(12) United States Patent
Chen et al.

(10) Patent No.: US 7,572,783 B2
(45) Date of Patent: Aug. 11, 2009

(54) SUBSTITUTED BENZOFUSED HETEROCYCLES

(75) Inventors: Xi Chen, Palo Alto, CA (US); Xiaoqi Chen, San Mateo, CA (US); Richard Victor Connors, Pacifica, CA (US); Kang Dai, Albany, CA (US); Ying Fu, Menlo Park, CA (US); Juan C. Jaen, Burlingame, CA (US); Yong-Jae Kim, Foster City, CA (US); Leping Li, Burlingame, CA (US); Mike E. Lizarzaburu, San Diego, CA (US); Jeffrey T. Mihalic, San Francisco, CA (US); Stephen J. Shuttleworth, Bourne End (GB)

(73) Assignee: Amgen Inc., Thousand Oaks, CA (US)

( * ) Notice: Subject to any disclaimer, the term of this patent is extended or adjusted under 35 U.S.C. 154(b) by 425 days.

(21) Appl. No.: 11/203,562

(22) Filed: Aug. 12, 2005
(Under 37 CFR 1.47)

(65) Prior Publication Data
US 2006/0199796 A1    Sep. 7, 2006

Related U.S. Application Data

(60) Provisional application No. 60/601,223, filed on Aug. 13, 2004.

(51) Int. Cl.
A61K 31/4709    (2006.01)
A61K 31/553     (2006.01)
C07D 217/02     (2006.01)
C07D 267/02     (2006.01)

(52) U.S. Cl. .................. 514/211.09; 514/221; 514/307; 514/412; 540/490; 540/500; 540/504; 546/140; 548/469

(58) Field of Classification Search ........................ None
See application file for complete search history.

(56) References Cited

U.S. PATENT DOCUMENTS

| | | | |
|---|---|---|---|
| 5,438,035 A | 8/1995 | Guaciaro et al. | |
| 5,532,237 A | 7/1996 | Gallant et al. | |
| 5,552,524 A | 9/1996 | Basinski et al. | |
| 5,624,941 A | 4/1997 | Barth et al. | |
| 5,705,515 A | 1/1998 | Fisher et al. | |
| 5,705,890 A | 1/1998 | Blackburn et al. | |
| 5,739,106 A | 4/1998 | Rink et al. | |
| 6,028,084 A | 2/2000 | Barth et al. | |
| 6,358,951 B1 | 3/2002 | Carpino | |
| 6,362,331 B1 | 3/2002 | Kamal et al. | |
| 6,365,633 B1 | 4/2002 | Cheetham et al. | |
| 6,602,867 B1 * | 8/2003 | Starck et al. ........... | 514/217.07 |
| 2002/0006964 A1 | 1/2002 | Young et al. | |

FOREIGN PATENT DOCUMENTS

| WO | WO99/00123 | 1/1999 |
|---|---|---|
| WO | WO99/43813 | 9/1999 |
| WO | WO00/21509 | 4/2000 |
| WO | WO00/56721 | 9/2000 |
| WO | WO01/09120 | 2/2001 |
| WO | WO01/10799 | 2/2001 |
| WO | WO01/62341 | 8/2001 |
| WO | WO01/77094 | 10/2001 |
| WO | WO01/89528 | 11/2001 |
| WO | WO02/15845 | 2/2002 |
| WO | WO02/15905 | 2/2002 |
| WO | WO02/40457 | 5/2002 |
| WO | WO02/40487 | 5/2002 |
| WO | WO02/051809 | 7/2002 |
| WO | WO02/076949 | 10/2002 |
| WO | WO02/098865 | 12/2002 |
| WO | WO03/009847 | 2/2003 |
| WO | WO03/041715 | 5/2003 |
| WO | WO2004/002961 | 6/2004 |
| WO | WO2004/021984 | 9/2004 |

OTHER PUBLICATIONS

Bray, George A. and Greenway, Frank L., "Current and Potential Drugs for Treatment of Obesity," *Endocrine Reviews*, vol. 20, No. 6, pp. 805-875 (1999).

Connacher, A.A., et al., "Weight Loss in Obese Subjects on a Restricted Diet Given BRL 26830A, a New Atypical β Adrenoceptor Agonist," *British Medical Journal*, vol. 296, pp. 1217-1220 (1988).

Daniels, A.J., et al., "Food Intake Inhibition and Reduction in Body Weight Gain in Lean and Obese Rodents Treated with GW438014A, a Potent and Selective NPY-Y5 Receptor Antagonist," *Regulatory Peptides*, vol. 106 pp. 47-54 (2002).

(Continued)

*Primary Examiner*—Zinna N Davis
(74) *Attorney, Agent, or Firm*—Jones Day

(57) ABSTRACT

The present invention relates to the compounds of Formula I, their preparation and pharmaceutical compositions comprising them. The compounds and pharmaceutical compositions are useful, for example, for the treatment and prevention of obesity, obesity-related disorders and eating disorders.

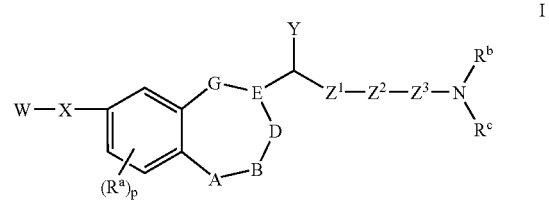

20 Claims, No Drawings

OTHER PUBLICATIONS

Gale, Susan M., et al., "Energy Homeostasis, Obesity and Eating Disorders: Recent Advances in Endocrinology," *J. Nutr.*, vol. 134 No. 2, pp. 295-298 (2004).

Goff, Dane A. and Zuckermann, Ronald N., "Solid-Phase Synthesis of Defined 1,4-Benzodiazepine-2,5-dione Mixtures," *J. Org. Chem.*, vol. 60, pp. 5744-5745 (1995).

Gualillo, Oreste, et al., Ghrelin, a Widespread Hormone: Insights into Molecular and Cellular Regulation of its Expression and Mechanism of Action, *FEBS Letters*, vol. 552, pp. 105-109 (2003).

Halaas, J.L., et al., "Weight-Reducing Effects of the Plasma Protein Encoded by the Obese Gene," *Science*, vol. 269, pp. 543-546 (1995).

Hataya, Yuji, et al., "A Low Dose of Ghrelin Stimulates Growth Hormone (GH) Release Synergistically with GH-Releasing Hormone in Humans," *Journal of Clinical Endocrinology & Metabolism*, vol. 86, No. 9, pp. 4552-4555 (2001).

Kamal, Ahmed, "Enzymatic Approach to the Synthesis of the Pyrrolo[1,4]benzodiazepine Antibiotics," *J. Org. Chem.*, vol. 56, pp. 2237-2240 (1991).

Keating, Thomas A. and Armstrong, Robert W., "A Remarkable Two-Step Synthesis of Diverse 1,4-Benzodiazepine-2,5-diones Using the Ugi Four-Component Condensation," *J. Org. Chem.*, vol. 61, pp. 8935-8939 (1996).

Kojima, Masayasu, et al., "Ghrelin is a Growth-Hormone-Releasing Acylated Peptide from Stomach," *Nature*, vol. 402, pp. 656-660 (1999).

Kopelman, Peter G., "Obesity as a Medical Problem," *Nature*, vol. 404, pp. 635-643 (2000).

Lazewska, D., et al., "Piperidine-containing Histamine $H_3$-receptor Antagonists of the Carbamate Series: Variation of the Spacer Length," *Pharmazie*, vol. 56, pp. 927-932 (2001).

Mayer, John P., et al., "Solid Phase Synthesis of 1,4-Benzodiazepine-2,5-diones," *Tetrahedron Letters*, vol. 37, No. 45, pp. 8081-8084 (1996).

Mori, Miwako, et al., "A One Step Synthesis of 1,4-Benzodiazepines: Synthetic Studies on Neothramycin," *Tetrahedron Letters*, vol. 26, No. 48, pp. 5947-5950 (1985).

Nakazato, Masamitsu, et al., "A Role for Ghrelin in the Central Regulation of Feeding," *Nature*, vol. 409, pp. 194-198 (2001).

Peino, Roberto, et al., "Ghrelin-induced Growth Hormone Secretion in Humans," *European Journal of Endocrinology*, vol. 143, pp. R11-R14 (2000).

Schwartz, Michael W., et al., "Central Nervous System Control of Food Intake," *Nature*, vol. 404, pp. 661-671 (2000).

Strack, Alison M., et al., "Regulation of Body Weight and Carcass Composition by Sibutramine in Rats," *Obesity Research*, vol. 10, No. 3, pp. 173-181 (2002).

Sturm, Roland, "The Effects of Obesity, Smoking, and Drinking on Medical Problems and Costs," *Health Affairs*, vol. 21, No. 2, pp. 245-253 (2002).

Tschöp, Matthias, et al., "Ghrelin Induces Adiposity in Rodents," *Nature*, vol. 407, pp. 908-913 (2000).

Wren, Alison M., et al., "Ghrelin Causes Hyperphagia and Obesity in Rats," *Diabetes*, vol. 50, pp. 2540-2547 (2001).

Wren, A.M., et al., "Ghrelin Enhances Appetite and Increases Food Intake in Humans," *The Journal of Clinical Endocrinology & Metabolism*, vol. 86, No. 12, pp. 5992-5995 (2001).

Zhang, Puwen, et al., "Synthesis of Novel Imidazobenzodiazepines as Probes of the Phamacophore for 'Diazepam-Insensitive' $GABA_A$ Receptors," *J. Med. Chem.*, vol. 38, pp. 1679-1688 (1995).

Zigman, Jeffrey M. and Elmquist, Joel K., "Minireview: From Anorexia to Obesity—The Yin and Yang of Body Weight Control," *Endocrinology*, vol. 144, No. 9, pp. 3749-3756 (2003).

International Preliminary Report on Patentability, dated Feb. 13, 2007 of PCT Application No. PCT/US2005/028935, filed Aug. 12, 2005.

Written Opinon, dated Feb. 13, 2007, 2008 of PCT Application No. PCT/US2005/028935, filed Aug. 12, 2005.

* cited by examiner

SUBSTITUTED BENZOFUSED HETEROCYCLES

CROSS REFERENCE TO RELATED APPLICATION

This application claims the benefit of U.S. Provisional Application No. 60/601,223 filed Aug. 13, 2004, which is incorporated herein by reference in its entirety.

FIELD OF THE INVENTION

This invention pertains generally to compounds and compositions comprising useful for the treatment and prevention of obesity, obesity-related disorders and eating disorders. Further, the invention described herein relates to methods of treating or preventing obesity and obesity-related disorders in a subject in need thereof by administering a composition of the present invention.

BACKGROUND OF THE INVENTION

Health problems resulting from obesity could offset many of the recent health gains achieved by modern medicine, and obesity may replace tobacco as the number one health risk for developed societies. It is estimated that about 97 million adults in the United States are overweight or obese. Approximately 300,000 deaths per year and significant morbidity are directly attributable to obesity, mainly due to heart disease, diabetes, cancer, asthma, sleep apnea, arthritis, reproductive complications and psychological disturbances (Gale et al., J. Nutr. 2004 February; 134(2): 295-8). Obesity results from a positive energy balance, as a consequence of increased ratio of caloric intake to energy expenditure. A lack of physical activity and high fat diets are major factors contributing to this condition. It has been shown that the genetic predisposition of individuals and ethnic groups to obesity also plays a significant role, although the genetic factors leading to obesity are not completely understood.

Increasing degrees of excess body fat and obesity are important predictors of decreased life expectancy. Obesity increases the risk of heart disease, high blood pressure, type II diabetes and other chronic diseases as much as does 20 years of aging (Sturm (2002) Health Affairs 21: 245-253). Additionally, it causes or exacerbates numerous health problems, such as hypertension, elevated plasma insulin concentrations, insulin resistance, dyslepidemias, obstructive sleep apnea, breast, endometrial, prostate and colon cancer, osteoarthritis, arteriosclerosis, abnormal heart rhythms and heart arrhythmias, cholelithiasis, and gallstones (Kopelman (2000) Nature 404: 635-643). Obesity is also associated with an increase in mortality and morbidity from stroke, myocardial infarction, congestive heart failure, coronary heart disease and premature death. Obesity shortens women's lives by seven years and men's lives by six years (Peeters, et al. (2003) Annals of Internal Medicine 138: 24-32).

Over the years, numerous therapeutic modalities have been used for the treatment of obesity, but none have been found to be entirely safe and effective for all patient populations (Bray et al. (1999) Endocrine Reviews 20(6): 805-875). Thyroid extract was reportedly used as early as 1893 (Putnam (1893) Am J Med Sci 106: 125-148). To achieve the effects on body weight, the doses required produced some measure of hyperthyroidism with catabolic consequences on bone, muscle, and the heart. When dinitrophenol was first used in 1933 (Masserman et al. (1934) JAMA 102: 523-525), it was accompanied by neuropathy and cataracts, which led to its discontinuation. The introduction of amphetamine in 1937 (Lesses et al. (1938) N. Engl. J. Med. 218: 119-124) was followed by reports of addiction, a problem that has plagued all of the chemicals that are structurally similar to amphetamine. The use of pills containing amphetamine, digitalis, and diuretics led to several deaths in 1967 and prompted the US Senate to hold hearings. In 1971 aminorex, or aminoxaphen, a new appetite suppressant, was taken off the market in Europe shortly after marketing because of an outbreak of pulmonary hypertension linked to this drug (Kramer et al. (1998) J. Clin. Epidemiol. 51: 361-364). A few years later in 1978, 17 deaths were reported with the use of very-low-calorie diets containing collagen as the principal source of protein (Sours et al. (1981) Am. J. Clin. Nutr. 34: 453-461). Problems with diet clinics led to another set of congressional hearings in 1991, again with little impact except the bankruptcy of several commercial weight loss programs. The final problem has been the valvular heart disease associated with the combined use of fenfluramine and phentermine (Connolly et al. (1997) N. Engl. J. Med. 337:581-588).

Thus, to slow the obesity epidemic, the source needs to be tackled through fundamental research into the mechanisms by which obesity is manifest, and education on the risks and how to prevent it. In order to understand the pathophysiology of obesity it is necessary to investigate the physiology of body weight regulation. Energy intake and body weight are regulated at a very consistent "set-point" by control systems in the hypothalamus. These systems receive feedback from peripheral signals (Schwartz et al. (2000) Nature 404(6778): 661-671). The adipocyte-derived hormone leptin signals the state of fat stores to the brain, inhibiting further food intake and fat accumulation. On the other hand, ghrelin, produced in oxyntic glands in the stomach, serves as an important indicator of energy insufficiency (Zigman et al. (2003) Endocrinology 144(9): 3749-3756).

Ghrelin has been recently identified as an endogenous ligand for the growth hormone secretagogue receptor (GHSR). It is synthesized primarily in the stomach and found in the circulation of healthy humans. Ghrelin is a 28 amino acid peptide hormone with an octanoyl side chain at the third amino acid of its N-terminus (serine 3). This modification is required for the interaction at the GHS receptor and its activity. Ghrelin levels in plasma are influenced by nutritional status and are believed to regulate growth hormone (GH), appetite and fat deposition (Hataya et al. (2001) J. Clin. Endocrinol. Metab. 86: 4552; Nakazato et al. (2001) Nature 409: 194-198; Peino et al. (2000) Eur. J. Endocrinol. 143: R11-R14; Tschop et al. (2000) Nature 407: 908-913; Wren et al. (2001) Diabetes 50: 2540-2547). The observation that ghrelin administration in rats resulted in weight gain as a consequence of changes in energy intake and/or fuel utilization supports such a role. Moreover, systemic ghrelin administration in humans causes sensations of hunger and induces overeating (Wren et al. (2001) J. Clin. Endocrinol. Metab. 86(12): 5992-5995). Based on these findings ghrelin is believed to play a crucial role in the regulation of appetite and body weight, and circulating ghrelin levels serve as an acute as well as a chronic signal of an underfed state. Therefore, ghrelin receptor modulators acting as agonists or antagonists would be able to enhance or reduce appetite and food intake, respectively; these molecules would receive obvious interest for treatment of eating disorders and obesity.

What are needed are alternative modalities for the treatment and prevention of obesity, obesity-related disorders and eating disorders.

SUMMARY OF THE INVENTION

The present invention provides compounds, that are modulators of, for example, ghrelin receptor (GHSR) activity, and methods of use thereof to treat or prevent conditions associated with, for example, obesity, obesity-related disorders or eating disorders. In particular, the present invention provides antagonists of GHSR, compositions comprising them and methods for treating or preventing conditions and disorders associated with eating behavior.

It is an object of this invention to identify compositions comprising specific modulators of ghrelin receptor (GHSR), useful for the treatment of obesity, obesity-related disorders and eating disorders. It is another object of the invention to identify methods of treating obesity and methods of preventing obesity. Yet another object of this invention is to provide pharmaceutical compositions comprising ghrelin receptor antagonists, either by itself or in combination with other anti-obesity agents.

The invention provides compounds of Formula I, as well as their pharmaceutically acceptable salts, solvates, stereoisomers, or prodrugs thereof.

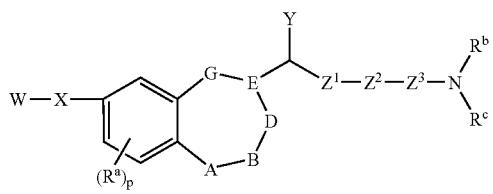

I

In Formula I, the substituents, subscripts and variables have the following meanings.

The symbols A, B and D represent a direct bond, —C($R^1$)($R^2$)—, —C($R^3$)=, —C(O)—, —N($R^4$)—, —N=, —O—, and —S(O)$_m$—, wherein m is an integer from 0 to 2, with the proviso that at least one of A, B, and D is other than a bond. In one aspect, when one of A and B is —C($R^1$)($R^2$)— or —C($R^3$)=, and the other is —N($R^4$)—, $R^4$ can be optionally combined with $R^1$, $R^2$ or $R^3$ to form a five or six-membered fused ring containing the nitrogen atom to which $R^4$ is attached and from 0 to 2 additional heteroatoms selected from the group consisting of N, O and S.

E is N or CH.

$R^1$, $R^2$, $R^3$ and $R^4$ are independently selected from the group consisting of hydrogen, halogen, amine, hydroxyl, cyano, ($C_1$-$C_8$) alkyl, ($C_2$-$C_8$) alkenyl, ($C_2$-$C_8$) alkynyl, and ($C_1$-$C_8$) alkoxy.

G is —C(O)—, —C(S)—, —C(NO$R^5$)—, —C(N—NH$R^6$)—, or —C($R^7$)($R^8$)—.

Each $R^a$ is independently selected from the group consisting of halogen, hydroxyl, cyano, ($C_1$-$C_8$) alkyl, ($C_2$-$C_8$) alkenyl, ($C_2$-$C_8$) alkynyl, ($C_1$-$C_8$) alkoxy and —N$R^9R^{10}$.

p is an integer from 0 to 3.

X is selected from the group consisting of —C($R^{11}$)($R^{12}$)—, —C(O)—, —C(S)—, —O—, —S(O)$_n$—, —N($R^{13}$)—, and —N(O$R^{14}$)—. The subscript n is an integer from 0 to 2.

$R^5$, $R^6$, and $R^{14}$ are independently selected from the group consisting of hydrogen, ($C_1$-$C_8$) alkyl, ($C_2$-$C_8$) alkenyl, and ($C_2$-$C_8$) alkynyl.

$R^7$, $R^8$, $R^9$, $R^{10}$, $R^{11}$, $R^{12}$, and $R^{13}$ are independently selected from the group consisting of hydrogen, ($C_1$-$C_8$) alkyl, ($C_2$-$C_8$) alkenyl, ($C_2$-$C_8$) alkynyl, and ($C_1$-$C_8$) alkoxy.

W is a ring selected from the group consisting of aryl, heteroaryl, ($C_3$-$C_8$) cycloalkyl, ($C_5$-$C_6$) heterocycloalkyl, ($C_5$-$C_8$) cycloalkenyl, and ($C_5$-$C_6$) heterocycloalkenyl.

Y is selected from the group consisting of hydrogen, ($C_1$-$C_8$) alkyl, ($C_2$-$C_8$) alkenyl, ($C_2$-$C_8$) alkynyl, aryl, heteroaryl, ($C_3$-$C_8$) cycloalkyl, ($C_3$-$C_8$) heterocycloalkyl, ($C_5$-$C_8$) cycloalkenyl and ($C_5$-$C_8$) heterocycloalkenyl.

$Z^1$ and $Z^3$ are independently selected from the group consisting of a bond and ($C_1$-$C_8$) alkylene. In one aspect, $Z^3$ can be combined with $R^b$ or $R^c$ to form a 3-, 4-, 5-, 6-, 7- or 8-membered ring containing the nitrogen atom to which $Z^3$ is attached and from 0 to 2 additional heteroatoms selected from the group consisting of N, O, and S.

$Z^2$ is selected from the group consisting of ($C_2$-$C_8$) alkenylene, ($C_2$-$C_8$) alkynylene, —C(O)O—, —N(R')(R")—, —C(O)N(R')—, —O—, —S(O)$_k$—, —N(R')C(O)N(R")—, —N(R')C(O)O—, —OC(O)O—, arylene, heteroarylene, aryl-($C_1$-$C_5$) alkylene, ($C_3$-$C_8$) cycloalkylene, ($C_3$-$C_8$) heterocycloalkylene, ($C_5$-$C_8$) cycloalkenylene, ($C_5$-$C_8$) heterocycloalkenylene, and ($C_5$-$C_8$) heterocycloalkylene-C(O)—. The subscript k is 0, 1, or 2.

R' and R" are independently selected from the group consisting of hydrogen, ($C_1$-$C_8$) alkyl, ($C_2$-$C_8$) alkenyl, and ($C_2$-$C_8$) alkynyl.

$R^b$ and $R^c$ are independently selected from the group consisting of hydrogen, ($C_1$-$C_8$) alkyl, ($C_2$-$C_8$) alkenyl, ($C_2$-$C_8$) alkynyl, ($C_3$-$C_8$) cycloalkyl, ($C_3$-$C_8$) heterocycloalkyl, ($C_3$-$C_8$) cycloalkenyl, ($C_3$-$C_8$) heterocycloalkenyl, aryl, heteroaryl, halo-($C_1$-$C_8$) alkyl, aryl-($C_1$-$C_5$) alkyl, ($C_3$-$C_8$) cycloalkyl-($C_1$-$C_5$)alkyl, ($C_3$-$C_8$) heterocycloalkyl-($C_1$-$C_5$) alkyl, ($C_3$-$C_8$) heterocycloalkenyl-($C_1$-$C_5$) alkyl, heteroaryl-($C_1$-$C_5$) alkyl, —C$R^{15}$CO$_2R^{16}$, —C$R^{15}$N($R^{16}$)SO$_2R^{17}$, —CO$_2R^{15}$, —C(O)N$R^{15}R^{16}$, —C(O)N($R^{15}$)O$R^{16}$, —C(=NO$R^{15}$)N$R^{16}R^{17}$, —C($R^{15}$)=NO$R^{16}$, —C(O)$R^{17}$C(O)N$R^{15}R^{16}$, —N$R^{15}R^{16}$, —N$R^{15}$SO$_2R^{16}$, —N$R^{15}$(O$R^{16}$), —N$R^{17}$C(O)N$R^{15}$C(O)$R^{16}$, —N$R^{15}$C(O)N$R^{16}R^{17}$, —O$R^{15}$, and —SO$_2$N$R^{15}R^{16}$. In one aspect, $R^b$ and $R^c$ may be combined to form a 3-, 4-, 5-, 6-, 7-, or 8-membered ring containing the nitrogen atom to which they are attached and from 0 to 3 additional heteroatoms selected from the group consisting of N, O and S.

$R^{15}$, $R^{16}$, and $R^{17}$ are independently selected from the group consisting of hydrogen, ($C_1$-$C_8$) alkyl, ($C_2$-$C_8$) alkenyl, ($C_2$-$C_8$) alkynyl, halo-($C_1$-$C_4$)alkyl, hetero($C_1$-$C_4$)alkyl, ($C_3$-$C_8$) cycloalkyl, ($C_3$-$C_8$) heterocycloalkyl, ($C_3$-$C_8$) cycloalkenyl, ($C_3$-$C_8$) heterocycloalkenyl, aryl, heteroaryl and aryl-($C_1$-$C_4$)alkyl.

In one aspect, the invention provides a group of compounds represented by the formula II(a):

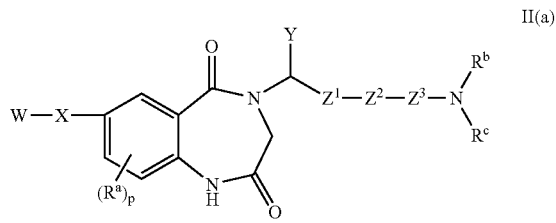

II(a)

In another aspect, the invention provides compounds represented by the formula II(b):

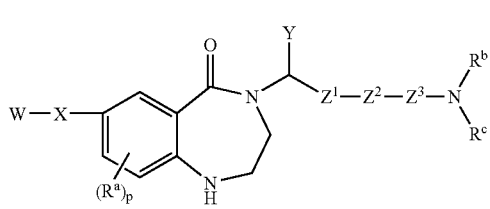

II(b)

In another aspect, the invention provides compounds represented by the formula II(c):

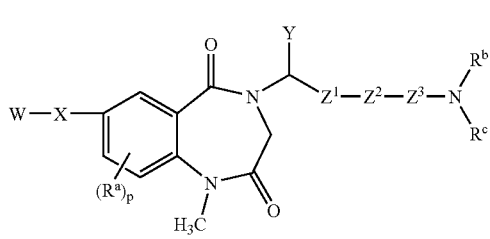

II(c)

In another aspect, the invention provides compounds represented by the formula II(d):

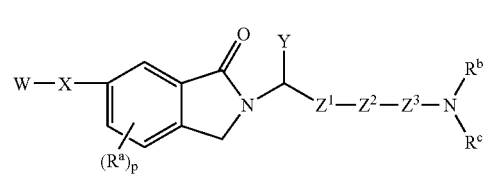

II(d)

In another aspect, the invention provides compounds represented by the formula II(e):

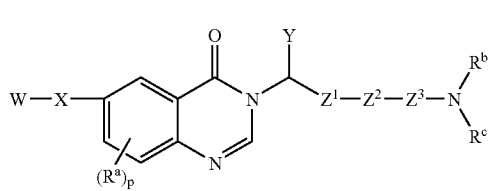

II(e)

In another aspect, the invention provides compounds represented by the formula II(f):

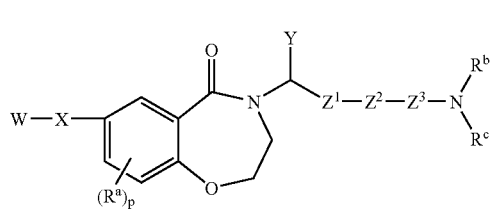

II(f)

In another aspect, the invention provides compounds represented by the formula II(g):

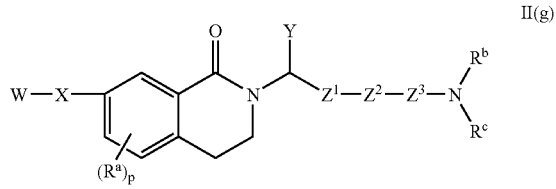

II(g)

In another aspect, the invention provides compounds represented by the formula II(h):

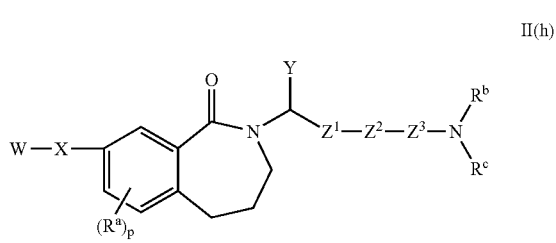

II(h)

In another aspect, the invention provides compounds represented by the formula II(i):

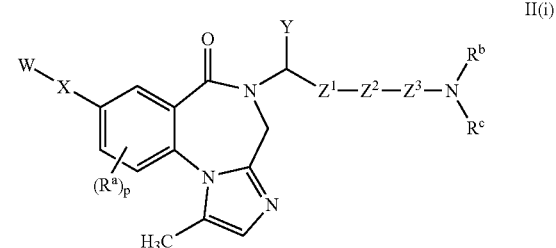

II(i)

In yet another aspect, the invention provides compounds represented by the formula II(j):

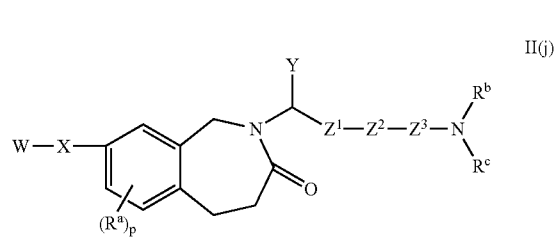

II(j)

In a further aspect, the invention provides compounds represented by the formula II(k):

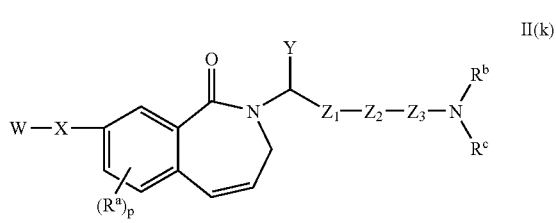

II(k)

In each of these groups of the embodiments represented by the Formulas II(a-k) W, X, Y, $Z^1$, $Z^2$, $Z^3$, $R^a$, p, $R^b$, and $R^c$ have the meanings as provided above.

In one aspect, the invention provides compounds of Formulas I and II(a-k) and their pharmaceutically acceptable salts, solvates, and stereoisomers.

Within each of these groups of embodiments are several further groups, described below.

In one aspect, p=0.

In one aspect, Y is $(C_1-C_8)$ alkyl or $(C_3-C_8)$ cycloalkyl.

In one aspect, X is S. In another aspect, X is O.

In one aspect, $Z^2$ can be piperidinyl-1-carbonyl or phenylene. In another aspect, $Z^2$ can be propenylene or thiazolediyl.

In one aspect, $Z^3$ can combined with $R^b$ to form a 3-, 4-, 5-, 6-, 7- or 8-membered ring containing the nitrogen atom to which $Z^3$ is attached and from 0 to 2 additional heteroatoms selected from the group consisting of N, O and S.

In one aspect, W is aryl.

In one aspect, $R^b$ and $R^c$ are independently selected from the group consisting of hydrogen,

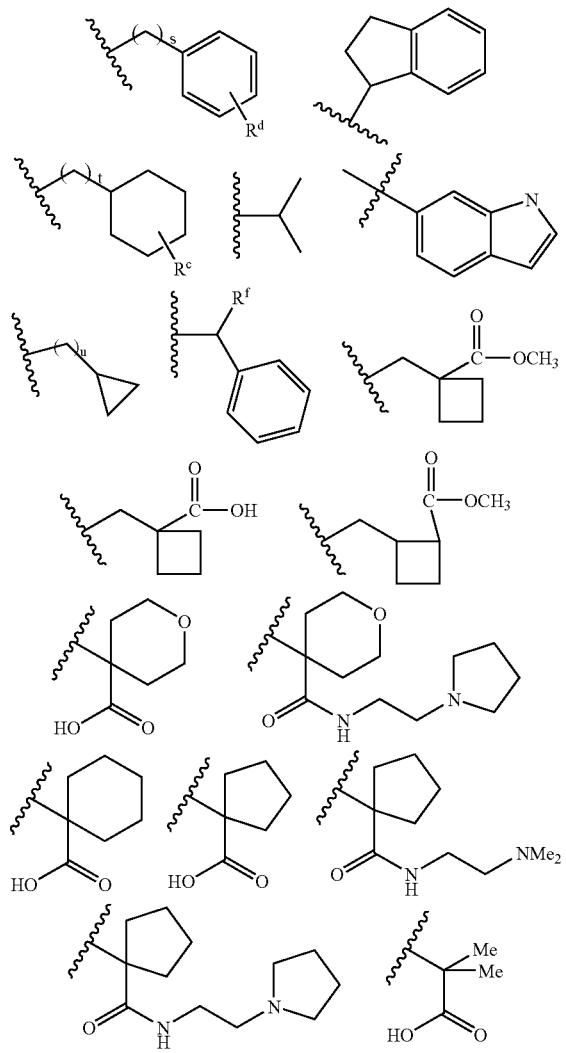

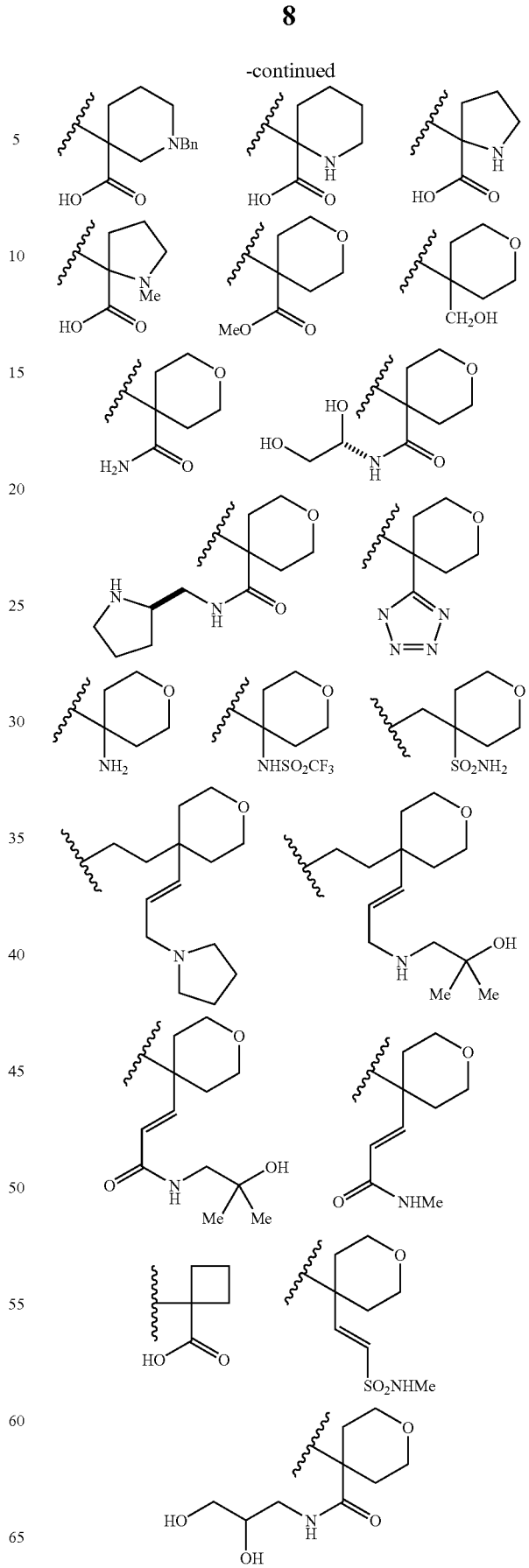

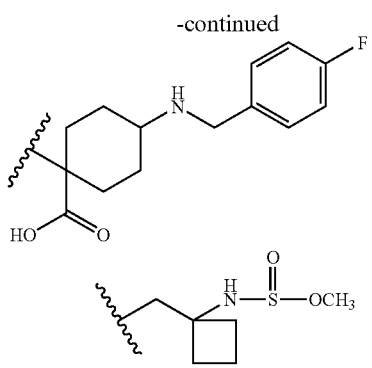

The subscripts s, t, and u are independently an integer from 0 to 5. In one aspect, $R^d$, $R^e$, and $R^f$ are independently selected from the group consisting of hydrogen, halogen, hydroxyl, amine, ($C_1$-$C_8$) alkyl and ($C_2$-$C_8$) alkenyl.

In one aspect, the invention provides the following compounds:

N-(1-benzyl-piperidin-4-yl)-2-(2,5-dioxo-7-phenoxy-1,2,3,5-tetrahydro-benzo[e][1,4]diazepin-4-yl)-3-methyl-butyramide, N-(1-benzyl-piperidin-4-yl)-2-(2,5-dioxo-7-phenoxy-1,2,3,5-tetrahydro-benzo[e][1,4]diazepin-4-yl)-3,3-dimethyl-butyramide, 2-[7-(2,6-dimethyl-phenoxy)-2,5-dioxo-1,2,3,5-tetrahydro-benzo[e][1,4]diazepin-4-yl]-3-methyl-N-[1-(1-phenyl-ethyl)-piperidin-4-yl]butyramide 2-[7-(2,6-dimethyl-phenoxy)-2,5-dioxo-1,2,3,5-tetrahydro-benzo[e][1,4]diazepin-4-yl]-N-(1-indan-1-yl-piperidin-4-yl)-3-methyl-butyramide, 4-{1-[2-(1-cyclopropylmethyl-piperidin-4-yl)-ethyl]-2-methyl-propyl}-7-(2,6-difluoro-phenoxy)-3,4-dihydro-1H-benzo[e][1,4]diazepine-2,5-dione, 7-(2-ethyl-phenoxy)-4-{1-[4-(4-fluoro-benzylamino)-piperidine -1-carbonyl]-2-methyl-propyl}-3,4-dihydro-1H-benzo[e][1,4]diazepine-2,5-dione, 4-[1-(4-cyclopropylamino-piperidine-1-carbonyl)-2-methyl-propyl]-7-(2-ethyl-phenoxy)-3,4-dihydro-1H-benzo[e][1,4]diazepine-2,5-dione, 7-(2,4-difluoro-phenoxy)-4-[1-(3-dimethylaminomethyl-phenyl)-2-methyl-propyl]-3,4-dihydro-1H-benzo[e][1,4]diazepine-2,5-dione, 7-(2,4-difluoro-phenoxy)-4-{1-[3-(isopropylamino-methyl)-phenyl]-2-methyl-propyl}-3,4-dihydro-1H-benzo[e][1,4]diazepine-2,5-dione, 2-(2,5-dioxo-7-phenoxy-1,2,3,5-tetrahydrobenzo[e][1,4]diazepin-4-yl)-3-methyl-butyric acid 1-benzyl-piperidin-4-yl ester, 1-benzyl-piperidine-4-carboxylic acid 2-[7-(4-fluoro-phenoxy)-2,5-dioxo-1,2,3,5-tetrahydro-benzo[e][1,4]diazepin-4-yl]-3-methyl-butyl ester, (1-benzyl-piperidin-4-yl)-carbamic acid 2-[7-(4-fluoro-phenoxy)-2,5-dioxo-1,2,3,5-tetrahydro-benzo[e][1,4]diazepin-4-yl]-3-methyl-butyl ester,

[1-(4-fluoro-benzyl)-piperidin-4-yl]-carbamic acid 2-[7-(4-fluoro-phenoxy)-2,5-dioxo-1,2,3,5-tetrahydro-benzo[e][1,4]diazepin-4-yl]-3-methyl-butyl ester, N-(1-benzyl-piperidin-4-yl)-2-(2,5-dioxo-7-phenoxy-1,2,3,5-tetrahydro-benzo[e][1,4]diazepin-4-yl)-3-methyl-butyramide, 7-(2-tert-butyl-phenoxy)-4-[1-(4-cyclopropylamino-piperidine-1-carbonyl)-2-methyl-propyl]-3,4-dihydro-1H-benzo[e][1,4]diazepine-2,5-dione, N-(1-benzyl-piperidin-4-yl)-2-(2,5-dioxo-7-phenoxy-1,2,3,5-tetrahydro-benzo[e][1,4]diazepin-4-yl)-2-thiophen-2-yl-acetamide, N-(1-benzyl-piperidin-4-yl)-2-cyclohexyl-2-(2,5-dioxo-7-phenoxy-1,2,3,5-tetrahydro-benzo[e][1,4]diazepin-4-yl)-acetamide, 2-{1-[2-(1-cyclopropylmethyl-piperidin-4-yl)-ethyl]-2-methyl-propyl}-7-(2,4-difluoro-phenoxy)-3,4-dihydro-2H-isoquinolin-1-one, 2-[1-(4-cyclopropylamino-piperidine-1-carbonyl)-2-methyl-propyl]-7-(2,4-difluoro-phenoxy)-3,4-dihydro-2H-isoquinolin-1-one, 7-(2,4-difluoro-phenoxy)-2-{1-[4-(4-fluoro-benzylamino)-piperidine-1-carbonyl]-2-methyl-propyl}-3,4-dihydro-2H-isoquinolin-1-one, 7-(2,4-difluoro-phenoxy)-2-(1-{4-[2-(4-fluoro-phenyl)-ethylamino]-piperidine-1-carbonyl}-2-methyl-propyl)-3,4-dihydro-2H-isoquinolin-1-one, 2-[1-(1-cyclopropylmethyl-piperidin-4-yloxymethyl)-2-methyl-propyl]-7-(2,4-difluoro-phenoxy)-3,4-dihydro-2H-isoquinolin-1-one, 2-(cyclopropyl-{3-[2-(cyclopropylmethyl-amino)-ethyl]-phenyl}-methyl)-7-(2,4-difluoro-phenoxy)-3,4-dihydro-2H-isoquinolin-1-one, 2-{1-[4-(cyclopropylmethyl-amino)-piperidine-1-carbonyl]-2-methyl-propyl}-7-(2,4-difluoro-phenoxy)-3,4-dihydro-2H-isoquinolin-1-one, N-(1-benzyl-piperidin-4-yl)-3-methyl-2-(4-oxo-6-o-tolyloxy-4H-quinazolin-3-yl)-butyramide, N-(1-benzyl-piperidin-4-yl)-2-[8-(4-fluoro-2-methyl-phenoxy)-1-methyl-6-oxo-4H,6H-3,5,10b-triaza-benzo[e]azulen-5-yl]-3-methyl-butyramide, 4-{1-[4-(indan-2-ylamino)-piperidine-1-carbonyl]-2-methyl-propyl}-7-o-tolyloxy-1,2,3,4-tetrahydro-benzo[e][1,4]diazepin-5-one, 8-(2,4-difluoro-phenoxy)-2-{1-[4-(4-fluoro-benzylamino)-piperidine-1-carbonyl]-2-methyl-propyl}-2,3-dihydro-benzo[c]azepin-1-one, 2-[1-(4-cyclopropylamino-cyclohexylmethyl)-2-methyl-propyl]-8-(2,4-difluoro-phenoxy)-2,3,4,5-tetrahydro-benzo[c]azepin-1-one, 2-(1-{4-[(cyclopropylmethyl-amino)-methyl]-thiazol-2-yl}-2-methyl-propyl)-8-(2,4-difluoro-phenoxy)-2,3,4,5-tetrahydro-benzo[c]azepin-1-one, 2-{1-[4-(cyclopropylmethyl-amino)-piperidine-1-carbonyl]-2-methyl-propyl}-8-(2,4-difluoro-phenoxy)-1,2,4,5-tetrahydro-benzo[c]azepin-3-one, 4-(1-{4-[2-(4-fluoro-phenyl)-ethylamino]-piperidine-1-carbonyl}-2-methyl-propyl)-1-methyl-7-o-tolyloxy-1,2,3,4-tetrahydro benzo[e][1,4]diazepin-5-one, 2-[7-(4-fluoro-phenoxy)-2,5-dioxo-1,2,3,5-tetrahydro-benzo[e][1,4]diazepin-4-yl]-3-methyl-N-(1-phenyl-piperidin-4-yl)-butyramide, 7-(2,6-dimethyl-phenoxy)-4-{1-[4-(4-fluoro-benzylamino)-piperidine-1-carbonyl]-2-methyl-propyl}-3,4-dihydro-1H-benzo[e][1,4]diazepine-2,5-dione, 7-(2,6-dimethyl-phenoxy)-4-1-{4-[2-(4-fluoro-phenyl)-ethylamino]-piperidine-1-carbonyl}-2-methyl-propyl)-3,4-dihydro-1H-benzo[e][1,4]diazepine-2,5-dione, 7-(2-tert-butyl-phenoxy)-4-(1-{4-[2-(4-fluoro-phenyl)-ethylamino]-piperidine-1-carbonyl}-2-methyl-propyl)-3,4-dihydro-1H-benzo[e][1,4]diazepine-2,5-dione, 2-(cyclopropyl(6-((cyclopropylmethylamino)methyl)pyridin-2-yl)methyl)-7-(2,4-difluorophenoxy)-3,4-dihydroisoquinolin-1(2H)-one, 2-(cyclopropyl(6-((cyclopropylamino)methyl)pyridin-2-yl)methyl)-7-(2,4-difluorophenoxy)-3,4-dihydroisoquinolin-1(2H)-one, 2-(cyclopropyl(6-(1-hydroxypropan-2-ylamino)methyl)pyridin-2-yl)methyl)-7-(2,4-difluorophenoxy)-3,4-dihydroisoquinolin-1(2H)-one, 2-(cyclopropyl(6-((1-hydroxy-2-methylpropan-2-ylamino)methyl)pyridin-2-yl)methyl)-7-(2,4-difluorophenoxy)-3,4-dihydroisoquinolin-1(2H)-one, 2-(cyclopropyl(6-((2-fluoroethylamino)methyl) pyridine-2-yl)methyl)-7-(2,4-difluorophenoxy)-3,4-dihydroisoquinolin-1(2H)-one and 2-(cyclopropyl(6-((2,2-difluoroethylamino) methyl)pyridin-2-yl)methyl)-7-(2,4-difluorophenoxy)-3,4-dihydroisoquinolin-1(2H)-one.

In one aspect, the invention provides pharmaceutical compositions comprising a compound of the invention of Formulas I and II(a-k), their pharmaceutically acceptable salts, solvates, stereoisomers, and prodrugs thereof and a pharmaceutically acceptable carrier, excipient or diluent. In another aspect, the invention provides pharmaceutical compositions comprising a compound of the invention of Formulas I and II(a-k), their pharmaceutically acceptable salts, solvates, and stereoisomers, and a pharmaceutically acceptable carrier, excipient or diluent.

In one aspect, the pharmaceutical composition can comprise the compound of the invention and an additional anti-obesity agent. In one aspect, the additional anti-obesity agent is selected from the group consisting of a serotonin transporter inhibitor, a norepinephrine transporter inhibitor, a cannabinoid-1 antagonist/inverse agonist, a histamine 3 antagonist/inverse agonist, a melanin concentrating hormone 1R antagonist, a melanin concentrating hormone 2R agonist/antagonist, leptin, a leptin derivative, an opioid antagonist, an orexin antagonist, a bombesin receptor subtype 3, a cholecystokinin-A agonist, a Ciliary neurotrophic factor, a Ciliary neurotrophic factor derivative, a growth hormone secretagogue receptor agonist/antagonist, a serotonin receptor 2C agonist, a melanocortin 4 receptor agonist, a monoamide reuptake inhibitor, an uncoupling protein-1, -2, or -3 activator, a beta adrenergic receptor 3 agonist, a thyroid hormone β agonist, a phosphodiesterase inhibitor, a fatty acid synthase inhibitor, a diacylglycerol acyltransferase-1 inhibitor, a diacylglycerol acyltransferase-2 inhibitor, an acetyl-CoA carboxylase 2 inhibitor, a glucocorticoid antagonist, an acyl-estrogen, a lipase inhibitor, a fatty acid transporter inhibitor, a dicarboxylate transporter inhibitor, a glucose transporter inhibitor, metformin and topiramate.

The invention further provides methods for treating a condition or disorder selected from the group consisting of obesity, an eating disorder, a cardiovascular disease, a gastrointestinal disorder, a dermatological disorder, and a cancer, comprising administering to a subject in need thereof a therapeutically effective amount of a compound or a composition of the invention. The compounds and compositions of the invention encompass all meanings defined above. In one aspect, the condition or disorder can be overeating, bulimia, diabetes, hypertension, elevated plasma insulin concentrations, insulin resistance, dyslipidemia, hyperlipidemia, breast, prostate, endometrial, kidney and colon cancer, heart disease, abnormal heart rhythms, arrhythmias, myocardial infarction, congestive heart failure, coronary heart disease, angina pectoris, cerebral infarction, cerebral thrombosis, transient ischemic attack, arthritis deformans, sudden death, osteoarthritis, cholelithiasis, gallstones, gallbladder disease, lumbodynia, emmeniopathy, obstructive sleep apnea, stroke, polycystic ovary disease, craniopharyngioma, the Prader-Willi Syndrome, Frohlich's syndrome, GH-deficiency, normal variant short stature, Turner syndrome, metabolic syndrome, impaired fasting glucose, impaired glucose tolerance, reproductive hormone abnormalities, sexual and reproductive dysfunction, fetal defects associated with maternal obesity, gastrointestinal motility disorders, respiratory disorders, fatty liver, breathlessness, dermatological disorders, inflammation, arteriosclerosis, hypercholesterolemia, hyperuricaemia, gout, and left ventricular hypertrophy.

In one aspect, the invention provides methods for modulating ghrelin receptor, comprising contacting a cell with a compound of the invention or a composition of the invention. In one aspect, the compound is a ghrelin receptor antagonist.

In one aspect, the invention provides methods for treating a condition or disorder selected from the group consisting of obesity, an eating disorder, a cardiovascular disease, a gastrointestinal disorder, a dermatological disorder, and a cancer, comprising administering to a subject in need thereof a therapeutically effective amount of a compound of the invention or a composition of the invention and an additional anti-obesity agent. The compounds and compositions of the invention include all meanings defined above. In one aspect, the additional anti-obesity agent is selected from the group consisting of a serotonin transporter inhibitor, a norepinephrine transporter inhibitor, a cannabinoid-1 antagonist/inverse agonist, a histamine 3 antagonist/inverse agonist, a melanin concentrating hormone 1R antagonist, a melanin concentrating hormone 2R agonist/antagonist, leptin, a leptin derivative, an opioid antagonist, an orexin antagonist, a bombesin receptor subtype 3, a cholecystokinin-A agonist, a Ciliary neurotrophic factor, a Ciliary neurotrophic factor derivative, a growth hormone secretagogue receptor agonist/antagonist, a serotonin receptor 2C agonist, a melanocortin 4 receptor agonist, a monoamide reuptake inhibitor, an uncoupling protein-1, -2, or -3 activator, a beta adrenergic receptor 3 agonist, a thyroid hormone β agonist, a phosphodiesterase inhibitor, a fatty acid synthase inhibitor, a diacylglycerol acyltransferase-1 inhibitor, a diacylglycerol acyltransferase-2 inhibitor, an acetyl-CoA carboxylase 2 inhibitor, a glucocorticoid antagonist, an acyl-estrogen, a lipase inhibitor, a fatty acid transporter inhibitor, a dicarboxylate transporter inhibitor, a glucose transporter inhibitor, metformin and topiramate.

Further objects, features and advantages of the invention will be apparent from the following detailed description.

DETAILED DESCRIPTION OF THE INVENTION

The present invention provides novel compounds, useful, for example, in the treatment of obesity. While not being bound by any particular mechanism of action, the compounds are believed to act as modulators of ghrelin activity, and, more particularly, as antagonists of GHSR. The compounds provided herein can be formulated into pharmaceutical compositions that are useful in treating patients with eating or obesity-related disorders. The invention also provides methods of treating or preventing obesity and obesity-related disorders in a subject in need thereof by administering a composition of the present invention.

Abbreviations

The following abbreviations are used throughout this application:
- ACN Acetonitrile
- aq Aqueous
- Bn Benzyl
- BnOH Benzyl alcohol
- Boc t-butoxycarbonyl
- DCE Dichloroethane
- DCM Dichloromethane
- DIEA Diisopropylethylamine
- DMA N,N-Dimethylacetamide
- DME 1,2-Dimethoxyethane
- DMF N,N-Dimethylformamide
- DMSO Dimethylsulfoxide
- DPPA Diphenylphosphoryl azide
- DTT Dithiothreitol
- EDC Ethylcarbodiimide hydrochloride
- EDCI 1-Ethyl-3-[3-(dimethylamino) propyl]carbodiimide hydrochloride
- EDTA Ethylene diamine tetraacetic acid
- ESI Electrospray Ionization
- $Et_3N$ Triethylamine
- EtOAc, EtAc Ethyl acetate
- EtOH Ethanol
- g Gram(s)
- h Hour(s)
- HBTU O-Benzotriazol-1-yl-N,N,N',N'-tetramethyluronium hexafluorophosphate
- HOBt 1-Hydroxybenzotriazole
- $IC_{50}$ The concentration of an inhibitor that causes a 50% reduction in a measured activity
- LAH Lithium aluminum hydride
- LDA Lithium diisopropylamide
- LRMS Low Resolution Mass Spectrometry
- MeI Methyl Iodate
- MeOH Methanol
- min Minute(s)
- mmol Millimole(s)
- NMM 4-Methylmorpholine
- NMP N-methylpyrrolidinone
- PG Protective Group
- Py Pyridine
- rt Room temperature
- TEA Triethylamine
- Tf Trifluoromethanesulfonate
- TFA Trifluoroacetic acid
- TFAA Trifluoroacetic anhydride
- THF Tetrahydrofuran
- TLC Thin Layer Chromatography General Definitions The term "ghrelin" refers to the natural endogenous ligand of the growth hormone secretagogue receptor (GHSR). Human ghrelin is a 28 amino acid peptide hormone with an octanoyl acid side chain at the third amino acid of its N-terminus (serine 3) (Kojima et al. (1999) Nature 42: 656-660).

GH refers to Growth Hormone.

GHSR or GHS-R refers to Growth Hormone Secretagogue Receptor, or ghrelin receptor. Upon activation, GHSR stimulates secretion of growth hormone (GH). Terms "GHSR" and "ghrelin receptor" are used interchangeably throughout the application.

The term "modulate" refers to the ability of a compound to increase or decrease the function, or activity, of ghrelin receptor. Modulation, as described herein, includes the antagonism or agonism of GHSR, either directly or indirectly. Antagonists are compounds that, e.g., partially or totally block stimulation, decrease, prevent, delay activation, inactivate, inhibit, desensitize, or down-regulate signal transduction. Agonists are compounds that, e.g., stimulate, increase, activate, open, facilitate, enhance activation, sensitize or up-regulate signal transduction.

The compositions of the present invention are useful for the treatment or prevention of obesity-related or eating disorders. The obesity herein may be due to any cause, whether genetic or environmental.

"Obesity" is a condition characterized by an excess of body fat. The operational definition of obesity is based on the Body Mass Index (BMI), which is calculated as body weight per height in meter squared ($kg/m^2$). Obesity refers to a condition whereby an otherwise healthy subject has a BMI greater than or equal to 30 $kg/m^2$, or a condition whereby a subject with at least one co-morbidity has a BMI greater than or equal to 27 $kg/m^2$. An "obese subject" is an otherwise healthy subject with a BMI greater than or equal to 30 $kg/m^2$ or a subject with at least one co-morbidity with a BMI greater than or equal 27 $kg/m^2$. A "subject at risk of obesity" is an otherwise healthy subject with a BMI of 25 $kg/m^2$ to less than 30 $kg/m^2$ or a subject with at least one co-morbidity with a BMI of 25 $kg/M^2$ to less than 27 $kg/m^2$.

The increased risks associated with obesity may occur at a lower BMI in people of Asian descent. In Asian and Asian-Pacific countries, including Japan, "obesity" refers to a condition whereby a subject with at least one obesity-induced or obesity-related co-morbidity that requires weight reduction or that would be improved by weight reduction, has a BMI greater than or equal to 25 $kg/m^2$. An "obese subject" in these countries refers to a subject with at least one obesity-induced or obesity-related co-morbidity that requires weight reduction or that would be improved by weight reduction, with a BMI greater than or equal to 25 $kg/m^2$. In these countries, a "subject at risk of obesity" is a person with a BMI of greater than 23 $kg/m^2$ to less than 25 $kg/m^2$.

The term "obesity-related disorders" encompasses disorders that are associated with, caused by, or result from obesity. Examples of obesity-related disorders include overeating and bulimia, diabetes, hypertension, elevated plasma insulin concentrations and insulin resistance, dyslipidemia, hyperlipidemia, breast, prostate, endometrial and colon cancer, heart disease, cardiovascular disorders, abnormal heart rhythms and arrhythmias, myocardial infarction, congestive heart failure, coronary heart disease, angina pectoris, cerebral infarction, cerebral thrombosis, transient ischemic attack, arthritis deformans, sudden death, osteoarthritis, cholelithiasis, gallstones and gallbladder disease, lumbodynia, emmeniopathy, obstructive sleep apnea, stroke, polycystic ovary disease, craniopharyngioma, the Prader-Willi Syndrome, Frohlich's syndrome, GH-deficiency, normal variant short stature, and Turner syndrome. Other examples include pathological conditions showing reduced metabolic activity or a decrease in resting energy expenditure as a percentage of total fat-free mass, such as in children with acute lymphoblastic leukemia. Further examples of obesity-related disorders include metabolic syndrome, also known as syndrome X, insulin resistance syndrome, impaired fasting glucose, impaired glucose tolerance, reproductive hormone abnormalities, sexual and reproductive dysfunction, such as impaired fertility, infertility, hirsutism in females and hypogonadism in males, fetal defects associated with maternal obesity, gastrointestinal motility disorders, such as obesity-related gastro-esophageal reflux, respiratory disorders, such as obesity-hypoventilation syndrome (Pickwickian syndrome), and breathlessness, fatty liver, dermatological disorders, inflammation, such as systemic inflammation of the vasculature, arteriosclerosis, hypercholesterolemia, hyperuricaemia, lower back pain, orthopedic disorders, gout, kidney cancer and increased anesthetic risk, as well as secondary outcomes of obesity such as left ventricular hypertrophy.

The term "metabolic syndrome," or syndrome X, as used herein, is present if a person has three or more of the following symptoms: abdominal obesity, hyperglyceridemia, low HDL cholesterol, high blood pressure, and high fasting plasma glucose. The criteria for these symptoms are defined in the 3rd Report of the National Cholesterol Education Program Expert Panel in Detection, Evaluation and Treatment of High blood Cholesterol in Adults (Ford, E. S. et al. (2002), JAMA 287(3): 356-359).

The term "diabetes" includes both insulin-dependent diabetes mellitus (IDDM, or Type I diabetes) and non-insulin dependent diabetes mellitus (NIDDM, or Type II diabetes). Type I diabetes results from an absolute deficiency of insulin, the hormone regulating glucose utilization. Type II diabetes often occurs when levels of insulin are normal or even elevated and appears to result from the inability of tissues to respond appropriately to insulin. Most of the Type II diabetics are also obese. The compositions of the present invention can be used for treating both Type I and II diabetes and for treating and/or preventing gestational diabetes mellitus indirectly by preventing obesity. The compositions of the invention can also be useful for treating and preventing diabetes directly.

As used herein, the terms "eating disorder", "feeding disorder", and the like refer to an emotional and/or behavioral disturbance associated with an excessive decrease in body weight and/or inappropriate efforts to avoid weight gain, e.g., fasting, self-induced vomiting, laxative or diuretic abuse. Depression is commonly associated with eating disorders. Exemplary eating disorders include anorexia nervosa and bulimia.

The terms "treat", "treating" and "treatment" refer to a method of alleviating or abrogating a disease and/or its attendant symptoms. Treatment of obesity and obesity-related disorders refers to the administration of compounds of the invention to reduce or maintain the body weight of an obese subject. One outcome of treatment may be reducing the body weight of the subject relative to that subject's body weight immediately before the administration of the compounds of the invention. Another outcome of treatment may be maintaining weight loss or preventing regain of body weight previously lost as a result of diet, exercise, or pharmacotherapy. Yet another outcome of treatment may be decreasing in occurrence and/or severity of obesity-related diseases. The treatment may result in a reduction in food or calorie intake by the subject, including a reduction in total food intake, or a reduction of intake of specific components of diet such as fats or carbohydrates, and/or inhibition of nutrient absorption and in weight reduction. The treatment may also result in an alteration of metabolic rate, such as an increase in metabolic rate, and/or an inhibition of the reduction of metabolic rate, and/or minimization of the metabolic resistance that may result from weight loss.

The terms "prevent", "preventing" and "prevention" refer to a method of decreasing the probability or eliminating the possibility that a disease will be contracted. Prevention of obesity and obesity-related disorders refers to the administration of the compounds of the invention to reduce or maintain the body weight of a subject at risk of obesity. One outcome of prevention may be reducing the weight of a subject relative to that subject's weight before the administration of the compounds of the invention. Another outcome of prevention may be preventing regain of weight previously lost as a result of diet, exercise of pharmacotherapy. Further outcome may be preventing obesity from occurring if the compounds are administered prior to the onset of obesity in a subject at risk of obesity or preventing weight regain or prolonging resistance to weight gain. Another outcome of prevention may be decreasing the occurrence and/or severity of obesity-related disorders if the compounds of the invention are administered prior to the onset of obesity in a subject at risk of obesity. If treatment is administered to already obese subjects, such treatment may prevent occurrence, progression or severity of obesity-related disorders.

The terms "administration" of or "administering" a compound as used herein refer to providing a compound of the invention or a prodrug thereof to a subject in need of treatment. Administration of the pharmaceutical composition of the invention includes administration of a single pharmaceutical dosage formulation containing ghrelin receptor modulators either in its own separate dosage formulation or in combination with a second anti-obesity agent. Where separate dosage formulations are used, the individual components of the composition can be administered either concurrently or sequentially prior to or subsequent to the administration of the other component of the composition. The terms "administration" or "administering" therefore include all such regimes of simultaneous or alternating treatment. If ghrelin receptor modulators are used in the combination with other anti-obesity agents, administration of the compositions of the invention can be done in the various ways as long as the most beneficial pharmaceutical effect of the combination of the ghrelin receptor modulator and another anti-obesity agent is achieved.

The term "subject" refers to an animal, preferably a mammal, preferably a human, who has been the object of treatment, observation or experiment.

The term "subject in need thereof" as used herein, refers to a subject who is in need of treatment or prophylaxis as determined by a researcher, medical doctor, veterinarian or other clinician. In one aspect, the subject in need of treatment can be an obese mammal. In another aspect, the subject in need of treatment can be an obese human without obesity related disorders or an obese human with one or more obesity-related co-morbidities.

The term "therapeutically effective amount" refers to that amount of the compound being administered sufficient to elicit the biological or medical response in a tissue, system, or subject, which includes preventing development of or alleviation to some extent of one or more of the symptoms of the condition or disorder being treated. A therapeutically effective dose may vary depending upon the route of administration and dosage form. The therapeutic index is the dose ratio between toxic and therapeutic effects which can be expressed as the ratio between LD50 and ED50. The LD50 is the dose lethal to 50% of the population and the ED50 is the dose therapeutically effective in 50% of the population. The LD50 and ED50 are determined by standard pharmaceutical procedures in animal cell cultures or experimental animals. Dosing regimens that achieve high therapeutic indexes are preferred.

The term "prophylactically effective amount" means the amount of the compound in the composition that will elicit the biological or medical response in a tissue, system or subject to prevent the onset of obesity or an obesity-related disorder in subject at risk for obesity or obesity-related disorders.

Chemical Definitions

As used herein, the terms have the following meanings:

The term "alkyl" by itself or as part of another substituent, means, unless otherwise stated, a straight or branched chain, saturated hydrocarbon having the indicated number of carbon atoms (i.e., $C_1$-$C_8$ means one to eight carbons). For example, ($C_1$-$C_8$) alkyl is meant to include, but is not limited to methyl, ethyl, propyl, isopropyl, butyl, sec-butyl, tert-butyl, pentyl, isopentyl, neopentyl, hexyl, isohexyl, cyclohexyl, (cyclohexyl)methyl, cyclopropylmethyl and neohexyl. An alkyl group can be unsubstituted or optionally substituted with one or more substituents as described herein below.

The term "alkenyl" as used herein refers to a straight or branched chain unsaturated hydrocarbon having the indicated number of carbon atoms (i.e., $C_2$-$C_8$ means two to eight carbons) and at least one double bond. Examples of a ($C_2$-$C_8$) alkenyl group include, but are not limited to, ethylene, propylene, 1-butylene, 2-butylene, isobutylene, sec-butylene, 1-pentene, 2-pentene, isopentene, 1-hexene, 2-hexene, 3-hexene, isohexene, 1-heptene, 2-heptene, 3-heptene, isoheptene, 1-octene, 2-octene, 3-octene, 4-octene, and isooctene.

The term "alkynyl" as used herein refers to a straight or branched chain unsaturated hydrocarbon having the indicated number of carbon atoms (i.e., $C_2$-$C_8$) means two to eight carbons) and at least one triple bond. Examples of a ($C_2$-$C_8$) alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne.

The term "alkylene" refers to a divalent alkyl group (e.g., an alkyl group attached to two other moieties, typically as a linking group). Examples of a ($C_1$-$C_8$) alkylene include —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, and —$CH_2CH_2CH_2CH_2CH_2CH_2CH_2$—, as well as branched versions thereof. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "alkenylene" refers to a divalent alkenyl group (e.g., an alkenyl group attached to two other moieties, typically as a linking group). Examples of a ($C_2$-$C_8$) alkenylene group include —CH=CH—, —$CH_2$CH=CH—, —$CH_2$CH=CHCH$_2$—, as well as branched versions thereof.

The term "alkynylene" refers to a divalent alkynyl group (e.g., an alkynyl group attached to two other moieties, typically as a linking group). Examples of a ($C_2$-$C_8$) alkynylene group include —C≡C—, —C≡C—$CH_2$—, —$CH_2$—C≡C—$CH_2$—$CH_2$—, as well as branched versions thereof.

The term "heteroatom" is meant to include oxygen (O), nitrogen (N), silicon (Si) and sulfur (S).

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Up to two heteroatoms may be consecutive, such as, for example, —$CH_2$—NH—O$CH_3$ and —$CH_2$—O—Si($CH_3$)$_3$. Also included in the term "heteroalkyl" are those radicals described in more detail below as "heteroalkylene" and "heterocycloalkyl."

The term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini. Still further, for alkylene and heteroalkylene linking groups, no orientation of the linking group is implied.

The term "cycloalkyl" by itself or in combination with other terms, represents, unless otherwise stated, cyclic version of "alkyl". Thus, the term "cycloalkyl" is meant to be included in the terms "alkyl". Examples of cycloalkyl include cyclopentyl, cyclohexyl, 1-cyclohexenyl, 3-cyclohexenyl, cycloheptyl, cyclobutylene, cyclohexylene and the like.

The terms "heterocycloalkyl" and "heterocycloalkylene" as used herein, refer to cyclic versions of heteroalkyl and heteroalkylene as described above. Examples of heterocycloalkyl include pyrrolidinyl, tetrahydrofuranyl, dioxolanyl, imidazolinyl, pyrazolidinyl, piperidinyl, morpholinyl, dithanyl, thiomorpholinyl, piperainyl, and trithanyl. Examples of heterocycloalkenyl include pyrrolinyl. imidazolinyl, and 2H-pyranyl.

The term "aryl" as used herein refers to a 6- to 14-membered monocyclic, bicyclic or tricyclic aromatic hydrocarbon ring system. Examples of an aryl group include phenyl and naphthyl. An aryl group can be unsubstituted or optionally substituted with one or more substituents as described herein below.

The term "heteroaryl" as used herein refers to an aromatic heterocycle ring of 5 to 14 members and having at least one heteroatom selected from nitrogen, oxygen and sulfur, and containing at least 1 carbon atom, including monocyclic, bicyclic, and tricyclic ring systems. Representative heteroaryls are triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, oxetanyl, azepinyl, piperazinyl, morpholinyl, dioxanyl, thietanyl and oxazolyl. A heteroaryl group can be unsubstituted or optionally substituted with one or more substituents as described herein below.

The term "arylalkyl" is meant to include those radicals in which an aryl group is attached to an alkyl group (e.g., benzyl, phenethyl, pyridylmethyl and the like) or a heteroalkyl group (e.g., phenoxymethyl, 2-pyridyloxymethyl, 3-(1-naphthyloxy)propyl, and the like). "Heteroarylalkyl" is meant to include those radicals in which a heteroaryl group is attached to an alkyl group.

The term "heterocycle" and "heterocyclic residue" as used herein refer to 3- to 14-membered ring systems which are either saturated, unsaturated, or aromatic, and which contain from 1 to 4 heteroatoms independently selected from nitrogen, oxygen and sulfur, and wherein the nitrogen and sulfur heteroatoms may be optionally oxidized, and the nitrogen heteroatom may be optionally quaternized, including monocyclic, bicyclic, and tricyclic ring systems. The bicyclic and tricyclic ring systems may encompass a heterocycle or heteroaryl fused to a benzene ring. The heterocycle may be attached via any heteroatom or carbon atom. Heterocycles include heteroaryls, heterocycloalkyls, and heterocycloalkenyls as defined above. Representative examples of heterocycles include, but are not limited to, aziridinyl, oxiranyl, thiiranyl, triazolyl, tetrazolyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, triazinyl, tetrazinyl, imidazolyl, tetrazolyl, pyrrolidinyl, isoxazolyl, furanyl, furazanyl, pyridinyl, oxazolyl, benzoxazolyl, benzisoxazolyl, thiazolyl, benzthiazolyl, thiophenyl, pyrazolyl, triazolyl, pyrimidinyl, benzimidazolyl, isoindolyl, indazolyl, benzodiazolyl, benzotriazolyl, benzoxazolyl, benzisoxazolyl, purinyl, indolyl, isoquinolinyl, quinolinyl, and quinazolinyl. A heterocycle group can be unsubstituted or optionally substituted with one or more substituents as described herein below.

Each of the above terms (e.g., "alkyl," "heteroalkyl," "aryl," "heteroaryl" and "heterocycle") is meant to include both substituted and unsubstituted forms of the indicated radical. Preferred substituents for each type of radical are provided below.

Substituents for the alkyl radicals (as well as those groups referred to as alkylene, alkenyl, alkynyl, cycloalkyl, heterocycloalkyl, cycloalkenyl, heterocycloalkenyl, aryl and heteroaryl) include, but are not limited to, —OR', =O, =NR', =N—OR', —NR'R", —SR', -halo, —SiR'R"R'", —OC(O)R', —C(O)R', —CO₂R', —CONR'R", —OC(O)NR'R", —NR"C(O)R', —NR"C(O)NR'R", —NR"SO₂NR'R", —NR"CO₂R', —NHC(NH₂)=NH, —NR'C(NH₂)=NH, —NHC(NH₂)=NR', —S(O)R', —SO₂R', —SO₂NR'R", —NR"SO₂R', —CN and —NO₂, in a number ranging from zero to three, with those groups having zero, one or two substituents being particularly preferred. R', R" and R'" each independently refer to hydrogen, unsubstituted ($C_1$-$C_8$) alkyl, unsubstituted hetero($C_1$-$C_8$)alkyl, unsubstituted aryl and aryl substituted with one to three substituents selected from -halo, unsubstituted alkyl, unsubstituted alkoxy, unsubstituted thioalkoxy and unsubstituted aryl($C_1$-$C_4$)alkyl. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl. Typically, an alkyl or heteroalkyl group will have from zero to three substituents, with those groups having two or fewer substituents being preferred in the present invention. More preferably, an alkyl or heteroalkyl radical will be unsubstituted or monosubstituted. From the above discussion of substituents, one of skill in the art will understand that the term "alkyl" is meant to include groups such as trihaloalkyl (e.g., —CF₃ and —CH₂CF₃).

Preferred substituents for the alkyl and heteroalkyl radicals are selected from: —OR', =O, —NR'R", —SR', -halo, —SiR'R"R'", —OC(O)R', —C(O)R', —CO₂R', —C(O)NR'R", —OC(O)NR'R", —NR"C(O)R', —NR"CO₂R', —NR'"SO₂NR'R", —S(O)R', —SO₂R', —SO₂NR'R", —NR"SO₂R', —CN and —NO₂, where R', R" and R'" are as defined above. Further preferred substituents are selected from: —OR', =O, —NR'R", -halo, —OC(O)R', —CO₂R', —C(O)NR'R", —OC(O)NR'R", —NR"C(O)R', —NR"CO₂R', —NR"SO₂NR'R", —SO₂R', —SO₂NR'R", —NR"SO₂R'—CN and —NO₂.

Similarly, substituents for the aryl and heteroaryl groups are varied and include: -halo, —OR', —OC(O)R', —NR'R", —SR', —R', —CN, —NO₂, —CO₂R', —C(O)NR'R", —C(O)R', —OC(O)NR'R", —NR"C(O)R', —NR"CO₂R', —NR'"C(O)NR'R", —NR'"SO₂NR'R", —NHC(NH₂) =NH, —NR'C(NH₂)=NH, —NH—C(NH₂)⊕NR', —S(O) R', —SO₂R', —SO₂NR'R", —NR"SO₂R', —N₃, —CH(Ph)₂, perfluoroalkoxy and perfluoro($C_1$-$C_4$)alkyl, in a number ranging from zero to the total number of open valences on the aromatic ring system; and where R', R" and R'" are independently selected from hydrogen, unsubstituted ($C_1$-$C_8$)alkyl, unsubstituted hetero($C_1$-$C_8$)alkyl, unsubstituted aryl, unsubstituted heteroaryl, unsubstituted aryl($C_1$-$C_4$)alkyl and unsubstituted aryloxy($C_1$-$C_4$)alkyl. Typically, an aryl or heteroaryl group will have from zero to three substituents, with those groups having two or fewer substituents being preferred in the present invention. In one aspect of the invention, an aryl or heteroaryl group will be monosubstituted. In another aspect, an aryl or heteroaryl group will be unsubstituted.

Preferred substituents for aryl and heteroaryl groups are selected from: -halo, —OR', —OC(O)R', —NR'R", —SR', —R', —CN, —NO₂, —CO₂R', —CONR'R", —C(O)R', —OC(O)NR'R", —NR"C(O)R', —S(O)R', —SO₂R', —SO₂NR'R", —NR"SO₂R', —N₃, —CH(Ph)₂, perfluoroalkoxy and perfluoro($C_1$-$C_4$)alkyl, where R' and R" are as defined above. Further preferred substituents are selected from: -halo, —OR', —OC(O)R', —NR'R", —R', —CN, —NO₂, —CO₂R', —CONR'R", —NR"C(O)R', —SO₂R', —SO₂NR'R", —NR"SO₂R', perfluoroalkoxy and perfluoro ($C_1$-$C_4$)alkyl.

Two of the substituents on adjacent atoms of the aryl or heteroaryl ring may optionally be replaced with a substituent of the formula -T-C(O)—(CH₂)$_q$—U—, wherein T and U are independently —NH—, —O—, —CH₂— or a single bond, and q is an integer of from 0 to 2. Alternatively, two of the substituents on adjacent atoms of the aryl or heteroaryl ring may optionally be replaced with a substituent of the formula -A-(CH₂)$_r$—B—, wherein A and B are independently —CH₂—, —O—, —NH—, —S—, —S(O)—, —S(O)₂—, —S(O)₂NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH₂)$_s$—X—(CH₂)$_t$—, where s and t are independently integers of from 0 to 3, and X is —O—, —NR'—, —S—, —S(O)—, —S(O)₂—, or —S(O)₂NR'—. The substituent R' in —NR'— and —S(O)₂NR'— is selected from hydrogen or unsubstituted ($C_1$-$C_6$)alkyl.

The term "alkoxy" as used herein refers to an —O-alkyl group or —O-aryl. For example, an alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, —O-neohexyl, and —O-phenyl. The term "alkoxyalkyl" refers to an alkoxy group appended to an alkyl radical. The term "alkoxyaryl" refers to an alkoxy group attached to an aryl radical.

The term "amino" refers to a chemical functionality —NR'R", wherein R' and R' are independently hydrogen, alkyl or aryl.

The term "aminoalkyl," or "alkylamino," as used herein, refers to an alkyl group (typically one to eight carbon atoms) wherein from one or more of the $C_1$-$C_8$ alkyl group's hydrogen atoms is replaced with an amine of formula -N(Rd)2, wherein each occurrence of $R^d$ is independently —H or ($C_1$-$C_8$)alkyl. Examples of aminoalkyl groups include, but are not limited to, —CH₂NH₂, —CH₂CH₂NH₂—, —CH₂CH₂CH₂NH₂, —CH₂CH₂CH₂CH₂NH₂, —CH₂CH₂CH₂CH₂CH₂NH₂, —CH₂CH₂CH₂CH₂CH₂CH₂NH₂, —CH₂CH₂CH₂N(CH₃)₂, t-butylaminomethyl, isopropylaminomethyl and the like. Similarly, the term "dialkylamino" refers to an amino group having two attached alkyl groups that can be the same or different.

The term "carbonyl-containing group" refers to any substituent containing a —C(O)—, including substituents based on —C(O)R or —RCHO where R is an alkyl, aryl, hydroxyl, or a secondary, tertiary, or quaternary amine. Carbonyl-containing groups include, for example, aldehydes, ketones, carboxylic acids, and esters. Alternatively, "carbonyl-containing group" refers to —R'C(O)R" groups wherein R' and R" are independently alkyl, aryl, hydroxyl, or secondary, tertiary, or quaternary amine. Examples include —COOH, $CH_2COOH$, —$CH_2COOCH_3$, —$CH_2CONH_2$, —$CH_2CON(CH_3)_2$.

The term "acyl" is meant to encompass radicals of a general formula —C(O)R, in which a carbonyl group —C(O)— is attached to an alkyl group (alkyl carbonyl) or to an aryl group (aryl carbonyl).

The term "alkyl carbonyl" is meant to encompass radicals of the general formula —C(O)R', wherein R' refers to ($C_1$-$C_8$) alkyl and hetero($C_1$-$C_8$)alkyl. Typically, an alkyl or heteroalkyl group will have from zero to three substituents, with those groups having two or fewer substituents being preferred in the present invention.

The term "aryl carbonyl" is meant to encompass radicals of the general formula —C(O)R", wherein R" refers to aryl and heteroaryl.

The term "carboxyl" or "carboxy" refers to the radical —COOH, and alkyl carboxyl or aryl carboxyl refers to —(R)C(O)OH, wherein R is respectively hydrogen, alkyl, aryl, heteroalkyl or heteroaryl.

The term "ester" refers to the radical —R'C(O)OR"—, wherein R' and R" are independently ($C_1$-$C_8$) alkyl, hetero ($C_1$-$C_8$)alkyl, aryl, or heteroaryl.

The term "amide" is meant to encompass radicals of a general formula N(R')(R")C(O)—, wherein R' and R" are each independently hydrogen, alkyl or aryl. Examples of amide groups include, but are not limited to, formamide, acetamide, hexanamide and 3-oxopentamide.

The term "halo" or "halogen" as used herein refers to —F, —Cl, —Br or —I.

The term "haloalkyl," as used herein, refers to a $C_1$-$C_6$ alkyl group wherein from one or more of the $C_1$-$C_6$ alkyl group's hydrogen atoms is replaced with a halogen atom, which can be the same or different. Examples of haloalkyl groups include, but are not limited to, trifluoromethyl, 2,2,2-trifluoroethyl, 4-chlorobutyl, 3-bromopropyl, pentachloroethyl, and 1,1,1-trifluoro-2-bromo-2-chloroethyl. Thus, the term "haloalkyl" includes monohaloalkyl (alkyl substituted with one halogen atom) and polyhaloalkyl (alkyl substituted with halogen atoms in a number ranging from two to (2m'+1) halogen atoms, where m' is the total number of carbon atoms in the alkyl group). The term "perhaloalkyl" means, unless otherwise stated, alkyl substituted with (2m'+1) halogen atoms, where m' is the total number of carbon atoms in the alkyl group. For example, the term "perhalo($C_1$-$C_4$)alkyl", is meant to include trifluoromethyl, pentachloroethyl, 1,1,1-trifluoro-2-bromo-2-chloroethyl, and the like.

The term "hydroxyalkyl," as used herein, refers to an alkyl group having the indicated number of carbon atoms wherein one or more of the alkyl group's hydrogen atoms are replaced with an —OH group. Examples of hydroxyalkyl groups include, but are not limited to, —$CH_2OH$, —$CH_2CH_2OH$, —$CH_2CH_2CH_2OH$, —$CH_2CH_2CH_2CH_2OH$, —$CH_2CH_2CH_2CH_2CH_2OH$, —$CH_2CH_2CH_2CH_2CH_2CH_2OH$, and branched versions thereof.

The term "protected" with respect to hydroxyl groups, amine groups, carboxyl groups and sulfhydryl groups refers to forms of these functionalities which are protected from undesirable reaction with a protecting group known to those skilled in the art such as those set forth in Protective Groups in Organic Synthesis, Greene, T. W.; Wuts, P. G. M., John Wiley & Sons, New York, N.Y., ($3^{rd}$ Edition, 1999) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methythiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate. Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals; and others.

The compounds of the invention can also exist in various isomeric forms, including configurational, geometric and conformational isomers, as well as existing in various tautomeric forms, particularly those that differ in the point of attachment of a hydrogen atom. As used herein, the term "isomer" is intended to encompass all isomeric forms of the compounds of the invention, including tautomeric forms of the compound.

Certain compounds of the invention may have asymmetric centers and therefore exist in different enantiomeric and diastereomeric forms. A compound of the invention can be in the form of an optical isomer or a diastereomer. Accordingly, the invention encompasses ghrelin receptor modulators and their uses as described herein in the form of their optical isomers, diasteriomers and mixtures thereof, including a racemic mixture. Optical isomers of the ghrelin receptor modulators can be obtained by known techniques such as asymmetric synthesis, chiral chromatography, simulated moving bed technology or via chemical separation of stereoisomers through the employment of optically active resolving agents.

As used herein and unless otherwise indicated, the term "stereoisomer" means one stereoisomer of a compound that is substantially free of other stereoisomers of that compound. For example, a stereomerically pure compound having one chiral center will be substantially free of the opposite enantiomer of the compound. A stereomerically pure a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

The term "pharmaceutically acceptable salts" is meant to include salts of the active compounds which are prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge et al. (1977) J. Pharm. Sci. 66:1-19). Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that readily undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester, but then is metabolically hydrolyzed to the carboxylic acid, the active entity. Additional examples include peptidyl derivatives of a compound of the invention.

Certain compounds of the invention can exist in unsolvated forms as well as solvated forms, including hydrated forms. In general, the solvated forms are equivalent to unsolvated forms and are intended to be encompassed within the scope of the invention. Certain compounds of the invention may exist in multiple crystalline or amorphous forms. In general, all physical forms are equivalent for the uses contemplated by the invention and are intended to be within the scope of the invention.

Certain compounds of the invention possess asymmetric carbon atoms (optical centers) or double bonds; the racemates, enantiomers, diastereomers, geometric isomers and individual isomers are all intended to be encompassed within the scope of the invention. These isomers can be resolved or asymmetrically synthesized using conventional methods to render the isomers "optically pure", i.e., substantially free of its other isomers.

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). Radiolabeled compounds are useful as therapeutic or prophylactic agents, e.g., cancer therapeutic agents, research reagents, e.g., ghrelin assay reagents, and diagnostic agents, e.g., in vivo imaging agents. All isotopic variations of the compounds of the invention, whether radioactive or not, are intended to be encompassed within the scope of the invention.

It should be noted that if there is a discrepancy between a depicted structure and a name given that structure, the depicted structure controls. In addition, if the stereochemistry of a structure or a portion of a structure is not indicated with, for example, bold or dashed lines, the structure or portion of the structure is to be interpreted as encompassing all stereoisomers of it.

Embodiments of the Invention

A class of compounds that, for example, modulate the ghrelin receptor or GHSR has been discovered. Depending on the biological environment (e.g., cell type, pathological condition of the host, etc.), these compounds can activate or inhibit the actions of ghrelin receptor. By activating or inhibiting ghrelin receptor, the compounds will find use as therapeutic agents capable of modulating diseases and conditions responsive to modulation of ghrelin receptor. As noted above, examples of such diseases and conditions include obesity and obesity-related disorders. Additionally, the compounds are useful for the treatment and/or prevention of complications of these diseases and disorders (e.g., cardiovascular disease).

While the compounds of the invention are believed to exert their effects by interacting with GHSR, the mechanism of action by which the compounds act is not a limiting embodiment of the invention. For example, compounds of the invention may interact with ghrelin receptor subtypes other than GHSR.

Compounds contemplated by the invention include, but are not limited to, the exemplary compounds provided herein.

Compounds

The invention provides compounds of Formula I:

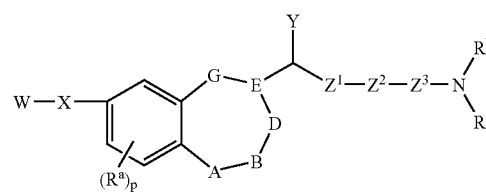

or a pharmaceutically acceptable salt or prodrug thereof. In formula I, the symbols A, B and D represent a direct bond, —C(R$^1$)(R$^2$)—, —C(R$^3$)═, —C(O)—, —N(R$^4$)—, —N═, —O—, and —S(O)$_m$—, wherein m is an integer from 0 to 2, with the proviso that at least one of A, B, and D is other than a bond. Exemplary A, B, and D groups are a single or a double bond, —CH$_2$—, ═CH—, —C(O)—, —O—, ═N—, —NH—, and —S(O)—.

It is to be understood that A, B and D are combined to form a stable moiety -A-B-D-. For example, compounds wherein -A-B- or -B-D- is —O—O— (peroxides) and the like are not intended to be within the scope of the invention.

In one aspect, when one of A and B is —C($R^1$)($R^2$)— or —C($R^3$)=, and the other is —N($R^4$)—, $R^4$ can be optionally combined with $R^1$, $R^2$, or $R^3$ to form a five- or six-membered fused ring containing the nitrogen atom to which $R^4$ is attached and from 0 to 2 additional heteroatoms selected from the group consisting of N, O and S. This ring may be a saturated, unsaturated, or aromatic ring. Exemplary rings formed by A, B, $R^1$, $R^2$, $R^3$ and $R^4$ are pyrroline, pyrrolidine, imidazole, piperidine, 5-methyl-1H-imidazole, and thiazole.

E is N or CH.

$R^1$, $R^2$, $R^3$ and $R^4$ are independently selected from the group consisting of hydrogen, halogen, amine, hydroxyl, cyano, ($C_1$-$C_8$) alkyl, ($C_2$-$C_8$) alkenyl, ($C_2$-$C_8$) alkynyl, and ($C_1$-$C_8$) alkoxy.

G is —C(O)—, —C(S)—, —(NOR$^5$)—, —C(N—NHR$^6$)—, or —C($R^7$)($R^8$)—. Examples of G include, but are not limited to, —C(O)—, —C(S)—, —C(NOCH$_3$)—, —C(N—NH$_2$)—, —C(N—NHC$_2$H$_5$)—, —CH$_2$—.

Each $R^a$ is independently selected from the group consisting of halogen, hydroxyl, cyano, ($C_1$-$C_8$) alkyl, ($C_2$-$C_8$) alkenyl, ($C_2$-$C_8$) alkynyl, ($C_1$-$C_8$) alkoxy and —NR$^9$R$^{10}$.

The subscript p 0, 1, 2 or 3.

X is selected from the group consisting of —C($R^{11}$)($R^{12}$)—, —C(O)—, —C(S)—, —O—, —S(O)$_n$—, —N($R^{13}$)—, and —N(OR$^{14}$)—. The subscript n is an integer from 0 to 2. Exemplary groups include —CH$_2$—, —C(O)—, —O—, —S—, —S(O)—, —S(O)$_2$—, —NH—, —N(OCH$_3$)—.

$R^5$, $R^6$, and $R^{14}$ are independently selected from the group consisting of hydrogen, ($C_1$-$C_8$) alkyl, ($C_2$-$C_8$) alkenyl, and ($C_2$-$C_8$) alkynyl.

$R^7$, $R^8$, $R^9$, $R^{10}$, $R^{11}$, $R^{12}$, and $R^{13}$ are independently selected from the group consisting of hydrogen, ($C_1$-$C_8$) alkyl, ($C_2$-$C_8$) alkenyl, ($C_2$-C8) alkynyl, and ($C_1$-$C_8$) alkoxy.

W is a ring selected from the group consisting of aryl, heteroaryl, ($C_3$-$C_8$) cycloalkyl, ($C_5$-$C_6$) heterocycloalkyl, ($C_5$-$C_8$) cycloalkenyl, and ($C_5$-$C_6$) heterocycloalkenyl. Examples include cyclopropyl, cyclobutyl, cyclopentyl, cyclohexyl, cycloheptyl, phenyl, tolyl, naphthyl, pyrrolyl, imidazolyl, pyrazinyl, oxazolyl, thiazolyl, furyl, thienyl, pyridinyl, pyrimidinyl, benzothiazolyl, benzimidazolyl, indolyl, isoquinolyl, quinolyl, fluorophenyl, diflurophenyl, trifluorophenyl, m-xylenyl, 1-methyl-3-fluorophenyl, 1,6-difluorophenyl, 3,6-difluorobenzyl, methylphenyl, ehtylphenyl, and mesityl.

Y is selected from the group consisting of hydrogen, ($C_1$-$C_8$) alkyl, ($C_2$-$C_8$) alkenyl, ($C_2$-$C_8$) alkynyl, aryl, heteroaryl, ($C_3$-$C_8$) cycloalkyl, ($C_3$-$C_8$) heterocycloalkyl, ($C_5$-$C_8$) cycloalkenyl and ($C_5$-$C_8$) heterocycloalkenyl. Examples of Y include isopropyl, t-butyl, cyclopropyl, cyclobutyl, cyclopentyl, cyclohexyl, phenyl and tiophenyl.

$Z^1$ and $Z^3$ are independently selected from the group consisting of a bond and ($C_1$-$C_8$) alkylene. Exemplary $Z^1$ and $Z^3$ groups include a single bond, methyl, ethyl, propyl, isopropyl, and butyl. In one aspect, $Z^3$ can be combined with $R^b$ or $R^c$ to form a 3-, 4-, 5-, 6-, 7- or 8-membered ring containing the nitrogen atom to which $Z^3$ is attached and from 0 to 2 additional heteroatoms selected from the group consisting of N, O, and S. This ring may be a saturated, unsaturated, or aromatic ring. Examples of rings formed by $Z^3$ and $R^b$ or $R^c$ include piperidinediyl, piperazinediyl, pyrrolidinediyl, and pyrrolinediyl.

$Z^2$ is selected from the group consisting of ($C_2$-$C_8$) alkenylene, ($C_2$-$C_8$) alkynylene, —C(O)O—, —N(R')(R")—, —C(O)N(R')—, —O—, —S(O)$_k$—, —N(R')C(O)N(R")—, —N(R')C(O)O—, —OC(O)O—, arylene, heteroarylene, aryl-($C_1$-$C_5$) alkylene, ($C_3$-$C_8$) cycloalkylene, ($C_3$-$C_8$) heterocycloalkylene, ($C_5$-$C_8$) cycloalkenylene, ($C_5$-$C_8$) heterocycloalkenylene, and ($C_5$-$C_8$) heterocycloalkylene-C(O)—. The subscript k is 0, 1, or 2. Examples of $Z^2$ include —C(O)NH—, —C(O)NH—CH$_2$—, —C(O)-piperidinyl, phenylene, cyclohexylene, and oxypiperidinyl.

R' and R" are independently selected from the group consisting of hydrogen, ($C_1$-$C_8$) alkyl, ($C_2$-$C_8$) alkenyl, and ($C_2$-$C_8$) alkynyl.

$R^b$ and $R^c$ are independently selected from the group consisting of hydrogen, ($C_1$-$C_8$) alkyl, ($C_2$-$C_8$) alkenyl, ($C_2$-$C_8$) alkynyl, ($C_3$-$C_8$) cycloalkyl, ($C_3$-$C_8$) heterocycloalkyl, ($C_3$-$C_8$) cycloalkenyl, ($C_3$-$C_8$) heterocycloalkenyl, aryl, heteroaryl, halo-($C_1$-$C_8$) alkyl, aryl-($C_1$-$C_5$) alkyl, ($C_3$-$C_8$) cycloalkyl-($C_1$-$C_5$)alkyl, ($C_3$-$C_8$) heterocycloalkyl-($C_1$-$C_5$) alkyl, ($C_3$-$C_8$) heterocycloalkenyl-($C_1$-$C_5$) alkyl, heteroaryl-($C_1$-$C_5$) alkyl, —CR$^{15}$CO$_2$R$^{16}$, —CR$^{15}$N(R$^{16}$)SO$_2$R$^{17}$, —CO$_2$R$^{15}$, —C(O)NR$^{15}$R$^{16}$, —C(O)N(R$^{15}$)OR$^{16}$, —C(=NOR$^{15}$)NR$^{16}$R$^{17}$, —C(R$^{15}$)=NOR$^{16}$, —C(O)R$^{17}$C(O)NR$^{15}$R$^{16}$, —NR$^{15}$R$^{16}$, —NR$^{15}$SO$_2$R$^{16}$, —NR$^{15}$(OR$^{16}$), —NR$^{17}$C(O)NR$^{15}$C(O)R$^{16}$, —NR$^{15}$C(O)NR$^{16}$R$^{17}$—OR$^{15}$, and —SO$_2$NR$^{15}$R$^{16}$. In one aspect, $R^b$ and $R^c$ may be combined to form a 3-, 4-, 5-, 6-, 7-, or 8-membered ring containing the nitrogen atom to which they are attached and containing from 0 to 3 additional heteroatoms selected from the group consisting of N, O and S. This ring may be a saturated, unsaturated, or aromatic ring. Examples of $R^b$ and $R^c$ include hydrogen, methyl, ethyl, propyl, isopropyl, butyl, propylenyl, butylenyl, propenyl, cyclopropyl, cyclopropyl methyl, cyclopropyl ethyl, cyclobutyl, cyclohexyl, cyclopentylenyl, cyclohexylenyl, phenyl, tolyl, naphthyl, pyrrolyl, imidazolyl, pyrazinyl, oxazolyl, thiazolyl, furyl, thienyl, pyridinyl, pyrimidinyl, benzothiazolyl, benzimidazolyl, indolyl, isoquinolyl, quinolyl, fluorophenyl, diflurophenyl, trifluorophenyl, m-xylenyl, 1-methyl-3-fluorophenyl, 1,6-difluorophenyl, 3,6-difluorobenzyl, methylphenyl, ehtylphenyl, mesityl, indanyl, ethyl-cyclobutanecarboxylic acid methyl ester, methyl-cyclopentanecarboxylic acid (2-dimethylamino-ethyl)-amide, and N-(2-hydroxy-2-methyl-propyl)-3-(4-methyl-tetrahydro-pyran-4-yl)-acrylamide.

$R^{15}$, $R^{16}$, and $R^{17}$ are independently selected from the group consisting of hydrogen, ($C_1$-$C_8$) alkyl, ($C_2$-$C_8$) alkenyl, ($C_2$-$C_8$) alkynyl, halo-($C_1$-$C_4$)alkyl, hetero($C_1$-$C_4$)alkyl, ($C_3$-$C_8$) cycloalkyl, ($C_3$-$C_8$) heterocycloalkyl, ($C_3$-$C_8$) cycloalkenyl, ($C_3$-$C_8$) heterocycloalkenyl, aryl, heteroaryl and aryl-($C_1$-$C_4$)alkyl.

The invention further provides one group of embodiments of the invention represented by the formula II(a):

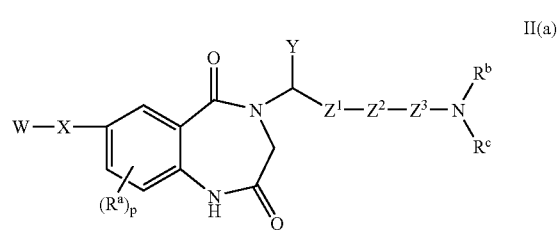

Another group of compounds of the invention is represented by the formula II(b):

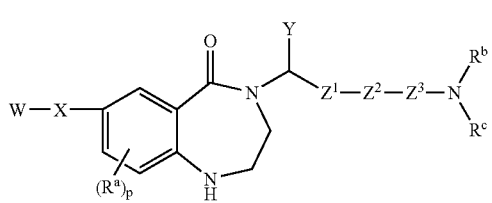

II(b)

Another group of embodiments is represented by the formula II(c):

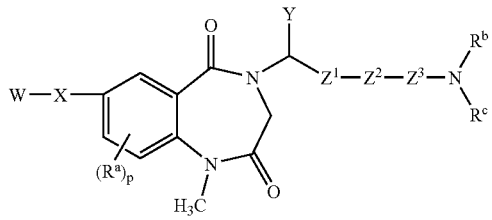

II(c)

Another group of compounds of the invention is represented by the formula II(d):

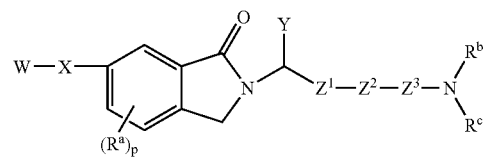

II(d)

Another group of compounds of the present invention is represented by the formula II(e):

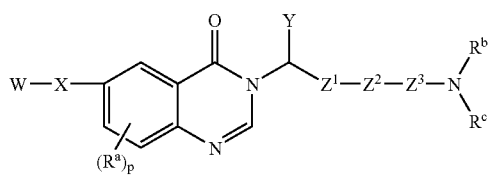

II(e)

Another aspect of the invention involves embodiments represented by the formula II(f):

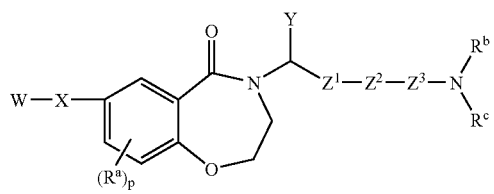

II(f)

Another group of embodiments is represented by the formula II(g):

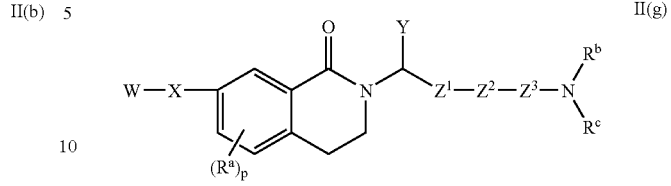

II(g)

Another group of compounds is represented by the formula II(h):

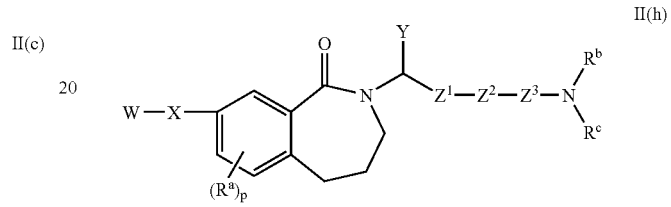

II(h)

Another aspect of the instant invention involves embodiments represented by the formula II(i):

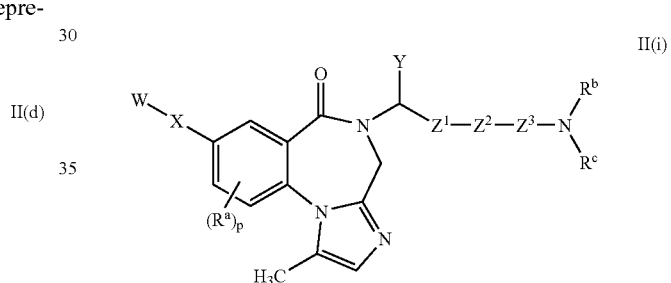

II(i)

Another group of embodiments of the invention is represented by the formula II(j):

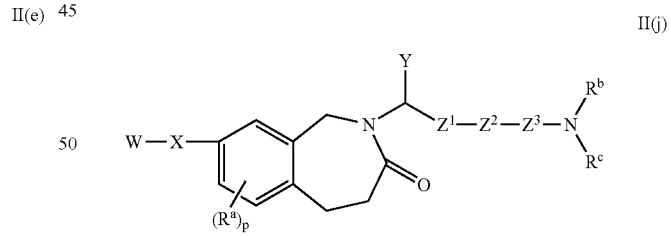

II(j)

Another group of compounds of the invention is represented by the formula II(k):

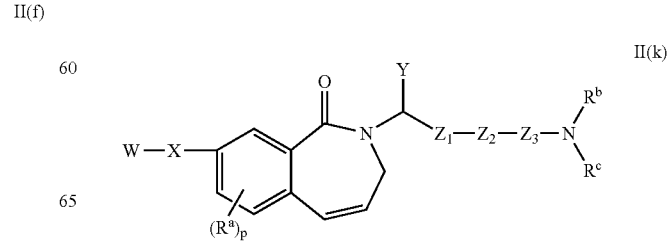

II(k)

In each of these groups of the embodiments represented by the Formulas II(a-k) W, X, Y, $Z^1$, $Z^2$, $Z^3$, $R^a$, p, $R^b$, and $R^c$ have the meanings as provided above.

Within each of these groups of embodiments are several further groups, described below.

In one aspect, p is 0.

In one aspect, Y is ($C_1$-$C_8$) alkyl or ($C_3$-$C_8$) cycloalkyl. For example, Y can be isopropyl or tert-butyl. In another aspect, Y is a cyclopropyl, cyclobutyl, cyclopentyl or cyclohexyl. In one aspect, Y can be cyclopentadienyl or tiophenyl.

In one aspect, X is S. In another aspect, X is O.

In one aspect, $Z^2$ can be piperidinyl-1-carbonyl or phenylene. In another aspect, $Z^2$ can be propenylene or thiazolediyl. In yet another aspect, $Z^2$ can be cyclohexylene, isoxazolediyl, pyridinediyl or imidazolediyl.

In one aspect, $Z^3$ can combined with $R^b$ to form a 3-, 4-, 5-, 6-, 7- or 8-membered ring containing the nitrogen atom to which $Z^3$ is attached and from 0 to 2 additional heteroatoms selected from the group consisting of N, O and S. Exemplary values for -$Z^3$-$R^b$— combinations include piperidinediyl and pyrrolidinediyl.

In one aspect, W is aryl. Exemplary values for W include phenyl, tolyl, xylenyl, mesitylenyl, fluoromethylbenzyl, flurobenzyl, difluorobenzyl, ethylbenzyl, and tert-butylbenzyl.

In one aspect, $R^b$ and $R^c$ are independently selected from the group consisting of hydrogen,

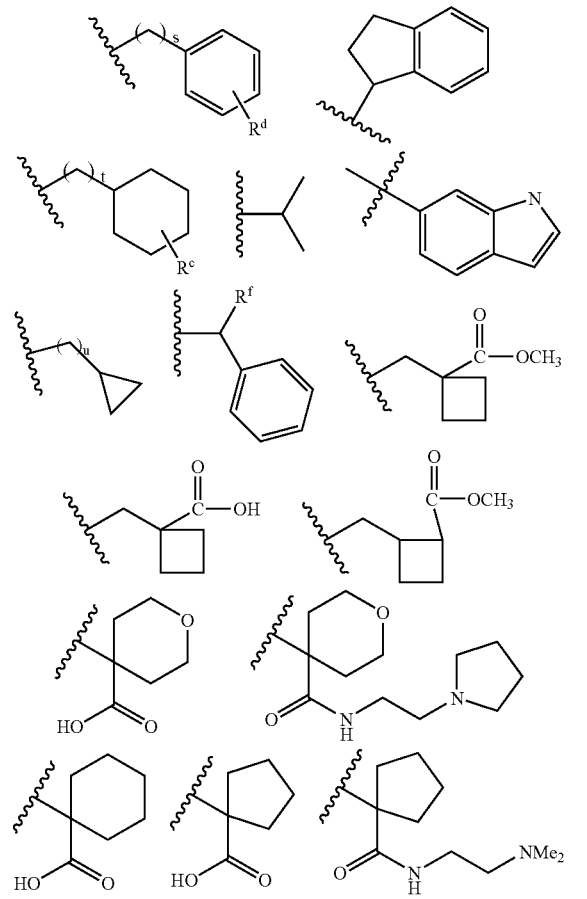

-continued

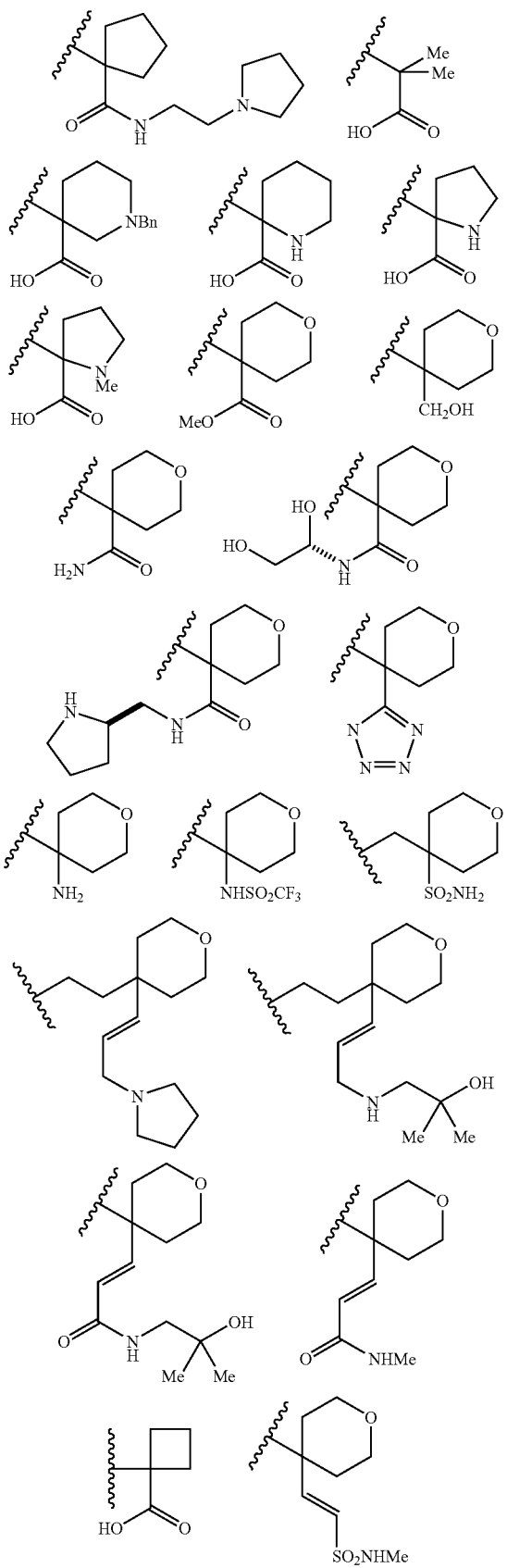

-continued

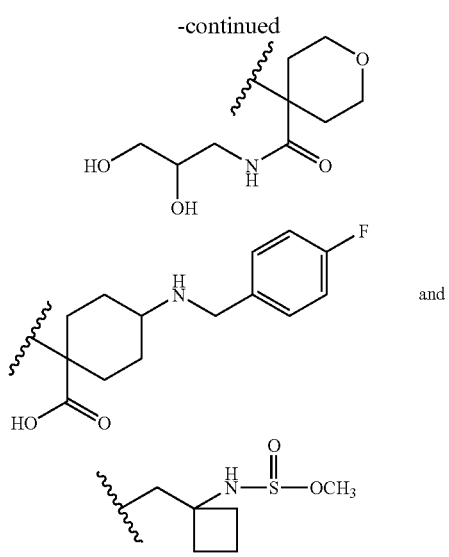

The subscripts s, t, and u are independently an integer from 0 to 5. In one aspect, $R^d$, $R^e$, and $R^f$ are independently selected from the group consisting of hydrogen, halogen, hydroxyl, amine, ($C_1$-$C_8$) alkyl and ($C_2$-$C_8$) alkenyl. Exemplary values for $R^d$, $R^e$, and $R^f$ include hydrogen, halogen, —$NH_2$, —NH($CH_3$), —OH, —$CH_3$, —$C_2H_5$, and —CH=$CH_2$.

Some embodiments of the invention combine the aspects of the invention outlined above. Accordingly, one group of embodiments includes the following compounds:

N-(1-benzyl-piperidin-4-yl)-2-(2,5-dioxo-7-phenoxy-1,2,3,5-tetrahydro-benzo[e][1,4]diazepin-4-yl)-3-methyl-butyramide, N-(1-benzyl-piperidin-4-yl)-2-(2,5-dioxo-7-phenoxy-1,2,3,5-tetrahydro-benzo[e][1,4]diazepin-4-yl)-3,3-dimethyl-butyramide, 2-[7-(2,6-dimethyl-phenoxy)-2,5-dioxo-1,2,3,5-tetrahydro-benzo[e][1,4]diazepin-4-yl]-3-methyl-N-[1-(1-phenyl-ethyl)-piperidin-4-yl]-butyramide, 2-[7-(2,6-dimethyl-phenoxy)-2,5-dioxo-1,2,3,5-tetrahydro-benzo[e][1,4]diazepin-4-yl]-N-(1-indan-1-yl-piperidin-4-yl)-3-methyl-butyramide, 4-{1-[2-(1-cyclopropylmethyl-piperidin-4-yl)-ethyl]-2-methyl-propyl}-7-(2,6-difluoro-phenoxy)-3,4-dihydro-1H-benzo[e][1,4]diazepine-2,5-dione, 7-(2-ethyl-phenoxy)-4-{1-[4-(4-fluoro-benzylamino)-piperidine -1-carbonyl]-2-methyl-propyl}-3,4-dihydro-1H-benzo[e][1,4]diazepine-2,5-dione, 4-[1-(4-cyclopropylamino-piperidine-1-carbonyl)-2-methyl-propyl]-7-(2-ethyl-phenoxy)-3,4-dihydro-1H-benzo[e][1,4]diazepine-2,5-dione, 7-(2,4-difluoro-phenoxy)-4-[1-(3-dimethylaminomethyl-phenyl)-2-methyl-propyl]-3,4-dihydro-1H-benzo[e][1,4]diazepine-2,5-dione, 7-(2,4-difluoro-phenoxy)-4-{1-[3-(isopropylamino-methyl)-phenyl]-2-methyl-propyl}-3,4-dihydro-1H-benzo[e][1,4]diazepine-2,5-dione, 2-(2,5-dioxo-7-phenoxy-1,2,3,5-tetrahydrobenzo[e][1,4]diazepin-4-yl)-3-methyl-butyric acid 1-benzyl-piperidin-4-yl ester, 1-benzyl-piperidine-4-carboxylic acid 2-[7-(4-fluoro-phenoxy)-2,5-dioxo-1,2,3,5-tetrahydro-benzo[e][1,4]diazepin-4-yl]-3-methyl-butyl ester, (1-benzyl-piperidin-4-yl)-carbamic acid 2-[7-(4-fluoro-phenoxy)-2,5-dioxo-1,2,3,5-tetrahydro-benzo[e][1,4]diazepin-4-yl]-3-methyl-butyl ester,

[1-(4-fluoro-benzyl)-piperidin-4-yl]-carbamic acid 2-[7-(4-fluoro-phenoxy)-2,5-dioxo-1,2,3,5-tetrahydro-benzo[e][1,4]diazepin-4-yl]-3-methyl-butyl ester, N-(1-benzyl-piperidin-4-yl)-2-(2,5-dioxo-7-phenoxy-1,2,3,5-tetrahydro-benzo[e][1,4]diazepin-4-yl)-3-methyl-butyramide, 7-(2-tert-butyl-phenoxy)-4-[1-(4-cyclopropylamino-piperidine-1-carbonyl)-2-methyl-propyl]-3,4-dihydro-1H-benzo[e][1,4]diazepine-2,5-dione, N-(1-benzyl-piperidin-4-yl)-2-(2,5-dioxo-7-phenoxy-1,2,3,5-tetrahydro-benzo[e][1,4]diazepin-4-yl)-2-thiophen-2-yl-acetamide, N-(1-benzyl-piperidin-4-yl)-2-cyclohexyl-2-(2,5-dioxo-7-phenoxy-1,2,3,5-tetrahydro-benzo[e][1,4]diazepin-4-yl)-acetamide, 2-{1-[2-(1-cyclopropylmethyl-piperidin-4-yl)-ethyl]-2-methyl-propyl}-7-(2,4-difluoro-phenoxy)-3,4-dihydro-2H-isoquinolin-1-one, 2-[1-(4-cyclopropylamino-piperidine-1-carbonyl)-2-methyl-propyl]-7-(2,4-difluoro-phenoxy)-3,4-dihydro-2H-isoquinolin-1-one, 7-(2,4-difluoro-phenoxy)-2-{1-[4-(4-fluoro-benzylamino)-piperidine-1-carbonyl]-2-methyl-propyl}-3,4-dihydro-2H-isoquinolin-1-one, 7-(2,4-difluoro-phenoxy)-2-(1-{4-[2-(4-fluoro-phenyl)-ethylamino]-piperidine-1-carbonyl}-2-methyl-propyl)-3,4-dihydro-2H-isoquinolin-1-one, 2-[1-(1-cyclopropylmethyl-piperidin-4-yloxymethyl)-2-methyl-propyl]-7-(2,4-difluoro-phenoxy)-3,4-dihydro-2H-isoquinolin-1-one, 2-(cyclopropyl-{3-[2-(cyclopropylmethyl-amino)-ethyl]-phenyl}-methyl)-7-(2,4-difluoro-phenoxy)-3,4-dihydro-2H-isoquinolin-1-one, 2-{1-[4-(cyclopropylmethyl-amino)-piperidine-1-carbonyl]-2-methyl-propyl}-7-(2,4-difluoro-phenoxy)-3,4-dihydro-2H-isoquinolin-1-one, N-(1-benzyl-piperidin-4-yl)-3-methyl-2-(4-oxo-6-o-toly-loxy-4H-quinazolin-3-yl)-butyramide, N-(1-benzyl-piperidin-4-yl)-2-[8-(4-fluoro-2-methyl-phenoxy)-1-methyl-6-oxo-4H,6H-3,5,10b-triaza-benzo[e]azulen-5-yl]-3-methyl-butyramide, 4-{1-[4-(indan-2-ylamino)-piperidine-1-carbonyl]-2-methyl-propyl}-7-o-tolyloxy-1,2,3,4-tetrahydro-benzo[e][1,4]diazepin-5-one, 8-(2,4-difluoro-phenoxy)-2-{1-[4-(4-fluoro-benzylamino)-piperidine-1-carbonyl]-2-methyl-propyl}-2,3-dihydro-benzo[c]azepin-1-one, 2-[1-(4-cyclopropylamino-cyclohexylmethyl)-2-methyl-propyl]-8-(2,4-difluoro-phenoxy)-2,3,4,5-tetrahydro-benzo[c]azepin-1-one, 2-(1-{4-[(cyclopropylmethyl-amino)-methyl]-thiazol-2-yl}-2-methyl-propyl)-8-(2,4-difluoro-phenoxy)-2,3,4,5-tetrahydro-benzo[c]azepin-1-one, 2-{1-[4-(cyclopropylmethyl-amino)-piperidine-1-carbonyl]-2-methyl-propyl}-8-(2,4-difluoro-phenoxy)-1,2,4,5-tetrahydro-benzo[c]azepin-3-one, 4-(1-{4-[2-(4-fluoro-phenyl)-ethylamino]-piperidine-1-carbonyl}-2-methyl-propyl)-1-methyl-7-o-tolyloxy-1,2,3,4-tetrahydrobenzo[e][1,4]diazepin-5-one, 2-[7-(4-fluoro-phenoxy)-2,5-dioxo-1,2,3,5-tetrahydro-benzo[e][1,4]diazepin-4-yl]-3-methyl-N-(1-phenyl-piperidin-4-yl)-butyramide, 7-(2,6-dimethyl-phenoxy)-4-{1-[4-(4-fluoro-benzylamino)-piperidine-1-carbonyl]-2-methyl-propyl}-3,4-dihydro-1H-benzo[e][1,4]diazepine-2,5-dione, 7-(2,6-dimethyl-phenoxy)-4-(1-{4-[2-(4-fluoro-phenyl)-ethylamino]-piperidine-1-carbonyl}-2-methyl-propyl)-3,4-dihydro-1H-benzo[e][1,4]diazepine-2,5-dione, 7-(2-tert-butyl-phenoxy)-4-(1-{4-[2-(4-fluoro-phenyl)-ethylamino]-piperidine-1-carbonyl}-2-methyl-propyl)-3,4-dihydro-1H-benzo[e][1,4]diazepine-2,5-dione, 2-(cyclopropyl(6-((cyclopropylmethylamino)methyl)pyridin-2-yl)methyl)-7-(2,4-difluorophenoxy)-3,4-dihydroisoquinolin-1(2H)-one, 2-(cyclopropyl(6-((cyclopropylamino)methyl)pyridin-2-yl)methyl)-7-(2,4-difluorophenoxy)-3,4-dihydroisoquinolin-1(2H)-one, 2-(cyclopropyl(6-(1-hydroxypropan-2-ylamino)methyl)pyridin-2-yl)methyl)-7-(2,4-difluorophenoxy)-3,4-dihydroisoquinolin-1(2H)-one, 2-(cyclopropyl(6-((1-hydroxy-2-methylpropan-2-ylamino)methyl)pyridin-2-yl)methyl)-7-(2,4-difluorophenoxy)-3,4-dihydroisoquinolin-1(2H)-one, 2-(cyclopropyl(6-((2-fluoroethylamino)methyl) pyridine-2-yl)methyl)-7-(2,4-difluorophenoxy)-3,4-dihydroisoquinolin-1(2H)-one and 2-(cyclopropyl(6-((2,2-difluoroethylamino) methyl)pyridin-2-yl)methyl)-7-(2,4-difluorophenoxy)-3,4-dihydroisoquinolin-1(2H)-one.

The compounds of the invention can have asymmetric centers and therefore exist in different enantiomeric and diastereomeric forms. This invention relates to the use of all optical isomers and stereoisomers of the compounds of the invention, and mixtures thereof, and to all pharmaceutical compositions and methods of treatment that may employ or contain them.

It should be noted that racemates, racemic mixtures, and stereoisomers, particularly diastereomeric mixtures or diastereomerically pure compounds and enantiomers or enantiomerically pure compounds of the above are all encompassed.

The invention further provides compounds of Formula I and Formulas II(a-k) that are in isolated and purified form.

Preparation of the Compounds

Schemes 1-9 below provide exemplary synthetic methods for the preparation of the compounds of the present invention. One of skill in the art will understand that additional methods are also useful. In other words, the compounds of the invention can be made using organic synthesis using starting materials, reagents and reactions well known in the art.

Certain compounds of the invention may be conveniently prepared by a general process outlined in Scheme 1. Carboxylic acid B can be obtained via nucleophilic aromatic substitution of aryl nitro fluoride with the commercially available compounds such as phenol, thiophenol or aniline derivatives as described in Examples. Acid B is converted to amide C by coupling with amine A in the presence of a carbonyldiimide dehydrating agent, such as EDC, or by conversion first to an acyl chloride with oxalyl chloride. The nitro group of amide C can be easily reduced with SnCl2 or another reducing agent such as palladium on carbon under a hydrogen atmosphere to produce aniline D. Treatment of D with chloroacetyl chloride under basic conditions produces benzodiazepine E. Upon removal of the protecting group PG, E can be coupled with amine intermediate A in the presence of EDC, HOBT and NMP to produce amide F, in which an end amino group can be installed via reductive amination to produce a compound of the invention T1. A skilled practitioner will recognize that a variety of amine intermediates can be used to prepare the intermediates such as amide F. The preparation of these amine intermediates is described in more detail in Examples. Alternatively, the nitrogen atom of benzodiazepine ring of amide F can be further functionalized, for example, by methylation with CH3I in the presence of sodium hydride and DMF to produce methylated benzodiazepine YY, which, in turn, can be subjected to reductive amination analogous to step e of Scheme 1 to generate a number of compounds of the invention.

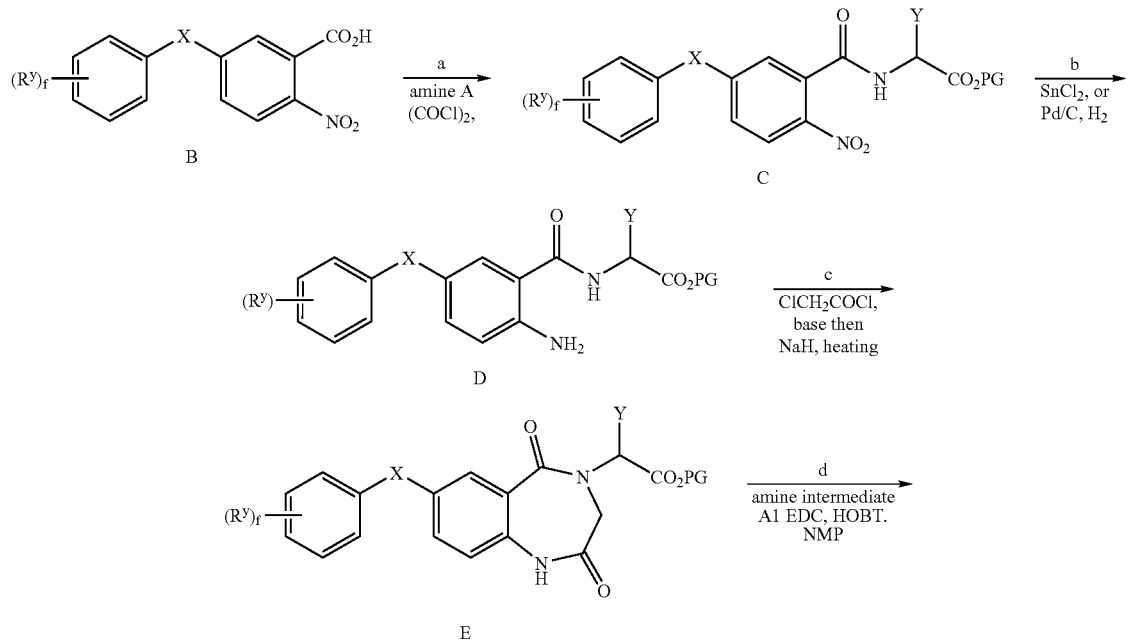

Scheme 1

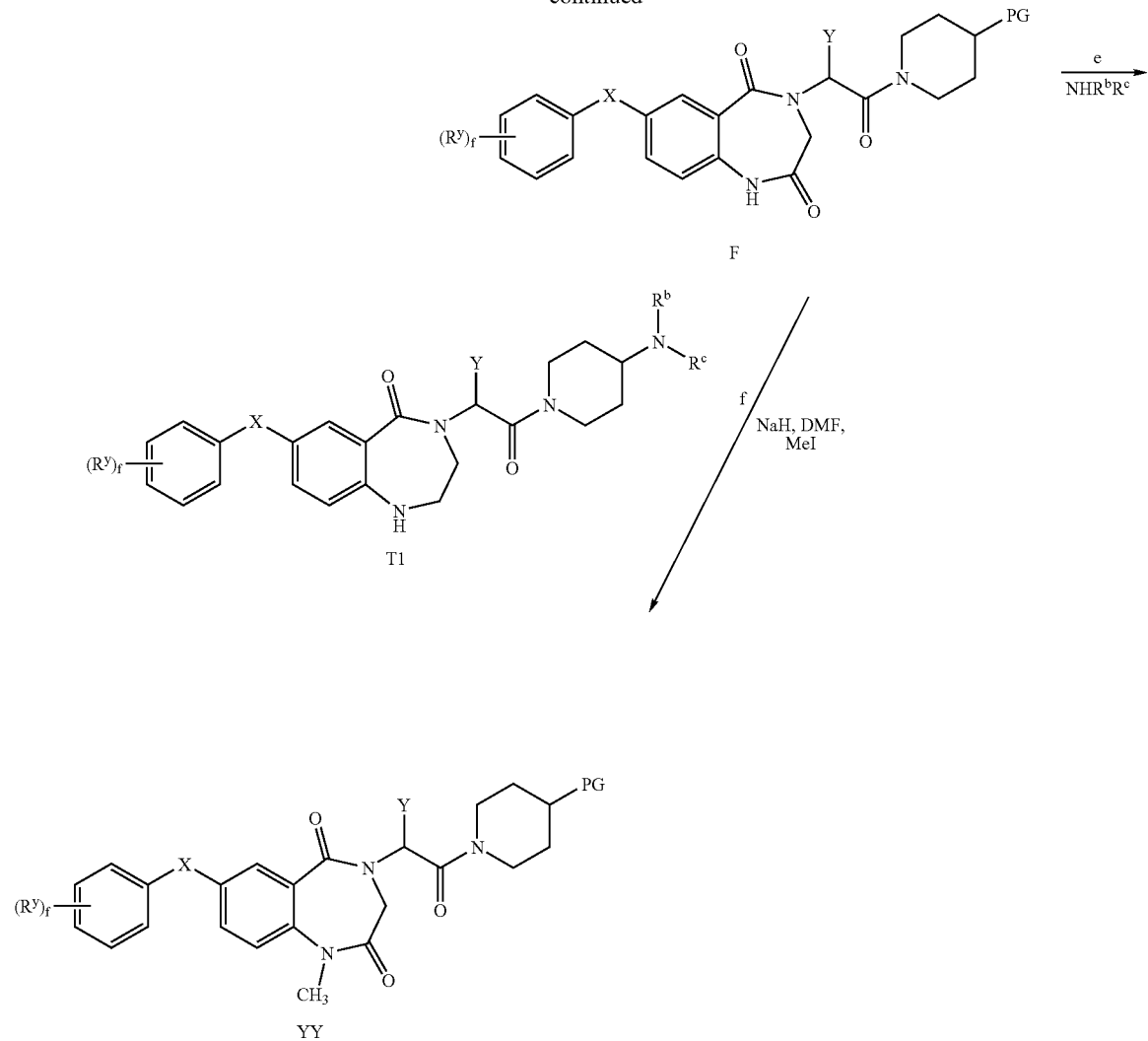

Other compounds of the invention can be assembled via the synthetic route depicted in Scheme 2. Aryl nitro-compound B can be esterified and reduced to an aniline intermediate, which can be transformed to aryliodide ester G under Sandemye conditions. Ester G can be converted under palladium-mediated conditions to compounds of the general formula ZZ. Coupling of compound ZZ with amine A2, typically under reductive amination conditions, yields compound J. Cyclization of J followed by reductive amination results in the production of compounds such as T2 or T3.

Scheme 2

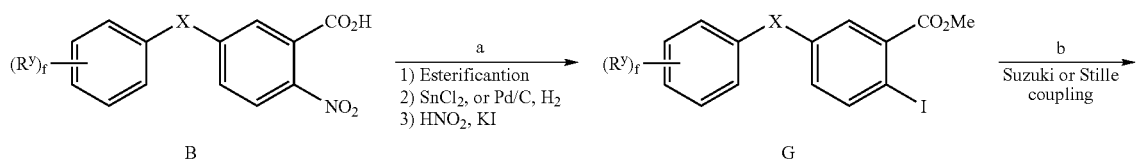

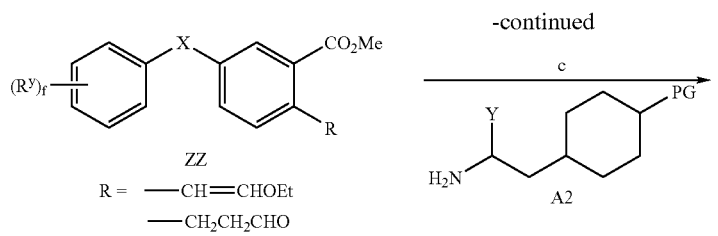

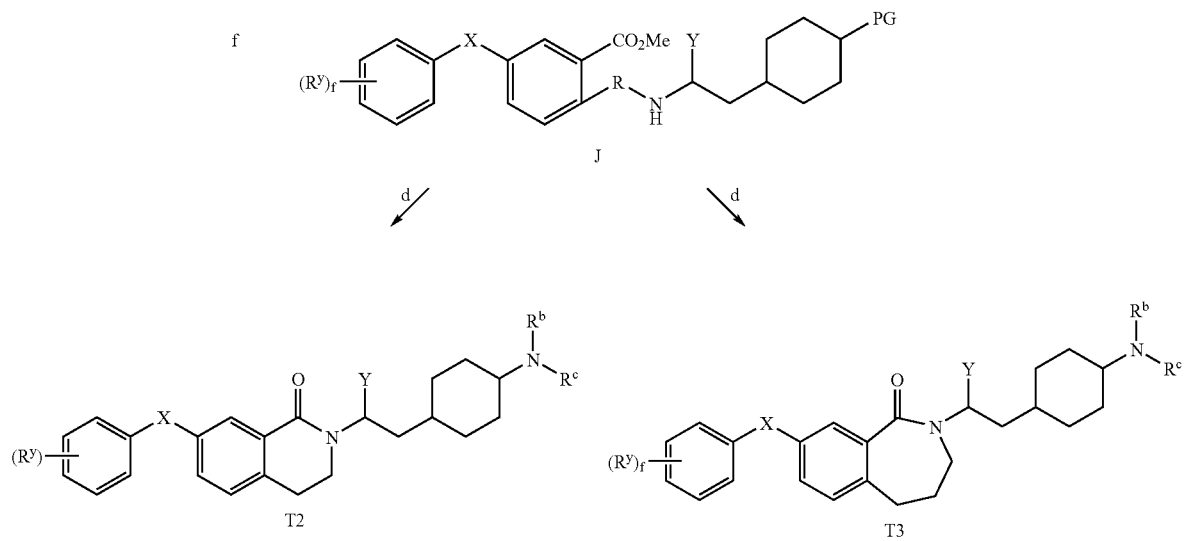

A variant of Scheme 1 is also useful for generation of a library of compounds of 5 the invention as depicted in Scheme 3. One of the amide groups present in benzodiazepinedione E can be converted to a thioamide group by treatment with Lawesson's reagent to produce compound K (for review, see Cava et al. (1985) Tetrahedron 41: 5061-5087). Heterocyclization of thioamide K yields imidazole L. Imidazole L can be used to afford a variety of compounds of the invention via steps analogous to steps d and e of Scheme 1.

Scheme 3

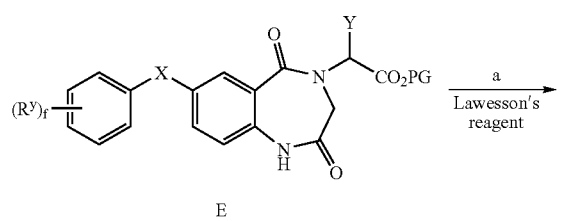

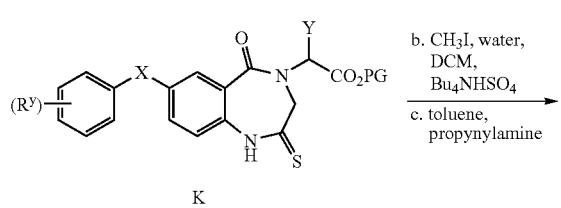

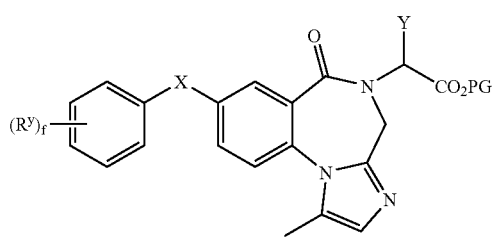

Some compounds of the invention can be assembled via a synthetic route exemplified in Scheme 4. Iodide G can be obtained as outlined in step a of Scheme 2. Stille coupling of ester iodide G with tributylvinyltin in the presence of Pd(PPh$_3$)$_4$ in THF results in styrene compound M, which can be saponified under basic conditions to carboxylic acid N. Acid N can be converted into acyl chloride O by treatment with oxalyl chloride in DCM. Coupling of acyl chloride O with amine intermediate A3 in the presence of diisopropylethylamine in a dichloroethane solution affords compound P, which can undergo Grubbs' intramolecular olefin metathesis to form ketal Q. Ketal Q can then be dissolved in a TFA solution and extracted with ethyl acetate to generate ketone R. This product can be used in the reaction of reductive amination with the variously substituted amines similar to step e illustrated in Scheme 1 to afford compounds of the invention.

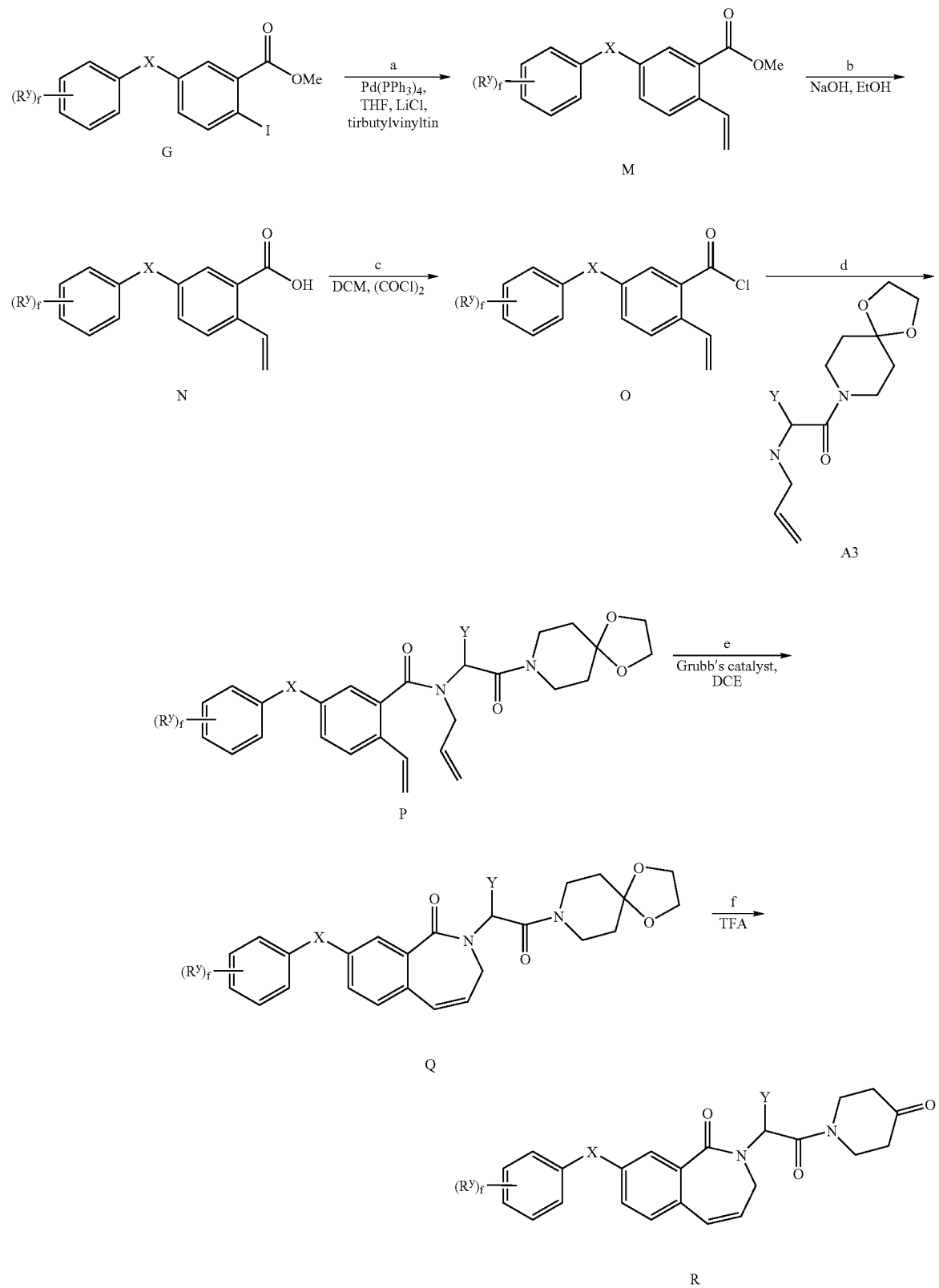

Alternatively, other compounds of the invention can be synthesized according to the scheme depicted below. Aniline S can be easily produced from compound D assembled according to steps a-c of Scheme 1. Ethanolic solution of aniline S can be converted into carboxylic acid T via heterocycle formation followed by saponification of the ester intermediate by adding acetic acid and triethylorthoformate under nitrogen and heating the mixture. Subsequent acidification of the reaction mixture with HCl affords acid T. A number of compounds of the invention of the general formula U can be produced through amide formation by coupling acid T with an amine intermediate such as 4-amino-1-benzylpiperidine (demonstrated below) in a dichloromethane solution containing triethylamine and HBTU. Other amines can be used in place of 4-amino-1-benzylpiperidine if desired.

Some compounds of the invention can be prepared as shown in Scheme 6. Acyl chloride V can be synthesized as demonstrated in step a of Scheme 2. V can be coupled with amine A3 in the presence of diisopropylethylamine to produce amide W. Amide W can be oxidized in dioxane solution containing catalytic amounts of osmium oxide and sodium periodate thereby producing aldehyde X. X, in ethanol, can be reduced to an aniline intermediate followed by a ring formation performed via catalytic hydrogenation to provide ketal Y. Ketal Y can be easily deprotected to form ketone Z by dissolving in a TFA solution followed by heating. Keto group of compound Z is useful for generating a variety of compounds of the invention via reductive amination as described above. For example, the reaction of ketone Z with a dichloromethane

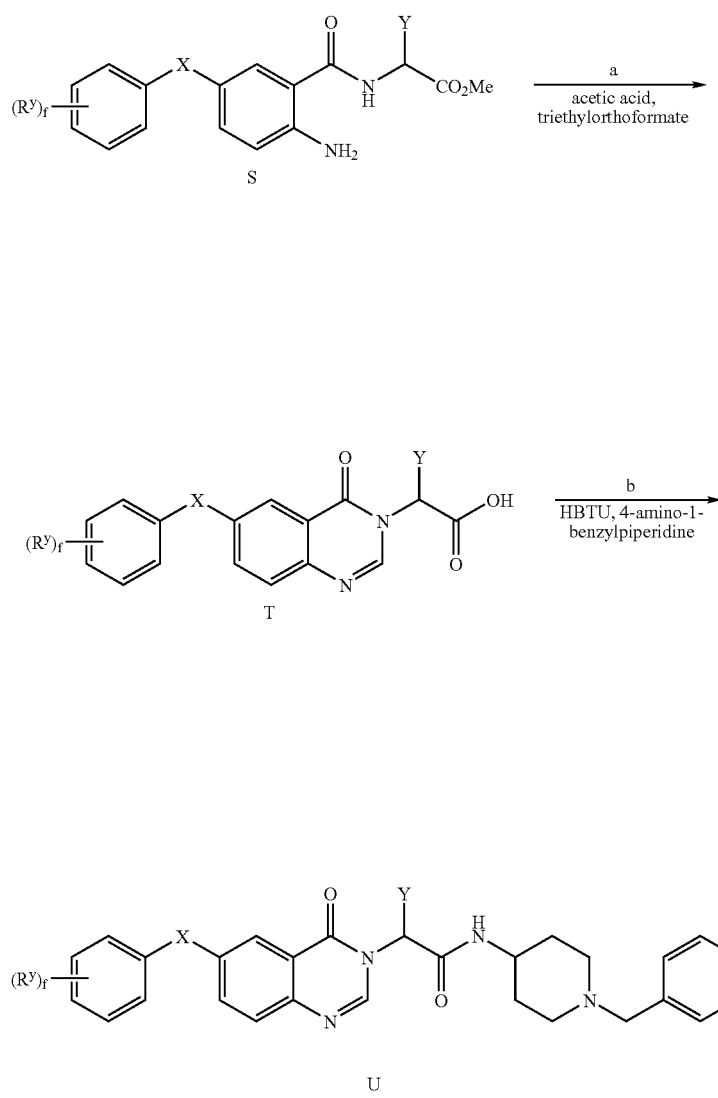

solution of aminoindane A4 in the presence of NaBH(OAc)$_3$ and triethylamine affords compounds of formula BB.
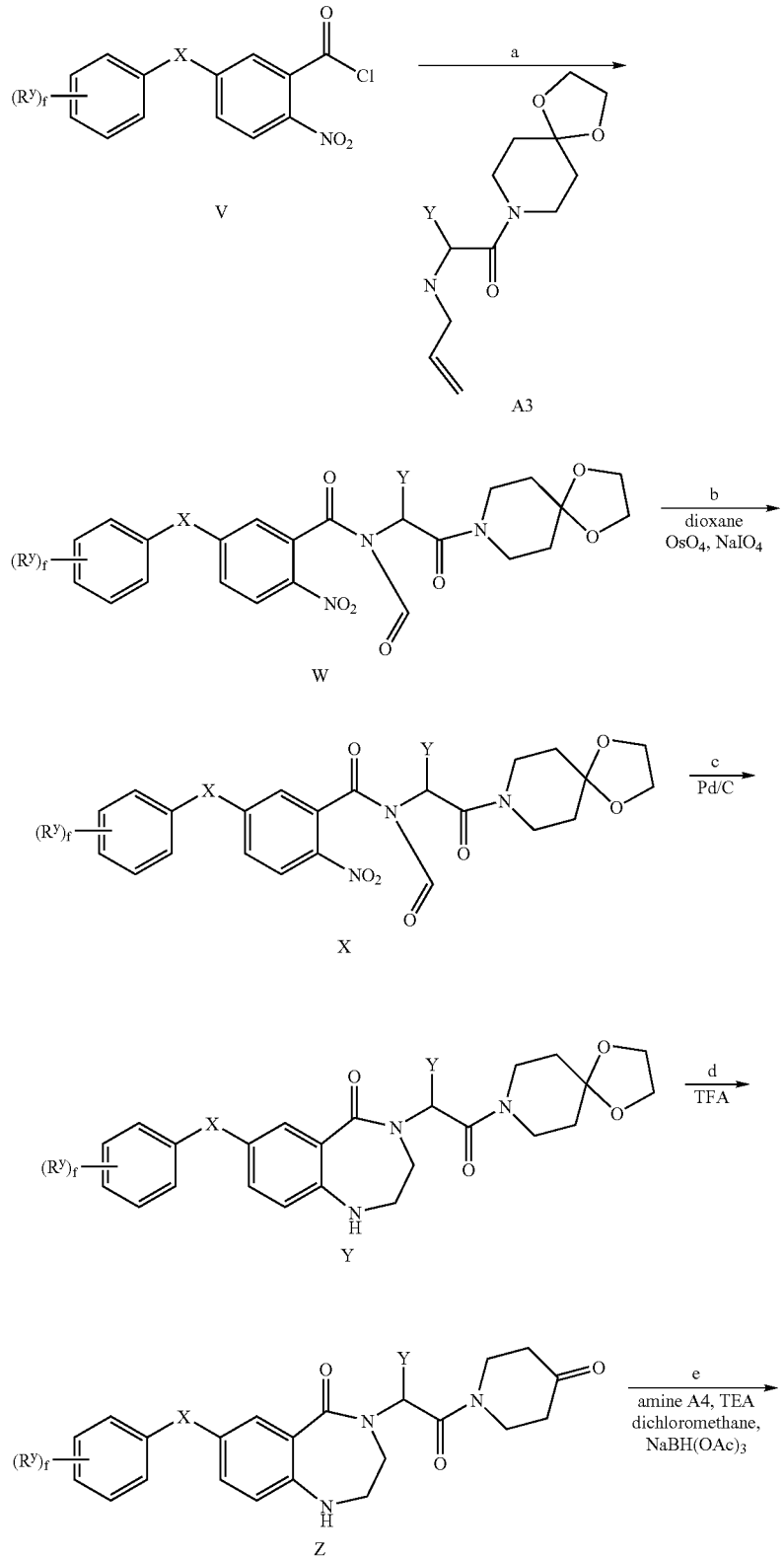
Scheme 6

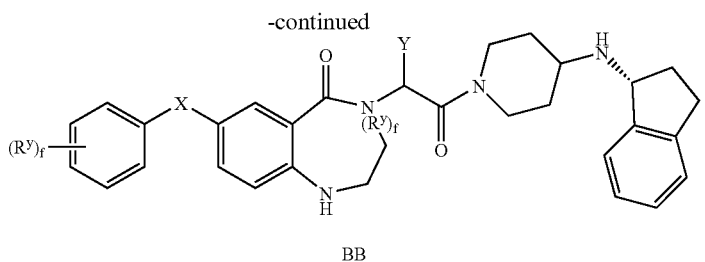

BB

Other compounds of the invention can be generated according to Scheme 7. Alcohol of formula DD can be generated via reduction of acid CC with the borane tetrahydrofurane complex. Alcohol DD can be oxidized to aldehyde EE in the presence of manganese oxide in DCM. Heck coupling of aldehyde EE with benzyl acrylate in acetonitrile in the presence of palladium acetate and tri-o-tolylphosphine and triethylamine affords compound FF, which can be coupled via reduction amination with amine A5 and sodium triacetoxyborohydride in DCE to produce amine GG. GG can be reduced via catalytic hydrogenation over palladium on carbon to carboxylic acid HH, which can be converted through the ring formation via amide coupling in the solution of EDC, HOBt and 4-methylmorpholine in DCM to lactam II. Reductive amination of the ketone group in lactam II with cyclopropyl-methylamine A6 generates compound of the invention JJ. Similarly, other amines can be used to provide variously substituted compounds of the invention.

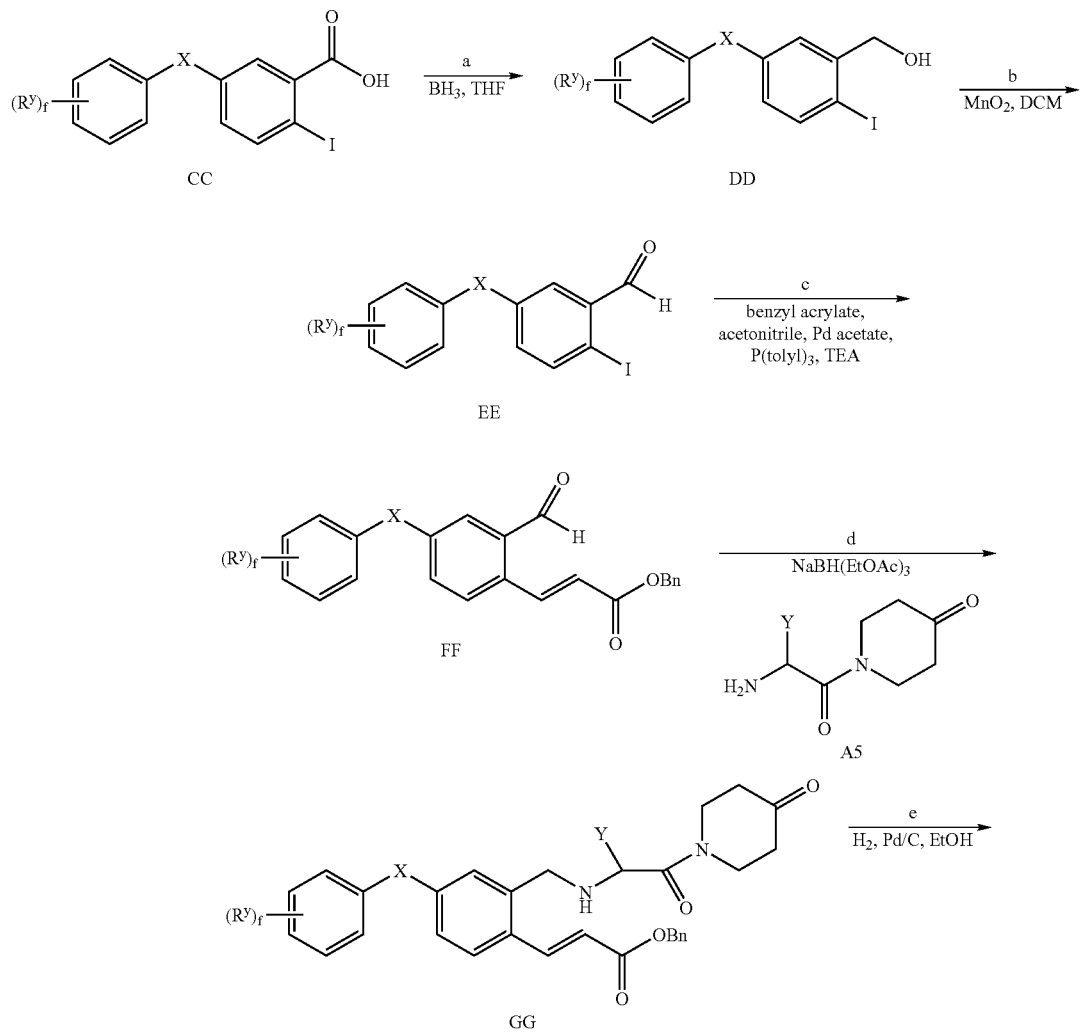

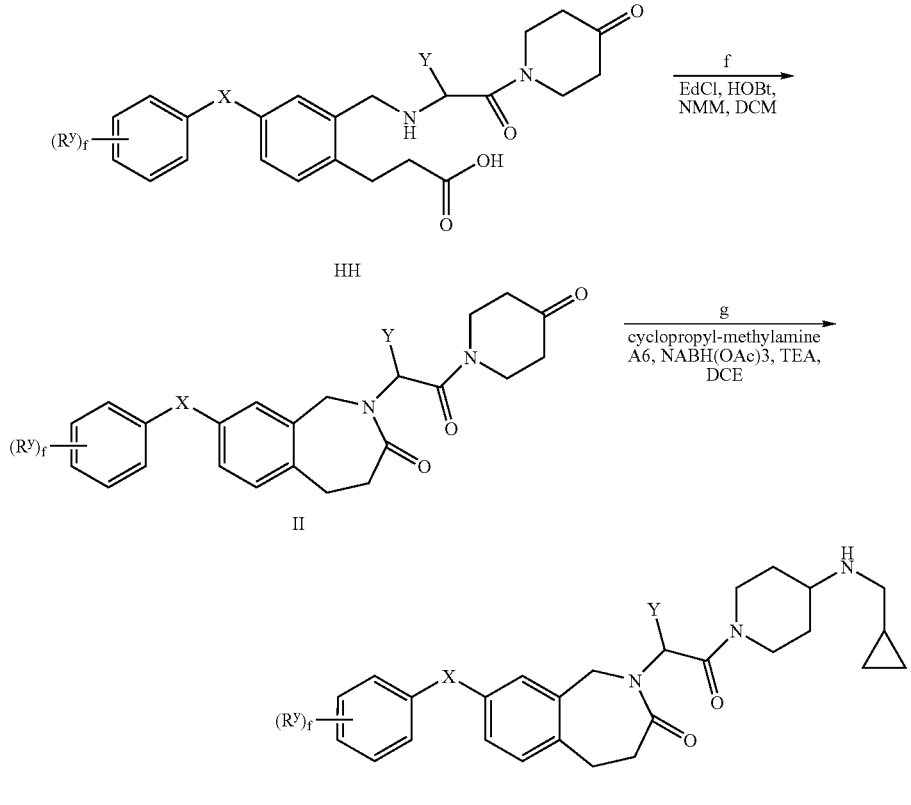

Compounds of the invention bearing the 2,3-dihydroisoindol-1-one ring can be assembled according to the synthetic route depicted in Scheme 8. Compound KK can be oxidized in the presence of ozone to generate aldehyde LL. Aldehyde LL can be coupled via reductive amination with amine A7 followed by cyclization to produce ketal MM, which can be converted to compounds of the invention via reactions analogous to steps d and e in Scheme 6. A skilled practitioner would appreciate that different amines can be used to generate a library of compounds.

Scheme 8

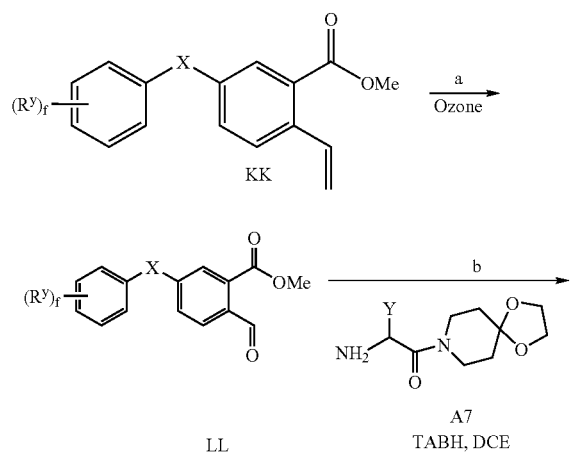

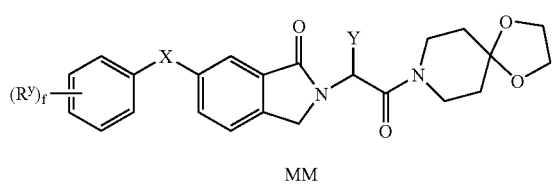

Other compounds of the invention can be generated according to the synthesis outlined in Scheme 9. Aniline NN can be converted to acid OO in the presence of HCl, NaNO$_2$, NaBF$_4$, TFA and K$_2$CO$_3$. Amide coupling of OO with amine A8 results in amide PP. Ring closure of PP with a dialkylating agent such as dichloroethane in the presence of a strong base such as NaH in DMF yields ketal QQ. Compounds of the invention of the general formula RR can be produced by deprotecting ketal QQ followed by reductive amination with amines such as A6. The free phenolic hydroxyl group in compound PP can be selectively functionalized to produce a ring-open structure such as compound SS. The ketal group can be removed, and the resulting ketone can then be functionalized to generate compound of the invention of the general formula TT.

Scheme 9

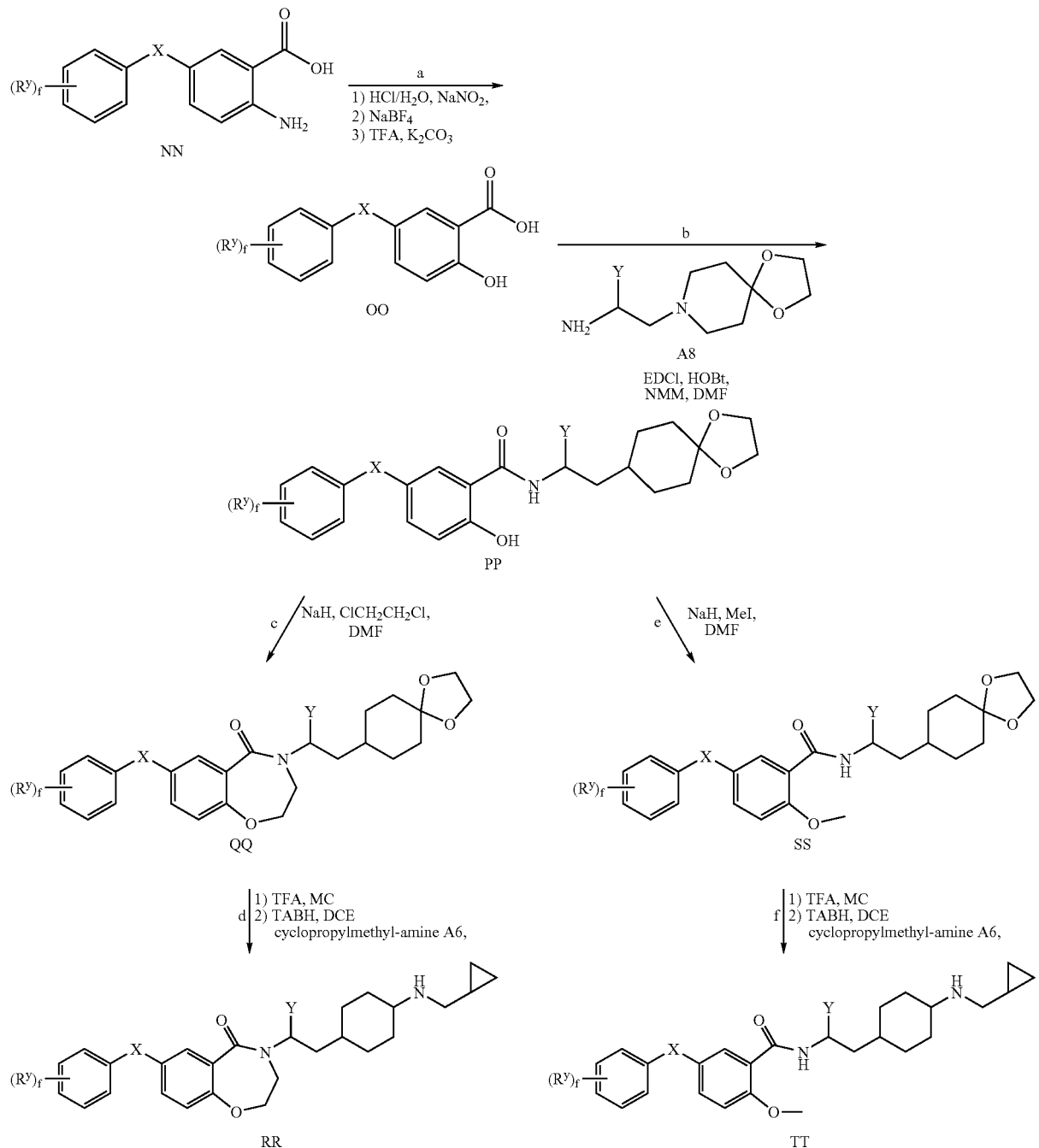

Regarding the molecular structures set forth in Schemes 1-9 above, one of skill in the art will readily appreciate that precursors and intermediates having aryl groups other than phenyl, e.g. naphthyl, can be used to practice the synthetic methods.

Schemes 1-9, each variable $R^y$ is independently selected from the group consisting of halogen, hydroxyl, cyano, ($C_1$-$C_8$) alkyl, ($C_2$-$C_8$) alkenyl, ($C_2$-$C_8$) alkynyl, ($C_1$-$C_8$) alkoxy and amino group. The subscript f can be 0, 1, 2, 3, 4, or 5.

It will also be appreciated that each group PG indicates, in a general sense, a carboxyl protecting group that can be removed under basic conditions (e.g., alkyl ester), see, e.g., Greene et al. (1991) *Protective Groups in Organic Synthesis*, 2$^{nd}$ Edition, New York: Wiley and Kocienski (1994) *Protecting Groups*, New York: Thieme, pp.224-276, and a leaving group (e.g., halogen, sulfonate, and the like), respectively.

The exemplary methods and the examples described herein are illustrative of the present invention and are not to be construed as limiting the scope thereof.

Compositions

The present invention also provides compositions comprising a therapeutically effective amount of a compound of the invention of the general Formula I and Formulas II(a-k) and a pharmaceutically acceptable carrier, diluent or excipient. Pharmaceutical compositions and single unit dosage forms comprising a compound of the invention, or a pharmaceutically acceptable stereoisomer, prodrug, salt, solvate, hydrate, or clathrate thereof, are also encompassed by the invention. Individual dosage forms of the invention may be suitable for oral, mucosal (including sublingual, buccal, rectal, nasal, or vaginal), parenteral (including subcutaneous, intramuscular, bolus injection, intraarterial, or intravenous), transdermal, or topical administration.

The term "pharmaceutical composition" is intended to encompass a product comprising the active ingredient(s), such as one or more compounds of the invention, or stereoisomers, solvates, pharmaceutically acceptable salts or tautomers thereof, and the inert ingredient(s), such as pharmaceutically acceptable carriers, excipients that make up the carrier, binders, diluents or the like, as well as any product which results, directly or indirectly, from combination, complexation or aggregation of any two or more ingredients, or from dissociation of one or more ingredients, or from other types of reactions or interaction of one or more ingredients. Additionally, the pharmaceutical compositions of the present invention include any composition made by admixing a ghrelin receptor modulator, additional active ingredient such as a second anti-obesity agent, and pharmaceutically acceptable excipients. By "pharmaceutically acceptable" it is meant that the carrier, diluent or excipient must be compatible with the other ingredients of the formulation and not deleterious to the recipient thereof.

Typical pharmaceutical compositions and dosage forms comprise one or more carriers, excipients or diluents. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. With that fact in mind, typical excipients include, but are not limited to, water, ethanol, ethylene glycol, propylene glycol, butane-1,3-diol, isopropyl myristate, isopropyl palmitate, mineral oil, and mixtures thereof, which are non-toxic and pharmaceutically acceptable. Examples of such additional ingredients are well known in the art. See, e.g., Remington's Pharmaceutical Sciences, 18th eds., Mack Publishing, Easton Pa. (1990).

The pH of a pharmaceutical composition or dosage form, or of the tissue to which the pharmaceutical composition or dosage form is applied, can also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

This invention further encompasses anhydrous (e.g., <1% water) pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Combination Therapy with Other Anti-Obesity Agents

The compositions of the instant invention may be advantageously combined and/or used in combination with agents useful in the treatment and/or prevention of obesity and eating disorders and pathologies associated therewith. In many instances, administration of the subject compounds or compositions in conjunction with these alternative agents enhances the efficacy of such agents. Accordingly, in some instances, the present compounds, when combined or administered in combination with, e.g., anti-obesity agents, can be used in dosages which are less than the expected amounts when used alone, or less than the calculated amounts for combination therapy.

The term "anti-obesity agent" refers to compounds that reduce total food intake by 5 to 30%, or reduce caloric intake or selectively reduce intake of specific components of the diet such as carbohydrates or fats by 5 to 30%; compounds which, when administered to a subject, act to increase the metabolic rate of the subject by 5-20% in 24 hour expenditure; and compounds that inhibit the absorption of 10 to 50% of the nutrients.

Suitable agents for combination therapy include those that are currently commercially available and those that are in development or will be developed. A skilled artisan can readily identify anti-obesity agents useful in compositions and methods of the present invention. Anti-obesity agents that decrease food intake can be evaluated in rodents according to the procedures described in the following publications: Halaas, J. L. et al. (1995) Science 269: 543-546; Daniels A. J. et al. (2002) Regulatory Peptides 106: 47-54 and Strack A. M. (2002) Obesity Research 10: 173-181. Anti-obesity agents that increase metabolic rate can be routinely evaluated in rodents as described in Himms-Hagan, J. (1994) American J. Physiology 266: R1371-1382 and Atgie C. (1998) Comp. Biochem. Physiol. A. Mol. Integr. Physiol. 119: 629-636; and, even when inactive in rodents, are tested in additional species such as dog and monkey before ultimately tested in humans (Connacher A. A. et al. (1992) Int'l J. Obesity 16: 685-694; Connacher A. A. et al. (1998) Brit. Med. J. 296: 1217-1220). The utility of anti-obesity agents that inhibit nutrient absorption can be evaluated using techniques described in Badr M. Z. & Chen, T. S. (1985) Toxicology 34: 333-340 and Sorribas, V. (1992) J. Pharm. Pharmacol. 44: 1030-1032.

The anti-obesity agents useful in the compositions of the present invention include, among others: a 5HT (serotonin) transporter inhibitor, a NE (norepinephrine) transporter inhibitor, a CB-1 (cannabinoid-1) antagonist/inverse agonist, an H3 (histamine 3) antagonist/inverse agonist, an MCHR1 (melanin concentrating hormone 1R) antagonist, an MCHR2 (melanin concentrating hormone 2R) agonist/antagonist, a NPY1 antagonist, leptin, a leptin derivative, an opioid antagonist, an orexin antagonist, a BRS3 (bombesin receptor subtype 3), a CCK-A (cholecystokinin-A) agonist, a CNTF (Ciliary neurotrophic factor), a CNTF derivative, a GHSR (growth hormone secretagogue receptor) agonist/antagonist, a 5HT2C (serotonin receptor 2C) agonist, a Mc4r (melanocortin 4 receptor) agonist, a monoamide reuptake inhibitor, an UCP-1, 2, or 3 (uncoupling protein) activator, a β3 (beta adrenergic receptor 3) agonist, a thyroid hormone β agonist, a PDE (phosphodiesterase) inhibitor, a FAS (fatty acid synthase) inhibitor, a DGAT1 (diacylglycerol acyltransferase) inhibitor, a DGAT2 inhibitor, an ACC2 (acetyl-CoA carboxylase 2) inhibitor, a glucocorticoid antagonist, an acyl-estrogen, a lipase inhibitor, a fatty acid transporter inhibitor, a dicarboxylate transporter inhibitor, a glucose transporter inhibitor, a serotonin reuptake inhibitors, metformin and topiramate.

Serotonin (5HT) transport inhibitors can include, for example, paroxetine, fluoxetine, fenfluramine, fluvoxamine, sertraline and imipramine. Norepinephrine (NE) transport inhibitors may include GW 320659, despiramine, talsurpam and nomifensine.

Cannabinoid receptor 1 (CB-1) antagonist/inverse agonists can include compounds described in U.S. Pat. Nos. 5,532,237; 4,972,587; 5,013,837; 5,081,122; 5,624,941 and 6,028,084; PCT Applications Nos. WO 96/33159, WO 98/43635; WO 99/02499; WO 00/10968; WO 01/09120 and WO 02/076949; EPO Application No. EP 658546. Specific CB-1 antagonist/inverse agonists may include rimonabant and SR-147778 (Sanofi Sythelabo).

Histamine 3 (H3) antagonist/inverse agonists useful in the compositions of this invention may include compounds described in PCT Application WO 02/15905; O-[3-(1H-imidazol-4-yl)propanol]carbamates (Kiec-Kononowicz, K. et al. (2000) 55: 349-355); piperidine-containing histamine H3-receptor antagonists (Lazewska, D. et al. (2001) Pharmazie, 56: 927-932), benzophenone derivatives and related compounds (Sasse, A. et al. (2001) Arch. Pharm. (Weinheim) 334: 45-52; substituted N-phenylcarbamates (Reidmeister, S. et al. (2000) Pharmazie 55: 83-86); and proxifan derivatives (Sasse, A. et al. (2000) J. Med. Chem. 43: 3335-3343). Specific H3 antagonist/inverse agonists may include thioperamide, 3-(1H-imidazol-4-yl)propyl N-(4-pentenyl)carbamate, clobenpropit, iodophenopropit, imoproxifan and GT2394 (Gliatech).

MCHR1 and MCHR2 agonists and antagonists may include the compounds described in PCT Application Nos. WO 01/82925, WO 01/87834, WO 02/04433 and WO 02/51809 and Japanese Patent Application No. JP 13226269. Specific MCHR1 antagonists may include T-226296 (Takeda).

Neuropeptide Y1 antagonists can include compounds described in U.S. Pat. No. 6,001,836; in PCT Application Nos. WO 96/14307, WO 99/51600, WO 01/23387, WO 01/85173 and WO 01/89528. Specific examples of NPY1 antagonists can include BIBP3226, J-115814, BIBO 3304, LY-357897, CP-671906 and GI-264879A.

Leptin includes recombinant human leptin (PEG-OB, Hoffman La Roche) and recombinant methionyl human leptin (Amgen). Leptin derivatives include compounds described in U.S. Pat. Nos. 5,552,524 and 5,521,283; PCT Application Nos. WO 96/23513, WO 96/23518 and WO 96/23520.

Opioid antagonists can include compounds described in PCT Application No. WO 00/21509. Specific opioid antagonists can include nalmefene (Revex®), 3-methoxynaltrexone naloxene and naltrexone. Orexin antagonists can include compounds described in PCT Application Nos. WO 01/68609, WO 01/96302, WO 02/51838 and WO 02/51232. Specific orexin antagonists may include SP-334867-A. An acyl-estrogen useful in this invention can include oleoyl-estrone (del Mar-Grasa, M. et al. (2001) Obesity Research 9: 202-209).

Cholecystokinin-A agonists can include those described in U.S. Pat. No. 5,739,106. Specific CCK-A agonists can include AR-R 15849, GI 181771, JMV-180, A-71378, A-71623 and SR146131.

Specific ciliary neurotrophic factors can include compounds GI-181771 (Glaxo-SmithKline), SR146131 (Sanofi Synthelabo), butabindide, PD170292, PD149164 (Pfizer). CNTF derivatives can include compounds described in PCT Application Nos WO 94/09134, WO 98/22128, WO 99/43813 and axokine (Regeneron).

Growth hormone secretagogue agonists and antagonists can include compositions described in U.S. Pat. No. 6,358,951 and PCT Applications Nos. WO 01/56592 and WO 02/32888. Specific GHS agonists may include NN703, hexarelin, MK-0677, SM-130686, CP-424391, L-692492 and L-163255.

5HT2C agonists can include compounds and compositions described in PCT application Nos. WO 02/36596, WO 02/10169, WO 02/40456 and WO 02/40457. Specific 5HT2C agonists can include BVT933, DPCA37215, WAY161503 and R-1065.

Mc4r agonists may include compounds and compositions described in PCT application Nos. WO 01/991752, WO 01/70708, WO 02/059108, WO 02/059117, WO 02/068388 and WO 03/009847. Specific Nc4r agonists can include CHIR86036 (Chiron), ME-10142 and ME-10145 (Melacure).

Monoamine reuptake inhibitors can include compounds and compositions described in PCT application Nos. WO 01/27068 and WO 01/62341. Specific monoamine reuptake inhibitors include sibutramine (Meridia®/Reductil®) disclosed in U.S. Pat. Nos. 4,746,680, 4,806,570 and 5,436,272 and U.S. Patent Publication 2002/0006964. Sibutramine can be used as a racemic mixture, optically pure isomers (+) and (−), or a pharmaceutically acceptable salt, solvent, hydrate, clathrate or prodrug thereof, particularly sibutramine hydrochloride monohydrate.

Serotonin reuptake inhibitor sibutramine can include compounds and compositions described in U.S. Pat. No. 6,365,633 and PCT Application Nos. WO 01/27060 and WO 01/162341.

Uncoupling Protein (UCP-1, UCP-2 and UCP-3) activators can include compounds and compositions described in PCT Application No. WO 99/00123. Specific uncoupling protein activators can include phytanic acid, 4-[(E)-2-(5,6,7,8-tetrahydro-5,5,8,8,-tetramethyl-2-napthalenyl)-1-propenyl]benzoic acid (TTNPB) and retinoic acid.

β3 adrenergic receptor agonists can include compounds and compositions described in U.S. Pat. Nos. 5,705,515 and 5,451,677, and PCT Applications Nos. WO 01/74782 and WO 02/32987. Specific β3 agonists can include AD9677/TAK677 (Dainippon/Takeda), CL-316243, SB 418790, BRL-37344, L-796568, BMS-196085, BRL-35135A, CGP12177A, BTA-243, Trecadrine, Zeneca D7114 and SR 59119A.

Thyroid hormone β agonists can include compounds and compositions described in PCT Application No. WO 02/15845 and Japanese Application No. JP 2000256190. Specific Thyroid hormone β agonists can include KB-2611 (KaroBioBMS).

Specific fatty acid synthase inhibitors can include Cerulenin and C75. Specific phosphodiesterase inhibitors can include theophylline, pentoxifylline, zaprinast, sildenafil, amrinone, milrinone, cilostamide, rolipram and cilomilast.

Lipase inhibitors can include compounds and compositions described in PCT Application No. WO 01/77094. Specific lipase inhibitors can include orlistat (Xenical®), Triton WR1339, RHC80267, lipstatin, tetrahydrolipstatin, teasaponin and diethylumbelliferyl phosphate.

Other compounds may include Topiramate (Topimax®), an anti-convulsant, which has been shown to increase weight loss; Metformin (Glucophage®), for patients with non-insulin dependent diabetes mellitus, particularly those with refractory obesity (Physician's Desk Reference (2002), 56th ed., 1080-1086). The compounds may also include zonisamide, an antiepileptic drug with serotonergic and dopaminergic activity in addition to the ability to block sodium and calcium channels. Zonisamide has been shown to result in weight loss in epileptic and obese adults.

Specific bombesin agonists can include, for example, [D-Phe6, beta-Ala11 ,Phe13,Nle14]Bn(6-14) and [D-Phe6, Phe 13]Bn(6-13)propylamide.

This listing of compounds is only illustrative of the anti-obesity agents that can be used in the compositions of the present invention and is not meant to be comprehensive.

Administration

The pharmaceutical compositions of the instant invention can be manufactured by methods well known in the art such as conventional granulating, mixing, dissolving, encapsulating, lyophilizing, emulsifying or levigating processes, among others. The compositions can be in the form of, for example, granules, powders, tablets, capsules, syrup, suppositories, injections, emulsions, elixirs, suspensions or solutions. Depending on the disease to be treated and the patient's condition, the compounds and compositions of the invention may be administered by oral, parenteral (e.g., intramuscular, intraperitoneal, intravenous, ICV, intracistemal injection or infusion, subcutaneous injection or implant), inhalation, nasal, vaginal, rectal, sublingual, or topical (e.g., transdermal, local) routes of administration and may be formulated, alone or together, in suitable dosage unit formulations containing conventional non-toxic pharmaceutically acceptable carriers, adjuvants and vehicles appropriate for each route of administration. The invention also contemplates administration of the compounds of the invention in a depot formulation, in which the active ingredient is released over a defined time period.

The instant compositions can be formulated for various routes of administration, for example, by oral administration, by transmucosal administration, by rectal administration, or subcutaneous administration as well as intrathecal, intravenous, intramuscular, intraperitoneal, intranasal, intraocular or intraventricular injection. The compound or compounds of the instant invention can also be administered in a local rather than a systemic fashion, such as injection as a sustained release formulation. The following dosage forms are given by way of example and should not be construed as limiting the instant invention.

Oral Dosage Forms

For oral, buccal, and sublingual administration, powders, suspensions, granules, tablets, pills, capsules, gelcaps, and caplets are acceptable as solid dosage forms. These can be prepared, for example, by mixing one or more compounds of the instant invention, or stereoisomers, solvates, prodrugs, pharmaceutically acceptable salts or tautomers thereof, with at least one additive or excipient such as a starch or other additive. Suitable additives or excipients are sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethyl-cellulose, and/or polyvinylpyrrolidone. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Additionally, dyestuffs or pigments may be added for identification. Tablets and pills may be further treated with suitable coating materials known in the art.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, PA), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Liquid dosage forms for oral administration may be in the form of pharmaceutically acceptable emulsions, syrups, elixirs, suspensions, slurries and solutions, which may contain an inactive diluent, such as water. Pharmaceutical formulations may be prepared as liquid suspensions or solutions using a sterile liquid, such as, but not limited to, an oil, water, an alcohol, and combinations of these. Pharmaceutically suitable surfactants, suspending agents, and/or emulsifying agents may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Controlled-release Dosage Forms

Controlled-release or delayed release pharmaceutical products can improve drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized. Controlled-release of an active ingredient can be stimulated by various conditions including, but not limited to, pH, temperature, enzymes, water, or other physiological conditions or compounds.

The instant compositions may also comprise, for example, micelles or liposomes, or some other encapsulated form, or may be administered in an extended release form to provide a prolonged storage and/or delivery effect. Examples include, but are not limited to, those described in U.S. Pat. Nos.: 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions.

Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release. Furthermore, the pharmaceutical formulations may be compressed into pellets or cylinders and implanted intramuscularly or subcutaneously as depot injections or as implants such as stents. Such implants may employ known inert materials such as silicones and biodegradable polymers. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

In one embodiment, a pump can be used (Sefton, CRC Crit. Ref Biomed Eng., 1987, 14, 201; Buchwald et al., Surgery, 1980, 88, 507; Saudek et al., N. Engl. J Med, 1989, 321, 574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J Macromol. Sci. Rev. Macromol. Chem., 1983, 23, 61; see also Levy et al., Science 1985, 228, 190; During et al., Ann. Neurol., 1989,25,351; Howard et al., 1989, J. Neurosurg. 71, 105). In yet another embodiment, a controlled-release system can be placed in proximity of the target of the compounds of the invention, e.g., the lung, thus requiring only a fraction of the systemic dose (see, e.g., Goodson, in Medical Applications of Controlled Release, supra, vol. 2, pp. 115 (1984)). Other controlled-release system can be used (see e.g., Langer, Science, 1990, 249, 1527).

Parenteral Dosage Forms

Parenteral dosage forms can be administered to patients by various routes including, but not limited to, subcutaneous, intravenous (including bolus injection), intramuscular, and intra-arterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. For example, lyophilized sterile compositions suitable for reconstitution into particulate-free dosage forms suitable for administration to humans.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

Transdermal and Topical Dosage Forms

Transdermal and topical dosage forms of the invention include, but are not limited to, creams, lotions, ointments, gels, solutions, emulsions, suspensions, or other forms known to one of skill in the art. See, e.g., Remington's Pharmaceutical Sciences, 18th eds., Mack Publishing, Easton Pa. (1990); and Introduction to Pharmaceutical Dosage Forms, 4th ed., Lea & Febiger, Philadelphia (1985). Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal and topical dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, 18th eds., Mack Publishing, Easton Pa. (1990).

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Mucosal Dosage Forms and Lung Delivery

Mucosal dosage forms of the invention include, but are not limited to, ophthalmic solutions, sprays and aerosols, or other forms known to one of skill in the art. See, e.g., Remington's Pharmaceutical Sciences, 18th eds., Mack Publishing, Easton Pa. (1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. In one embodiment, the aerosol comprises a carrier. In another embodiment, the aerosol is carrier free.

A compound of the invention can also be administered directly to the lung by inhalation (see e.g., Tong et al., PCT Application, WO 97/39745; Clark et al, PCT Application, WO 99/47196). For administration by inhalation, a compound of the invention can be conveniently delivered to the lung by a number of different devices. For example, a Metered Dose Inhaler ("MDI") which utilizes canisters that contain a suitable low boiling propellant, e.g., dichlorodifluoromethane, trichlorofluoromethane, dichlorotetrafluoroethane, carbon dioxide or other suitable gas can be used to deliver a ghrelin receptor modulator directly to the lung. MDI devices are available from a number of suppliers such as 3M Corporation.

Alternatively, a Dry Powder Inhaler (DPI) device can be used to administer a compound of the invention to the lung (see, e.g., Raleigh et al., Proc. Amer. Assoc. Cancer Research Annual Meeting, 1999, 40, 397). DPI devices typically use a mechanism such as a burst of gas to create a cloud of dry powder inside a container, which can then be inhaled by the patient. DPI devices are also well known in the art and can be purchased from a number of vendors which include, for example, Fisons, Inhale Therapeutic Systems, ML Laboratories, Qdose and Vectura. A popular variation is the multiple dose DPI ("MDDPI") system, which allows for the delivery of more than one therapeutic dose. MDDPI devices are available from companies such as SkyePharma and Vectura. For example, capsules and cartridges of gelatin for use in an inhaler or insufflator can be formulated containing a powder mix of the compound and a suitable powder base such as lactose or starch for these systems.

Another type of device that can be used to deliver a compound of the invention to the lung is a liquid spray device supplied, for example, by Aradigm Corporation. Liquid spray systems use extremely small nozzle holes to aerosolize liquid drug formulations that can then be directly inhaled into the lung.

In one embodiment, a nebulizer device is used to deliver a compound of the invention to the lung. Nebulizers create aerosols from liquid drug formulations by using, for example, ultrasonic energy to form fine particles that can be readily inhaled (See e.g., Verschoyle et al., British J Cancer, 1999, 80, Suppl 2, 96). Examples of nebulizers include devices supplied by Sheffield/Systemic Pulmonary Delivery Ltd. (See, Armer et al., U.S. Pat. No. 5,954,047; van der Linden et al., U.S. Pat. No. 5,950,619; van der Linden et al., U.S. Pat. No. 5,970,974), Batelle Pulmonary Therapeutics.

Liquid drug formulations suitable for use with nebulizers and liquid spray devices and EHD aerosol devices will typically include a compound of the invention with a pharmaceutically acceptable carrier. Preferably, the pharmaceutically acceptable carrier is a liquid such as alcohol, water, polyethylene glycol or a perfluorocarbon. Optionally, another material may be added to alter the aerosol properties of the solution or suspension of a ghrelin receptor modulator. Preferably, this material is liquid such as an alcohol, glycol, polyglycol or a fatty acid. Other methods of formulating liquid drug solutions or suspension suitable for use in aerosol devices are known to those of skill in the art (See, e.g., Biesalski, U.S. Pat. No. 5,112,598; Biesalski, U.S. Pat. No. 5,556,611).

Other Delivery Systems

Alternatively, other pharmaceutical delivery systems can be employed. Liposomes and emulsions are well known examples of delivery vehicles that can be used to deliver a ghrelin receptor modulator. Certain organic solvents such as dimethylsulfoxide can also be employed, although usually at the cost of greater toxicity.

A compound of the invention can also be formulated in rectal or vaginal compositions such as suppositories or retention enemas, e.g., containing conventional suppository bases such as cocoa butter or other glycerides.

Combined Administration

In the case of a combined administration, a compound of the invention may be administered simultaneously with other another therapeutic agent that is useful for the treatment or prevention of diabetes, obesity or other disease or may be administered at a time prior to or subsequent to another therapeutic agent. In the case of combined administration, a pharmaceutical composition containing a compound of the invention and an additional therapeutic agent can be administered. Alternatively, a pharmaceutical composition containing a compound of the invention and a pharmaceutical composition containing an additional therapeutic agent may be administered separately. The administration routes of respective pharmaceutical compositions may be the same or different.

Dosage

In order to practice the present methods of therapy, a therapeutically effective amount of the compounds of the invention is administered in a composition to a subject in need of such treatment or prophylaxis. The need for a prophylactic administration is determined by the use of well-known risk factors. The effective amount of an individual compound is generally determined by a physician, and depends on factors such as the disease or condition to be treated, the severity of the disease and other diseases from which the patient suffers, other drugs and/or treatments which the patient may concomitantly require, the chosen route of administration and other factors in the physician's judgment.

The magnitude of prophylactic or therapeutic dose of the active compounds of the composition will vary with the nature or the severity of the condition to be treated, with the particular compound in the composition and its route of administration. It will also vary according to the age, sex, weight and response of the individual patient. In general, the daily dose range of each compound lies within the range of from about 0.0001 mg/kg to about 100 mg/kg body weight of a subject in single or divided doses. However, in some cases it may be necessary to use dosages outside these limits. If a composition of the invention is administered intravenously, a suitable dosage range can be from about 0.0001 mg/kg to about 50 mg/kg per day. Where the composition of the invention is administered orally, a suitable dosage range can be from about 0.001 mg/kg to about 100 mg/kg per day.

This dosage regimen may be adjusted to provide the optimal therapeutic response. Generally, treatment is initiated with smaller dosages that are less than the optimum dose of the compound. Thereafter, the dosage is increased by small increments until the optimum effect under the circumstances is reached. For convenience, the total daily dosage may be divided and administered in portions during the day, if desired. In the case of combined administration, a compound of the invention may be administered at a dose of 50 mg to 800 mg per administration, which is given once to several times a day. In addition, the compound may be administered at a smaller dose. The combined pharmaceutical agent can be administered at a dose generally employed for the prophylaxis or treatment of diabetes or obesity or at a smaller dose than that.

The dosage regimen utilizing the compositions of the present invention can be selected in accordance with a variety of factors including type of the compounds, species, age, general health, body weight, diet, sex and medical condition of the subject, the severity of the condition to be treated, the renal and hepatic function of the patient, the drug combination, the particular compounds employed and their route of administration. As alluded to above, a physician, clinician or veterinarian of ordinary skill can readily determine and prescribe the effective amount of the drug required to prevent, counter or arrest the progress of the condition.

Therapeutic Uses of the Compounds of the Invention

The invention provides methods for treating a condition or disorder selected from the group consisting of obesity, an eating disorder, a cardiovascular disease, a gastrointestinal disorder, a dermatological disorder, and a cancer, comprising administering to a subject in need thereof a therapeutically effective amount of a compound comprising administering to a patient in need thereof a therapeutically effective amount of a compound of Formula I or Formulas II(a)-II(k).

Obesity can be treated or prevented by administration of a therapeutically effective amount of a compound of the invention. Obesity may have genetic, environmental (e.g., expending less energy than is consumed) and regulatory determinants. Obesity includes exogenous, hyperinsulinar, hyperplasmic, hypothyroid, hypothalamic, symptomatic, infantile, upper body, alimentary, hypogonadal, simple and central obesity, hypophyseal adiposity and hyperphagia. Metabolic disorders, such as hyperlidemia and diabetes, and cardiovascular disorders, such as hypertension and coronary artery disease, are commonly associated with obesity.

The invention provides methods for treatment or prevention of diabetes and diabetic conditions by administration of a therapeutically effective amount of ghrelin receptor modulator. Types of diabetes that can be treated or prevented by administering a therapeutically effective amount of a compound of Formula I or Formulas II(a)-II(k) include type I diabetes mellitus juvenile onset diabetes, insulin dependent-diabetes mellitus or IDDM), type II diabetes mellitus (non-insulin-dependent diabetes mellitus or NIDDM), insulinopathies, diabetes associated with pancreatic disorders, diabetes associated with other disorders (such as Cushing's Syndrome, acromegaly, pheochromocytoma, glucagonoma, primary aldosteronism, and somatostatinoma), type A and type B insulin resistance syndromes, lipatrophic diabetes, and diabetes induced by □-cell toxins.

Other conditions or disorders that can be treated or prevented by administering a therapeutically effective amount of a compound of Formula I or Formulas II(a)-II(k) include, but are not limited to any condition which is responsive to the modulation, preferably inhibition, of ghrelin receptor and thereby benefits from administration of such a modulator. Representative conditions in this regard include, but are not limited to, overeating, bulimia, diabetes, hypertension, elevated plasma insulin concentrations, insulin resistance, dyslipidemia, hyperlipidemia, breast, prostate, endometrial, kidney and colon cancer, heart disease, abnormal heart rhythms, arrhythmias, myocardial infarction, congestive heart failure, coronary heart disease, angina pectoris, cerebral infarction, cerebral thrombosis, transient ischemic attack, arthritis deformans, sudden death, osteoarthritis, cholelithiasis, gallstones, gallbladder disease, lumbodynia, emmeniopathy, obstructive sleep apnea, stroke, polycystic ovary disease, craniopharyngioma, the Prader-Willi Syndrome, Frohlich's syndrome, GH-deficiency, normal variant short stature, Turner syndrome, metabolic syndrome, impaired fasting glucose, impaired glucose tolerance, reproductive hormone abnormalities, sexual and reproductive dysfunction, fetal defects associated with maternal obesity, gastrointestinal motility disorders, respiratory disorders, fatty liver, breathlessness, dermatological disorders, inflammation, arteriosclerosis, hypercholesterolemia, hyperuricaemia, gout, and left ventricular hypertrophy.

The invention also provides methods for modulating ghrelin receptor, comprising contacting a cell with a compound of Formula I or Formulas II(a)-II(k). In one aspect, the compound of Formula I or Formulas II(a)-II(k) is a ghrelin receptor antagonist.

The invention further provides methods for treating a condition or disorder selected from the group consisting of obesity, an eating disorder, a cardiovascular disease, a gastrointestinal disorder, a dermatological disorder, and a cancer, comprising administering to a subject in need thereof a therapeutically effective amount of a compound of Formula I or Formulas II(a)-II(k) and an additional anti-obesity agent. In one aspect, the additional anti-obesity agent is selected from the group consisting of a serotonin transporter inhibitor, a norepinephrine transporter inhibitor, a cannabinoid-1 antagonist/inverse agonist, a histamine 3 antagonist/inverse agonist, a melanin concentrating hormone 1R antagonist, a melanin concentrating hormone 2R agonist/antagonist, leptin, a leptin derivative, an opioid antagonist, an orexin antagonist, a bombesin receptor subtype 3, a cholecystokinin-A agonist, a Ciliary neurotrophic factor, a Ciliary neurotrophic factor derivative, a growth hormone secretagogue receptor agonist/antagonist, a serotonin receptor 2C agonist, a melanocortin 4 receptor agonist, a monoamide reuptake inhibitor, an uncoupling protein-1, -2, or -3 activator, a beta adrenergic receptor 3 agonist, a thyroid hormone β agonist, a phosphodiesterase inhibitor, a fatty acid synthase inhibitor, a diacylglycerol acyltransferase-1 inhibitor, a diacylglycerol acyltransferase-2 inhibitor, an acetyl-CoA carboxylase 2 inhibitor, a glucocorticoid antagonist, an acyl-estrogen, a lipase inhibitor, a fatty acid transporter inhibitor, a dicarboxylate transporter inhibitor, a glucose transporter inhibitor, metformin and topiramate.

Kits

The invention encompasses kits that can simplify the administration of compounds of the invention or compositions of the invention to a patient.

A typical kit of the invention comprises a unit dosage of a compound of the invention. In one aspect, the unit dosage form is in a container, which can be sterile, containing a therapeutically effective amount of a compound of the invention and a pharmaceutically acceptable vehicle. In another aspect, the unit dosage form is in a container containing a therapeutically effective amount of a compound of the invention as a lyophilate or pharmaceutically acceptable salt. In this instance, the kit can further comprise another container that contains a solution useful for the reconstitution of the lyophilate or dissolution of the salt. The kit can also comprise a label or printed instructions for use.

In a further aspect, the kit comprises a unit dosage form of a composition of the invention.

Kits of the invention can further comprise one or more devices that are useful for administering the unit dosage forms of a compound of the invention or a composition of the invention. Examples of such devices include, but are not limited to, a syringe, a drip bag, a patch or an enema, which optionally contain the unit dosage forms.

The present invention, thus generally described, will be understood more readily by reference to the following examples, which are provided by way of illustration and are not intended to be limiting of the present invention. Compounds of the invention may be synthesized from simple starting molecules and commercially available materials as illustrated in Examples.

The present invention is not to be limited in scope by the specific embodiments disclosed in the Examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims. To this end, it should be noted that one or more hydrogen atoms or methyl groups may be omitted from the drawn structures consistent with accepted shorthand notation of such organic compounds, and that one skilled in the art of organic chemistry would readily appreciate their presence.

EXAMPLES

Examples 1-49 below provide exemplary synthetic methods for the preparation of the compounds of the present invention. One of skill in the art will understand that additional methods are also useful. In other words, the compounds of the invention can be made using conventional organic synthesis using starting materials, reagents and reactions well known in the art.

Reagents and solvents used below can be obtained from commercial sources such as Aldrich Chemical Co. (Milwaukee, Wis., USA). 1H-NMR spectra were recorded on a Bruker 400 MHz or 500 MHz NMR spectrometer. Significant peaks are tabulated in the order: multiplicity (s, singlet; d, doublet; t, triplet; q, quartet; m, multiplet; br s, broad singlet), coupling constant(s) in Hertz (Hz) and number of protons. Electron Ionization (EI) mass spectra were recorded on a Hewlett Packard 5989A mass spectrometer. Mass spectrometry results are reported as the ratio of mass over charge, followed by the relative abundance of each ion (in parentheses) or a single m/z value for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard 1100 MSD electrospray mass spectrometer using the HP1 100 HPLC for sample delivery. Normally the analyte was dissolved in methanol at 0.1 mg/mL and 1 microliter was infused with the delivery solvent into the mass spectrometer, which scanned from 100 to 1500 daltons. All compounds could be analyzed in the positive ESI mode, using 1:1 acetonitrile/water with 1% acetic acid as delivery solvent. The compounds provided below could also be analyzed in the negative ESI mode, using 2 mM NH4OAc in acetonitrile/water as delivery solvent. Enantiomeric purity was determined using a Hewlett-Packard Series 1050 system equipped with a chiral HLPC column (ChiralPak AD, 4.6 mm×150mm) and isocratic elution using 5:95 isopropanol-hexane as a mobile phase.

The compounds were named using ISIS.

Example 1

This example illustrates the chiral synthesis of amine intermediate A2 from alcohol S1 and compound 1.

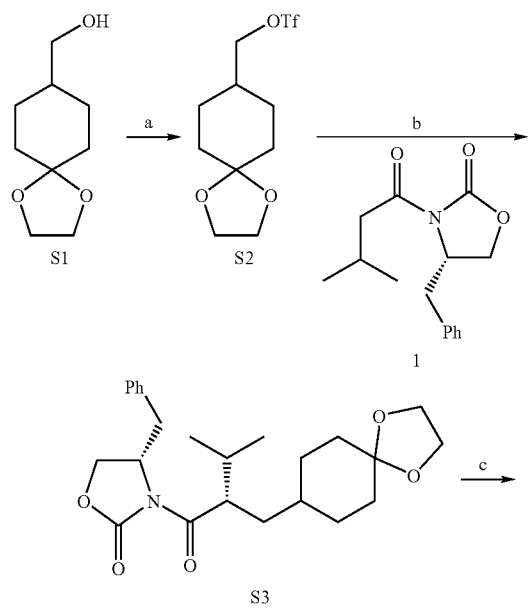

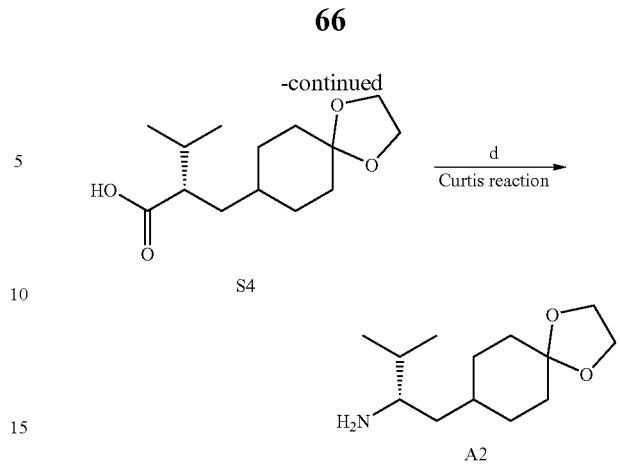

Step a. Trifluoromethanesulfonic anhydride (10.87 mL, 64.61 mmol, 1.0 equiv) was added to a solution of alcohol SI (11.13 g, 64.63 mmol, 1 equiv) and pyridine (6.27 mL, 77.60 mmol, 1.2 equiv) in dichloromethane (50 mL) at −78° C. and was slowly warmed to −20° C. The reaction was diluted with brine (300 mL) and extracted with dichloromethane (2×200 mL). The organic layer was combined, dried over sodium sulfate and concentrated. The residue was purified by silica gel flash column chromatography (20% ethyl acetate in hexane) to afford triflate S2 (12.8 g, 65% yield) as colorless oil. $^1$H NMR (400 MHz, CDCl$_3$) δ 4.35 (d, J=6.4 Hz, 2H), 3.95 (dd, J=9.4, 3.9 Hz, 2H), 3.92 (dd, J=9.0, 3.6 Hz, 2H), 1.91~1.84 (m, 1H), 1.83~1.77 (m, 4H), 1.57 (dd, J=14.1, 5.1 Hz, 1H), 1.53 (dd, J=14.1, 5.1H), 1.42~1.32 (m, 2H).

Step b. Lithium diisopropylamide (2.0 M solution in heptane/THF/ethylbenzene, 12.4 mL, 24.8 mmol, 1.1 equiv) was added drop-wise to a solution of compound 1 (5.91 g, 23.61 mmol, 1 equiv) in THF (50 mL) at −78° C. The reaction was stirred at this temperature for 1 h, whereupon a solution of triflate S2 (5.6 g, 18.4 mmol, 0.81 equiv) in THF (10 mL) at −78° C. was added to the reaction vessel via cannula and stirred at −25° C. The mixture was slowly warmed to 23° C. overnight. The reaction was diluted with water (30 mL) and extracted with ethyl acetate (3×50 mL). The organic layer was combined, dried over magnesium sulfate and concentrated. The residue was purified by silica gel flash column chromatography (20% ethyl acetate in hexane) to afford oxazolidinone S3 (5.87 g, 62% yield) as colorless oil. $^1$H NMR (400 MHz, CDCl$_3$) δ 7.36~7.22 (m, 5H), 4.75~4.69 (m, 1H), 4.16~4.10 (m, 2H), 3.94 (s, 4H), 3.90 (ddd, J=11.0, 5.8, 3.1 Hz, 1H), 3.33 (dd, J=12.9, 3.1 Hz, 1H), 2.73 (dd, J=13.3, 9.8 Hz, 1H), 1.93~1.69 (m, 6H), 0.97 (d, J=6.8 Hz, 3H), 0.93 (d, J=6.7 Hz, 3H); LRMS (ESI) m/z: Calculated for $C_{24}H_{34}NO_5$ (M+H) 416.3, found 416.4.

Step c. Lithium hydroxide (4 N in H2O, 14 mL, 56 mmol, 4.0 equiv) was added to a solution of oxazolidinone S3 (5.87 g, 14.13 mmol, 1 equiv) and hydrogen peroxide (30 wt % solution in H2O, 12 mL, 106 mmol, 7.5 equiv) in THF (85 mL) and H20 (21 mL), and the mixture was warmed to 23° C. overnight. The reaction was slowly quenched with Na2SO3 (1.5 M in H2O, 77 mL) at 0° C. and diluted with the saturated sodium bicarbonate solution (21 mL). Subsequently, THF was evaporated under reduced pressure in a rotary evaporator and the residue was washed with dichloromethane (3×40 mL). The aqueous layer was acidified to pH 4~5 at 0° C. with 2 N HCl solution and subsequently extracted with dichloromethane (3×60 mL), dried over sodium sulfate and concentrated to afford acid S4. The residue was carried to the next step without any further purification. LRMS (ESI) m/z: calculated for C14H25O4 (M+H) 257.2, found 257.2.

Step d. A solution of acid S4 (1.92 g, 7.5 mmol, 1.0 equiv), triethylamine (1.1 mL, 7.89 mmol, 1.1 equiv) and diphenylphosphoryl azide (1.61 mL, 7.47 mmol, 1.0 equiv) in toluene (30 mL) was heated at 80° C. until bubbling ceased (~2 h). The reaction was cooled to 23° C., benzyl alcohol (2.3 mL, 22.2 mmol, 3.0 equiv) was injected and the mixture was stirred at 80° C. overnight. The reaction was concentrated and the residue was purified by silica gel flash column chromatography (40% ethyl acetate in hexane). The resulting product was dissolved in ethanol (40 mL), treated with Pd/C (2 scoops) and hydrogen gas (balloon) for 12 h. The reaction was filtered through Celite, concentrated and purified by silica gel flash column chromatography (17% methanol in dichloromethane with 1% ammonium hydroxide) to afford amine A2 (1.51 g, 88% yield) as colorless oil. 1H NMR (400 MHz, CD3OD) δ 3.91 (s, 4H), 2.65~2.59 (m, 1H), 1.80~1.40 (m, 8H), 1.33~1.08 (m, 4H), 0.92 (d, J=6.9 Hz, 3H), 0.89 (d, J=6.9 Hz, 3H); LRMS (ESI) m/z: Calculated for C13H26NO2 (M+H) 228.2, found 228.2.

A skilled artisan would appreciate that other amine intermediates can be synthesized using the same synthetic scheme, starting with a corresponding alkylating agent S2 and making other necessary conditional modifications.

Example 2

This example illustrates the synthesis of amine A9 from bromide S5.

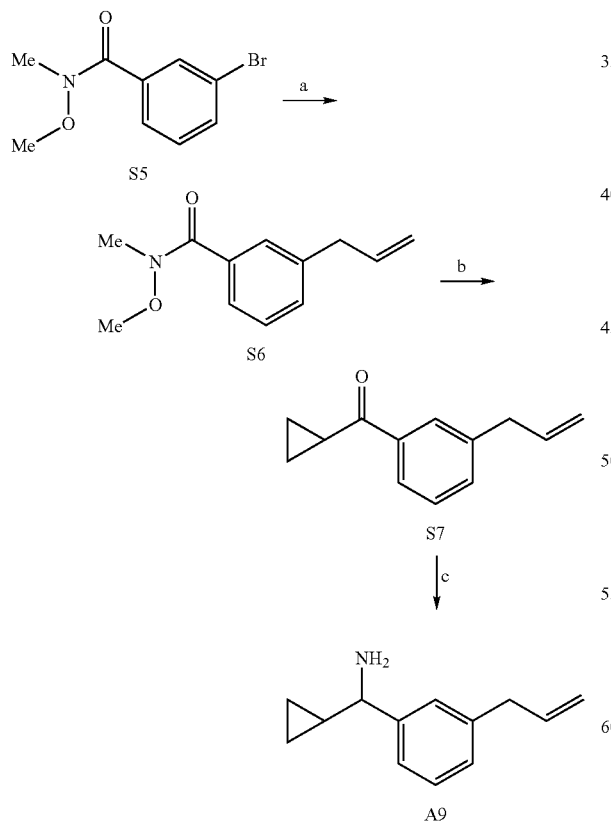

Step a. Pd(PPh$_3$)$_4$ (0.53 g, 0.4 mmol) was added to a dry, degassed THF solution (50 mL) containing bromide S5 (7 g, 29 mmol), LiCl (8.5 g, 201 mmol), and allyltributyltin (11.44 g, 37 mmol) under argon at room temperature. This mixture was then heated at reflux for 24 h. After cooling to room temperature, a 10% NH$_4$OH solution (150 mL) was added, and the mixture was stirred for 10 min. Next, the mixture was partitioned with ethyl acetate (250 mL), and the organic layer was washed with brine, dried with Na$_2$SO$_4$, and concentrated to give intermediate S6. Intermediate S6 was used in the next step without purification: ESI (MH$^+$) m/z 206.

Step b. A 0.6 M THF solution containing cyclopropylmagnesium bromide (46 mL, 28 mmol) was added to a dry THF solution (50 mL) containing intermediate S6 (4 g, 20 mmol) at −78° C. under nitrogen. This mixture was then allowed to slowly warm to room temperature and was stirred for 4 h. Next, the solution was poured into water (200 mL) and extracted with ethyl acetate (2×150 mL). The organic layers were washed with brine, dried over Na2SO4, and concentrated to give intermediate S7. Intermediate S7 was used in the next step without purification: ESI (MH+) m/z 187.

Step c. A HCl salt of ammonium hydroxide (2.91 g, 42 mmol) was added to an ethanolic solution containing intermediate S7 (3.99, 21 mmol) and pyridine (4.2 mL, 54 mmol). The resulting solution was heated at 50° C. for 3 h. Next, the solvent was removed under reduced pressure, and the resulting residue was taken up into ethyl acetate (150 mL), washed with water (100 mL), followed by washing with brine (50 mL), dried over Na$_2$SO$_4$, and concentrated. The residue was then dissolved in dry THF (50 mL); lithium aluminum hydride (0.8 g, 21 mmol) was added, and the resulting mixture was heated at reflux for 1.5 h. After heating, water (0.8 mL) was added followed by a 1 N solution of NaOH (0.8 mL), and then the final addition of water (1.6 mL). The resulting solid was filtered and washed with copious amounts of dichloromethane. The remaining oil was purified on silica eluting with 60% ethyl acetate/hexane solution. Fractions containing the desired product were pooled and concentrated to give amine A9 as light yellow oil: ESI (MH$^+$) m/z 188.

Example 3

This example illustrates the synthesis of amine A10 from 3-chloromethyl-benzoyl chloride S8 and Weinreb amine.

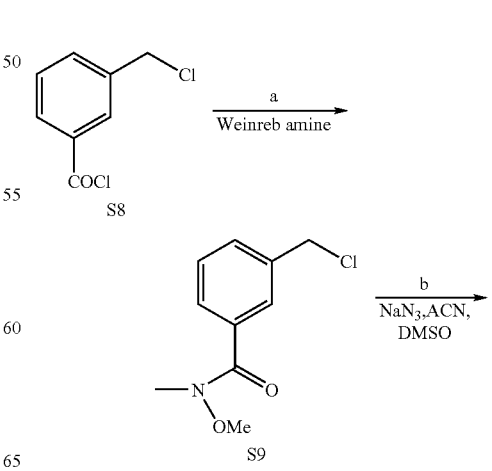

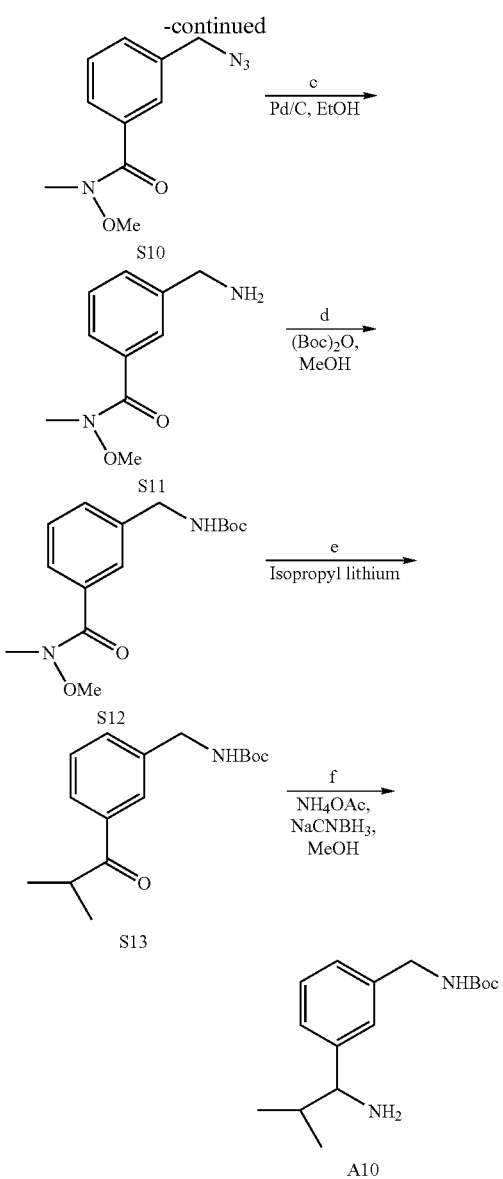

Step a. Benzoyl chloride S8 (5.00 g, 26.45 mmol, 1.0 equiv) was slowly added to a solution of the HCl salt of Weinreb amine (2.58 g, 26.45 mmol, 1.0 equiv) and triethylamine (8.0 mL, 29.10 mmol, 2.1 equiv) in dichloromethane (50 mL) at 0° C. and the mixture was warmed to room temperature. After 1 hr, 50 mL of DCM was added and the mixture was washed twice with 50 mL water, followed by washing with brine (50 mL). The organic layer was dried over sodium sulfate and concentrated. The residue was purified by silica gel flash column chromatography (30% ethyl acetate in hexane) to afford S9 (5.0 g, 90% yield) as a white solid.

Step b. S9 (2.26 g, 10.60 mmol, 1.0 equiv) was added to a mixture of ACN and DMSO (1:1, 30 mL), followed by the addition of sodium azide (1.03 g, 15.90 mmol, 1.5 equiv). The reaction was heated to 60° C. while stirring. After one hour, ACN was removed under vacuum and 100 mL of ethyl acetate were added. The mixture was washed with water (3×30 mL) and then dried over sodium sulfate. The solvent was removed and the resulting solid S10 was used in the next step without further purification.

Step c. Azide S10, dissolved in 20 mL ethanol, was treated with 10% Pd/C and hydrogen (balloon) at room temperature. The reaction was monitored by TLC and upon showing of the total consumption of S10, the reaction was stopped, the mixture was filtered through a pad of Celite and concentrated to afford amine S11 as light brown viscous oil, which was used in the next step.

Step d. Amine S11 was dissolved in 20 mL of methanol, and Boc anhydride (3.47 g, 15.9 mmol, 1.5 equiv) was added. The reaction was stirred at room temperature overnight. The solvent was removed under vacuum and the residue was subjected to silica gel flash chromatography (20-40% ethyl acetate in hexane) to produce S12 (2.17 g, 70% yield) as white solid. $^1$H NMR (400 MHz, CDCl$_3$) δ 7.50-7.53 (m, 2H), 7.28-7.33 (m, 2H), 5.08 (br, 1H), 4.28 (br, 2H), 3.49 (s, 3H), 3.25 (s, 3H), 1.40 (s, 9H), ESI (MH$^+$) m/z 295.

Step e. To Weinreb amide S12 (550 mg, 1.87 mmol, 1.0 equiv) in 15 mL THF at −78° C., 5.6 mL isopropyl lithium (0.7 M in pentane) was added drop-wise. The reaction mixture color turned from light orange to deep red. The flask was kept at −78° C. cold bath for 30 minutes. The saturated ammonium chloride aqueous solution (20 mL) was added at low temperature and the mixture was allowed to reach room temperature. Ethyl acetate (50 mL) was added, the organic layer was separated and further washed with 20 mL of brine. The organic layer was dried over sodium sulfate and concentrated. The resulted residue was purified through silica gel flash column chromatography (20% ethyl acetate in hexane) to deliver S12 (440 mg, 80% yield) as colorless oil. $^1$H NMR (500 MHz, CDCl$_3$) δ 7.85 (s, 1H), 7.81 (d, J=8.0 Hz, 1H), 7.46 (d, J=7.9 Hz, 1H), 7.40 (t, J=8.0 Hz, 1H), 5.12 (br, 1H), 4.34 (br, 2H), 3.53 (m, 1H), 1.44 (s, 9H), 1.18 (d, J=4.0 Hz, 6H), ESI (MH$^+$) m/z 278.

Step f. To ketone S12 (500 mg, 1.80 mmol, 1.0 equiv), the following reagents were added: THF (2.0 mL), methanol (8.0 mL), ammonium acetate (1.38 g, 18.0 mmol, 10.0 equiv) and sodium cyanoborohydride (1.13 g, 18.0 mmol, 10.0 equiv). The mixture was heated to 80° C. and was kept stirring overnight. Then the solvent was removed and 40 mL of ethyl acetate were added. The solution was washed by aqueous saturated sodium bicarbonate (20 mL), followed by brine (10 mL). The organic layer was dried over sodium sulfate and concentrated. The residue was purified by silica gel flash column chromatography (2-10% methanol in dichloromethane with 1% TEA) to yield A10 as colorless oil (355 mg, 71%). $^1$H NMR (400 MHz, CDCl$_3$) δ 7.20-7.35 (m, 4H), 5.26 (br, 1H), 4.24 (br, 2H), 3.87 (m, 1H), 2.20 (m, 1H), 1.40 (s, 9H), 1.10 (d, J=3.0 Hz, 3H), 0.88 (d, J=3.0 Hz, 3H) ESI (MH$^+$) m/z 279.

Example 4

This example illustrates the preparation of amine A11 from 1-bromo-3-methyl-butan-2-one S13 and 4-hydroxy-piperidine-1-carboxylic acid tert-butyl ester S14. Other amines with an ether or thioether linker can be easily prepared using the same scheme of synthesis making the necessary substitutions.

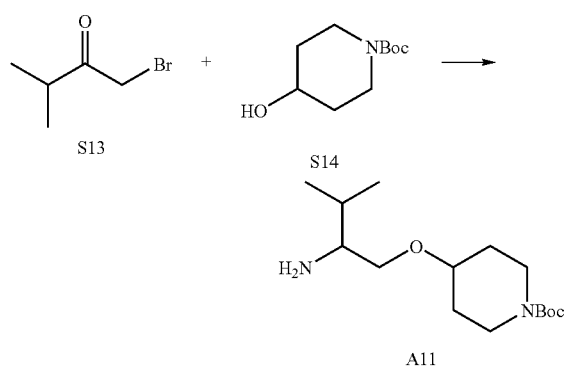

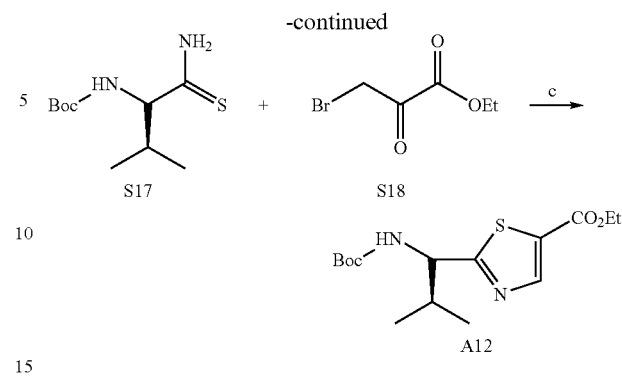

To a solution of 4-hydroxy-piperidine-1-carboxylic acid tert-butyl ester S14 (4.25 g, 21.1 mmol) in dry DMF NaH (759 mg, 60% mineral dispersion, 31.7 mmol) was added. The reaction was stirred at room temperature for 1 hour, then 1-bromo-3-methyl-butan-2-one S13 was added slowly and the mixture was stirred at room temperature for 16 hours. The mixture was then diluted with EtOAc (220 mL) and extracted with brine (2×100 mL). The organic layer was concentrated and the crude intermediate was filtered through a silica gel plug to remove base-line impurities (2% MeOH in $CH_2Cl_2$). The crude intermediate was used with no further purification.

The crude material was resuspended in methanol and placed in a sealed tube. $NH_4OAc$ (1.1 g, 14 mmol) and $NaBH_3CN$ (441 mg, 7 mmol) were added to the tube, which was then resealed and heated at 70° C. for 12 hours. The solvent was then removed and the crude material was loaded onto a silica gel column and eluted with 2% MeOH in $CH_2Cl_2$ to give 200 mg (3%) 4-(2-amino-3-methyl-butoxy)-piperidine-1-carboxylic acid tert-butyl ester A11 as clear oil. TLC, $R_f$=0.4 (10% MeOH in $CH_2Cl_2$); $^1$H NMR (500 mHz, $CDCl_3$) δ 0.98 (d, J=6.81 Hz , 3H), 1.03 (d, j=6.81 Hz, 3H), 1.45 (s, 9H), 1.60 (m, 2H), 1.81 (m, 2H), 1.92 (m, 1H), 2.98 (m, 1H), 3.18 (m, 2H), 3.49 (m, 1H), 3.55 (m, 1H), 3.69 (m, 3H), 3.91 (bs, 2H). M+1 found 287.1; $C_{15}H_{30}N_2O_3$ requires 286.23.

Example 5

This example illustrates the preparation of amine A12 from compound S15. A skilled practitioner would appreciate that other amines bearing a heteroaryl ring can be synthesized using the same scheme with the corresponding changes.

Step a. The mixture of S15 (10.0 g, 46 mmol), 1-(3-dimethylaminopropyl)-3-ethylcarbodiimide hydrochloride (17 g, 92 mmol), 1-hydroxybenzotriazle hydrate (6.2 g, 46 mmol) and 4-methylmorpholine (9.3 g, 92 mmol) in THF (100 mL) was stirred at room temperature for 35 minutes. Ammonium hydroxide (18 mL, 138 mmol) was then added and the mixture was stirred for 2½ h. The reaction was diluted with ethyl acetate and washed with the saturated sodium bicarbonate solution twice, then with brine. The mixture was dried and concentrated to yield 8 g of S16 as white solid.

Step b. The mixture of S16 (1.87 g, 8.76 mmol) and Lawesson's reagent (3.5 g, 8.67 mmol) in THF (35 mL) was stirred at 50° C. for 10 h. The reaction was concentrated, then purified by flash chromatography on silica gel and eluted with 5-25% EtOAc/hexane to yield 1.2 g of S17 as white solid.

Step c. Potassium hydrogen carbonate was added to the solution of S17 (1.2 g, 4.84 mmol) at −15° C. and the mixture was stirred for 7 min. 3-Bromo-2-oxo-propionic acid ethyl ester S18 was then added to the mixture at -15° C. and the reaction was stirred for 3 min. TFAA and pyridine, pre-mixed at −10° C., were added to the mixture at −15° C. The mixture was warmed to room temperature and stirred for 1 hr. The reaction was quenched with saturated sodium bicarbonate and extracted with DCM. The organic layer was washed with 0.1 N HCl, dried, concentrated, then purified by flash chromatography on silica gel eluted with 10-20% EtOAc/hexane to yield 1.5 g of amine A12 as brown oil.

Example 6

This example illustrates the preparation of 2-{1-[4-(cyclopropylmethyl-amino)-piperidine-1-carbonyl]-2-methyl-propyl}-7-(2,4-difluoro-phenoxy)-3,4-dihydro-2H-isoquinolin-1-one.

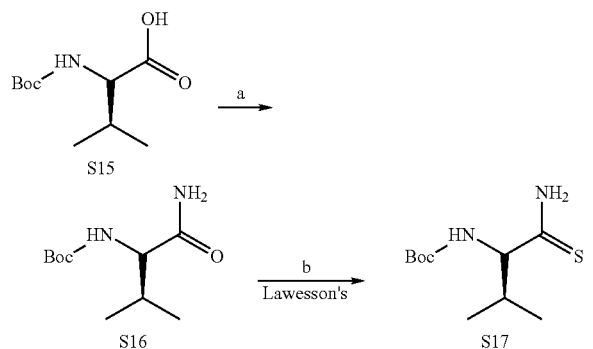

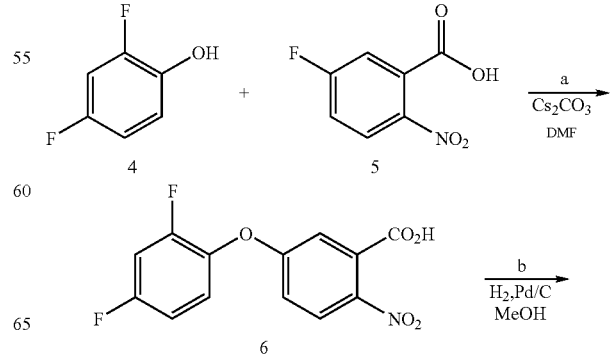

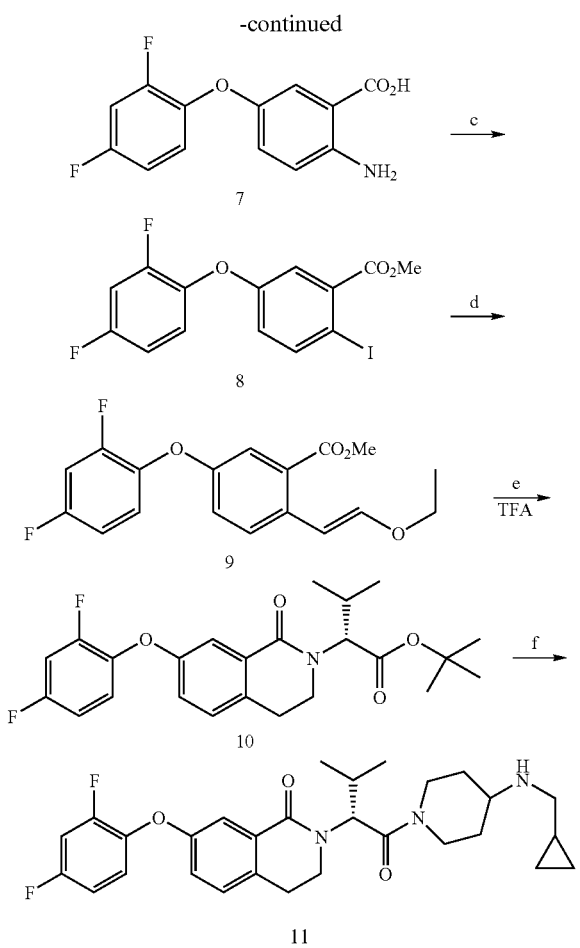

Step a. The mixture of 2,4-difluorophenol 4 (20 g, 153.9 mmol), 5-fluoro-2nitrobenzoic acid 5, (28.5 g, 153.9 mmol), and cesium carbonate (100 g, 307.7 mmol) in DMF (310 mL) was heated in a 100° C. oil bath for 10 hrs. At the completion of the reaction, the mixture was cooled down to room temperature and was treated with 1 N HCl solution to bring pH to acidic, and was extracted with ethyl acetate. The organic layer was washed three times with 300 mL of water, dried, and concentrated to yield 32 g of 2-nitro-5-(2,4-difluorophenoxy) benzoic acid 6 as a brown solid.

Step b. The mixture of 2-nitro-5-(2,4-difluorophenoxy)-benzoic acid 6 (16 g, 77 mmol) and palladium on carbon (10 wt %, 4 g) in methanol (200 mL) was charged in a hydrogenation par shaker. The mixture was hydrogenated at 60 psi of hydrogen atmosphere for 3 hrs. The reaction was filtered through a Celite pad, and the filtrate was concentrated to yield 14 g of aniline 7 as brown solid.

Step c. To a solution of 7 (14.4 g, 54.6 mmol) in methanol (200 mL) at 0° C. was added 60 mL of water, 60 mL of concentrated HCl followed by sodium nitrate (18.6 g, 270 mmol). The reaction was kept at 0° C. for one hour at which point KI (17.9 g, 108 mmol) was added. The reaction temperature was gradually raised to room temperature and maintained there for one hour, then raised to 60° C. for 2 hours. The crude reaction mixture was diluted with 1000 mL of AcOEt and extracted twice with lN $NaS_2O_3$ (500 mL). The aqueous layer was back-extracted with AcOEt (2×500 mL) and the organic layers were combined and concentrated by rotary evaporation. The crude intermediate was then re-suspended in 200 mL of methanol containing 10% of concentrated $H_2SO_4$ and refluxed for 16 hours. The crude mixture was then diluted with 1000 mL of EtOAc, extracted with water twice (500 mL) and then concentrated by rotary evaporation. The crude oil was loaded onto a silica gel column and eluted with 2% AcOEt in hexane to obtain 15.9 g (75% yield) of 5-(2,4-difluoro-phenoxy)-2-benzoic acid methyl ester 8 as a yellow solid. TLC, $R_f$=0.2 (2% EtOAc in hexane); $^1$H NMR (CDCl$_3$) δ 3.90 (s, 3H), 6.77 (dd, J=8.7, 3 Hz, 1H), 6.92 (m, 1H), 6.96 (m, 1H), 7.09 (m, 1H), 7.35 (d, J=3 Hz, 1H), 7.87 (d, J=8.7 Hz, 1H). M+1 found 391.1; $C_{14}H_9F_2IO_3$ requires 389.96.

Step d. To a solution of ethoxyethyne (5 g, 71.3 mmol) in dry THF (20 mL) and under a nitrogen atmosphere was slowly added 1 N BH$_3$ in THF (23.7 mL) over a fifteen-minute period. The reaction was kept at room temperature for one hour an then was refluxed for two additional hours. The crude trialkylborane solution was cooled to room temperature, at which time 5-(2,4-difluoro-phenoxy)-2-benzoic acid methyl ester 8 (9.2 g, 23.7 mmol), NaOH (1.42 g, 35.6 mmol), and Pd(PPh$_3$)$_4$ (1.36 g, 1.2 mmol) were added. The solution was refluxed for two hours then diluted with 200 mL of AcOEt and extracted with brine (2×100 mL). The organic layer was concentrated and loaded onto a silica gel column and eluted with 2% AcOEt in hexane to provide 3.2 g (41%) of 5-(2,4-difluoro-phenoxy)-2-(2-ethoxy-vinyl)-benzoic acid methyl ester 9 as light yellow oil. TLC, $R_f$=0.17 (2% AcOEt in hexane); $^1$H NMR (CDCl$_3$) δ 1.35 (t, J=7.0 Hz, 3H), 3.85 (s, 3H), 3.93 (q, J=7.0 Hz, 2H), 6.65 (d, J=13 Hz, 1H), 6.85 (d, J=13 Hz, 1H), 6.85 (m, 1H), 6.95 (m, 1H), 7.03 (m, 2H), 7.34 (d, J=8.7 Hz, 1H), 7.87 (d, J=2.7 Hz, 1H). M+1 found 335.1; $C_{18}H_{16}F_2O_4$ requires 334.10.

Step e. To a solution of 5-(2,4-difluoro-phenoxy)-2-(2-ethoxy-vinyl)-benzoic acid methyl ester 9 (1.2 g, 3.8 mmol) in dichloroethane (20 mL) was added 5 ml of TFA and five drops of water. The reaction was stirred at room temperature for ten minutes, at which time the solvent was removed. The crude reaction mixture was re-suspended in dichloroethane and D-valine t-butylester HCl (2.05 g, 9.75 mmol), triethylamine (1.36 mL, 9.75 mmol), and tiacetoxyborohydride (2.76 g, 13 mmol) were added. The reaction was stirred at room temperature for fifteen minutes and then at 60° C. for an additional 16 hours. The mixture was diluted with 100 mL dichloromethane and extracted with saturated brine (100 mL). The organic layer was concentrated, loaded onto a silica gel column and eluted with dichloromethane to yield 516 mg (77%) of 2-[7-(2,4-difluoro-phenoxy)-1-oxo-3,4-dihydro-1H-isoquinolin-2-yl]-3-methyl-butyric acid tert-butyl ester 10 as a light yellow solid. TLC, $R_f$=0.3 (2% MeOH CH$_2$Cl$_2$); $^1$H NMR (CDCl$_3$) δ 0.93 (d, J=6.7 Hz, 3H), 1.05 (d, J=6.6 Hz, 3H), 1.45 (s, 9H), 2.24 (m, 1H), 2.93 (m, 2H), 3.52 (m, 1H), 3.75 (m, 1H), 5.00 (d, J=6.7 Hz, 1H), 6.85 (m, 1H), 6.93 (m, 1H), 7.07 (m, 2H), 7.15 (d, J=8.3 Hz, 1H), 7.58 (d, J=2.6 Hz, 1H). M+1 found 432.10; $C_{24}H_{27}F_2NO_4$ requires 431.19.

Step f. To a solution of 2-[7-(2,4-difluoro-phenoxy)-1-oxo-3,4-dihydro-1H-isoquinolin-2-yl]-3-methyl-butyric acid tert-butyl ester 10 (447 mg, 1.19 mmol) in dichloromethane (20 mL) was added 5 mL of TFA and the mixture was stirred at room temperature for 2 hours, at which time the solvent was removed. The crude reaction mixture was re-suspended in dry DMF (20 mL), then 1,4dioxa-8-azaspiro-[4,5]decane (286 mg, 2.0 mmol), HBTU (754 mg, 1.2 mmol), and DIEA (515 mL, 4.0 mmol) were added. The reaction was stirred at room temperature for 16 hours and them diluted with EtOAc (200 mL) and extracted twice with saturated brine (100 mL). The solvent was removed and the crude material was used without further purification.

The crude intermediate was dissolved in a 50/50 mixture of water and acetic acid (20 mL) and heated at 100° C. After two hours, the solvent was removed and the crude material was resuspended in dichloromethane (200 mL) and extracted twice with NaHCO$_3$ (100 mL). The organic layer was concentrated and the crude material was re-suspended in dichloroethane. Cyclopropylmethylamine HCl salt (164 mg, 1.52 mmol), DIEA (269 mL, 1.52 mmol), and triacetoxyborohydride (428 mg, 2.02 mmol) were added and the reaction was stirred at 60° C. for six hours, then diluted with 200 mL of CH$_2$Cl$_2$ and extracted with saturated brine (2×100 ml). The organic layer was concentrated and the crude oil was loaded onto a silica gel column and eluted with 10% methanol in dichloromethanol to provide 280 mg of 2-{1-[4-(cyclopropylmethyl-amino)-piperidine-1-carbonyl]-2-methyl-propyl}-7-(2,4-difluoro-phenoxy)-3,4-dihydro-2H-isoquinolin-1-one 11 as a white solid. $^1$H NMR (CDCl$_3$) δ 0.24 (dd, J=23.5, 4.3 Hz, 2H), 0.59 (dd, J=16.4, 7.5 Hz, 2H), 0.94 (m, 6H), 1.00 (m, 2H), 2.0 (m. 1H), 1.27 (m, 0.5H), 1.45 (m, 1.5H), 2.40 (m, 1H), 1.90 (m, 1H), 2.62 (d, J=7.2 Hz, 1H), 2.64 (m, 1H), 2.71 (d, J=7.2 Hz, 1H), 2.86 (m, 1.5H), 2.95 (m, 1H), 3.09 (m, 1.5H), 3.48 (m, 1H), 3.68 (m, 1H), 4.42 (m, 1H), 4.61 (m, 1H), 5.21 (d, J=5.2 Hz, 0.5H), 5.27 (d, J=5.2 Hz, 0.5H), 6.86 (m, 1H), 6.95 (m, 1H), 7.06 (m, 2H), 7.14 (d, J=8.5 Hz, 1H), 7.54 (d, J=10.7, 2.6 Hz, 1H). ESI [M+1] found 512.1; C$_{29}$H$_{35}$F$_2$N$_3$O$_3$ requires 511.26.

Example 7

This example illustrates the preparation of 2-{1-[4-(cyclopropyl-amino)-piperidine-1-carbonyl]-2-methyl-propyl}-7-(2,4-difluoro-phenoxy)-3,4-dihydro-2H-isoquinolin-1-one 12. This compound was prepared according to Example 6 substituting cyclopropylamine for cyclopropylmethylamine in the final reductive amination step (f). $^1$H NMR (CDCl$_3$) δ 0.32 (m, 1H), 8 0.32 (m, 1H), 0.43 (dd, J=16.0, 6.7 Hz, 2H), 0.90 (m, 3H), 0.95 (m, 3H), 1.00 (m, 0.5H), 1.16 (m, 0.5H), 1.24 (m, 1H), 1.86 (m, 0.5H), 1.95 (m, 1.5H), 2.04 (m, 0.5H), 2.10 (m, 0.5H), 2.40 (m, 1H), 2.82 (m, 4H), 3.08 (m, 1H), 3.52 (m, 1H), 3.72 (m, 0.5H), 3.76 (m, 0.5H), 4.24 (m, 1H), 4.46 (m, 1H), 5.24 (d, J=10.7 Hz, 0.5H), 5.25 (d, J=10.7 Hz, 0.5H), 6.85 (m, 1H), 6.94 (m, 1H), 7.07 (m, 2H), 7.14 (d, J=8.2 Hz, 1H), 7.56 (s, 1H). ESI [M+1] found 498.2; C$_{28}$H$_{33}$F$_2$N$_3$O$_3$ requires 497.25.

Example 8

This example illustrates the preparation of 7-(2,4-difluoro-phenoxy)-2-{1-[4-(4-fluoro-benzylamino)-piperidine-1-carbonyl]-2-methyl-propyl}-3,4-dihydro-2H-isoquinolin-1-one 13. This compound was prepared according to the synthetic scheme described in Example 6 using 4-fluorobenzylamine instead of cyclopropylmethylamine in step f. 1H NMR (CDCl$_3$) δ 0.90 (m, 3H), 0.95 (m, 3H), 1.03 (m, 1H), 1.25 (m, 2H), 1.89 (m, 2H), 2.40 (m, 1H), 2.40 (m, 1H), 2.72 (m, 1H), 2.80 (m, 1H), 2.86 (d, J=8.4 Hz, 2H), 3.51 (m, 0.5H), 3.48 (m, 1H), 3.70 (m, 1.5H), 3.76 (m, 1H), 4.23 (m, 1H), 4.41 (m, 1H), 5.24 (d, J=10.7 Hz, 0.5H) 5.25 (d, J=10.7 Hz, 0.5H), 6.85 (m, 1H), 6.96 (m, 3H), 7.06 (m, 2H), 7.13 (m, 1H), 7.26 (m, 2H), 7.20 (dd, J=8.2, 2.7,1H). ESI [M+1] found 566.2; C$_{33}$H$_{34}$F$_3$N$_3$O$_3$ requires 565.26.

Example 9

This example illustrates the preparation of 7-(2,4-difluoro-phenoxy)-2-(1-{4-[2-(4-fluoro-phenyl)-ethylamino]-piperidine-1-carbonyl}-2-methyl-propyl)-3,4-dihydro-2H-isoquinolin-1-one 14. This compound was prepared according to the synthetic scheme described in Example 6 substituting 2-(4-flurophenyl)ethylamine for cyclopropylmethylamine in step f. 1H NMR (CDCl$_3$) δ 0.90 (m, 3H), 0.94 (m, 3H), 1.15 (m, 0.5H), 1.24 (m, 1.5H), 1.83 (m, 2H), 2.40 (m, 1H), 2.72 (m, 5H), 2.85 (m, 3H), 3.05 (d, 1H), 3.52 (m, 1H), 3.64 (m, 0.5H), 3.72 (m, 0.5H), 4.24 (m, 1H), 4.46 (m, 1H), 5.24 (d, J=10.6 Hz, 0.5H), 5.26 (d, J=10.7 Hz, 0.5H), 6.85 (m, 1H), 6.95 (m, 3H), 7.09 (m, 3H), 7.14 (m, 2H), 7.14 (d, J=8.5 Hz, 1H), 7.55 (d, J=6.9 Hz, 1H). ESI [M+1] found 580.3; C33H36F3N3O3 requires 579.27.

Example 10

This example illustrates the preparation of 2-[1-(1-cyclo-propylmethyl-piperidin-4-yloxymethyl)-2-methyl-propyl]-7-(2,4-difluoro-phenoxy)-3,4-dihydro-2H-isoquinolin-1-one 16. Compound 9 was prepared according to steps a-d of Example 6.

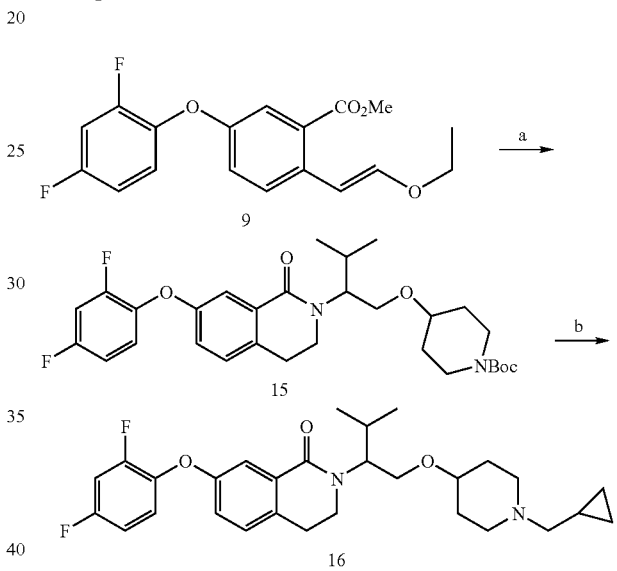

Step a. To the solution of 5-(2,4-difluoro-phenoxy)-2-(2-ethoxy-vinyl)-benzoic acid methyl ester 9 (194 mg, 0.6 mmol) in dichloromethane (5 mL) was added 1 mL of TFA and five drops of water. The reaction was stirred at room temperature for ten minutes, at which time the solvent was removed. The reaction mixture was re-suspended in dichloroethane and 4-(2-amino-3-methyl-butoxy)-piperidine-1-carboxylic acid tert-butyl ester A11 (200 mg, 0.70 mmol), DIEA (154 mL, 0.87 mmol), and sodium triacetoxyborohydride (184 mg, 1.87 mmol) were added. The mixture was stirred at room temperature for fifteen minutes and then at 60° C. for additional 16 hours. The reaction was diluted with 100 mL CH$_2$Cl$_2$ and extracted with saturated brine (100 mL). The organic layer was concentrated and loaded onto a silica gel column and eluted with 2% methanol in dichloromethane to give 250 mg (79%) of 4-{2-[7-(2,4-difluoro-phenoxy)-1-oxo-3,4-dihydro-1H-isoquinolin-2-yl]-3-methyl-butoxy}-piperidine-1-carboxylic acid tert-butyl ester 15 as light yellow solid. TLC, R$_f$=0.3 (2% MeOH CH$_2$Cl$_2$). $^1$H NMR (CDCl$_3$) δ 0.92 (d, J=6.6 Hz, 3H), 1.01 (d, J=6.5 Hz, 3H), 1.31 (m, 1H), 1.44 (s, 9H), 1.61 (m, 2H), 2.2 (m, 1H), 2.90 (m, 2H), 3.14 (m, 2H), 3.41(m, 1H), 3.51 (m, 1H), 3.73 (m, 1H), 2.63 (m, 4H), 4.02 (m, 1H), 4.56 (m, 1H), 6.84 (m, 1H), 6.93 (m, 1H), 7.06 (m, 2H), 7.14 (d, J=8.1 Hz, 1H), 7.54 (d, J=2.6 Hz, 1H), M+1 found 545.3; C$_{30}$H$_{38}$F$_2$N$_2$O$_5$ requires 544.27.

Step b. To the solution of 4-{2-[7-(2,4-difluoro-phenoxy)-1-oxo-3,4-dihydro-1H-isoquinolin-2-yl]-3-methyl-butoxy}-piperidine-1-carboxylic acid tert-butyl ester 15 (40 mg, 0.07 mmol) in dichloromethane (5 mL) was added 1 mL of TFA and the reaction was stirred at room temperature for 2 hours, at which time the solvent was removed and the crude material was re-suspended in dichloroethane, then carboxaldehyde cyclopropane (7.7 mg, 0.11 mmol), DIEA (39 mL, 0.22 mmol), and triacetoxyborohydride (31 mg, 0.148 mmol) were added. The mixture was stirred at 60° C. for six hours, then diluted with 10 mL of $CH_2Cl_2$ and extracted with saturated brine (10 mL). The solvent was removed and the crude oil was loaded onto a silica gel column and eluted with 10% MeOH in $CH_2Cl_2$ to yield 4.4 mg of 2-[1-(1-cyclopropylmethyl-piperidin-4-yloxymethyl)-2-methyl-propyl]-7-(2,4-difluoro-phenoxy)-3,4-dihydro-2H-isoquinolin-1-one 16 as a white solid. $^1$H NMR (CDCl$_3$) δ 0.08 (m, 2H), 0.2 (m, 2H), 0.85 (m, 1H), 0.91 (d, J=6.6 Hz, 3H), 1.01 (d, J=6.6 Hz, 3H), 1.62 (m, 2.5H), 1.70 (m, 1H), 1.87 (m, 2.5H), 2.10 (m, 1H), 2.25 (m 3H), 2.78 (m, 2H), 2.89 (m, 2H), 3.30 (n, 1H), 3.49 (m, 1H), 3.59 (m, 1H), 6.84 (m, 1H), 6.90 (m, 1H), 7.06 (m, 2H), 7.14 (d, J=8.3 Hz, 1H), 7.57 (d, J=2.6 Hz, 1H). ESI [M+1] found 499.3; $C_{29}H_{36}F_2N_2O_3$ requires 498.27.

Example 11

This example illustrates the preparation of 2-[1-(1-cyclopropylmethyl-piperidin-4-yloxymethyl)-2-methyl-propyl]-7-(2,4-difluoro-phenoxy)-3,4-dihydro-2H-isoquinolin-1-one 17. Generally, the title compound was prepared following procedures described in Example 10, using amine A 16 instead of 4-(2-amino-3-methyl-butoxy)-piperidine-1-carboxylic acid tert-butyl ester A11. Amine A16, in turn, was prepared according to the reaction scheme described in Example 1.

Step a. Trifluoroacetic acid (0.5 mL) was injected in the solution of enol ether 9 (339 mg, 1.01 mmol, 1.0 equiv) in ethyl acetate (8 mL) at 0° C. and the mixture was warmed to 23° C. and stirred for 2 h. The reaction was concentrated and pumped, then the residue was dissolved in dichloroethane (10 mL). Amine A16 (290 mg, 0.02 mmol, 1.0 equiv) and sodium triacetoxyborohydride (642 mg, 3.02 mmol, 3.0 equiv) were added and the reaction mixture was stirred for 3 h at 23° C. and 15 h at 50° C. The reaction was diluted with water and extracted with $CH_2Cl_2$ (3×20 mL). The organic layer was combined, dried over sodium sulfate and concentrated. The residue was purified by silica gel flash column chromatography (20% ethyl acetate in hexanes) and concentrated to afford amide 102 (211 mg, 39% yield); LRMS (ESI) m/z: calculated for $C_{31}H_{41}F_2N_2O_4$ (free base; M+H) 543.3, found 543.2.

Step b. Trifluoroacetic acid (1 mL) was injected into a solution of 102 (211 mg, 0.39 mmol, 1.0 equiv) in chloroform (5 mL) at 0° C. and the mixture was stirred for 1.2 h before the reaction was concentrated and pumped. The residue was dissolved in dichloroethane (5 mL); cyclopropanecarboxaldehyde (116 μL, 1.55 mmol, 4.0 equiv) and sodium triacetoxyborohydride (413 mg, 1.94 mmol, 5.0 equiv) were added and the reaction mixture was stirred for 3 h. The mixture was diluted with water and extracted with a solution of 30% IPA in CHCl$_3$ (3×10 mL). The organic layer was combined, dried over sodium sulfate and concentrated. The residue was purified by silica gel flash column chromatography (10% methanol in dichloromethane with 1% ammonium hydroxide) and concentrated. The product was dissolved in methanol, HCl (2.0 M in diethyl ether, 100 μL) was added, and solvent evaporated to afford amine salt 17 (160 mg, 76% yield) as a white solid; $^1$H NMR (500 MHz, CD$_3$OD) δ 7.42 (s, 1H), 7.29 (d, J=7.6 Hz, 1H), 7.21 (td, J=9.2, 5.4 Hz, 1H), 7.17~7.11 (m, 2H), 7.00 (t, J=8.4 Hz, 1H), 4.31 (s, 1H), 3.57 (t, J=10.7 Hz,

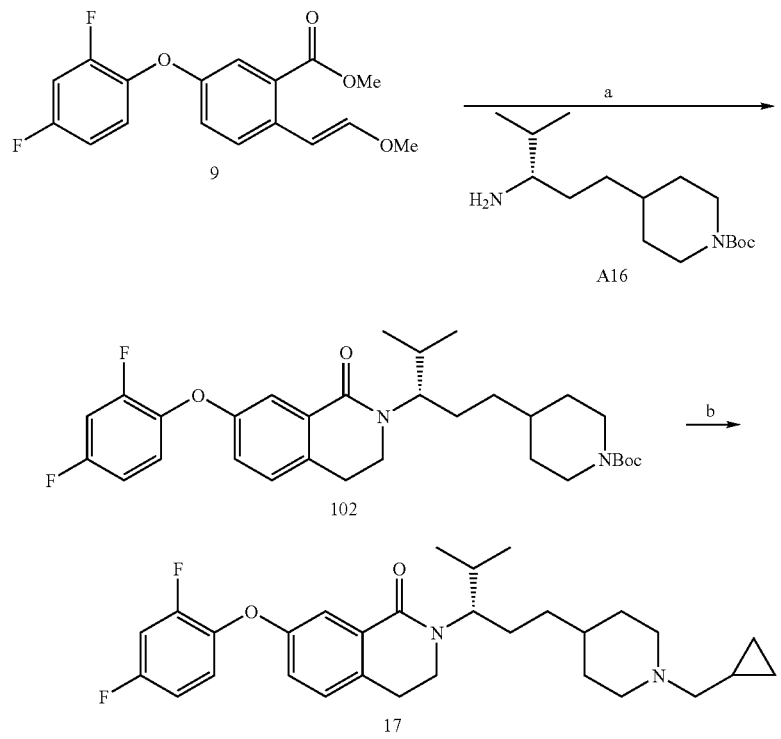

2H), 3.43 (t, J=6.1 Hz, 2H), 3.02~2.88 (m, 6H), 1.98~1.81 (m, 5H), 1.60 (br. s, 2H), 1.50~1.36 (m, 2H), 1.34~1.07 (m, 3H), 1.03 (d, J=6.9 Hz, 3H), 0.89 (d, J=6.9 Hz, 3H), 0.73 (dt, J=6.9, 6.1 Hz, 2H), 0.41 (dt, J=6.9, 4.6 Hz, 2H); LRMS (ESI) m/z: calculated for $C_{30}H_{39}F_2N_2O_2$ (free base; M+H) 497.3, found 497.3.

Example 12

This example illustrates the preparation of 2-(cyclopropyl-{3-[2-(cyclopropylmethyl-amino)-ethyl]-phenyl}-methyl)-7-(2,4-difluoro-phenoxy)-3,4-dihydro-2H-isoquinolin-1-one 105. Compound 9 was synthesized according to steps a-d of Example 6.

mic mixture of 103 was resolved using normal phase preparative Chiral HPLC (Chiral AD column, isocratic 2.5% isopropyl alcohol in hexane solution): ESI (MH+) m/z 446.

Step b. Compound 103 (0.23 g, 0.5 mmol) was dissolved in a 3:1 dioxane/water solution (30 mL) containing catalytic amount of $OSO_4$. After 10 min, the solution turned dark in color, and an aqueous solution containing $NaIO_4$ (0.33, 1.5 mmol) was added. After 2 h the reaction was completed, and the mixture was partitioned with water (50 mL) and ethyl acetate (50 mL). The organic layer was then washed with the saturated solution of $Na_2S_2O_3$, followed by brine, dried over $Na_2SO_4$, and concentrated to give intermediate 104. This material was used in the next step without purification.

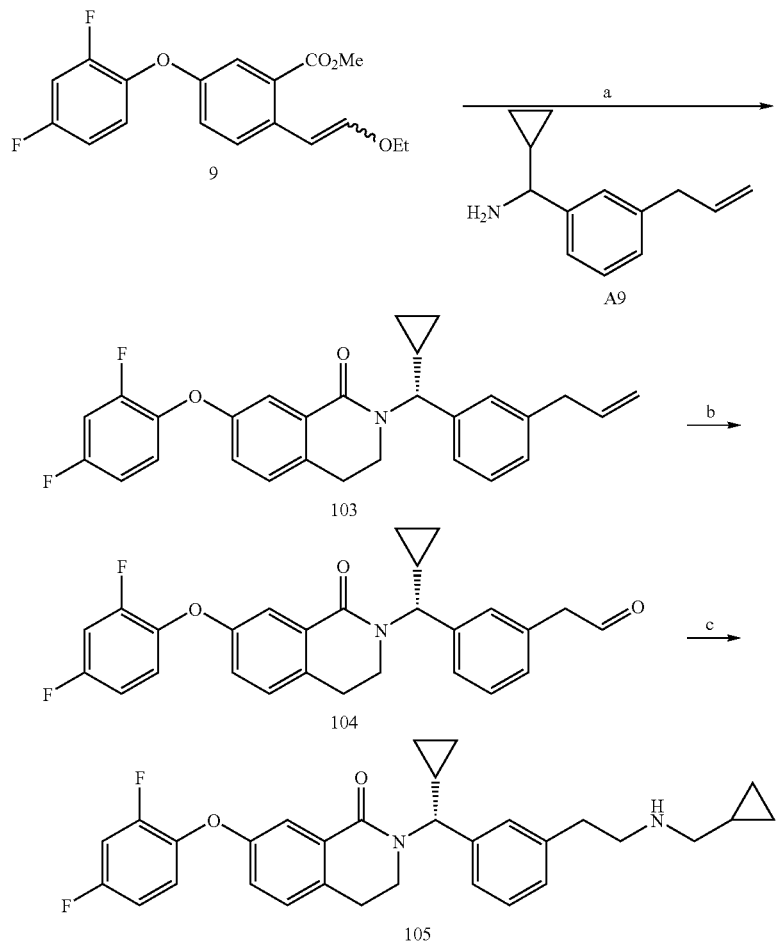

Step a. Compound 9 (0.32 g, 0.9 mmol) was dissolved in a 20% TFA/DCM (10 mL) solution at room temperature. After stirring for 2 min, excess solvent was removed using reduced pressure, and the resulting residue was taken up into dichloroethane (20 mL). Amine A9 (0.20 g, 1.0 mmol) was added, followed by the addition of $NaBH(OAc)_3$ (0.4 g, 1.9 mmol) and triethylamine (0.38 mL, 2.7 mmol). The mixture was then heated at 75° C. overnight, cooled to room temperature, washed with water (75 mL), dried with $Na_2SO_4$, and concentrated. The remaining oil was purified on silica gel column eluting with a 60% ethyl acetate/hexane solution. Fractions containing product were pooled and concentrated. The race- Step c. $NaBH(OAc)_3$ (50 mg, 0.2 mmol) was added to a DCM (10 mL) solution containing (aminomethyl)cyclopropane (48 mg, 0.7 mmol) and intermediate 104 (30 mg, 0.07 mmol) at room temperature. After stirring for 4 hours the solvent was removed using evaporation, and the remaining residue was purified using preparative HPLC (C18 column, 10%-90% acetonitrile/water gradient): $^1$H NMR (500 MHz, MeOD) δ 7.50 (d, J=7.75 Hz, 1 H), 7.47 (d, J=2.68 Hz, 1H), 7.39 (t, J=7.65 Hz, 1H), 7.36 (s, 1H), 7.28 (d, J=8.325 Hz, 1 H), 7.14-7.25 (m, 4H), 7.01 (m, 1H), 5.04 (d, J=10.30 Hz, 1H), 3.70 (m, 1H), 3.37 (m, 1 H), 3.24 (t, J=7.57, 2H), 3.00 (t, J=8.46 Hz, 2H), 2.95 (m, 1H), 2.87-2.94 (m, 3H), 1.54 (m, 1H), 1.05 (m, 1H), 0.92 (m, 1H), 0.69 (m, 3H), 0.48 (m, 1H), 0.38 (m, 2H); Analytical HPLC Method A@ 220 nm: rt=7.10 min.; ESI [M+H]$^+$ m/z a+503.
Example 13
This example illustrates the preparation of 2-{1-[4-(cyclopropylmethyl-amino)-cyclohexylmethyl]-2-methyl-propyl}-8-(2,4-difluoro-phenoxy)-2,3,4,5-tetrahydro-benzo[c]azepin-1-one 22. Compound 8 was prepared according to steps a-c of Example 6.
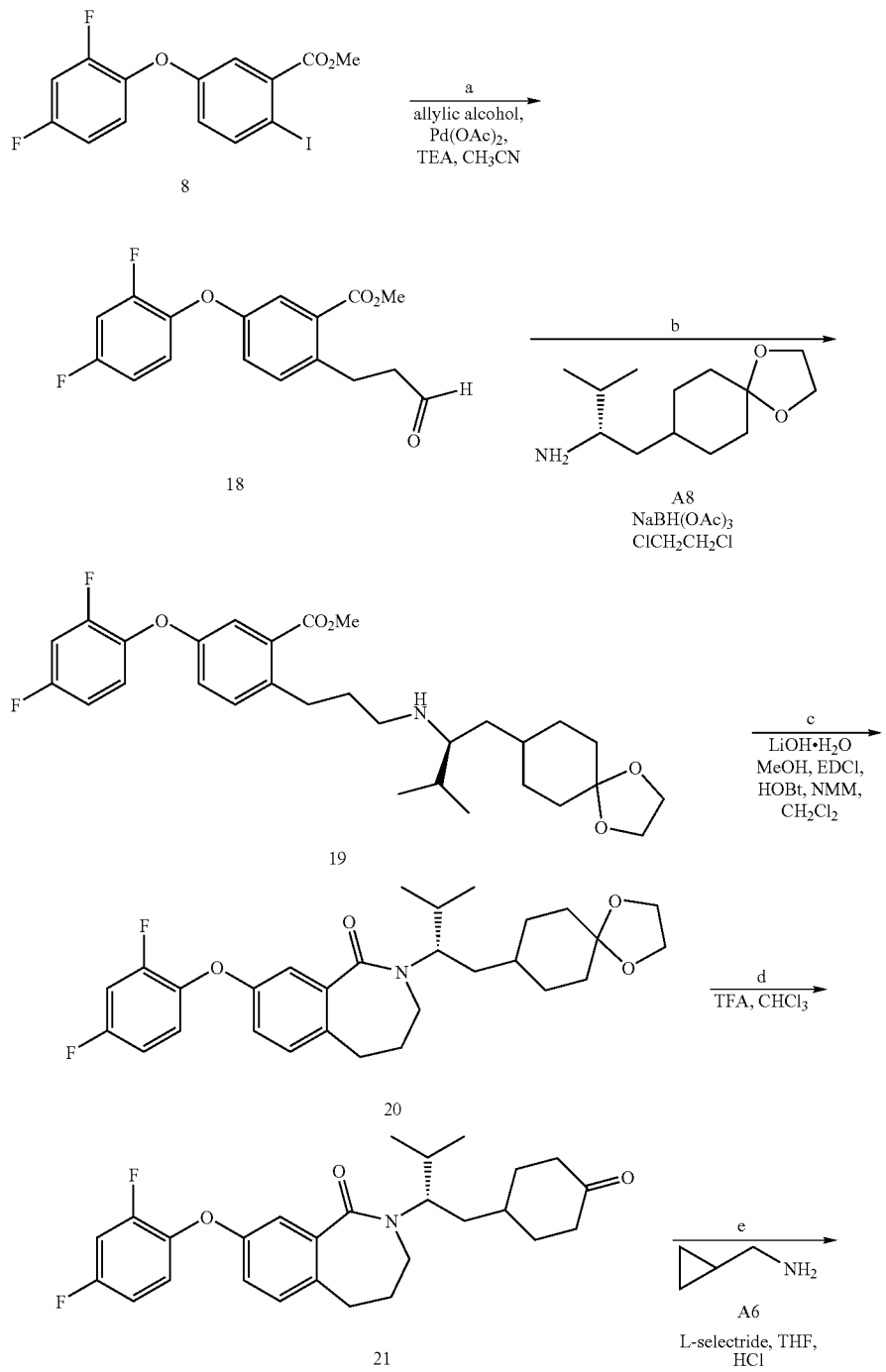

-continued

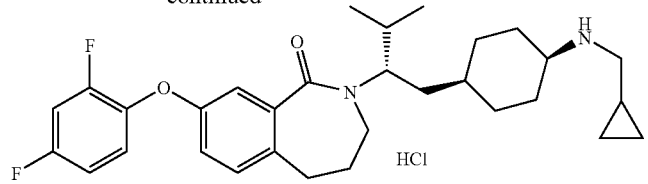

22

Step a. To an oven dried 10 mL round bottom flask was added a solution of 5-(2,4-difuoro-phenoxy)-2-iodo-benzoic acid methyl ester 8 (1.4 g, 3.59 mmol) in acetonitrile (2 mL), allylic alcohol (0.2 g, 4.49 mmol), palladium acetate (0.12 g, 0.54 mmol) and triethylamine (0.453 g, 4.49 mmol). The flask was equipped with condenser, under positive nitrogen pressure and put into an oil bath (100° C.) after being degassed for 20 min. After heating at refluxing for 1 hr, the mixture was cooled down to room temperature and diluted with water and ether. The ether phase was separated and washed 3 times with water, then it was dried over anhydrous sodium sulfate, filtered and concentrated. The residual material was purified by flash chromatography on silica gel eluted with 5% EtOAc/hexane to yield 0.6 g of aldehyde 18.

Step b. Sodium triacetoxyborohydride (2.5 g, 11.8 mmol, 3.1 equiv) was added to a solution of aldehyde 18 (1.23 g, 3.84 mmol, 1.0 equiv) and amine A8 (1.45 g, 6.37 mmol, 1.7 equiv) in dichloroethane (40 mL), and the mixture was stirred at 23° C. overnight. The reaction was diluted with 30 mL of water and extracted with dichloromethane (3×30 mL). The organic layer was combined and dried (sodium sulfate) and concentrated. The residue was purified by silica gel flash column chromatography (10% methanol in dichloromethane) to afford compound 19 (2.01 g, 98% yield) as white foam. LRMS (ESI) m/z: calculated for $C_{30}H_{40}F_2NO_5$ (M+H) 532.3, found 532.3.

Step c. Lithium hydroxide monohydrate (317 mg, 7.55 mmol, 2.0 equiv) was added to a solution of 19 (3.78 g, 3.78 mmol, 1.0 equiv) in methanol (40 mL) and $H_2O$ (12 mL) and the mixture was stirred at 80° C. for 2 h. The reaction was concentrated and re-dissolved in dichloromethane (50 mL). EDCI (2.2 g, 11.5 mmol, 3.0 equiv), HOBt (510 mg, 3.77 mmol, 1.0 equiv) and 4-methylmorpholine (1.6 mL, 14.55 mmol, 3.8 equiv) were added and the mixture was stirred at 40° C. for 2 h. The reaction was diluted with the saturated sodium bicarbonate solution (50 mL) and extracted with dichloromethane (3×50 mL). The organic layer was combined, dried over sodium sulfate and concentrated. The residue was purified by silica gel flash column chromatography (30% ethyl acetate in hexane) to afford lactam 20 (1.18 g, 63% yield) as colorless oil. LRMS (ESI) m/z: calculated for $C_{29}H_{36}F_2NO_4$ (M+H) 500.3, found 500.2.

Step d. Trifluoroacetic acid (1 mL) was injected in the solution of lactam 20 (260 mg, 0.52 mmol, 1.0 equiv) in chloroform (10 mL) at 0° C. and the mixture was stirred at 23° C. for 1 h. The reaction was concentrated and the residue was purified by silica gel flash column chromatography (gradient from 30% to 50% ethyl acetate in hexane) to afford ketone 21 (203 mg, 86% yield) as colorless oil. $^1$H NMR (400 MHz, $C_6D_6$) δ 7.62 (d, J=2.5 Hz, 1H), 6.88 (d, J=8.3, 2.9 Hz, 1H), 6.78 (d, J=8.8 Hz, 1H), 6.60 (td, J=8.8, 5.4 Hz, 1H), 6.44 (ddd, J=10.3, 8.3, 2.9 Hz, 1H), 6.27 (dddd, J=9.3, 7.8, 2.9, 2.0 Hz, 1H), 4.51 (br. t, J=12.7 Hz, 1H), 2.58~2.44 (m, 4H), 2.24~2.16 (m, 3H), 1.95~1.86 (m, 2H), 1.51~1.23 (m, 5H), 1.15~0.89 (m, 4H), 0.82 (d, J=6.9 Hz, 3H), 0.78 (d, J=6.9 Hz, 3H); LRMS (ESI) m/z: calculated for $C_{27}H_{32}F_2NO_3$ (M+H) 456.2, found 456.2.

Step e. Aminomethylcyclopropane A6 (160 mL, 7.55 mmol, 6.0 equiv) was added to a solution of ketone 21 (141 mg, 0.309 mmol, 1.0 equiv) and crushed 4 Å molecular sieves (~50 mg, oven-dried) in toluene (2.4 mL) for 1 h. The reaction was cooled and filtered and the solvent was evaporated. The residue was dissolved in THF (3 mL); L-selectride (1.0 M in THF, 2 mL, 2.0 mmol, 6.5 equiv) was added at 0C and the mixture was heated to 80° C. for 18 h. To the reaction was added water (160 mL), ethanol (1.2 mL) and potassium hydroxide (60 mg), the mixture was cooled to 0C and hydrogen peroxide (30% solution in $H_2O$, 500 mL) was added slowly and the reaction was stirred for 1 h. The mixture was diluted with water (20 mL) and extracted with 30% 2-propanol in chloroform (2×20 mL). The organic layer was combined, dried over sodium sulfate and concentrated. The residue was purified by silica gel flash column chromatography (10% methanol in dichloromethane with 1% ammonium hydroxide) and concentrated. The residue was dissolved in methanol, then hydrogen chloride (2.0 M in diethyl ether, 200 mL) was added and the solvents were evaporated to afford amine salt 22 (144.4 mg, 85% yield) as a 15:1 (cis/trans) diastereomeric mixture.

22-cis: $^1$H NMR (500 MHz, $CD_3OD$) δ 7.24~6.97 (m, 6H), 4.41 (br. s, 1H), 3.22~3.06 (m, 2H), 3.13~3.06 (m, 1H), 2.93 (d, J=7.34 Hz, 2H), 2.86~2.75 (m, 2H), 2.07~1.99 (m, 2H), 1.96~1.78 (m, 4H), 1.74~1.66 (m, 5H), 1.64~1.53 (m, 2H), 1.43 (t, J=10.3 Hz, 1H), 1.36~1.22 (m, 1H), 1.07 (d, J=6.9 Hz, 2H), 0.90 (d, J=6.4 Hz, 2H), 0.75~0.71 (m, 2H), 0.43~0.41 (m, 2H); LRMS (ESI) m/z: calculated for $C_{31}H_{41}F_2N_2O_2$ (free base; M+H) 511.3, found 511.3.

Example 14

This example illustrates the preparation of 2-(1-{4-[(cyclopropylmethyl-amino)-methyl]-thiazol-2-yl}-2-methyl-propyl)-8-(2,4-difluoro-phenoxy)-2,3,4,5-tetrahydro-benzo[c]azepin-1-one. In general, this compound was prepared according to steps a-e of Example 13 using A12 instead of A8. Amine A12 was prepared as described in Example 5. Aldehyde 18 was synthesized as detailed in Example 13, step a.

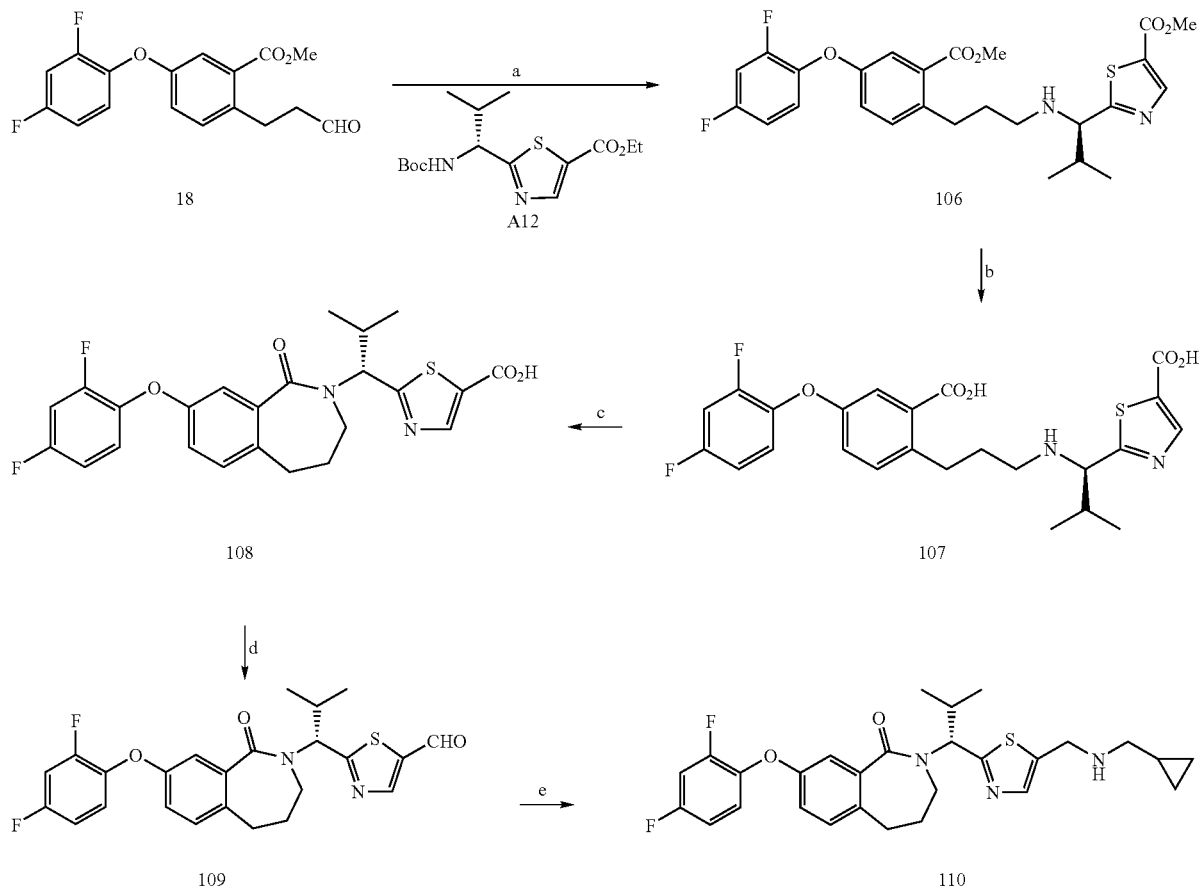

Step a. Amine A12 (0.688 g, 2.1 mmol) in DCM (3 mL) was treated with TFA (2 mL) for 1 h at room temperature, then the solvent was removed. A portion of this deprotected amine A12 (0.2 g, 0.86 mmol), compound 18 (0.24 g, 0.78 mmol), and sodium triacetoxyborohydride (0.42 g, 1.96 mmol) in DCE (0.2 M solution) were stirred at room temperature for 2 h. The reaction was treated with saturated sodium bicarbonate solution and extracted with ethyl acetate, the organic layer was washed with brine, dried, concentrated, and purified by flash chromatography on silica gel eluted with 5% MeOH/DCM to yield coupled product 106 (0.25 g) as brown oil.

Step b. The mixture of 106 (0.25 g, 0.47 mmol) and LiOH (0.5 g, 20 mmol) in methanol (5 mL) and water (1 mL) was stirred at 80° C. for 4 h. The reaction was cooled and extracted with EtOAc, the organic layer was discarded, and the aqueous layer was acidified with 1 N HCl and extracted with ethyl acetate. The organic layer was washed with brine, dried, and concentrated yielding 0.24 g of diacid 107 as brown solid.

Step c. Diacid 107 (0.24 g, 0.5 mmol) was treated with 1-(3-dimethylaminopropyl)-3-ethylcarbodiimide hydrochloride (0.29 g, 1.5 mmol), 1-hydroxybenzotriazle hydrate (0.068 g, 0.5 mmol) and 4-methylmorpholine (0.152 g, 1.5 mmol) in DCM (3 mL) at room temperature for 8 h to promote cyclization. The crude product was purified by flash chromatography on silica gel eluted with 10% EtOAc/hexane to yield 0.18 g of compound 108.

Step d. To the solution of acid 108 (0.18 g, 0.38 mmol) in THF (3 mL) borane was added and the mixture was stirred at room temperature for 4 h. The reaction was treated with the saturated sodium bicarbonate solution and extracted with ethyl acetate, the organic layer was washed with brine, dried, concentrated, then purified by flash chromatography on silica gel eluted with 10% EtOAc/hexane to yield 0.15 g of alcohol. Alcohol (0.15 g, 0.32 mmol) was treated with Dess-Martin reagent in DCM at rt for 3 h. At the completion of oxidation, the reaction was quenched with sodium bicarbonate and extracted with EtOAc. Organic layer was washed with sodium bicarbonate, then with brine, dried and concentrated to yield 0.1 g aldehyde 109 as brown solid.

Step e. The mixture of aldehyde 109 (0.1 g, 0.22 mmol), cyclopropylmethylamine (0.04 g, 0.4 mmol), TEA (0.025 g, 0.25 mmol) and sodium triacetoxyborohydride (0.14 g, 0.66 mmol) in DCE (2 mL) was stirred at room temperature for 2 h. The reaction was treated with saturated sodium bicarbonate solution and extracted with ethyl acetate. The organic layer was washed with brine, dried, concentrated, and purified by HPLC (0.1% TFA in acetonitrile and water) to yield 0.02 g of compound 110 as brown oil. 1H NMR (400 MHz, CDCl$_3$) δ 7.13 (s, 1H), 7.05-7.10 (m, 2H), 6.97 (m, 2H), 6.85 (m, 1H), 5.72 (d, J=11.1 Hz 1H), 3.98 ( s, 1H), 3.37 (m, 2H), 2.52-2.56 (m, 4H), 1.70 (m, 3H), 1.21 (m, 3 H), 1.0 (d, J=5.2 Hz, 3H), 0.97 (d, J=5.2 Hz, 3H), 0.95 (m, 1H), 0.5 (d, J=5.2 Hz, 2H), 0.1 (d, J=5.2 Hz, 2H). ESI (MH+) m/z 610.

Example 15

This example illustrates the synthesis of N-(1-benzyl-piperidin-4-yl)-3-methyl-2-(4-oxo-6-o-tolyloxy-4H-quinazolin-3-yl)-butyramide 25. Amine 23 was prepared by coupling D-valine tert-butyl ester with 2-amino-5-(2-methylphenoxy) benzoic acid, which, in turn, was prepared following the procedures detailed for compound 7 in Example 6 by substituting 2-methylphenol for 2,4-difluorophenol.

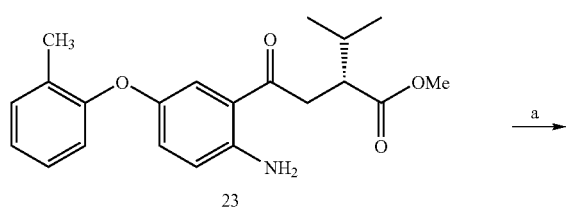

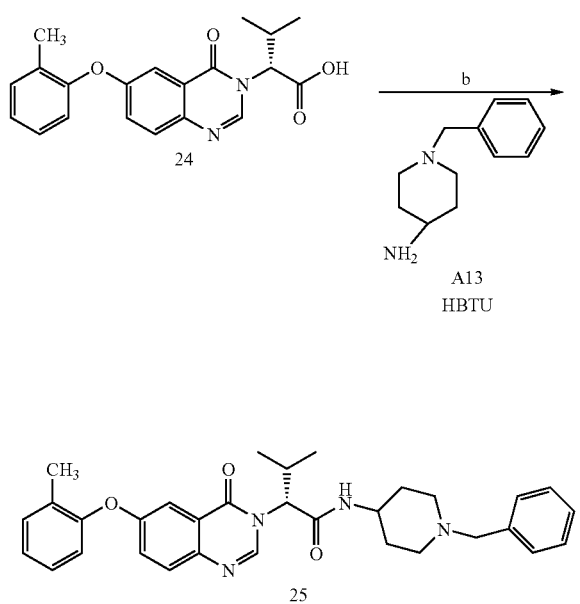

Step a. Acetic acid (80 μL, 1.4 mmol) was added to an ethanolic solution (25 mL) containing amine 23 (0.52 g, 1.5 mmol) and triethylorthoformate (0.24 mL, 1.4 mmol) under an atmosphere of nitrogen. The resulting solution was then heated at reflux overnight. After heating, the mixture was concentrated using reduced pressure, and the remaining residue was dissolved in a methanol (10 mL) solution containing 3N aqueous NaOH (10 mL). This mixture was heated at reflux for 4 h. After cooling, the solution was acidified with aqueous 3 N HCl, extracted with ethyl acetate (50 mL), washed with brine, dried with $Na_2SO_4$, and concentrated to give carboxylic acid 24. This material was used in the next step without purification: ESI (MH+) m/z 353.

Step b. HBTU (75 mg, 0.2 mmol) was added to a dichloromethane solution (1 mL) containing triethylamine (50 μL, 0.3 mmol), carboxylic acid 24 (25 mg, 0.07 mmol), and 4-amino-1-benzylpiperidine (50 mg, 0.3 mmol) at room temperature. After stirring for 4 hours, the solvent was removed using evaporation, and the remaining residue was purified using preparative HPLC (C 18 column, 10%-90% acetonitrile/water gradient) to yield compound 25. $^1$H NMR (400 MHz, $CD_3OD$) δ 8.52 (s, 1H), 7.73 (d, J=10.63 Hz, 1H), 7.48-7.53 (m, 6H), 7.40 (d, J=2.77 Hz, 1H), 7.34 (d, J=7.62 Hz, 1H), 7.26 (t, J=5.85 Hz, 1H), 7.16 (m, 1H), 6.99 (d, J=8.10 Hz, 1H), 5.13 (d, J=11.04, 1H), 4.29 (s, 2H), 3.90 (m, 1H), 3.49 (m, 2H), 3.15 (m, 2H), 2.49 (m, 1H), 2.19 (s, 1H), 2.05 (d, J=13.76 Hz, 1H), 1.74 (m, 2H), 1.10 (d, J=6.47 Hz, 3H), 1.01 (dd, J=3.22 Hz, J=6.83 Hz, 1H), 0.83 (d, J=6.57, 3 H); Analytical HPLC Method A @ 220 nm: RT =7.53 min.; ESI [M+H]+ m/z 525.

Example 16

This example illustrates the preparation of 4-{1-[4-(indan-2-ylamino)-piperidine-1-carbonyl]-2-methyl-propyl}-7-o-tolyloxy-1,2,3,4-tetrahydro-benzo[e][1,4]diazepin-5-one. Acyl chloride 26 was derived from its corresponding acid, which in turn was obtained similar to compound 7 using 2-methylphenol and 5-fluoro-2-nitrobenzoic acid as starting compounds.

Amine A3 was prepared as follows:

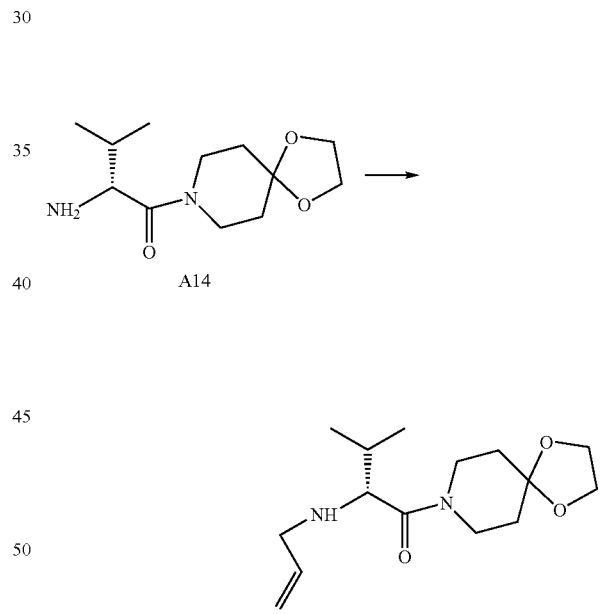

Allylbromide (0.74, 8.7 mmol) was added to an acetonitrile solution (30 mL) containing amine A14 (2.12 g, 8.7 mmol) and $Na_2CO_3$ (4.6 g, 43 mmol) at room temperature. After stirring overnight, the solvent was removed and the remaining residue was dissolved in ethyl acetate (100 mL), washed with water (50 mL), then brine (50 mL), dried over $Na_2SO_4$, and concentrated to give amine A3: ESI (MH+) m/z 283.

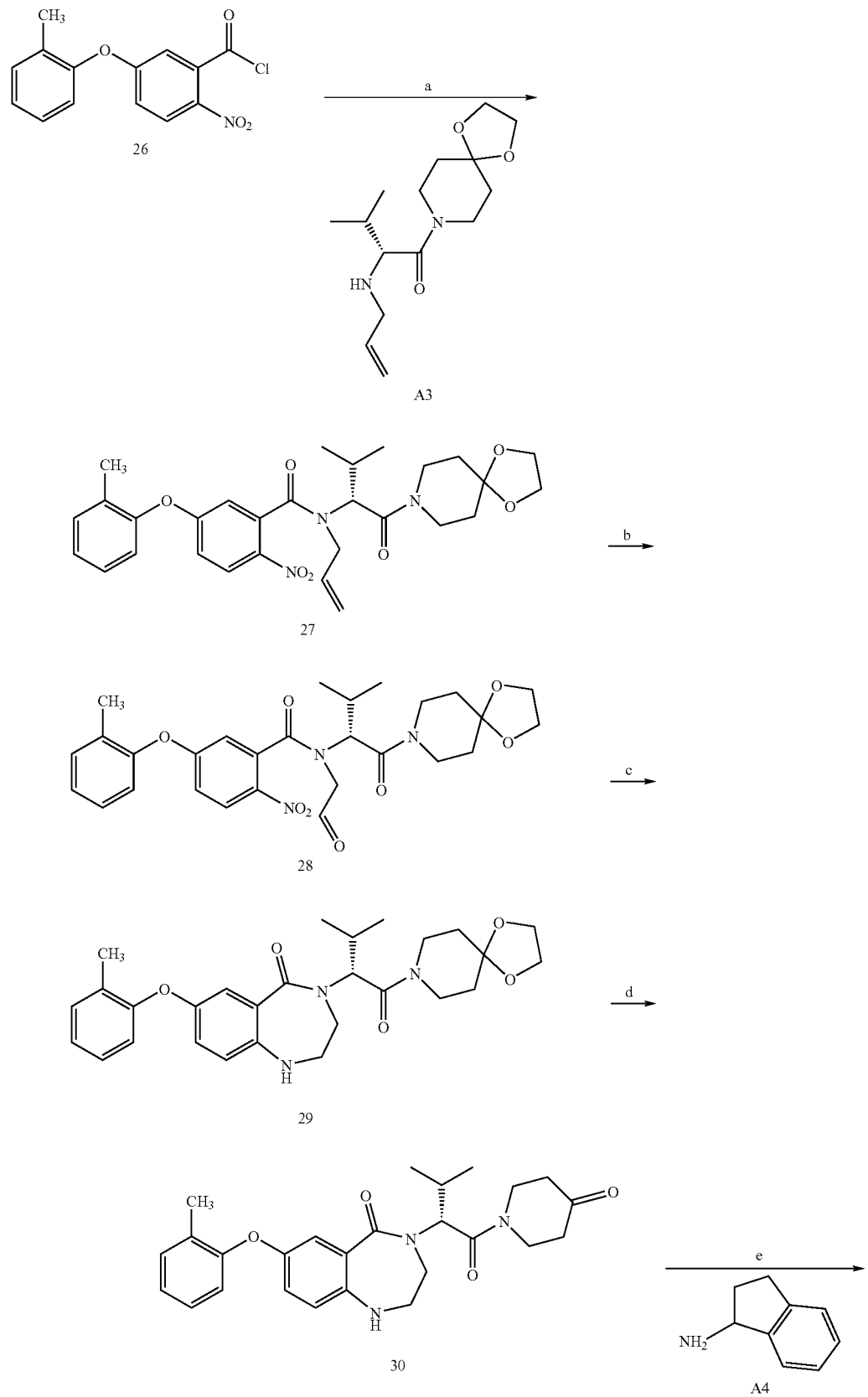

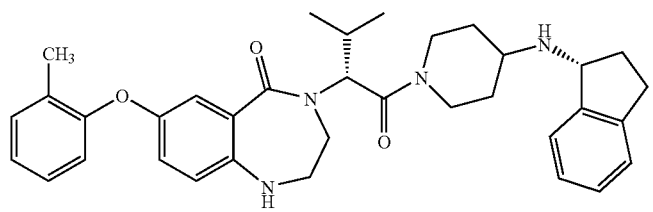

31

Step a. Diisopropylethylamine (0.35 mL, 2.0 mmol) was added to a dichloroethane solution (20 mL) containing acid chloride 26 (0.3 g, 1.0 mmol) and amine A3 (0.29 g, 1.0 mmol). The resulting solution was heated at reflux for 24 h. Next, the solution was cooled to room temperature, washed with water, then with brine, dried over $Na_2SO_4$, and concentrated. The remaining residue was purified on silica eluting with a 40% hexane/ethyl acetate solution. Similar fractions were pooled and concentrated to yield amide 27: ESI (MH$^+$) m/z 538.

Step b. Amide 27 (0.45 g, 0.8 mmol) was dissolved in a 3:1 dioxane/water solution (30 mL) containing catalytic amounts of $OsO_4$. After 10 minutes, the solution turned dark in color, and an aqueous solution containing $NaIO_4$ (0.51 g, 2.4 mmol) was added. After 2 hr the reaction was completed and the mixture was partitioned with water (50 mL) and ethyl acetate (50 mL). The organic layer was then washed with a saturated solution of $Na_2S_2O_3$, followed by brine, then dried over $Na_2SO_4$, and concentrated. The remaining residue was purified on silica eluting with 60% hexane/ethyl acetate solution. Similar fractions were pooled and concentrated to give aldehyde 28: ESI (MH$^+$) m/z 540.

Step c. 10% Palladium on carbon was added to an ethanol solution (25 mL) containing aldehyde 28 (0.31 g, 0.6 mmol) under an atmosphere of nitrogen at room temperature. The nitrogen atmosphere was then replaced with a hydrogen atmosphere (60 psi), and the mixture was mixed in a Parr shaker for 36 h. The suspension was then filtered over Celite, and excess solvent was removed using reduced pressure. Aniline 29 was used in the next step without purification.

Step d. Aniline 29 (0.32 g, 0.6 mmol) was dissolved in a 1:1 TFA/$H_2O$ solution (15 mL) and heated to 80° C. for 25 min. Excess TFA was removed using reduced pressure, and the resulting aqueous solution was extracted with ethyl acetate (50 mL), dried over $Na_2SO_4$, and concentrated to give ketone 30. This material was used in the next reaction without further purification: ESI (MH$^+$) m/z 450.

Step e. NaBH(OAc)3 (50 mg, 0.2 mmol) was added to a dichloromenthane solution (1 mL) containing (R)-(−)-1-aminoindane A4 (30 mg, 0.2 mmol), triethylamine (75 μL, 0.5 mmol), and ketone 30 (15 mg, 0.03 mmol) at room temperature. After stirring for 3 hours, the solvent was evaporated, and the remaining residue was purified using preparative HPLC (C18 column, 10%-90% acetonitrile/water gradient). Compound 31 exists as a mixture of conformational isomers: 1H NMR (400 MHz, CD$_3$OD) δ 7.34 (d, J=7.20, 1H), 7.10-7.25 (m, 5H), 6.91-7.07 (m, 3, H), 6.78 (m, 2H), 5.27 (t, J=10.21 Hz, 1H), 4.53-4.68 (m, 1H), 4.22-4.42 (m, 1H), 3.43-3.67 (m, 6H), 3.10-3.18 (m, 2H), 2.82 (m, 2H), 2.40 (m, 2H), 2.2 (s, 3H), 1.85-2.10 (m, 2H), 1.29-1.42 (m, 3H), 0.94 (m, 6H); Analytical HPLC Method A@220 nm: RT=7.56 min.; ESI (MH+) m/z 567.

Example 17

This example illustrates the preparation of 8-(2,4-difluoro-phenoxy)-2-{1-[4-(4-fluoro-benzylamino)-piperidine-1-carbonyl]-2-methyl-propyl}-2,3-dihydro-benzo[c]azepin-1-one. The preparation of iodoester compound 8 was described in Example 6. Amine A3 was synthesized as described in Example 16.

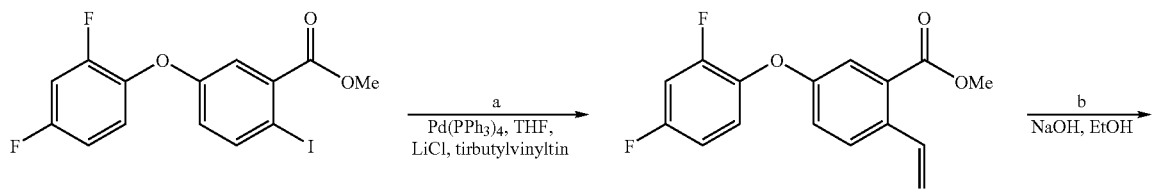

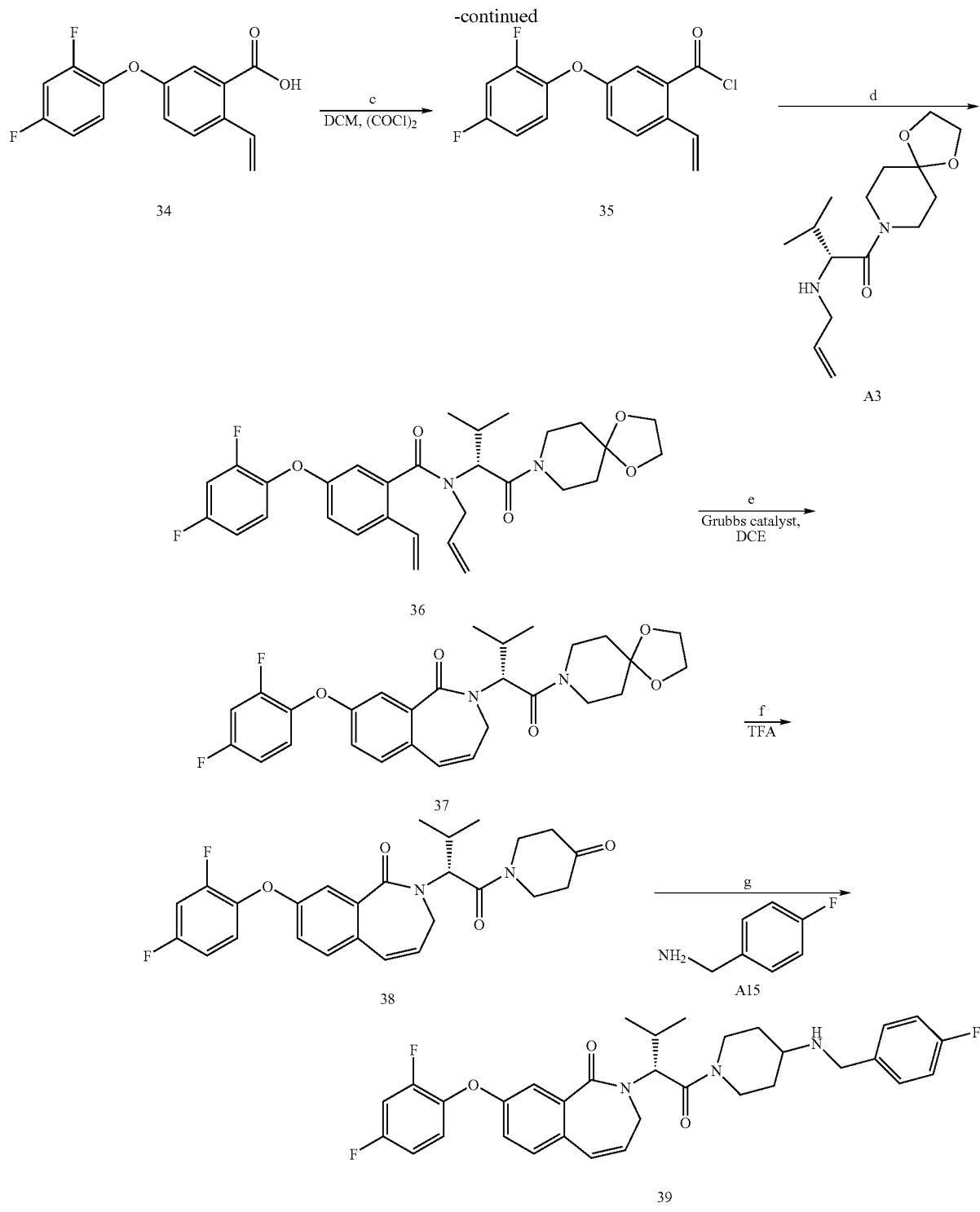

Step a. Pd(PPh$_3$)$_4$ (160 mg, 0.1 mmol) was added to a dry, degassed THF solution (50 mL) containing ester iodide 8 (3.46 g, 8.9 mmol), LiCl (2.63 g, 62 mmol), and tributylvinyltin (3.1 mL, 11 mmol) under an atmosphere of argon at room temperature. This mixture was then heated at reflux for 24 h. After cooling to room temperature, a 10% NH$_4$OH solution (20 mL) was added, and the mixture was stirred for an additional 10 min. Next, the mixture was partitioned with ethyl acetate (250 mL), and the organic layer was washed with brine, dried with Na$_2$SO$_4$, and concentrated to give ester 33, which was used in the next step without purification: ESI (MH$^+$) m/z 291.

Step b. A 3 N NaOH aqueous solution (20 mL) was added to an ethanolic solution (30 mL) containing ester 33 (1.6 g, 5.5 mmol) and the mixture was heated at reflux for 4 hours. Excess ethanol was removed using reduced pressure, and the resulting aqueous solution was acidified with 3 N HCl and extracted with ethyl acetate, washed with brine, dried with Na₂SO₄, and concentrated to give carboxylic acid 34. Acid 34 was used in the next step without further purification: ESI (MH⁺) m/z 277.

Step c. Oxalyl chloride (0.73 mL, 8 mmol) was added to a dichloromethane solution containing carboxylic acid 34 (1.16 g, 4.2 mmol) at room temperature. Next, 5 drops of DMF were added, and the mixture was stirred for 2 h. The solvent was then removed using reduced pressure to give acid chloride 35. This material was used in the next step without further purification.

Step d. Diisopropylethylamine (1.46 mL, 8 mmol) was added to a dichloroethane solution containing acid chloride 35 (1.2 g, 4.2 mmol) and amine A3 (1.25 g, 4.4 mmol). The resulting solution was then heated at reflux for 24 h. Next, the solution was cooled to room temperature, washed with water followed by brine, dried over Na₂SO₄, and concentrated. The remaining residue was purified on silica eluting with a 30% hexane/ethyl acetate solution. Similar fractions were pooled and concentrated to give intermediate 36: ESI (MH⁺) m/z 541.

Step e. Grubb's catalyst was added to a degassed DCE solution containing intermediate 36 (0.5 g, 0.9 mmol) under an atmosphere of argon. The mixture was then heated at 45° C. for 2 days. The solvent was removed using reduced pressure, and the resulting residue was purified on silica eluting with a 60% hexane/ethyl acetate solution. Similar fractions were pooled and concentrated to give ketal 37: ESI (MH⁺) m/z 513.

Step f. Ketal 37 (0.32 g, 0.6 mmol) was dissolved in a 1:1 TFA/H₂O solution (20 mL) and heated to 80° C. for 30 min. Excess TFA was removed using reduced pressure, and the resulting aqueous solution was extracted with ethyl acetate (50 mL), dried over Na₂SO₄, and concentrated to produce ketone 38. This material was used in the next reaction without further purification: ESI (MH⁺) m/z 469.

Step g. NaBH(OAc)₃ (50 mg, 0.2 mmol) was added to a DCM solution (1 mL) containing 4-fluorobenzylamine A15 (30 μL, 0.3 mmol) and ketone 38 (20 mg, 0.04 mmol) at room temperature. After stirring for 4 hours the solvent was removed using evaporation, and the remaining residue was purified using preparative HPLC (C 18 column, 10%-90% acetonitrile/water gradient); compound 39 exists as a mixture of conformational isomers. ¹H NMR (500 MHz, CD₃OD) δ 7.41 (d, J=2.74 Hz, 0.6H), 7.38 (d, J=2.74 Hz, 0.4H), 7.33 (m, 3H), 7.27 (m, 1H), 7.16 (m, 2H), 7.02 (m 3H), 6.92 (d, J=9.87 Hz, 0.6H), 6.84 (d, J=9.87 Hz, 0.4H), 6.24 (m, 0.6H), 6.17 (m, 0.4), 5.12 (d, J=10.65 Hz, 0.6H), 5.09 (d, J=10.65 Hz, 0.4H), 4.51 (d, J=12 Hz, 0.6H), 4.40 (d, J=12 Hz, 0.4H), 4.42 (d, J=12 Hz, 0.6H), 400 (d, J=12 Hz, 0.4H), 3.62-3.77 (m, 3H), 3.06 (t, J=12 Hz, 0.6H), 2.90 (t, J=12 Hz, 0.4H), 2.70 (m, 2H), 2.40 (m. 1H), 1.93 (d, J=12 Hz, 1H), 1.80 (d, J=12 Hz, 1H), 1.33 (m, 1H), 1.24 (m, 1H), 0.90-0.98 (m, 6H); Analytical HPLC Method A @ 220 nm: RT=7.14 min.; ESI (MH⁺) m/z 578.

Example 18

This example illustrates the preparation of 2-{1-[4-(cyclopropylmethyl-amino)-piperidine-1-carbonyl]-2-methyl-propyl}-8-(2,4-difluoro-phenoxy)-1,2,4,5-tetrahydro-benzo[c]azepin-3-one. Iodide 40 was prepared similarly to compound 8 as described in Example 6.

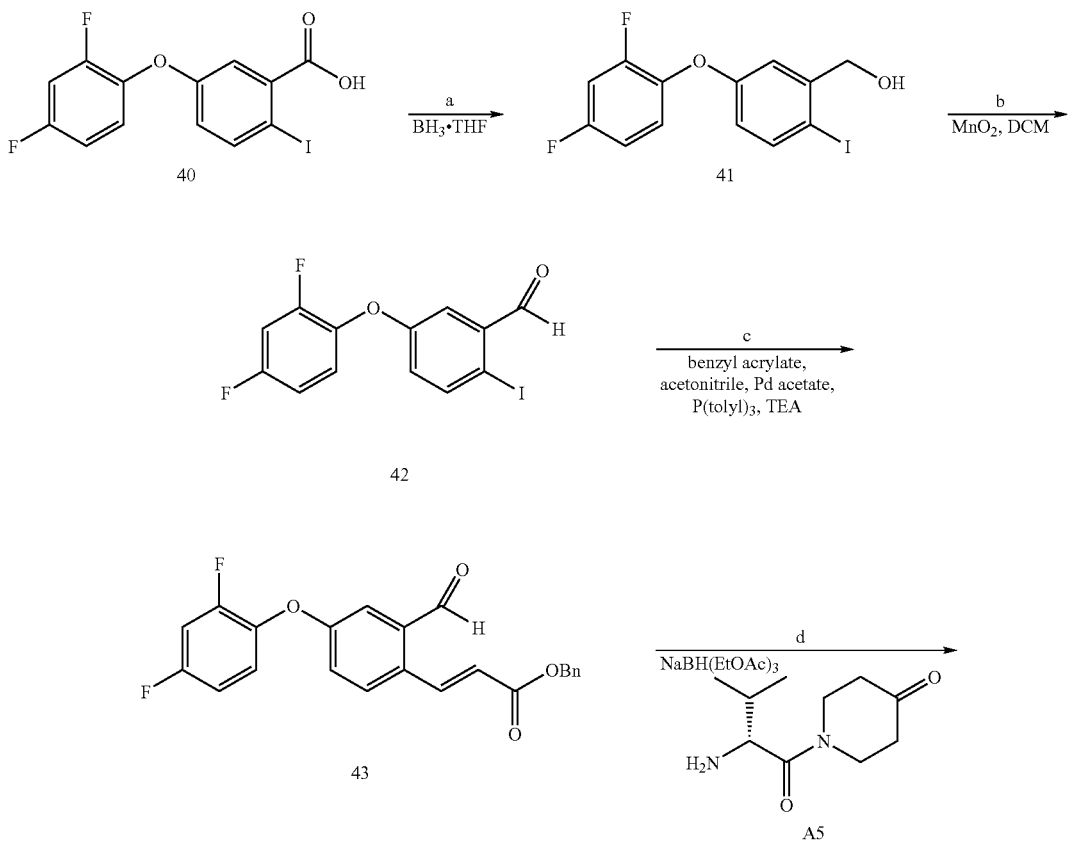

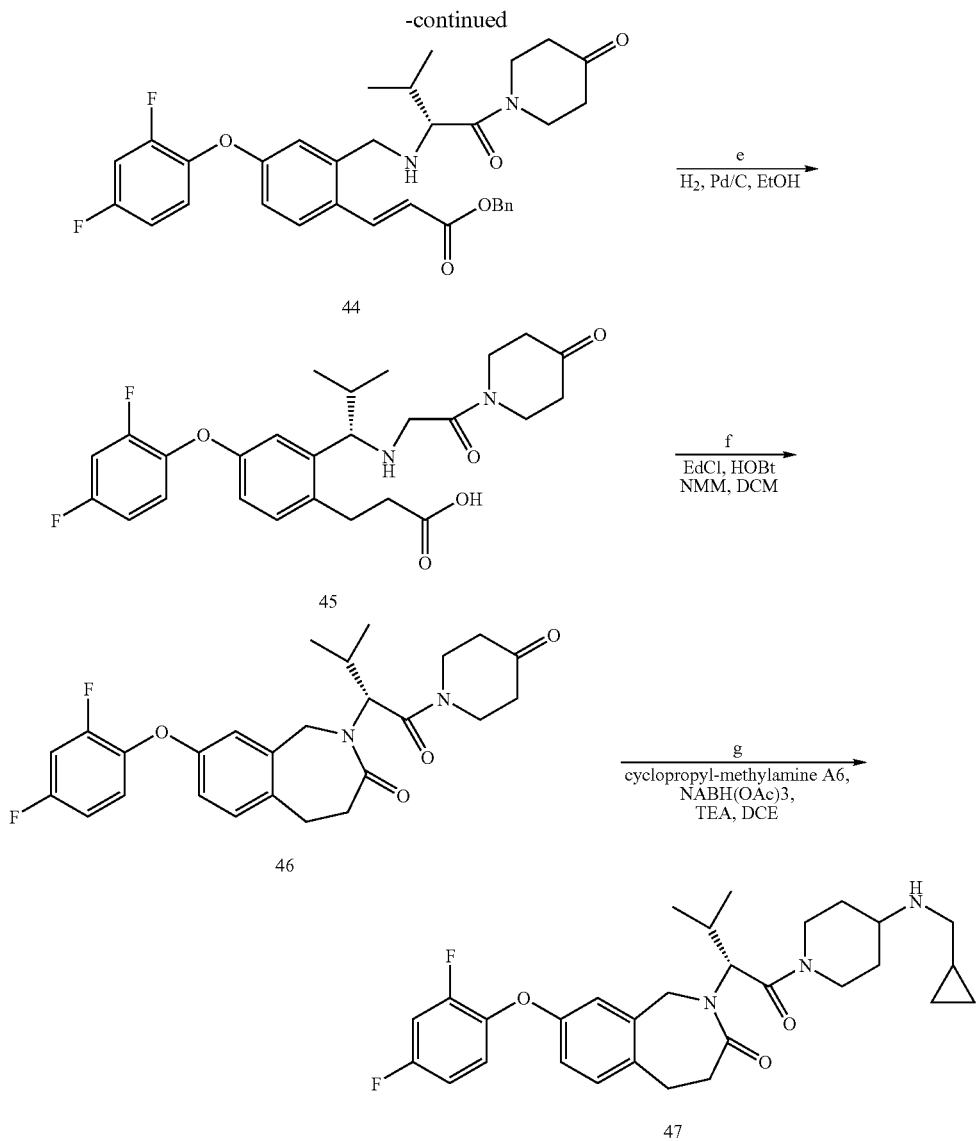

Step a. To a solution of iodide 40 (2 g, 5.32 mmol) in THF (22 mL) was added borane tetrahydrofuran complex (8 mL, 1.0 M, 8 mmol) over 20 min. The reaction mixture was stirred at room temperature for 10 h. The solvent was evaporated to yield 1.8 g of alcohol 41 as brown oil.

Step b. To a solution of alcohol 41 (1.8 g, 5 mmol) in DCM (25 mL) was added manganese (IV) oxide (9.5 g, 109 mmol). The mixture was stirred at room temperature for 10 h. The reaction was filtered through Celite and concentrated to yield 1.4 g of aldehyde 42 as brown oil.

Step c. To an oven dried 10 mL round bottom flask, was added a solution of 5-(2,4-difuoro-phenoxy)-2-iodo-benzaldehyde (1.4 g, 3.9 mmol) in acetonitrile (6.5 mL), benzyl acrylate (1.9 g, 11.7 mmol), palladium acetate (0.175 g, 0.78 mmol), tri-o-tolylphosphine (0.473 g, 1.56 mmol) and triethylamine (6.5 g, 8.95 mL, 88.6 mmol). The flask was equipped with a condenser, under positive nitrogen pressure and put into an oil bath (80° C.) after it had been degassed for 30 min. The mixture was allowed to react at 80° C. for 1½ hr before it was cooled down to rt, diluted with EtOAc and filtered through celite. The organic phase was washed with 1 N HCl solution, then dried over anhydrous sodium sulfate, filtered, concentrated, and purified by flash chromatography on silica gel eluted with 5-10% EtOAc/Hexane to yield 1 g of compound 43.

Step d. The mixture of compound 43 (0.5 g, 1.27 mmol), amine A5 (0.276 g, 1.40 mmol), and sodium triacetoxyborohydride (0.673 g, 3.17 mmol) in DCE (6.5 mL) was stirred at room temperature for 2 h. The reaction was treated with saturated sodium bicarbonate solution and extracted with ethyl acetate. The organic layer was washed with brine, dried, concentrated and then purified by flash chromatography on silica gel eluted with 5-10% MeOH/DCM to yield 0.3 g of ester 44.

Step e. The mixture of ester 44 (0.25 g, 0.43 mmol), palladium on carbon (10 wt %, 0.06 g) in EtOH (5 mL) was charged with hydrogen balloon and stirred at room temperature for 1 h. The reaction was filtered trough Celite, then purified by flash chromatography on silica gel eluted with 5-10% MeOH/DCM to yield 0.2 g of acid 45.

Step f. The mixture of acid 45 (0.15 g, 0.31 mmol.), 1-(3-dimethylaminopropyl)-3-ethylcarbodiimide hydrochloride (0.177 g, 0.92 mmol), 1-hydroxybenzotriazle hydrate (0.041 g, 0.31 mmol) and 4-methylmorpholine (0.093 g, 0.92 mmol) in DCM (3 mL) was stirred at room temperature for 8 h. The reaction was treated with saturated sodium bicarbonate solution and extracted with ethyl acetate. The organic layer was washed with brine, dried, concentrated, then purified by flash chromatography on silica gel eluted with 10% EtOAc/hexane to yield 0.1 g of ketone 46 as brown solid.

Step g. The mixture of ketone 46 (0.02 g, 0.04 mmol), cyclopropyl methylamine A6, (0.01 g, 0.09 mmol), TEA (0.015 g, 0.15 mmol) and sodium triacetoxyborohydride (0.021 g, 0.1 mmol) in DCE (1 mL) was stirred at room temperature for 2 h. The reaction was treated with the saturated sodium bicarbonate solution and extracted with ethyl acetate. The organic layer was washed with brine, dried, concentrated, then purified by preparative HPLC (0.1% TFA in acetonitrile and water) to yield 0.0015 g of compound 47 as brown oil. ESI (MH+) m/z 526.

Example 19

This example illustrates the preparation of 4-(1-{4-[2-(4-fluoro-phenyl)-ethylamino]-piperidine-1-carbonyl}-2-methyl-propyl)-1-methyl-7-o-tolyloxy-1,2,3,4-tetrahydrobenzo[e][1,4]diazepin-5-one. Aniline 29 was synthesized according to steps a-c, Example 16.

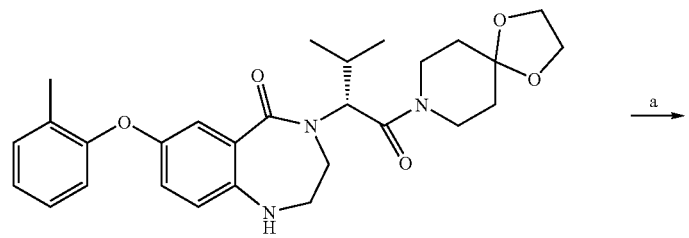

29

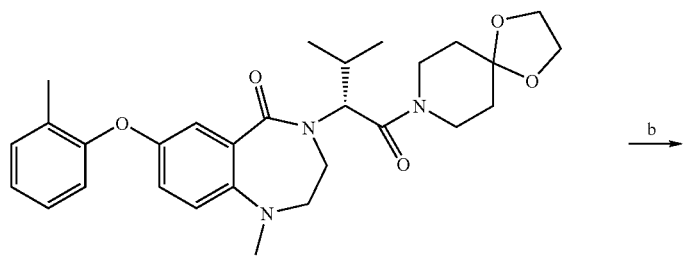

111

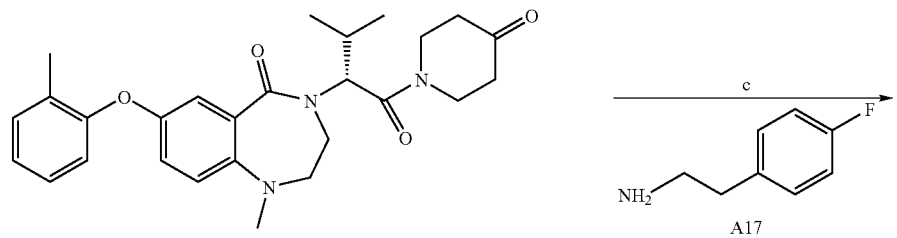

112

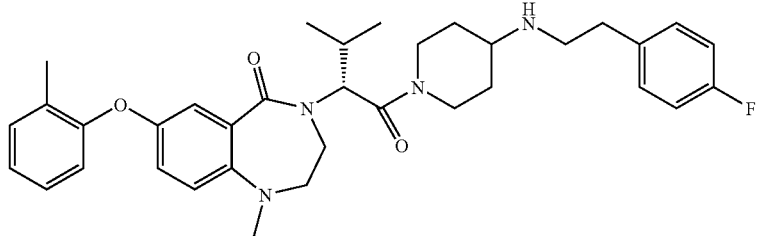

113

Step a. NaBH(OAc)₃ (172 mg, 0.8 mmol) was added to a dichloromenthane solution (10 mL) containing aniline 29 (200 mg, 0.4 mmol) and formaldehyde (37% aqueous solution, 32 µL, 0.4 mmol) at room temperature. After stirring overnight, this solution was washed with water, followed by washing with brine, dried over Na₂SO₄, and concentrated. This material was used in the next step without purification: ESI (MH⁺) m/z 508.

Step b. Ketal 111 (0.25 g, 0.5 mmol) was dissolved in a 1:1 TFA/H₂O solution (15 mL) and heated to 80° C. for 25 min. Excess TFA was removed using reduced pressure, and the resulting aqueous solution was extracted with ethyl acetate (50 mL), dried over Na₂SO₄, and concentrated to give ketone 112. This material was used in the next reaction without further purification: ESI (MH⁺) m/z 464.

Step c. NaBH(OAc)₃ (50 mg, 0.2 mmol) was added to a dichloromenthane solution (1 mL) containing 4-fluorophenethylamine A17 (30 mg, 0.2 mmol), triethylamine (75 µL, 0.5 mmol), and ketone 112 (30 mg, 0.06 mmol) at room temperature. After stirring for 5 hours, the solvent was evaporated, and the remaining residue was purified using preparative HPLC (C18 column, 10%-90% acetonitrile/water gradient) yielding compound of the invention 113. ¹H NMR (compound 113 exists as a mixture of conformational isomers) (500 MHz, CD₃OD) δ 7.26-7.33 (m, 3H), 7.14-7.18 (m, 1H). 7.00-7.10 (m, 6H), 6.85 (d, J=8 Hz, 0.5H), 6.82 (d, J=8 Hz, 0.5H), 5.26 (d, J=11 Hz, 0.5H), 5.18 (d, J=11 Hz, 0.5H), 4.57 (m, 0.5H), 4.40 (m, 0.5H), 3.42-3.59 (m, 3H), 3.16-3.26 (m, 2H), 3.09 (m, 1H), 2.96 (m, 2 H), 2.78 (s, 3H), 2.39 (m, 1H), 2.15-2.37 (m, 4H), 1.50-1.60 (m, 1H), 1.37 (m, 1H), 1.08 (m, 1H), 0.93-0.99 (m, 6H); Analytical HPLC Method A@ 220 nm: rt=8.26 min.; ESI (MH⁺) m/z 587.

Example 20

This example illustrates the preparation of 2-[7-(4-fluorophenoxy)-2,5-dioxo-1,2,3,5-tetrahydro-benzo[e][1,4]diazepin-4-yl]-3-methyl-N-( 1 -phenyl-piperidin-4-yl)-butyramide 58. 5-(4-Fluoro-phenoxy)-2-nitrobenzoic acid 54 was generated as described in step a of Example 6 using 4-fluorophenol instead of 2,4-difluorophenol.

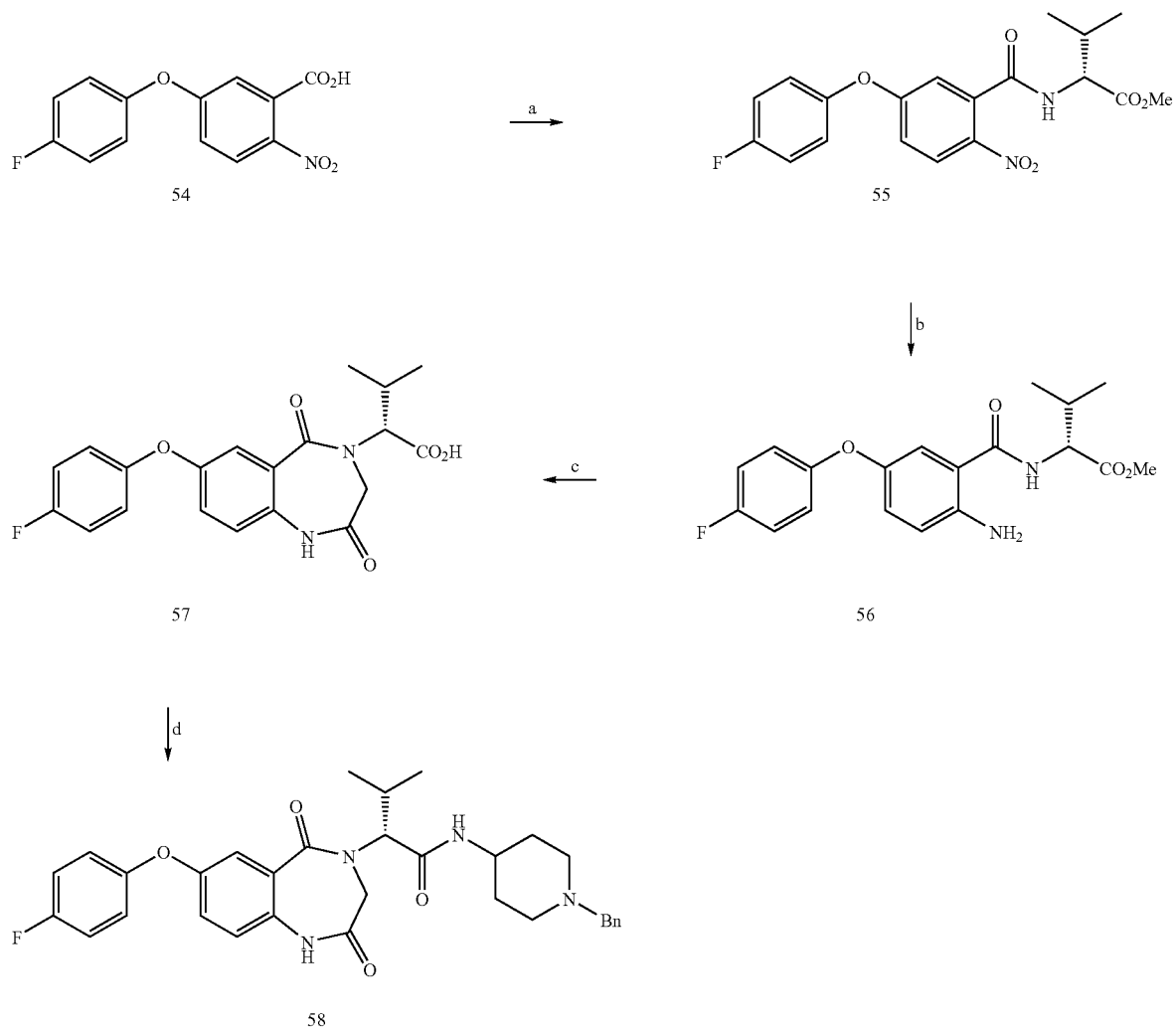

Step a. A solution of acid 54 (40.0 g, 50.5 mmol) in DCM (100 mL) was treated with oxalyl chloride (12.8 g, 101.0 mmol) for 5 min at room temperature. Upon removal of solvents, the residual material was dissolved in DCM (100 mL), a solution of D-valine methyl ester hydrochloride (10.6 g, 50.5 mmol). TEA (15.3 g, 151.6 mmol) was then added, the mixture was stirred for 4 h, and then poured into 10% HCl and extracted with DCM. The organic layer was washed with sodium bicarbonate and with brine, dried, and concentrated to yield 17 g of amide 55 as brown oil.

Step b. The solution of amide 55 (12.0 g, 27.8 mmol) and palladium on carbon (1.5 g) in methanol (100 mL) was put on a hydrogenation Parr shaker (45 psi) for 5 h. At the completion of the reaction, the mixture was filtered through a plug of Celite and concentrated yielding 11 g of aniline 56 as brown oil.

Step c. The mixture containing 56 (1.9 g, 4.73 mmol), TEA (0.96 g, 9.45 mmol) in DCM (70 mL), and chloroacetyl chloride (1.07 g, 9.45 mmol) in DCM (10 mL) was stirred for 30 min at room temperature. The reaction mixture was poured into 3N HCl (10 mL) and extracted with DCM. The organic layer was washed with sodium bicarbonate and brine, dried, and concentrated to yield 1.5 g of an acylated product. This intermediate (0.76 g, 1.74 mmol) was dissolved in DMF (7 mL), then treated with sodium hydride (0.348 g, 60%, 8.7 mmol) for 8 h. Saturated ammonium chloride was added to the reaction, the mixture was extracted with DCM, organic layer was acidified with 3 N HCl, separated, washed with brine, and concentrated to yield 0.6 g of acid 57 as brown solid.

Step d. The mixture of acid 57 (0.50 g, 1.30 mol), 4-amino-1-benzylpiperidine (0.27 g, 1.42 mol.), 1-(3-dimethylamino-propyl)-3-ethylcarbodiimide hydrochloride (0.27 g, 1.42 mol), HOBt (0.181 g, 0.134 mmol) and 4-methylmorpholine (0.41 g, 4 mmol) in DCM (30 mL) was stirred at room temperature for 8 h. The reaction mixture was diluted with ethyl acetate and washed with the saturated sodium bicarbonate solution and brine. The organic layer was dried over $Na_2SO_4$, concentrated; and crude product was purified by flash chromatography on silica gel eluted with 10% EtOAc/hexane with 1% ammonium hydroxyl added to yield 0.58 g of compound 58 as off-white foam. 1H NMR (400 MHz, $CDCl_3$) δ 8.00 (s, 1H), 7.55 (d, J=2.8 Hz, 1H), 7.29 (m, 5H), 7.13 (dd, J=8.8, 2.8 Hz, 1H), 7.05 (dd, J=9.1, 8.0 Hz, 2H), 7.02 (dd, J=9.1, 4.5 Hz, 2H), 6.94 (d, J=8.8 Hz, 1H), 6.05 (d, J=7.2 Hz, 1H), 4.56 (d, J=10.9 Hz, 1H), 4.45 (bd, J=15.0 Hz, 1H), 3.80 (bd, J=15.0 Hz, 1H), 3.76 (m, 1H), 3.47 (s, 2H), 2.75 (t, J=13.0 Hz, 1H), 2.43 (m, 1H), 2.13 (d, J=11.3 Hz, 1H), 2.07 (d, J=11.5 Hz, 1H), 1.92 (d, J=12.3 Hz, 1H), 1.81 (d, J=12.3 Hz, 1H), 1.44 (m, 2H), 1.00 (d, J=6.5 Hz, 3H), 0.88 (d, J=6.5 Hz, 3H). MS SEI m/z: [M+H]+ at 559.

Example 21

This example illustrates the preparation of 1-benzyl-piperidine-4-carboxylic acid 2-[7-(4-fluoro-phenoxy)-2,5-dioxo-1,2,3,5-tetrahydro-benzo[e][1,4]diazepin-4-yl]-3-methyl-butyl ester. 5-(4-Fluoro-phenoxy)-2-nitrobenzoic acid 54 was generated as described in step a of Example 6 using 4-fluorophenol instead of 2,4-difluorophenol.

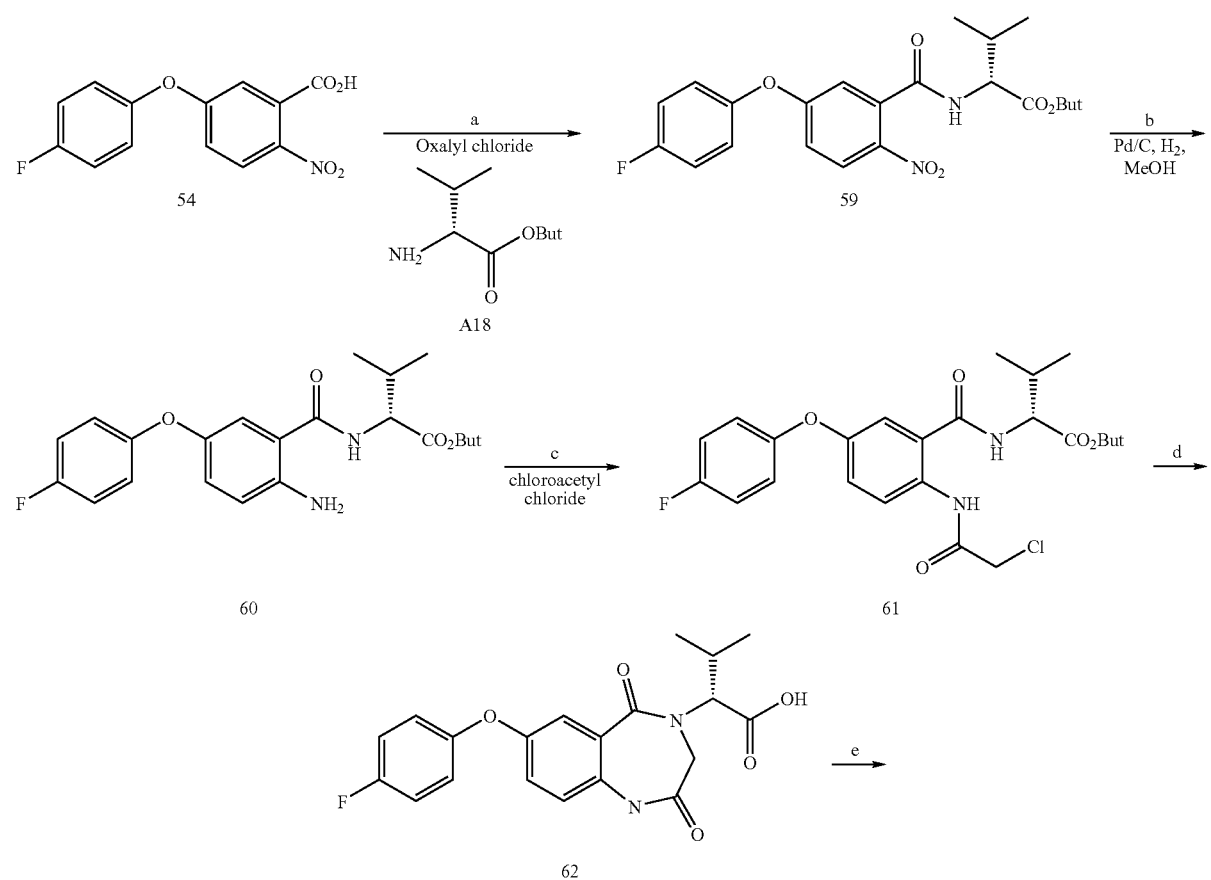

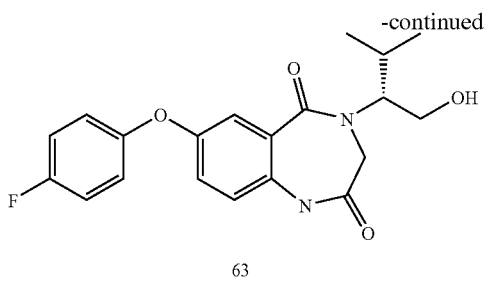

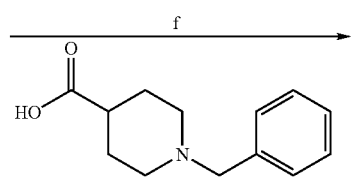

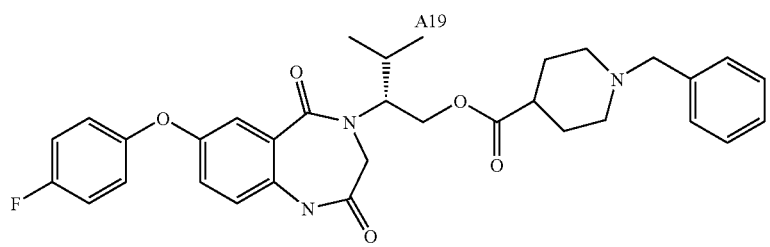

Step a. A solution of acid 54 (40.0 g, 50.5 mmol) in DCM (100 mL) was treated with oxalyl chloride (12.8 g, 101.0 mmol) for 5 min at room temperature. Upon removal of solvents, the residual material was dissolved in DCM (100 mL), and a solution of amine A18 (10.6 g, 50.5 mmol) and TEA (15.3 g, 151.6 mmol) was then added and the mixture was stirred for 4 h. The mixture was poured into 10% HCl, extracted with DCM, and the organic layer was washed with sodium bicarbonate, and brine, dried and concentrated to yield 17 g of amide 59 as brown oil.

Step b. The solution of amide 59 (12.0 g, 27.8 mmol) and palladium on carbon (1.5 g) in methanol (100 mL) was put on a hydrogen par shaker (45 psi) for 5 h, filtered through a plug of Celite and concentrated, yielding 11 g of aniline 60 as brown oil.

Step c. To the solution of aniline 60 (1.9 g, 4.73 mmol), and TEA (0.96 g, 9.45 mmol) in DCM (70 mL), chloroacetyl chloride (1.07 g, 9.45 mmol) in DCM (10 mL) was added drop-wise, and the mixture was stirred for 30 min. The reaction mixture was poured into 3N HCl (10 mL), extracted with DCM, the organic layer was washed with sodium bicarbonate and brine, dried, and concentrated to yield 1.5 g of compound 61 as brown solid.

Step d. To the solution of compound 61 (7.6 g, 17.4 mmol) in DMF (70 mL), sodium hydride (3.48 g, 60%, 87 mmol) was added, the mixture was stirred for 8 h. Saturated ammonium chloride was added and the reaction was extracted with DCM, the organic layer was acidified with 3 N HCl, separated, washed with brine, and concentrated to yield 6 g of acid 62 as brown solid.

Step e. To the solution of acid 62 (1.45 g, 3.76 mmol) in THF (10 mL), (trimethylsilyl) diazomethane (7.5 mL, 2.0 M, 15.0 mmol) was added, and the mixture was stirred for 3 h. LAH (0.29 g, 7.5 mmol) was then added into the mixture, stirred for 30 min, and the reaction mixture was quenched by sodium bicarbonate and extracted with isopropyl alcohol/chloroform. The organic layer was washed with brine and concentrated to yield 0.85 g of alcohol 63 as brown oil.

Step f. The mixture of alcohol 63 (0.05 g, 0.134 mmol), intermediate A19 (0.03 g, 0.134 mmol), 1-(3-dimethylaminopropyl)-3-ethylcarbodiimide hydrochloride (0.078 g, 0.4 mmol), HOBt (0.018 g, 0.134 mmol) and 4-methylmorpholine (0.041 g, 0.4 mmol) in DCM (3 mL) was stirred at room temperature for 8 h. The reaction was treated with the saturated sodium bicarbonate solution and extracted with ethyl acetate. The organic layer was washed with brine, dried, concentrated, and then purified by flash chromatography on silica gel eluted with 10% EtOAc/Hexane to yield 0.006 g of compound 64 as off-white film. $^1$H NMR (400 MHz, CDCl$_3$) δ 7.64 (m, 1H), 7.2-7.3 (m, 4H), 6.8-7.10 (m, 7H), 4.64 (m, 1H), 4.37 (m, 1H), 4.16 (m, 1H), 4.03 (m, 1H), 3.85 ( m, 2H), 2.78 (m, 2H), 2.26 (m, 1H), 2.0 (m, 4H), 1.81 (m, 5H), 1.07 (d, J=5.2 Hz, 3H), 0.95 (d, J=5.2 Hz, 3H). ESI (MH$^+$) m/z 610.

Example 22

This example illustrates the preparation of N-(1-benzyl-piperidin-4-yl)-2-(2,5-dioxo-7-phenoxy-1,2,3,5-tetrahydro-benzo[e][1,4]diazepin-4-yl)-3-methyl-butyramide. This compound was prepared according to steps a-e of Example 20 using 2-nitro-5-phenoxybenzoic acid instead of 2-nitro-5-(4-fluorophenoxy)benzoic acid in step a. MS SEI [M+H]+ m/e at 541.

Example 23

This example illustrates the preparation of 2-[7-(2,6-dimethyl-phenoxy)-2,5-dioxo-1,2,3,5-tetrahydro-benzo[e][1,4]diazepin-4-yl]-3-methyl-N-[1-(1-phenyl-ethyl)-piperidin-4-yl]-butyramide. This compound was synthesized starting from an acid intermediate 65, which was prepared according to steps a-c of Example 20 using 2-nitro-5-(2,6-dimethyl-phenoxy)-benzoic acid instead of 2-nitro-5-(4-fluorophenoxy)benzoic acid in step a.

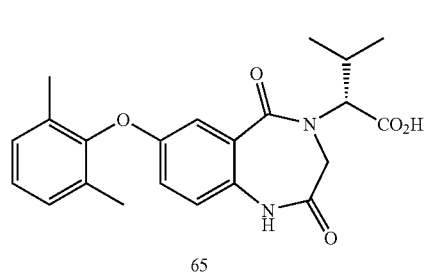
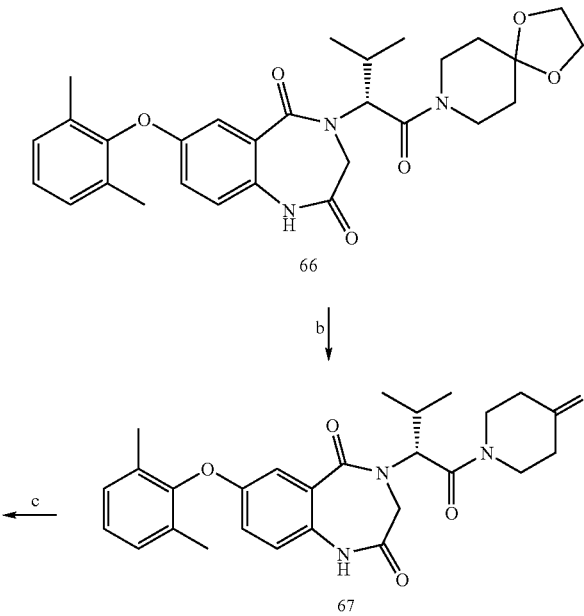

The mixture of compound 65 (400 mg, 1 mmol), 1,4 dioxa-8-azaspiro-[4,5] decane (286 mg, 2.0 mmol), HBTU (754 mg, 1.2 mmol), and DIEA (515 mL, 4.0 mmol) in dry DMF (3 mL) was stirred at room temperature for 16 hours and then diluted with EtAc (200 mL) and extracted with saturated brine (2×100 mL). The solvent was removed and compound 66 was used without further purification.

Intermediate 66 was dissolved in a 50/50 mixture of water and acetic acid (20 mL) and heated at 100° C. After two hours, the solvent was removed and the crude material was resuspended in dichloromethane (200 mL) and extracted with NaHCO₃ (2×100 mL). The organic layer was concentrated and the crude material was resuspended in dichloroethane. S-1-methylbenzylamine (184 mg, 1.52 mmol), DIEA (269 mL, 1.52 mmol), and triacetoxyborohydride (428 mg, 2.02 mmol) were added and the reaction was stirred at 60° C. for six hours, then diluted with 200 mL of CH₂Cl₂ and extracted with saturated brine (2×100 mL). The organic layer was concentrated and the crude oil was loaded onto a silica gel column and eluted with 10% methanol in dichloromethanol to provide 280 mg of compound 68.

NMR 500 (CD₃OD) δ 7.49 (m, 5H), 6.92-7.25 (m, 6H), 5.21 (m, 1H), 4.64 (d, 1H, J=1.3 Hz), 4.30 (m, 1H), 3.80(d, 1H, J=1.5 Hz), 3.16 (m, 2H), 2.60 (t, 1H, J=1.8 Hz), 2.41 (s, 2H), 2.20 (m, 2H), 2.11 (s, 6H), 1.66 (s, 3H), 1.48 (m, 2H), 1.37 (m, 1H), 0.94 (d, 6H, J=6 Hz). MS SEI m/z relative intensity: M+H, 583.3(100).

Example 24

This example illustrates the preparation of 7-(2,6-dimethyl-phenoxy)-4-{1-[4-(4-fluoro-benzylamino)-piperidine-1-carbonyl]-2-methyl-propyl}-3,4-dihydro-1H-benzo[e][1,4]diazepine-2,5-dione. This compound was prepared according to Example 23 using 4-fluorobenzylamine instead of α-methylbenzylamine in the last step of the synthesis.

¹H NMR 500 (CD₃OD) δ 7.52 (m, 2H), 7.02-7.22 (m, 8H), 5.25 (m, 1H), 4.66 (dd, 1H, J=1.3, 10 Hz), 4.23 (m, 3H), 3.86 (d, 1H, J=1.5 Hz), 3.45 (m, 1H), 3.10 (m, 1H), 2.73 (m, 1H), 2.43 (s, 1H), 2.25 (m, 1H), 2.10 (s, 6H), 1.56 (m, 2H), 1.37 (m, 1H), 0.94 (d 6H, J=8 Hz). MS SEI m/z relative intensity: M+H, 587.3(100).

Example 25

This example illustrates the preparation of 2-[7-(2,6-dimethyl-phenoxy)-2,5-dioxo-1,2,3,5-tetrahydro-benzo[e][1,4]diazepin-4-yl]-N-(1-indan-1-yl-piperidin-4-yl)-3-methyl-butyramide. This compound was prepared according to steps of Example 23 using 1-aminoindan instead of a-methylbenzylamine.

¹H NMR 500 (CD₃OD) δ 7.54 (s, 1H), 7.35 (m, 3H), 6.90-7.23 (m, 6H), 5.25 (m, 1H), 4.69 (t, 1H, J=10 Hz), 4.23 (m, 2H), 3.85 (d, 1H, J=1.5 Hz), 3.59 (m, 1H), 3.22 (m, 2H), 3.02 (s, 1H), 2.60 (m, 1H), 2.44 (s, 1H), 2.23 (m, 4H), 2.11 (s, 6H), 1.58 (m, 2H), 1.42 (m, 1H), 0.95 (d 6H, J=6 Hz). MS SEI m/z relative intensity: M+H, 595.1(100).

Example 26

This example illustrates the preparation of 7-(2,6-dimethyl-phenoxy)-4-(1-{4-[2-(4-fluoro-phenyl)-ethylamino]-piperidine-1-carbonyl}-2-methyl-propyl)-3,4-dihydro-1H-benzo[e][1,4]diazepine-2,5-dione. This compound was prepared according to steps of Example 23 using 2-(4-fluorophenyl)ethylamine instead of a-methylbenzylamine.

¹H NMR 500 (CD₃OD) δ 7.30 (m, 1H), 7.02-7.22 (m, 9H), 5.23 (m, 1H), 4.63 (dd, 1H, J=1.3, 10 Hz), 4.25 (m, 3H), 3.86 (d, 1H, J=1.5 Hz), 3.40 (m, 1H), 3.26 (m, 2H), 2.97 (s, 2H), 2.71(m, 1H), 2.42 (s, 1H), 2.15 (m, 3H), 2.10 (s, 6H), 1.48 (m, 2H), 0.94 (d 6H, J=6 Hz). MS SEI m/z relative intensity: M+H, 601.1(100).

Example 27

This example illustrates the preparation of 7-(2-tert-butyl-phenoxy)-4-(1-{4-[2-(4-fluoro-phenyl)-ethylamino]-piperidine-1-carbonyl}-2-methyl-propyl)-3,4-dihydro-1H-benzo

[e][1,4]diazepine-2,5-dione. This compound was prepared similar to compound of Example 26 starting with 2-nitro-5-(2-tert-butylphenoxy)benzoic acid instead of 2-nitro-5-(2,6-dimethylphenoxy) benzoic acid.

$^1$H NMR 500 (CD$_3$OD) δ 7.53 (m, 1H), 7.45 (m, 2H), 7.39 (m, 2H), 7.33 (m, 1H), 7.08-7.19 (m, 4H), 6.81 (d, 1H, J=8 Hz), 5.26 (m, 1H), 4.89 (m, 1H), 4.70 (t, 1H, J=14 Hz), 4.50 (m, 1H), 4.25 (m, 1H), 3.91 (d, 1H, J=15 Hz), 3.61 (m, 1H), 3.21 (m, 1H), 3.02 (m, 1H), 2.78 (m, 1H), 2.60 (m, 1H), 2.45 (m, 1H), 2.23 (m, 3H), 1.58 (m, 2H), 1.39 (s, 9H), 1.00 (d, J=6 Hz, 3H), 0.92 (d, 3H, J=6 Hz). MS SEI m/z relative intensity: M+H, 629.3 (100).

Example 28

This example illustrates the preparation of 4-{1-[2-(1-cyclopropylmethyl-piperidin-4-yl)-ethyl]-2-methyl-propyl}-7-(2,6-difluoro-phenoxy)-3,4-dihydro-1H-benzo[e][1,4]diazepine-2,5-dione. This compound was prepared according to steps a-c of Example 21 substituting 2-nitro-5-(4-fluorophenoxy) benzoic acid with 2-nitro-5-(2,4-difluorophenoxy) benzoic acid in step a and using 1-[2-(1-benzyl-piperidin-4-yl)-ethyl]-2-methyl-propylamine instead of D-valine methyl ester in step b. 1-[2-(1-Benzyl-piperidine-4-yl)-ethyl]-2-methyl-propylamine was prepared according to the synthesis described in Example 1.

$^1$H NMR (500 MHz, CD$_3$OD) δ 7.35~7.28 (m, 2H), 7.21~7.12 (m, 4H), 4.30 (br. s, 1H), 3.88 (br. s, 1H), 3.75 (br. s, 1H), 3.63 (br. t, 2H), 2.99 (d, J=7.3 Hz, 2H), 2.93 (t, J=13.2 Hz, 2H), 1.96 (m, 2H), 1.88~1.79 (m, 2H), 1.60 (br. s, 1H), 1.46~1.08 (m, 5H), 1.04 (d, J=6.4 Hz, 3H), 0.86 (d, J=6.4 Hz, 3H), 0.76 (dt, J=7.8, 5.9 Hz, 2H), 0.42 (dt, J=4.9, 4.9 Hz, 2H); LRMS (ESI) m/z: calculated for C$_{30}$H$_{38}$F$_2$N$_3$O$_3$ (free base; M+H) 526.64, found 526.64.

Example 29

This example illustrates the preparation of 7-(2-ethyl-phenoxy)-4-{1-[4-(4-fluoro-benzylamino)-piperidine-1-carbonyl]-2-methyl-propyl}-3,4-dihydro-1H-benzo[e][1,4]diazepine-2,5-dione. This compound was prepared similarly to Example 26 starting with 2-nitro-5-(2-ethylphenoxy) benzoic acid instead of 2-nitro-5-(2,6-dimethylphenoxy) benzoic acid.

$^1$H NMR 500 (CD$_3$OD) δ 7.67 (m, 1H), 7.59 (m, 1H), 7.55 (m, 2H), 7.40 (s, 1H), 7.35 (m, 1H), 7.31 (d, 1H, J=3 Hz), 7.23 (m, 3H), 7.16 (m, 2H), 6.91 (dd, 1H, J=6, 16 Hz), 5.12 (m, 1H), 4.78 (dd, 1H, J=2, 10 Hz), 4.25 (d, 2H, J=16 Hz), 3.92 (d, 1H, J=3 Hz), 3.38 (s, 1H), 3.17 (t, 1H, J=2.2 Hz), 2.60 (q, 1H, J=8 Hz), 2.6 6(q, 2H, J=12 Hz,), 2.19 (m, 1H), 2.21 (m, 2H), 1.48 (m, 2H), 1.20 (t, 3H, J=8 Hz), 0.97 (d, 3H, J=6 Hz), 0.92 (d 3H, J=6 Hz). MS SEI m/z relative intensity: M+H 587.5 (100).

Example 30

This example illustrates the preparation of 4-[1-(4-cyclopropylamino-piperidine-1-carbonyl)-2-methyl-propyl]-7-(2-ethyl-phenoxy)-3,4-dihydro-1H-benzo[e][1,4]diazepine-2,5-dione. This compound was prepared according to steps of Example 26 starting with 2-nitro-5-(2-tert-butylphenoxy) benzoic acid instead of 2-nitro-5-(2,6-dimethylphenoxy) benzoic acid.

$^1$H NMR 500 (CD$_3$OD) δ 7.39 (m, 1H), 7.36 (m, 1H), 7.24 (m, 1H), 7.12-7.19 (m, 3H), 6.92 (t, 1H, J=8 Hz), 5.11 (m, 1H), 4.78 (dd, 1H, J=2, 10 Hz), 4.18 (m, 1H), 3.92 (m, 1H), 3.42 (m, 1H), 3.10 (t, 1H, J=2.2 Hz), 2.76 (m, 2H), 2.66 (q, 2H, J=12 Hz), 2.37 (m, 1H), 2.19 (m, 2H), 1.40 (m, 2H), 1.30 (m, 1H), 1.20 (t, 3H, J=8 Hz), 1.05-0.84 (m, 11H), MS SEI m/z relative intensity: M+H, 519.4 (100).

Example 31

This example illustrates the preparation of 7-(2,4-difluorophenoxy)-4-[1-(3-dimethylaminomethyl-phenyl)-2-methyl-propyl]-3,4-dihydro-1H-benzo[e][1,4]diazepine-2,5-dione. This compound was prepared according to steps a-c of Example 20 by starting with 2-nitro-5-(2,4-difluorophenoxy) benzoic acid instead of 2-nitro-5-(4-difluorophenoxy) benzoic acid in Step a and substituting amine A10 for D-valine ester in Step b. The product from Step b was converted to the title compound by removing the Boc protecting group followed by a methylation step.

$^1$H NMR (500 MHz, CD$_3$Cl) δ 9.28 (br, 1H), 6.89-7.50 (m, 10H), 5.53 (d, J=10 Hz,1H), 4.00 (br, 2H), 3.76 (d, J=14 Hz, 1H), 3.64 (d, J=14 Hz,1H), 2.30 (s, 6H), 2.18 (m, 1H), 1.10 (d, J=5.0 Hz, 3H), 0.88 (d, J=5.0 Hz, 3H). ESI (MH$^+$) m/z 494.

Example 32

This example illustrates the preparation of 7-(2,4-difluorophenoxy)-4-{1-[3-(isopropylamino-methyl)-phenyl]-2-methyl-propyl}-3,4-dihydro-1H-benzo[e][1,4]diazepine-2,5-dione. This compound was prepared according to steps a-c of Example 20 by starting with 2-nitro-5-(2,4-difluorophenoxy) benzoic acid instead of 2-nitro-5-(4-difluorophenoxy) benzoic acid in step a and substituting amine A10 for D-valine ester in Step b. The product from Step b was converted to the title compound by a standard Boc-deprotection followed by reductive amination with acetone and sodium triacetoxyborohydride.

$^1$H NMR (400 MHz, CD$_3$Cl) δ 8.99 (br, 1H), 6.90-7.50 (m, 10H), 5.51 (d, J=10 Hz,1H), 3.95 (br, 2H), 3.75 (d, J=14 Hz, 1H), 3.66 (d, J=14 Hz,1H), 3.10 (m, 1H), 2.50 (m, 1H) 2.18 (m, 1H), 1.10 (d,J=5.0 Hz, 3H), 1.00 (d,J=4.8 Hz, 6H) 0.88 (d, J=5.0 Hz, 3H). ESI (MH+) m/z 508.

Example 33

This example illustrates the preparation of 2-(2,5-dioxo-7-phenoxy-1,2,3,5-tetrahydrobenzo[e][1,4]diazepin-4-yl)-3-methyl-butyric acid 1-benzyl-piperidin-4-yl ester. This compound was prepared according to steps a-d of Example 20 using 4-hydroxy-1-benzylpiperidine instead of 4-amino-1-benzylpiperidine in step d.

$^1$H NMR (500 MHz, MeOD) δ 7.50-7.59 (m, 9H), 7.39-7.47 (m, 4H), 7.28 (m, 1H), 7.14-7.24 (m, 3H), 7.05-7.08 (m, 2H), 5.2 (s, 1H), 4.00-4.35 (m, 4H), 3.8-3.6 (m, 2H), 3.19-3.31 (m, 1H), 3.08 (m, 1H), 2.33-2.50 (m, 3H), 2.00-2.21 (m, 2H), 1.85 (m, 1H), 1.11 (d, J=7 Hz, 3H), 0.96 (d, J=7 Hz, 3H),; Analytical HPLC Method A@220 nm: rt =7.583 min.; ESI (MH$^+$) m/z 542.

Example 34

This example illustrates the preparation of N-(1-benzyl-piperidin-4-yl)-2-(2,5-dioxo-7-phenoxy-1,2,3,5-tetrahydro-benzo[e][1,4]diazepin-4-yl)-3-methyl-butyramide. This compound was prepared according to steps a-e of Example 20 starting with 2-nitro-5-phenoxy-benzoic acid instead of 2-nitro-5-(4-fluorophenoxy)-benzoic acid in step a, and substituting threonine methyl ester for valine methyl ester in step b. $^1$H NMR (500 MHz, CDCl$_3$) δ 9.01 (br, 1H), 7.29-7.60 (m, 7H), 6.95-7.13 (m, 7H), 5.10 (m, 1H), 4.42 (m, 1H), 4.08-4.30 (m, 3H), 3.90 (m, 2H), 3.21-3.40 (m, 2H), 2.60-3.10 (m, 6H) 1.85-2.10(m, 4H). ESI (MH$^+$) m/z 543.

Example 35

This example illustrates the preparation of 7-(2-tert-butylphenoxy)-4-[1-(4-cyclopropylamino-piperidine-1-carbonyl)-2-methyl-propyl]-3,4-dihydro-1H-benzo[e][1,4]diazepine-2,5-dione. This compound was prepared according to steps a-e of Example 20 starting with 2-nitro-5-(2-tert-butylphenoxy)-benzoic acid instead of 2-nitro-5-(4-fluorophenoxy)-benzoic acid in step a. $^1$H NMR 500 (CD$_3$OD) d 7.39 (m, 1H), 7.36 (m, 1H), 7.24 (m, 1H), 7.12-7.19 (m, 3H), 6.92 (t, 1H, J=8 Hz), 5.11 (m, 1H), 4.7 8(dd, 1H, J=2, 10 Hz), 4.18 (m, 1H), 3.92 (m, 1H), 3.42 (m, 1H), 3.10 (t, 1H, J=2.2 Hz), 2.76 (m, 2H), 2.66 (q, 2H, J=12 Hz), 2.19 (m, 2H), 1.40 (m, 2H), 1.30 (m, 1H), 1.20 (t, J=8 Hz, 3H), 1.05(s, 9H), 1.02-0.84 (m, 5H). MS SEI m/z relative intensity: [M+H]+ at 547.

Example 36

This example illustrates the preparation of N-(1-benzyl-piperidin-4-yl)-2-(2,5-dioxo-7-phenoxy-1,2,3,5-tetrahydro-benzo[e][1,4]diazepin-4-yl)-2-thiophen-2-yl-acetamide. This compound was prepared according to steps a-e of Example 20 starting with 2-nitro-5-phenoxy-benzoic acid instead of 2-nitro-5-(4-fluorophenoxy)-benzoic acid in step a, and using 2-thiophenylglycine methyl ester instead of D-valine methyl ester in step b. $^1$H NMR (400 MHz, CDCl$_3$) δ 8.40 (br, 1H), 7.68 (d, J=8.0 Hz, 1H), 6.80-7.52 (m, 16H), 5.89 (s, 1H), 4.58 (m, 1H), 4.28-4.38 (m, 2H), 4.05 (m, 1H), 3.85 (m, 1H), 3.60-3.70 (m, 2H), 2.50-2.60 (m, 2H) 1.40-2.05 (m, 4H). ESI (MH$^+$) m/z 581.

Example 37

This example illustrates the preparation of N-(1-benzyl-piperidin-4-yl)-2-cyclohexyl-2-(2,5-dioxo-7-phenoxy-1,2,3,5-tetrahydro-benzo[e][1,4]diazepin-4-yl)-acetamide. This compound was prepared according to steps a-d of Example 20 starting with 2-nitro-5-phenoxy-benzoic acid instead of 2-nitro-5-(4-fluorophenoxy)-benzoic acid in step a, and using cyclohexylglycine methyl ester instead of D-valine methyl ester in step b. $^1$H NMR (400 MHz, CDCl$_3$) δ 8.70 (br, 1H), 7.60 (d, J=8.0 Hz, 1H), 7.00-7.50 (m, 13H), 5.15 (m, 1H), 4.67 (m, 1H), 4.29-4.36 (m, 2H), 4.10 (m, 1H), 3.95 (m, 1H), 3.63-3.74 (m, 2.50-2.62 (m, 3H) 1.40-2.15(m, 4H), 1.25-1.38 (m, 10H). ESI (MH$^+$) m/z 581

Example 38

This example illustrates the preparation of (1-benzyl-piperidin-4-yl)-carbamic acid 2-[7-(4-fluoro-phenoxy)-2,5-dioxo-1,2,3,5-tetrahydro-benzo[e][1,4]diazepin-4-yl]-3-methyl-butyl ester. Alcohol 63 was obtained according to steps a-e described in Example 21.

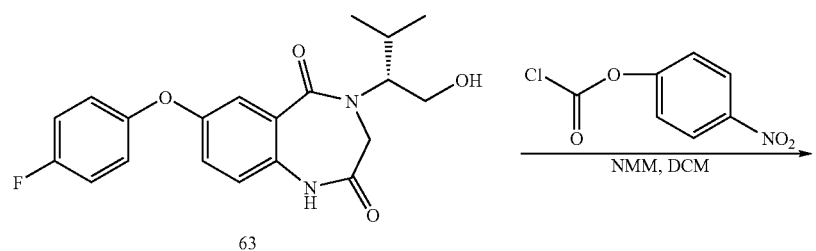

63

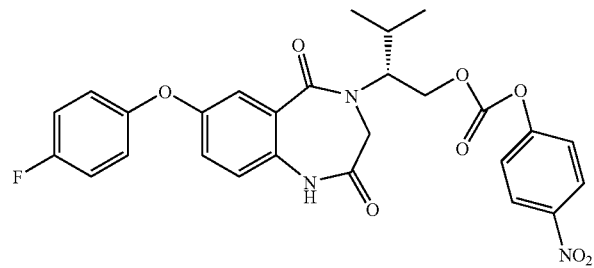

69

Alcohol 63 (0.11 g, 0.3 mmol) in DCM (1 mL) was treated with p-nitrophenylchloroformate (0.12 g, 0.6 mmol.) and 4-methylmorpholine (0.12 g, 1.2 mmol) for 3 h at 0° C., then the reaction was quenched with sodium bicarbonate and extracted with EtOAc. The organic layer was washed with sodium bicarbonate and brine, dried and concentrated to yield 0.15 g carbonate 69, which was allowed to react with 4-amino-1-benylpiperidine to yield the title compound.

Example 39

This example illustrates the preparation of N-(1-Benzyl-piperidin-4-yl)-2-(2,5-dioxo-7-phenoxy-1,2,3,5-tetrahydro-benzo[e][1,4]diazepin-4-yl)-3,3-dimethyl-butyramide. This compound was prepared according to steps a-e of Example 20 using tert-butylglycine methyl ester instead of D-valine methyl ester. $^1$H NMR 500 (CD$_3$OD) δ 7.39 (m, 1H), 7.36 (m, 1H), 7.24 (m, 1H), 7.12-7.19 (m, 3H), 6.92 (t, 1H, J=8 Hz), 5.11 (m, 1H), 4.78(dd, 1H, J=2, 10 Hz), 4.18 (m, 1H), 3.92 (m, 1H), 3.42 (m, 1H), 3.10 (t, 1H, J=2.2 Hz), 2.76 (m, 2H), 2.66 (q, 2H, J=12 Hz), 2.19 (m, 2H), 1.40 (m, 2H), 1.30 (m, 1H), 1.20 (t, J=8 Hz, 3H), 1.05(s, 9H), 1.02-0.84 (m, 5H). MS SEI m/z relative intensity: [M+H]+ at 547.

Example 40

This example illustrates the preparation of N-(1-benzyl-piperidin-4-yl)-2-[8-(4-fluoro-2-methyl-phenoxy)-1-methyl-6-oxo-4H,6H-3,5,10b-triaza-benzo[e]azulen-5-yl]-3-methyl-butyramide. Compound 70 was prepared according to steps a-c of Example 20 using 2-nitro-5-(4-fluoro-2-methyl-phenoxy)-benzoic acid instead of 2-nitro-5-(4-fluorophenoxy)-benzoic acid.

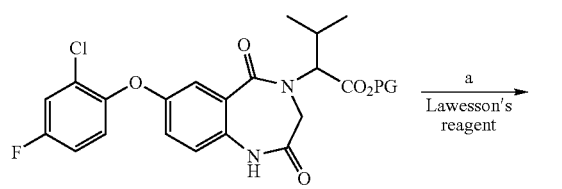

70

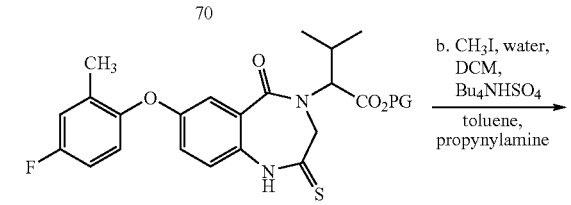

71

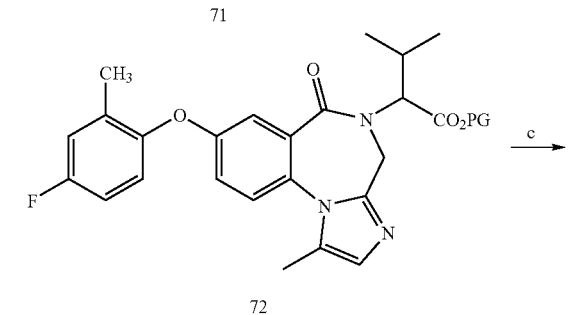

72

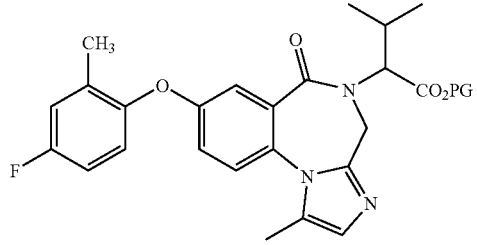

73

Step a. The mixture of 70 (0.2 g, 0.48 mmol) and Lawesson's reagent (0.2 g, 0.48 mmol) in THF (2 mL) was stirred at 50° C. for 3 h. The reaction was concentrated, then purified by flash chromatography on silica gel eluted with 30% EtOAc/hexane to yield 0.2 g of compound 71 as brown oil.

Step b. The mixture of compound 71 (0.13 g, 0.3 mmol.), methyl iodide (0.064 g, 0.453 mmol), water (1.5 mL), DCM (1.5 mL), 2 N sodium hydroxide (70 mL) and catalytic amount of tetrabutylammonium hydrogen sulfate was stirred at room temperature for 3 hours. The reaction was separated, aqueous layer was extracted with DCM, combined organic layers were dried, concentrated, and redissolved in toluene (3 mL). Propargyl amine (67 mg, 1.2 mmol, 4 equiv) and py.HCl (35 mg, 0.3 mmol, 1 equiv) were added into the mixture, the reaction was heated at 125° C. for 10 h, cooled to rt, concentrated, then purified by flash chromatography on silica gel eluted with 20% EtOAc/hexane to yield 0.1 g of 72 as brown oil.

Step c. Intermediate 72 was converted to the final compound following the procedures described in step d in Example 21. $^1$H NMR (400 MHz, CDCl$_3$) δ 7.51 (d, J=2.4 Hz,1H), 7.37 (m, 4H), 7.33 (s, 1H), 7.20 (d, J=7.2 Hz, 1H), 6.93-7.10 (m, 5H), 6.89 (s, 1 H), 5.21 (d, J=12.8 Hz, 1H), 4.61 (d, J=8.8 Hz, 1H), 4.04 (d, J=13.2 Hz, 1H), 3.83 (bd, 1 H), 3.61 (bd, 2H), 2.92 (bd, 1H), 2.34 (s, 3H), 2.30 (s, 1H), 2.26 (d, J=5.2 Hz, 4H), 1.98 (m, 3H), 1.68 (m, 3H), 0.97 (d, J=5.2 Hz, 3H), 0.49 (d, J=5.2 Hz, 3H). ESI (MH+) m/z 610.

Example 41

This example illustrates the preparation of cyclopropyl(6-vinylpyridin-2-yl)methanamine A20 from 6-Bromo-picolinic acid S19. Other cyclopropyl (vinylpyridine)methanamines can be easily prepared using the same scheme of synthesis making the necessary substitutions.

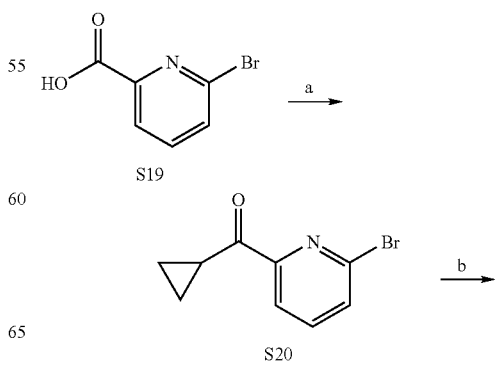

-continued

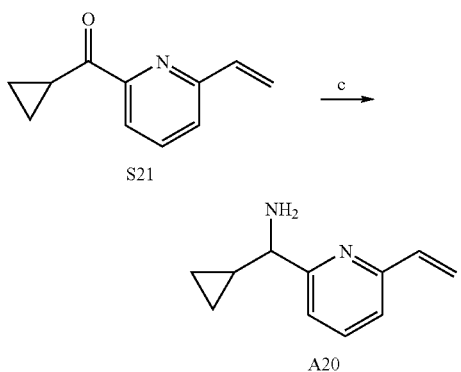

Step a. To a solution of 6-bromo-picolinic acid S19 (5.0 g, 24.7 mmol) in dry dichloromethane (150 ml) was added oxalyl chloride (4.3 ml, 49.4 mmol) and then slowly 0.5 ml of DMF. The reaction mixture was stirred at room temperature for three hours at which time the solvent was removed and the crude intermediate was temporarily set aside. A 0.5 M solution of cyclopropylmagnesium bromide (100 ml, 50.0 mmol) was added dropwise, over the course of 2 hours, to a solution of CuCN (3.23 g, 37.1 mmoles in 150 ml THF) at −78° C. A solution of the crude intermediate set aside (THF, 100 ml) was then added dropwise at −78° C. and stirred for 2 hours. The crude mixture was then diluted with dichloromethane (1000 mL) and extracted with brine (2×300 mL). The organic layer was concentrated and the crude intermediate was used in the next step with no further purification.

Step b. To a solution of Intermediate S20 (1.0 g, 4.4 mmol) in dry DMF (25 ml) was added tributyl(vinyl)tin (1.96 g, 6.2 mmol). The reaction was degassed with Nitrogen, $Pd(PPh_3)_2Cl_2$ (154 mg, 0.22 mmol) was added and placed under argon at 100° C. for 5 hours. The crude mixture was stirred with 10 ml of 0.5M NaOH for 10 minutes then diluted with EtOAc (200 mL) and extracted with brine (2×100 mL). The organic layer was concentrated, the crude material was loaded onto a silica gel column and eluted with 2% EtOAc in Hexane to give 640 mg of intermediate S21 as a light yellow oil. TLC, $R_f$=0.4 (10% EtOAc in Hexane); $^1$H NMR (400 mHz, $CDCl_3$) δ 7.88 (d, J=6.9, 1H), 7.75 (t, J=7.7, 1H), 7.47 (d, J=6.9, 1H), 6.87 (dd, J=10.7, 17.4, 1H), 6.34 (dd, J=1.2, 17.4, 1H), 5.53 (dd, J=1.2, 10.7, 1H), 3.62 (m, 1H), 1.22 (m, 2H), 1.09 (m, 2H), M+1 found 174.1; $C_{11}H_{11}NO$ requires 173.0

Step c. To a solution of intermediate S21 (1.2 g, 6.9 mmol) in MeOH/THF (40ml/10 ml) was added $NH_4OAc$ (2.6 g, 34 mmol) and $NaCNBH_3$ (2.1 g, 34 mmoles). The reaction was sealed in a high-pressure tube and heated at 90° C. for 16 hours. The crude mixture was diluted with a small quantity of water (50 mL) and extracted with dichloromethane (3×300 mL). The organic layer was concentrated, the crude material was loaded onto a silica gel column and eluted with 10% MeOH with 1% TEA in $CH_2Cl_2$ to give 996 mg of cyclopropyl(6-vinylpyridin-2-yl)methanamine A20 as a clear oil. TLC, $R_f$=0.3 (10% MeOH with 1% TEA in $CH_2Cl_2$); $^1$H NMR (400 mHz, Methanol-$D_4$) δ 7.81 (t, J=7.8, 1H), 7.44 (d, J=7.7, 1H), 7.37 (d, J=7.7, 1H), 6.88 (dd, J=10.8, 17.4, 1H), 6.43 (dd, J=1.4, 17.4, 1H), 5.53 (dd, J=1.4, 10.8, 1H), 3.77 (d, J=9.8, 1H), 1.26 (m, 1H), 0.84 (m, 1H), 0.73 (m, 1H), 0.64 (m, 2H), M +1 found 175.1; $C_{11}H_{14}N_2$ requires 174.0

Example 42

This example illustrates the preparation of product (R)-2-(cyclopropyl(6-vinylpyridin-2-yl)methyl)-7-(2,4-difluorophenoxy)-3,4-dihydroisoquinolin-1(2H)-one 74 from 5-(2,4-difluoro-phenoxy)-2-(2-ethoxy-vinyl)-benzoic acid methyl ester 9

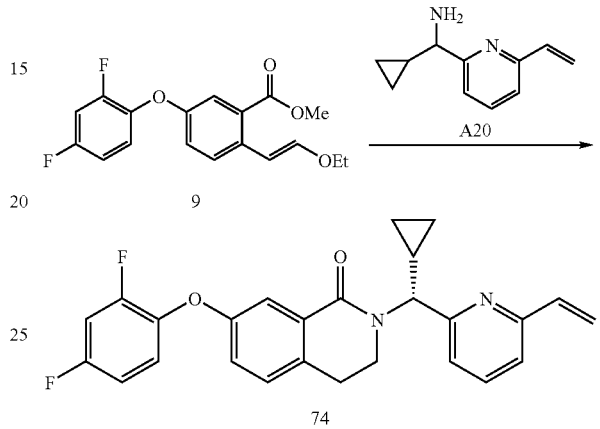

To the solution of 5-(2,4-difluoro-phenoxy)-2-(2-ethoxy-vinyl)-benzoic acid methyl ester 9 (2.09 g, 6.3 mmol) in dichloromethane (20 mL) was added 2 mL of TFA and five drops of water. The reaction was stirred at room temperature for ten minutes, at which time the solvent was removed. The crude reaction mixture was re-suspended in 100 ml of dichloromethane, extracted twice with 50 ml of saturated NaHCO3. The organic layer was dried with sodium sulfate and the solvent removed. The crude intermediate was re-suspended in 100 ml of dichloroethane and added drop wise to a 100 ml solution of dichloroethane containing cyclopropyl(6-vinylpyridin-2-yl)methanamine A20 (1.2 g, 6.9 mmol) and sodium triacetoxyborohydride (3.3 g, 15.7 mmol). The mixture was stirred at 70° C. during the drop wise addition and for additional 2 hours. The reaction was diluted with 500 mL dichloromethane and extracted with saturated brine (300 mL). The organic layer was concentrated and loaded onto a silica gel column and eluted with dichloromethane followed by separation of the enatiomers (AD-H column, 10% IPA/Hex) to give 115 mg of (R)-2-(cyclopropyl(6-vinylpyridin-2-yl)methyl)-7-(2,4-difluorophenoxy)-3,4-dihydroisoquinolin-1(2H)-one 74 as clear oil. The sterochemical configuration was assigned based on the compound 11 TLC, $R_f$=0.25 ($CH_2Cl_2$); $R_t$=20.2 min (45 min. run, AD-H chiral analalytical column, 1 ml/min, 5% IPA/Hex); $^1$H NMR (Methanol-$D_4$) δ 7.69 (t, J=7.6, 1H), 7.42 (s, 1H), 7.35 (d, J=7.5, 1H), 7.29 (d, J=7.6, 1H), 7.25 (d, J=8.3, 1H), 7.09 (m, 3H), 6.97 (m, 1H), 6.78 (dd, J=10.7, 17.4, 1H), 6.18 (d, J=17.4, 1H), 5.39 (d, J=10.7, 1H), 4.99 (d, J=10.1, 1H), 3.8 (m, 2H), 2.9 (m, 2H), 1.63 (m, 1H), 0.81 (m, 1H), 0.66 (m, 1H), 0.56 (m, 1H), 0.46 (m, 1H), M+1 found 433.1; $C_{26}H_{22}F_2N_2O_2$ requires 432.2

Example 43

This example illustrates the preparation of product (R)-2-(cyclopropyl(6-((cyclopropylmethylamino)methyl)pyridin- 2-yl)methyl)-7-(2,4-difluorophenoxy)-3,4-dihydroisoquino-lin-1(2H)-one 76 from (R)-2-(cyclopropyl(6-vinylpyridin-2-yl)methyl)-7-(2,4-difluorophenoxy)-3,4-dihydroisoquinolin-1 (2H)-one 74

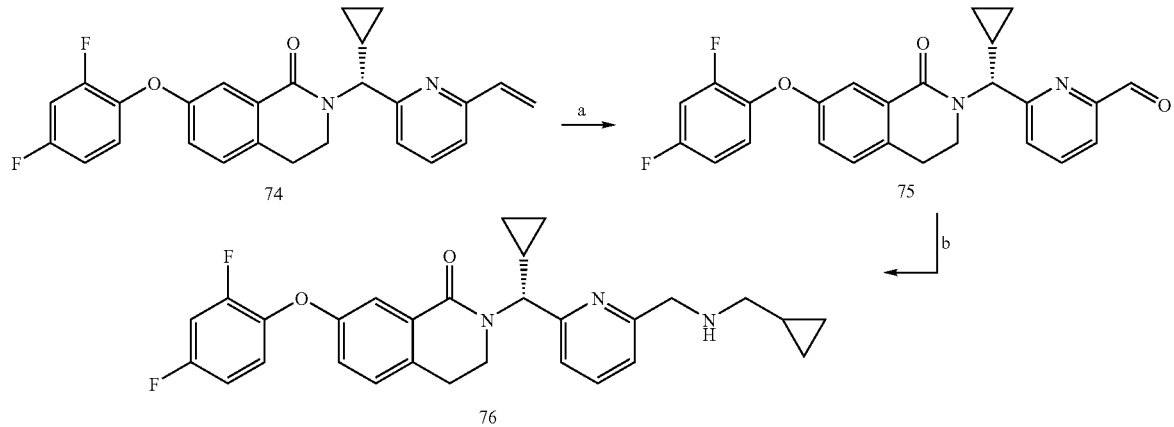

Step a. (R)-2-(cyclopropyl(6-vinylpyridin-2-yl)methyl)-7-(2,4-difluorophenoxy)-3,4-dihydroisoquinolin-1(2H)-one 74 (40 mg, 0.10 mmol) was dissolved in a 3:1 dioxane/water solution (5 mL) containing catalytic amount of $OsO_4$. After 10 min, the solution turned dark in color, $NaIO_4$ (36 mg, 0.34 mmol) was added. After 2 hours the reaction was completed, and the mixture was partitioned with water (50 mL) and ethyl acetate (50 mL). The organic layer was then washed with the saturated solution of $Na_2S_2O_3$, followed by brine, dried over $Na_2SO_4$, and concentrated to give intermediate 75. This material was used in the next step without purification.

Step b. $NaBH(OAc)_3$ (40 mg, 0.2 mmol) was added to a dichloroethane solution (5 mL) containing (aminomethyl)cyclopropane (13 mg, 0.2 mmol) and intermediate 75 (40 mg, 0.09 mmol). The reaction mixture was stirred at room temperature for 2 hours. After the reaction was complete the solvent was removed using evaporation, and the remaining residue was purified using preparative HPLC (C18 column, 10%-90% acetonitrile/water gradient) to provide 20 mg of (R)-2-(cyclopropyl(6-((cyclopropylmethylamino)methyl)pyridin-2-yl)methyl)-7-(2,4-difluorophenoxy)-3,4-dihydroisoquinolin-1 (2H)-one 76 as a white solid.

$^1$H NMR (400 MHz, Methanol-$D_4$) δ 7.77 (t, J=7.7 Hz, 1H), 7.50 (d, J=7.70 Hz, 1H), 7.43 (s, 1H), 7.27 (d, J=7.7 Hz, 2H), 7.10-7.28 (m, 3H), 6.98 (m, 1H), 5.01 (d, J=10.2, Hz, 1 H), 3.99 (s, 2H), 3.80 (m, 1H), 3.66 (m, 1H), 2.95 (m, 2H), 2.57 (m, 2H), 1.65 (m, 1H), 0.92 (m, 1H), 0.84 (m, 1H), 0.70 (m, 1H), 0.55 (m, 1H), 0.47 (m, 3H), 0.11 (m, 2H), M+1 found 490.1; $C_{29}H_{29}F_2N_3O_2$ requires 489.2

Example 44

This example illustrates the preparation of product (R)-2-(cyclopropyl(6-((cyclopropylamino)methyl)pyridin-2-yl)methyl)-7-(2,4-difluorophenoxy)-3,4-dihydroisoquinolin-1 (2H)-one 77 from (R)-2-(cyclopropyl(6-vinylpyridin-2-yl)methyl)-7-(2,4-difluorophenoxy)-3,4-dihydroisoquinolin-1 (2H)-one 74

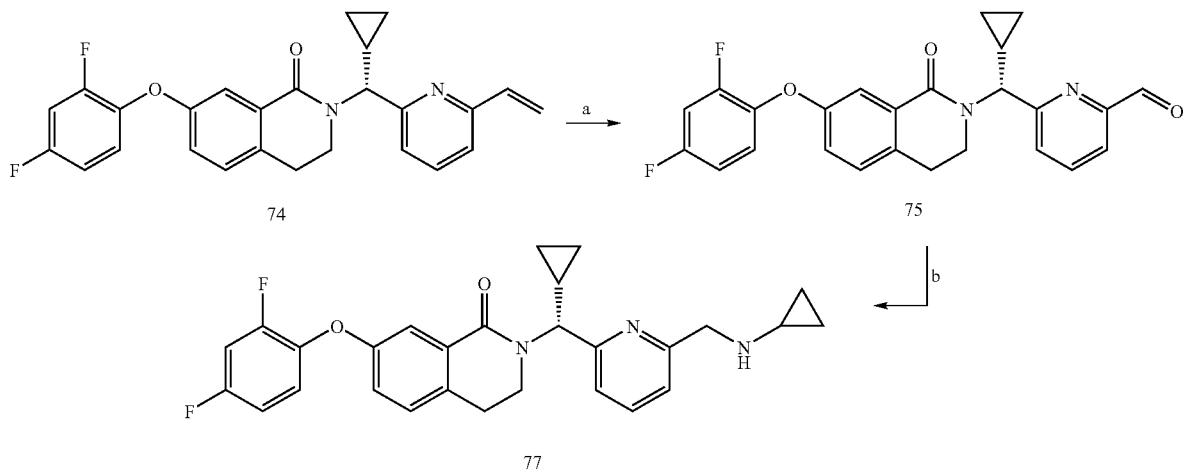

Step a. (R)-2-(cyclopropyl(6-vinylpyridin-2-yl)methyl)-7-(2,4-difluorophenoxy)-3,4-dihydroisoquinolin-1(2H)-one 74 (20 mg, 0.05 mmol) was dissolved in a 3:1 dioxane/water solution (5 mL) containing catalytic amount of $OsO_4$. After 10 min, the solution turned dark in color, $NaIO_4$ (18 mg, 0.17 mmol) was added. After 2 h the reaction was completed, and the mixture was partitioned with water (50 mL) and ethyl acetate (50 mL). The organic layer was then washed with the saturated solution of $Na_2S_2O_3$, followed by brine, dried over $Na_2SO_4$, and concentrated to give intermediate 75. This material was used in the next step without purification.

Step b. $NaBH(OAc)_3$ (20 mg, 0.1 mmol) was added to a dichloroethane (5 mL) solution containing aminocyclopropane (5.2 mg, 0.1 mmol) and intermediate 75 (20 mg, 0.05 mmol) at room temperature. After the reaction was complete the solvent was removed using evaporation, and the remaining residue was purified using preparative HPLC (C18 column, 10%-90% acetonitrile/water gradient) to provide 8.4 mg of (R)-2-(cyclopropyl(6-((cyclopropylamino)methyl)pyridin-2-yl)methyl)-7-(2,4-difluorophenoxy)-3,4-dihydroisoquinolin-1(2H)-one 77 as a white solid. $^1$H NMR (400 MHz, Methanol-$D_4$) δ 7.88 (t, J=7.8 Hz, 1H), 7.65 (d, J=7.8 Hz, 1H), 7.41 (m, 2H), 7.27 (d, J=8.3 Hz, 1H), 7.11-7.14 (m, 3H), 7.00 (m, 1H), 5.00 (d, J=10.4, Hz, 1H), 4.45 (s, 2H), 3.86 (m, 1H), 3.60 (m, 1H), 2.98 (m, 1H), 2.93 (m, 1H), 2.82 (m, 1H), 1.75 (m, 1H), 0.83 (m, 5H), 0.72 (m, 1H), 0.50 (m, 2H), M+1 found 476.2; $C_{28}H_{27}F_2N_3O_2$ requires 475.2

Example 45

This example illustrates the preparation of product 2-((R)-cyclopropyl(6-(((R)-1-hydroxypropan-2-ylamino)methyl)pyridin-2-yl)methyl)-7-(2,4-difluorophenoxy)-3,4-dihydroisoquinolin-1(2H)-one 78 from (R)-2-(cyclopropyl(6-vinylpyridin-2-yl)methyl)-7-(2,4-difluorophenoxy)-3,4-dihydroisoquinolin-1 (2H)-one 74

Step a. (R)-2-(cyclopropyl(6-vinylpyridin-2-yl)methyl)-7-(2,4-difluorophenoxy)-3,4-dihydroisoquinolin-1(2H)-one 74 (470 mg, 1.1 mmol) was dissolved in a 3:1 dioxane/water solution (20 mL) containing catalytic amount of $OsO_4$ (69 mg, 0.27 mmoles). After 10 min, the solution turned dark in color, $NaIO_4$ (933 mg, 4.4 mmol) was added. After 2 hours the reaction was completed, and the mixture was partitioned with water (200 mL) and ethyl acetate (200 mL). The organic layer was then washed with the saturated solution of $Na_2S_2O_3$, followed by brine, dried over $Na_2SO_4$, and concentrated to give intermediate 75. This material was used in the next step without purification. Step b. $NaBH(OAc)_3$ (203 mg, 0.96 mmol) was added to a dichloroethane (10 mL) solution containing (R)-2-aminopropan-1-ol (48 mg, 0.64 mmol) and intermediate 75 (140 mg, 0.32 mmol) 60° C. for 4 hours. The crude mixture was diluted with dichloromethane (300 mL) and extracted with 100 ml of water. The organic layer was concentrated, the crude material was loaded onto a silica gel column and eluted with 10% MeOH with 1% TEA in $CH_2Cl_2$ to give 100 mg of 2-((R)-cyclopropyl(6-(((R)-1-hydroxypropan-2-ylamino)methyl)pyridin-2-yl)methyl)-7-(2,4-difluorophenoxy)-3,4-dihydroisoquinolin-1 (2H)-one 78 as a white solid. TLC, Rf=0.27 (10% MeOH with 1% TEA in $CH_2Cl_2$): 1H NMR (400 MHz, Methanol-D4) δ 7.94 (t, J=7.8 Hz, 1H), 7.67 (d, J=7.8 Hz, 1H), 7.47 (d, J=7.0 Hz, 1H), 7.40 (d, J=2.6 Hz, 1H), 7.28 (d, J=8.3 Hz, 1H), 7.11-7.14 (m, 3H), 7.00 (m, 1H), 4.95 (d, J=10.3, Hz, 1 H), 4.46 (d, J=9.6 Hz, 1H), 4.44 (d, J=9.6 Hz, 1H), 3.95 (m, 1H), 3.79 (dd, J=11.8 Hz, 1H), 3.71 (m, 1H), 3.55 (dd, J=6.4, 11.8 Hz, 1H), 3.40 (m, 1H), 2.99 (m, 2H), 2.73 (m, 1H), 1.29 (d, J=6.7 Hz,

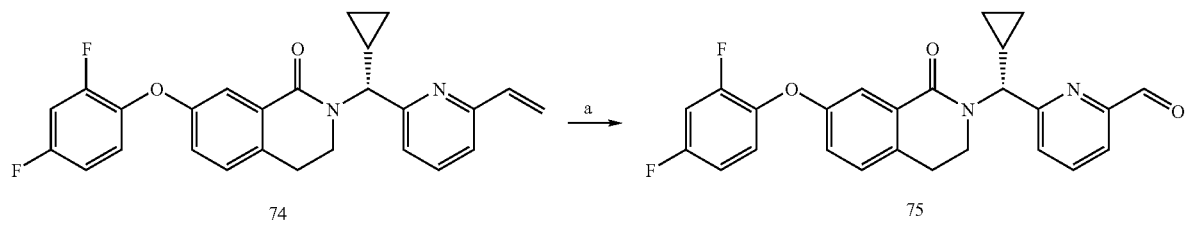

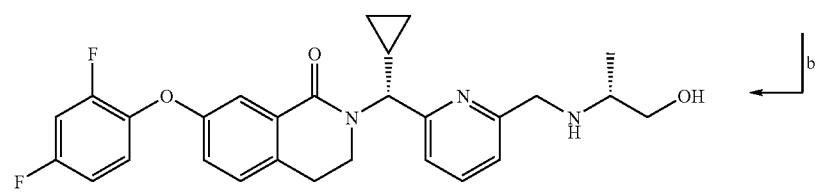

3H), 0.84 (m, 1H), 0.74 (m, 1H), 0.51 (m, 1H), 0.51 (m, 1H), M+1 found 494.1; C28H29F2N3O2 requires 493.2.

Example 46

This example illustrates the preparation of product (R)-2-(cyclopropyl(6-((1-hydroxy-2-methylpropan-2-ylamino)methyl)pyridin-2-yl)methyl)-7-(2,4-difluorophenoxy)-3,4-dihydroisoquinolin-1(2H)-one 79 from (R)-2-(cyclopropyl(6-vinylpyridin-2-yl)methyl)-7-(2,4-difluorophenoxy)-3,4-dihydroisoquinolin-1 (2H)-one 74 ylpropan-1-ol (10.2 mg, 0.12 mmol) and intermediate 75 (25 mg, 0.06 mmol) 60° C. for 4 hours. The crude mixture was diluted with dichloromethane (100 mL) and extracted with 50 ml of water. The organic layer was concentrated, the crude material was loaded onto a silica gel column and eluted with 10% MeOH with 0.5% TEA in CH$_2$Cl$_2$ to give 15.3 mg of (R)-2-(cyclopropyl(6-((1-hydroxy-2-methylpropan-2-ylamino)methyl)pyridin-2-yl)methyl)-7-(2,4-difluorophenoxy)-3,4-dihydroisoquinolin-1(2H)-one 79 as a light yellow solid. TLC, R$_f$=0.22 (10% MeOH with 0.5% TEA in

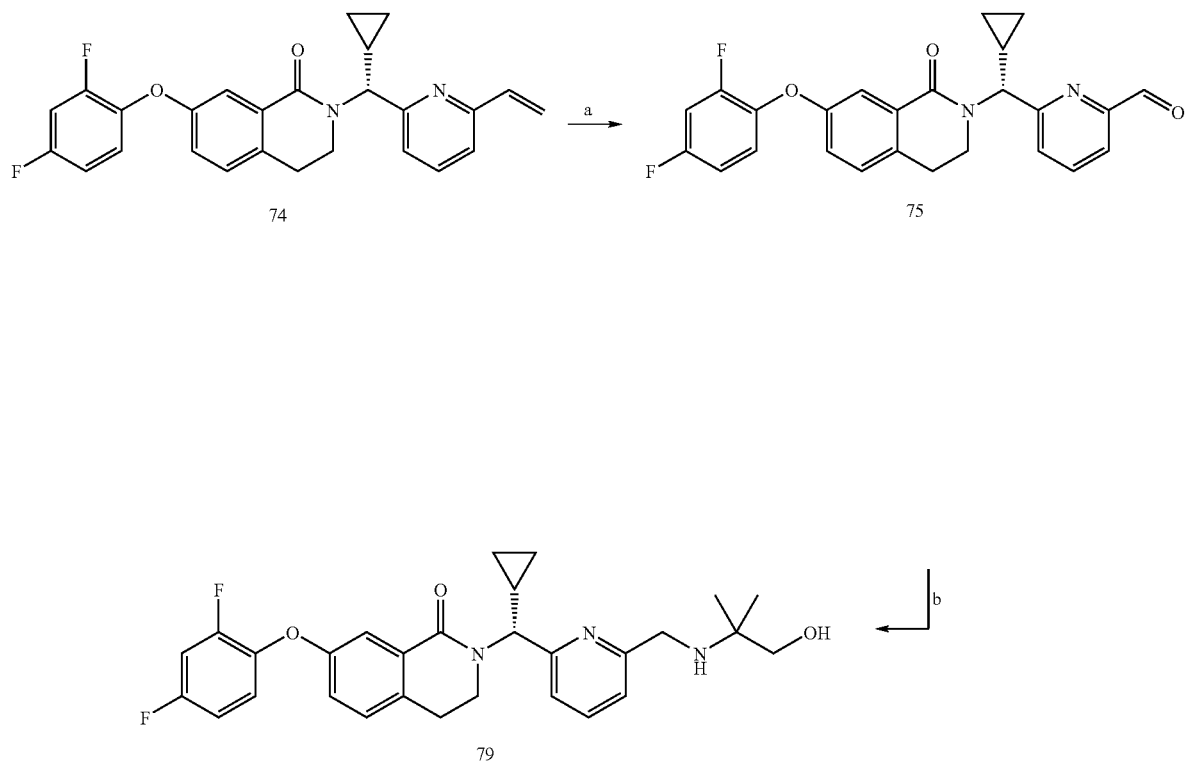

Step a. (R)-2-(cyclopropyl(6-vinylpyridin-2-yl)methyl)-7-(2,4-difluorophenoxy)-3,4-dihydroisoquinolin-1(2H)-one 74 (470 mg, 1.1 mmol) was dissolved in a 3:1 dioxane/water solution (20 mL) containing catalytic amount of OSO4 (69 mg, 0.27 mmoles). After 10 min, the solution turned dark in color, NaIO$_4$ (933 mg, 4.4 mmol) was added. After 2 hours the reaction was completed, and the mixture was partitioned with water (200 mL) and ethyl acetate (200 mL). The organic layer was then washed with the saturated solution of Na$_2$S$_2$O$_3$, followed by brine, dried over Na$_2$SO$_4$, and concentrated to give intermediate 75. This material was used in the next step without purification.

Step b. NaBH(OAc)$_3$ (36.6 mg, 0.17 mmol) was added to a dichloroethane (3 mL) solution containing 2-amino-2-meth- CH$_2$Cl$_2$): $^1$H NMR (400 MHz, Methanol-D$_4$) δ 7.72 (t, J=7.7 Hz, 1H), 7.41 (m, 2H), 7.27 (d, J=8.4 Hz, 2H), 7.20 (m, 1H), 7.11-7.12 (m, 2H), 6.98 (m, 1H), 4.97 (d, J=10.1, Hz, 1H), 3.84 (m, 4H), 3.38 (s, 2H), 2.99 (m, 2H), 1.64 (m, 1H), 1.11 (s, 6H), 0.81 (m, 1H), 0.69 (m, 1H), 0.56 (m, 1H), 0.46 (m, 1H), M+1 found 508.1; C$_{29}$H$_{31}$F$_2$N$_3$O$_2$ requires 507.2

Example 47

This example illustrates the preparation of product (R)-2-(cyclopropyl(6-((2-fluoroethylamino)methyl)pyridin-2-yl)methyl)-7-(2,4-difluorophenoxy)-3,4-dihydroisoquinolin-1(2H)-one 80 from (R)-2-(cyclopropyl(6-vinylpyridin-2-yl)methyl)-7-(2,4-difluorophenoxy)-3,4-dihydroisoquinolin-1(2H)-one 74

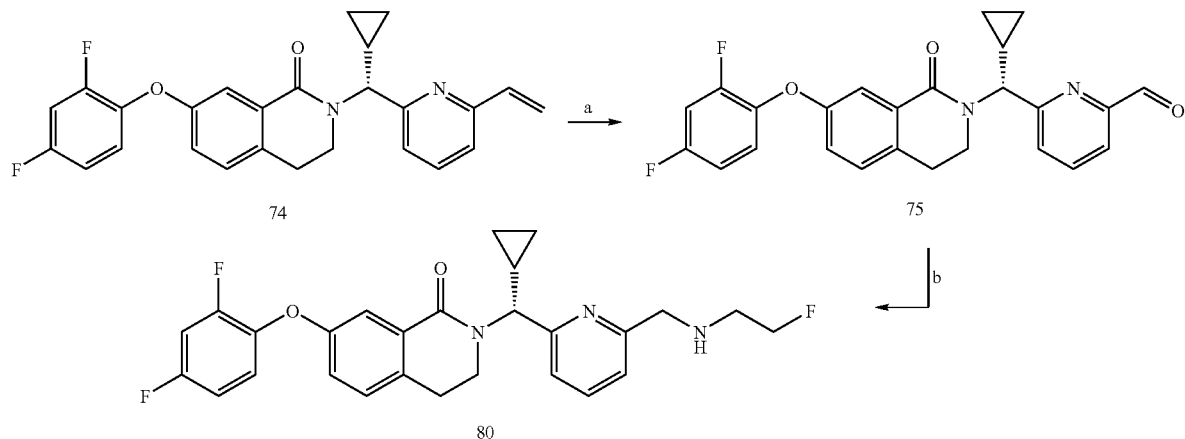

Step a. (R)-2-(cyclopropyl(6-vinylpyridin-2-yl)methyl)-7-(2,4-difluorophenoxy)-3,4-dihydroisoquinolin-1 (2H)-one 74 (470 mg, 1.1 mmol) was dissolved in a 3:1 dioxane/water solution (20 mL) containing catalytic amount of OSO4 (69 mg, 0.27 mmoles). After 10 min, the solution turned dark in color, NaIO$_4$ (933 mg, 4.4 mmol) was added. After 2 hours the reaction was completed, and the mixture was partitioned with water (200 mL) and ethyl acetate (200 mL). The organic layer was then washed with the saturated solution of Na$_2$S$_2$O$_3$, followed by brine, dried over Na$_2$SO$_4$, and concentrated to give intermediate 75. This material was used in the next step without purification.

Step b. NaBH(OAc)$_3$ (115 mg, 0.54 mmol) was added to a dichloroethane (4 mL) solution containing 2-fluoroethylamine HCl (36mg, 0.36 mmol), DIEA (64 µl, 0.36 mmoles) and intermediate 75 (80 mg, 0.18 mmol) 60° C. for 4 hours. The crude mixture was diluted with dichloromethane (100 mL) and extracted with 50 ml of water. The organic layer was concentrated, the crude material was loaded onto a silica gel column and eluted with 2% MeOH in CH$_2$Cl$_2$ to give 42 mg of (R)-2-(cyclopropyl(6-((2-fluoroethylamino)methyl) pyridine-2-yl)methyl)-7-(2,4-difluorophenoxy)-3,4-dihydroisoquinolin-1(2H)-one 80 as a white solid. TLC, R$_f$=0.23 (2% MeOH in CH$_2$Cl$_2$): $^1$H NMR (400 MHz, Methanol-D$_4$) δ 7.72 (t, J=7.7 Hz, 1H), 7.42 (m, 2H), 7.26 (d, J=8.1 Hz, 2H), 7.20 (m, 1H), 7.11-7.12 (m, 2H), 6.98 (m, 1H), 4.98 (d, J=10.2, Hz, 1H), 4.46 (dd, J=4.8, 47.6 Hz, 2H), 3.88 (s, 2H), 3.80 (m, 1H), 3.72 (m, 1H), 2.95 (m, 2H), 2.85 (dd, J=4.8, 27.9 Hz, 2H), 2.70 (m, 1H), 0.81 (m, 1H), 0.68 (m, 1H), 0.55 (m, 1H), 0.46 (m, 1H), M+1 found 482.1; C$_{27}$H$_{26}$F$_3$N$_3$O$_2$ requires 481.2

Example 48

This example illustrates the preparation of product (R)-2-(cyclopropyl(6-((2,2-difluoroethylamino)methyl)pyridin-2-yl)methyl)-7-(2,4-difluorophenoxy)-3,4-dihydroisoquinolin-1(2H)-one 81 from (R)-2-(cyclopropyl(6-vinylpyridin-2-yl)methyl)-7-(2,4-difluorophenoxy)-3,4-dihydroisoquinolin-1(2H)-one 74

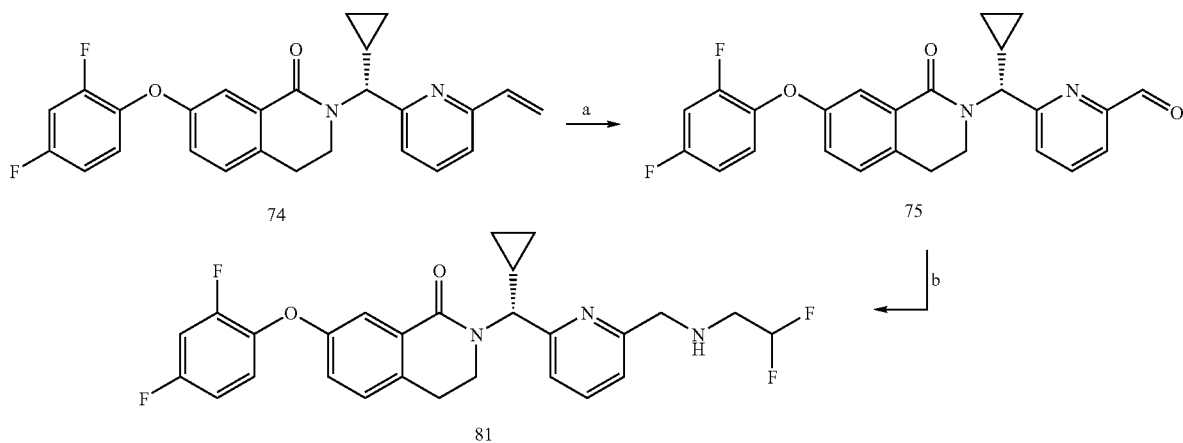

Step a. (R)-2-(cyclopropyl(6-vinylpyridin-2-yl)methyl)-7-(2,4-difluorophenoxy)-3,4-dihydroisoquinolin-1(2H)-one 74 (470 mg, 1.1 mmol) was dissolved in a 3:1 dioxane/water solution (20 mL) containing catalytic amount of OSO$_4$ (69 mg, 0.27 mmoles). After 10 min, the solution turned dark in color, NaIO$_4$ (933 mg, 4.4 mmol) was added. After 2 hours the reaction was completed, and the mixture was partitioned with water (200 mL) and ethyl acetate (200 mL). The organic layer was then washed with the saturated solution of $Na_2S_2O_3$, followed by brine, dried over $Na_2SO_4$, and concentrated to give intermediate 75. This material was used in the next step without purification.

Step b. $NaBH(OAc)_3$ (117 mg, 0.55 mmol) was added to a dichloroethane (4 mL) solution containing 2,2-difluoroethylamine (90 mg, 1.1 mmol) and intermediate 75 (120 mg, 0.28 mmol) 60 C for 4 hours. The crude mixture was diluted with dichloromethane (100 mL) and extracted with 50 ml of water. The organic layer was concentrated, the crude material was loaded onto a silica gel column and eluted with 2% MeOH in $CH_2Cl_2$ to give 95 mg of (R)-2-(cyclopropyl(6-((2,2-difluoroethylamino) methyl)pyridin-2-yl)methyl)-7-(2,4-difluorophenoxy)-3,4-dihydroisoquinolin-1(2H)-one 81 as a light yellow oil. TLC, $R_f$=0.25 (2% MeOH in $CH_2Cl_2$): $^1H$ NMR (400 MHz, Methanol-$D_4$) δ 7.73 (t, J=7.7 Hz, 1H), 7.42 (m, 2H), 7.26 (d, J=8.2 Hz, 2H), 7.20 (m, 1H), 7.09-7.12 (m, 2H), 6.98 (m, 1H), 5.86 (dd, J=4.3, 56.2 Hz, 1H), 4.99 (d, J=10.2, Hz, 1H), 3.90 (s, 2H), 3.82 (m, 1H), 3.72 (m, 1H), 2.93 (m, 4H), 2.60 (m, 1H), 0.81 (m, 1H), 0.68 (m, 1H), 0.54 (m, 1H), 0.47 (m, 1H), M+1 found 500. 1; $C_{27}H_{25}F_4N_3O_2$ requires 499.2

Example 49

Ghrelin Receptor Competitive Binding Assay

To determine the compounds' affinity to GHSR1a, competitive membrane binding assays were performed. Stable CHO cells expressing human GHSR1a were grown, their membranes were isolated and the isolated membranes were used in the binding assay. Reaction mixtures (200 μL) containing binding buffer (50 mM Tris-HCl, pH 7.4, 10 mM NaCl, 10 mM $MgCl_2$, 1 mM EDTA, 0.2% BSA, 30 μg/ml bacitracin, protease inhibitor cocktail), membrane (10 μg), [$^{125}I$]-ghrelin (0.1 nM), and testing compound dilutions were incubated at room temperature for 60 minutes. The membrane-ligand complex was harvested onto a filter plate using a cell harvester and washed 4 times with washing buffer (50 mM Tris-buffer, pH 7.4, 10 mM $MgCl_2$, 1 mM EDTA, 0.015% Triton X-100). Scintillation solution was added to the plate containing the retained membrane-ligand complex and read in a Parkard TopCount. Ki of each compound were calculated with Prism 4. [$^{125}I$]-ghrelin (2200 Ci/mmol) was purchased from PerkinElmer.

Aequorin Assay $IC_{50}$ values of inventive compounds may be assessed as follows. An aequorin (Euroscreen) luminescent assay (Stabels et al., 1997) measuring the intracellular $Ca^{2+}$ concentration was used as the functional assay to evaluate the potency of the compounds. A stable cell line, expressing human GHSR1a and apoaequorin in mitochondria was used in the aequorin assay. $5 \times 10^6$ cells per mL were incubated at room temperature in HyClone Media (Perbio) supplemented with 2 μM coelenterazine (Molecular Probes). After 2 hrs cells were diluted to $1 \times 10^6$ cells per ml in HyClone Medium.

50 μL of the cell suspension was added to each well of a 96-well plate containing 50 μL of compound, diluted in HyClone Medium. The cell suspension/compound mixture was incubated for 30 seconds before 50 μL of a 9× $EC_{50}$ concentrations of a human ghrelin solution, in HyClone Medium, was injected. The final Ghrelin concentration was $3 \times EC_{50}$ (20 nM). Aequorin luminescence elicited by intracellular $Ca^{2+}$ in the cells was recorded for a total of 60 seconds with a microplate luminometer (Microlumate, Berthold). $IC_{50}$ of the compounds in this assay was calculated with Prism 4.

Exemplary compounds of the invention having useful activity as measured by $K_i$ and $IC_{50}$ are shown in Table 1. All compounds were divided in four classes based on their $IC_{50}$ values. The range of the IC50 in each class is as follows:

| Class I:   | $IC_{50} \leq 10$ nM              |
|------------|-----------------------------------|
| Class II:  | $10$ nM $\leq IC_{50} \leq 50$ nM |
| Class III: | $50$ nM $\leq IC_{50} \leq 500$ nM |

TABLE 1

| Compound | Class |
|---|---|
| N-(1-Benzyl-piperidin-4-yl)-2-(2,5-dioxo-7-phenoxy-1,2,3,5-tetrahydro-benzo[e][1,4]diazepin-4-yl)-3-methyl-butyramide | I |
| N-(1-Benzyl-piperidin-4-yl)-2-(2,5-dioxo-7-phenoxy-1,2,3,5-tetrahydro-benzo[e][1,4]diazepin-4-yl)-3,3-dimethyl-butyramide | I |
| 2-[7-(2,6-Dimethyl-phenoxy)-2,5-dioxo-1,2,3,5-tetrahydro-benzo[e][1,4]diazepin-4-yl]-3-methyl-N-[1-(1-phenyl-ethyl)-piperidin-4-yl]-butyramide | I |
| 2-[7-(2,6-Dimethyl-phenoxy)-2,5-dioxo-1,2,3,5-tetrahydro-benzo[e][1,4]diazepin-4-yl]-N-(1-indan-1-yl-piperidin-4-yl)-3-methyl-butyramide | I |
| 4-{1-[2-(1-Cyclopropylmethyl-piperidin-4-yl)-ethyl]-2-methyl-propyl}-7-(2,6-difluoro-phenoxy)-3,4-dihydro-1H-benzo[e][1,4]diazepine-2,5-dione | I |
| 7-(2-Ethyl-phenoxy)-4-{1-[4-(4-fluoro-benzylamino)-piperidine-1-carbonyl]-2-methyl-propyl}-3,4-dihydro-1H-benzo[e][1,4]diazepine-2,5-dione | II |
| 4-[1-(4-Cyclopropylamino-piperidine-1-carbonyl)-2-methyl-propyl]-7-(2-ethyl-phenoxy)-3,4-dihydro-1H-benzo[e][1,4]diazepine-2,5-dione | II |
| 7-(2,4-Difluoro-phenoxy)-4-[1-(3-dimethylaminomethyl-phenyl)-2-methyl-propyl]-3,4-dihydro-1H-benzo[e][1,4]diazepine-2,5-dione | I |
| 7-(2,4-Difluoro-phenoxy)-4-{1-[3-(isopropylamino-methyl)-phenyl]-2-methyl-propyl}-3,4-dihydro-1H-benzo[e][1,4]diazepine-2,5-dione | I |
| 2-(2,5-Dioxo-7-phenoxy-1,2,3,5-tetrahydrobenzo[e][1,4]diazepin-4-yl)-3-methyl-butyric acid 1-benzyl-piperidin-4-yl ester | II |
| 1-Benzyl-piperidine-4-carboxylic acid 2-[7-(4-fluoro-phenoxy)-2,5-dioxo-1,2,3,5-tetrahydro-benzo[e][1,4]diazepin-4-yl]-3-methyl-butyl ester | II |
| (1-Benzyl-piperidin-4-yl)-carbamic acid 2-[7-(4-fluoro-phenoxy)-2,5-dioxo-1,2,3,5-tetrahydro-benzo[e][1,4]diazepin-4-yl]-3-methyl-butyl ester | III |
| [1-(4-Fluoro-benzyl)-piperidin-4-yl]-carbamic acid 2-[7-(4-fluoro-phenoxy)-2,5-dioxo-1,2,3,5-tetrahydro-benzo[e][1,4]diazepin-4-yl]-3-methyl-butyl ester | III |
| N-(1-Benzyl-piperidin-4-yl)-2-(2,5-dioxo-7-phenoxy-1,2,3,5-tetrahydro-benzo[e][1,4]diazepin-4-yl)-3-methyl-butyramide | III |
| 7-(2-tert-Butyl-phenoxy)-4-[1-(4-cyclopropylamino-piperidine-1-carbonyl)-2-methyl-propyl]-3,4-dihydro-1H-benzo[e][1,4]diazepine-2,5-dione | II |
| 2-[7-(4-Fluoro-phenoxy)-2,5-dioxo-1,2,3,5-tetrahydro-benzo[e][1,4]diazepin-4-yl]-3-methyl-N-(1-phenyl-piperidin-4-yl)-butyramide | II |
| 7-(2,6-Dimethyl-phenoxy)-4-{1-[4-(4-fluoro-benzylamino)-piperidine-1-carbonyl]-2-methyl-propyl}-3,4-dihydro-1H-benzo[e][1,4]diazepine-2,5-dione | I |
| 7-(2,6-Dimethyl-phenoxy)-4-(1-{4-[2-(4-fluoro-phenyl)-ethylamino]-piperidine-1-carbonyl}-2-methyl-propyl)-3,4-dihydro-1H-benzo[e][1,4]diazepine-2,5-dione | I |
| 7-(2-tert-Butyl-phenoxy)-4-(1-{4-[2-(4-fluoro-phenyl)-ethylamino]-piperidine-1-carbonyl}-2-methyl-propyl)-3,4-dihydro-1H-benzo[e][1,4]diazepine-2,5-dione | III |
| 2-{1-[2-(1-Cyclopropylmethyl-piperidin-4-yl)-ethyl]-2-methyl-propyl}-7-(2,4-difluoro-phenoxy)-3,4-dihydro-2H-isoquinolin-1-one | I |
| 2-[1-(4-Cyclopropylamino-piperidine-1-carbonyl)-2-methyl-propyl]-7-(2,4-difluoro-phenoxy)-3,4-dihydro-2H-isoquinolin-1-one | I |
| 7-(2,4-Difluoro-phenoxy)-2-{1-[4-(4-fluoro-benzylamino)-piperidine-1-carbonyl]-2-methyl-propyl}-3,4-dihydro-2H-isoquinolin-1-one | I |

TABLE 1-continued

| Compound | Class |
|---|---|
| 7-(2,4-Difluoro-phenoxy)-2-(1-{4-[2-(4-fluoro-phenyl)-ethylamino]-piperidine-1-carbonyl}-2-methyl-propyl)-3,4-dihydro-2H-isoquinolin-1-one | I |
| 2-[1-(1-Cyclopropylmethyl-piperidin-4-yloxymethyl)-2-methyl-propyl]-7-(2,4-difluoro-phenoxy)-3,4-dihydro-2H-isoquinolin-1-one | I |
| 2-(Cyclopropyl-{3-[2-(cyclopropylmethyl-amino)-ethyl]-phenyl}-methyl)-7-(2,4-difluoro-phenoxy)-3,4-dihydro-2H-isoquinolin-1-one | I |
| 2-{1-[4-(Cyclopropylmethyl-amino)-piperidine-1-carbonyl]-2-methyl-propyl}-7-(2,4-difluoro-phenoxy)-3,4-dihydro-2H-isoquinolin-1-one | I |
| N-(1-Benzyl-piperidin-4-yl)-3-methyl-2-(4-oxo-6-o-tolyloxy-4H-quinazolin-3-yl)-butyramide | II |
| N-(1-Benzyl-piperidin-4-yl)-2-[8-(4-fluoro-2-methyl-phenoxy)-1-methyl-6-oxo-4H,6H-3,5,10b-triaza-benzo[e]azulen-5-yl]-3-methyl-butyramide | I |
| 4-{1-[4-(Indan-2-ylamino)-piperidine-1-carbonyl]-2-methyl-propyl}-7-o-tolyloxy-1,2,3,4-tetrahydro-benzo[e][1,4]diazepin-5-one | I |
| 8-(2,4-Difluoro-phenoxy)-2-{1-[4-(4-fluoro-benzylamino)-piperidine-1-carbonyl]-2-methyl-propyl}-2,3-dihydro-benzo[c]azepin-1-one | I |
| 2-[1-(4-Cyclopropylamino-cyclohexylmethyl)-2-methyl-propyl]-8-(2,4-difluoro-phenoxy)-2,3,4,5-tetrahydro-benzo[c]azepin-1-one | I |
| 2-(1-{4-[(Cyclopropylmethyl-amino)-methyl]-thiazol-2-yl}-2-methyl-propyl)-8-(2,4-difluoro-phenoxy)-2,3,4,5-tetrahydro-benzo[c]azepin-1-one | I |
| 4-(1-{4-[2-(4-Fluoro-phenyl)-ethylamino]-piperidine-1-carbonyl}-2-methyl-propyl)-1-methyl-7-o-tolyloxy-1,2,3,4-tetrahydro enzo[e][1,4]diazepin-5-one | II |
| 2-(cyclopropyl(6-((cyclopropylmethylamino)methyl)pyridin-2-yl)methyl)-7-(2,4-difluorophenoxy)-3,4-dihydroisoquinolin-1(2H)-one | I |
| 2-(cyclopropyl(6-((cyclopropylamino)methyl)pyridin-2-yl)methyl)-7-(2,4-difluorophenoxy)-3,4-dihydroisoquinolin-1(2H)-one | I |
| 2-(cyclopropyl(6-((1-hydroxypropan-2-ylamino)methyl)pyridin-2-yl)methyl)-7-(2,4-difluorophenoxy)-3,4-dihydroisoquinolin-1(2H)-one | I |
| 2-(cyclopropyl(6-((1-hydroxy-2-methylpropan-2-ylamino)methyl)pyridin-2-yl)methyl)-7-(2,4-difluorophenoxy)-3,4-dihydroisoquinolin-1(2H)-one | I |
| 2-(cyclopropyl(6-((2-fluoroethylamino)methyl) pyridine-2-yl)methyl)-7-(2,4-difluorophenoxy)-3,4-dihydroisoquinolin-1(2H)-one | I |
| 2-(cyclopropyl(6-((2,2-difluoroethylamino)methyl)pyridin-2-yl)methyl)-7-(2,4-difluorophenoxy)-3,4-dihydroisoquinolin-1(2H)-one | I |

It is understood that the invention is not limited to the embodiments set forth herein for illustration, but embraces all such forms thereof as come within the scope of the following claims.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:
1. A compound of formula I

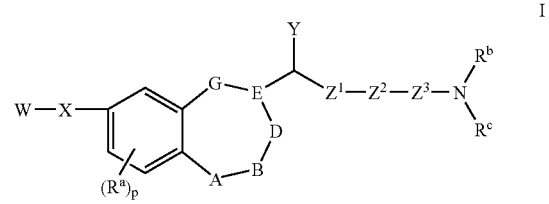

or a pharmaceutically acceptable salt thereof, wherein:
A, B, and D are independently selected from the group consisting of a direct bond, $—C(R^1)(R^2)—$, $—C(R^3)=$, $—C(O)—$, $—N(R^4)—$, $—N=$, $—O—$, and $—S(O)_m—$, wherein m is an integer from 0 to 2, and provided that at least one of A, B, and D is other than a bond; and further provided that when one of A and B is $—C(R^1)(R^2)—$ and the other is $—N(R^4)—$, $R^4$ can be optionally combined with $R^1$, $R^2$ or $R^3$ to form a five or six-membered fused ring containing the nitrogen atom to which $R^4$ is attached and from 0 to 2 additional heteroatoms selected from the group consisting of N, O and S;

E is N;

$R^1$, $R^2$, $R^3$ and $R^4$ are independently selected from the group consisting of hydrogen, halogen, amine, hydroxyl, cyano, $(C_1-C_8)$ alkyl, $(C_2-C_8)$ alkenyl, $(C_2-C_8)$ alkynyl, and $(C_1-C_8)$ alkoxy;

G is selected from the group consisting of $—C(O)—$, $—C(S)—$, $—C(NOR^5)—$, $—C(N—NHR^6)—$, and $—C(R^7)(R^8)—$;

Each $R^a$ is independently selected from the group consisting of halogen, hydroxyl, cyano, $(C_1-C_8)$ alkyl, $(C_2-C_8)$ alkenyl, $(C_2-C_8)$ alkynyl, $(C_1-C_8)$ alkoxy and $—NR^9R^{10}$;

p is an integer from 0 to 3;

X is $—S—$ or $—O—$;

$R^5$, $R^6$, and $R^{14}$ are independently selected from the group consisting of hydrogen, $(C_1-C_8)$ alkyl, $(C_2-C_8)$ alkenyl, and $(C_2-C_8)$ alkynyl;

$R^7$, $R^8$, $R^9$, $R^{10}$, $R^{11}$, $R^{12}$, and $R^{13}$ are independently selected from the group consisting of hydrogen, $(C_1-C_8)$ alkyl, $(C_2-C_8)$ alkenyl, $(C_2-C_8)$ alkynyl, and $(C_1-C_8)$ alkoxy;

W is a ring selected from the group consisting of aryl, heteroaryl, $(C_3-C_8)$ cycloalkyl, $(C_5-C_6)$ heterocycloalkyl, $(C_5-C_8)$ cycloalkenyl, and $(C_5-C_6)$ heterocycloalkenyl;

Y is selected from the group consisting of hydrogen, $(C_1-C_8)$ alkyl, $(C_2-C_8)$ alkenyl, $(C_2-C_8)$ alkynyl, aryl, heteroaryl, $(C_3-C_8)$ cycloalkyl, $(C_3-C_8)$ heterocycloalkyl, $(C_5-C_8)$ cycloalkenyl and $(C_5-C_8)$ heterocycloalkenyl;

$Z^1$ and $Z^3$ are independently selected from the group consisting of a bond and $(C_1-C_8)$ alkylene;

optionally, $Z^3$ can be combined with $R^b$ or $R^c$ to form a 3-, 4-, 5-, 6-, 7- or 8-membered ring containing the nitrogen atom to which $Z^3$ is attached and from 0 to 2 additional heteroatoms selected from the group consisting of N, O, and S;

$Z^2$ is selected from the group consisting of $(C_2-C_8)$ alkenylene, $(C_2-C_8)$ alkynylene, $—C(O)O—$, $—N(R')(R")—$, $—C(O)N(R')—$, $—O—$, $—S(O)_k—$, $—N(R')C(O)N(R")—$, $—N(R')C(O)O—$, $—OC(O)O—$, arylene, heteroarylene, aryl-$(C_1-C_5)$ alkylene, $(C_3-C_8)$ cycloalkylene, ($C_3$-$C_8$) heterocycloalkylene, ($C_5$-$C_8$) cycloalkenylene, ($C_5$-$C_8$) heterocycloalkenylene, and ($C_5$-$C_8$) heterocycloalkylene-C(O)—, wherein k is 0, 1, or 2;

R' and R" are independently selected from the group consisting of hydrogen, ($C_1$-$C_8$) alkyl, ($C_2$-$C_8$) alkenyl, and ($C_2$-$C_8$) alkynyl;

$R^b$ and $R^c$ are independently selected from the group consisting of hydrogen, ($C_1$-$C_8$) alkyl, ($C_2$-$C_8$) alkenyl, ($C_2$-$C_8$) alkynyl, ($C_3$-$C_8$) cycloalkyl, ($C_3$-$C_8$) heterocycloalkyl, ($C_3$-$C_8$) cycloalkenyl, ($C_3$-$C_8$) heterocycloalkenyl, aryl, heteroaryl, halo-($C_1$-$C_8$) alkyl, aryl-($C_1$-$C_5$) alkyl, ($C_3$-$C_8$) cycloalkyl-($C_1$-$C_5$)alkyl, ($C_3$-$C_8$) heterocycloalkyl-($C_1$-$C_5$) alkyl, ($C_3$-$C_8$) heterocycloalkenyl-($C_1$-$C_5$) alkyl, heteroaryl-($C_1$-$C_5$) alkyl, —$CR^{15}CO_2R^{16}$, —$CR^{15}N(R^{16})SO_2R^{17}$, —$CO_2R^{15}$, —$C(O)NR^{15}R^{16}$, —$C(O)N(R^{15})OR^{16}$, —$C(=NOR^{15})NR^{16}R^{17}$, —$C(R^{15})=NOR^{16}$, —$C(O)R^{17}C(O)NR^{15}R^{16}$, —$NR^{15}R^{16}$, —$NR^{15}SO_2R^{16}$, —$NR^{15}(OR^{16})$, —$NR^{17}C(O)NR^{15}C(O)R^{16}$, —$NR^{15}C(O)NR^{16}R^{17}$, —$OR^{15}$, and —$SO_2NR^{15}R^{16}$; optionally, $R^b$ and $R^c$ may be combined to form a 3-, 4-, 5-, 6-, 7-, or 8-membered ring containing the nitrogen atom to which they are attached from 0 to 3 additional heteroatoms selected from the group consisting of N, O and S; and $R^{15}$, $R^{16}$, and $R^{17}$ are independently selected from the group consisting of hydrogen, ($C_1$-$C_8$) alkyl, ($C_2$-$C_8$) alkenyl, ($C_2$-$C_8$) alkynyl, halo-($C_1$-$C_4$)alkyl, hetero($C_1$-$C_4$)alkyl, ($C_3$-$C_8$) cycloalkyl, ($C_3$-$C_8$) heterocycloalkyl, ($C_3$-$C_8$) cycloalkenyl, ($C_3$-$C_8$) heterocycloalkenyl, aryl, heteroaryl and aryl-($C_1$-$C_4$)alkyl.

2. The compound as set forth in claim 1 represented by a formula selected from the group consisting of formulas II(a), II(b), II(c), II(d), II(e), II(f), II(g), II(h), II(i), II(j) and II(k), II(a)

II(b)

II(c)

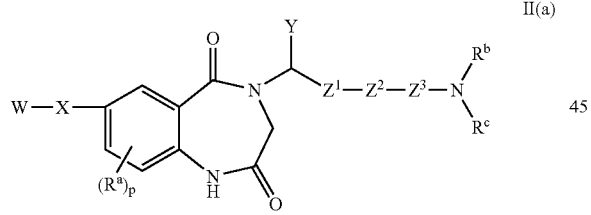
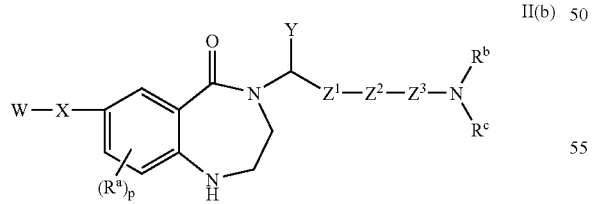
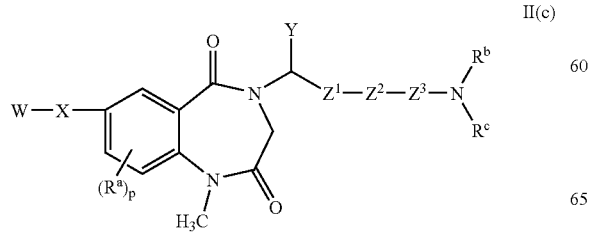

-continued

II(d)
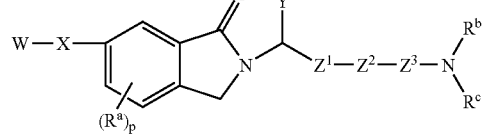

II(e)
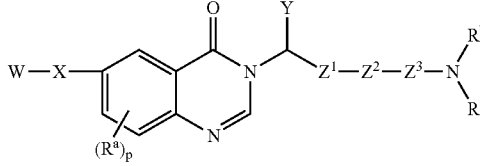

II(f)
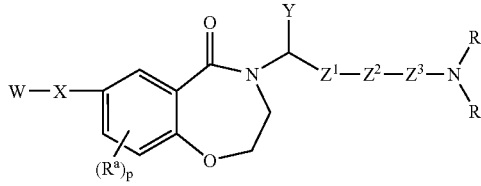

II(g)
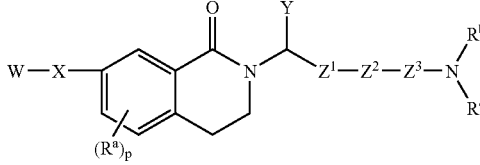

II(h)
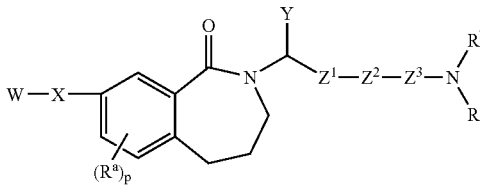

II(i)
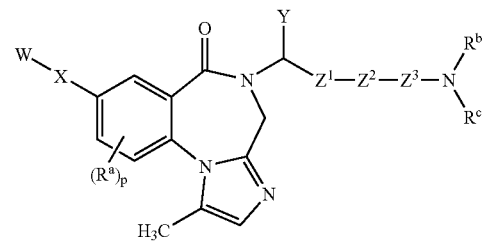

II(j)
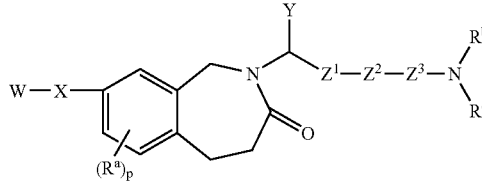

II(k)
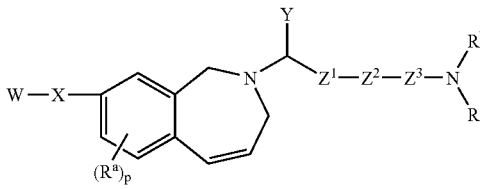

or a pharmaceutically acceptable salt thereof.

3. The compound as set forth in claim 2 represented by formula II(a) or formula II(g)

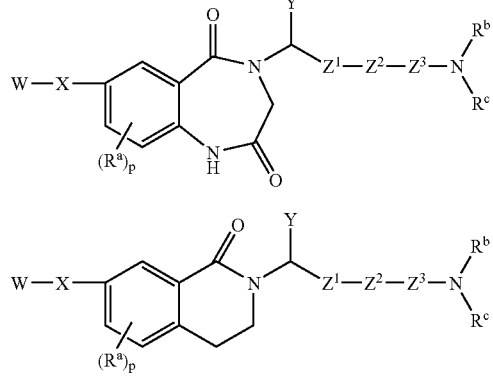

or a pharmaceutically acceptable salt thereof.

4. The compound of claim 2, wherein Y is selected from the group consisting of $(C_1-C_8)$ alkyl, $(C_2-C_8)$ alkenyl, $(C_2-C_8)$ alkynyl, $(C_3-C_8)$ cycloalkyl, $(C_3-C_8)$ heterocycloalkyl, aryl, heteroaryl and $(C_5-C_8)$ cycloalkenyl.

5. The compound of claim 4, wherein Y is selected from the group consisting of isopropyl, tert-butyl, cyclopropyl, cyclobutyl, cyclopentyl, cyclohexyl, thiophenyl, and cyclopentadienyl.

6. The compound of claim 1, wherein $Z^2$ is selected from the group consisting of:

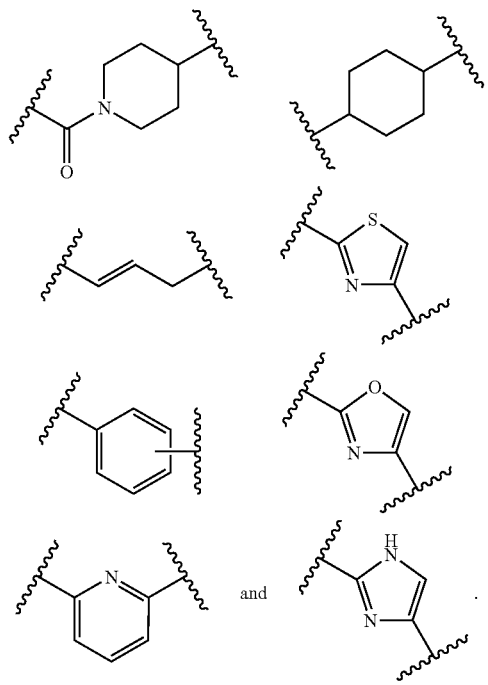

7. The compound of claim 1, wherein $Z^3$ is combined with $R^b$ to form a 3-, 4-, 5-, 6-, 7- or 8-membered ring containing the nitrogen atom to which $Z^3$ is attached and from 0 to 2 additional heteroatoms selected from the group consisting of N, O and S.

8. The compound of claim 7, wherein the ring resulting from combining $Z^3$ and $R^b$ is selected from the group consisting of:

9. The compound of claim 6, wherein W is aryl.

10. The compound of claim 9, wherein $R^b$ and $R^c$ are independently selected from the group consisting of hydrogen,

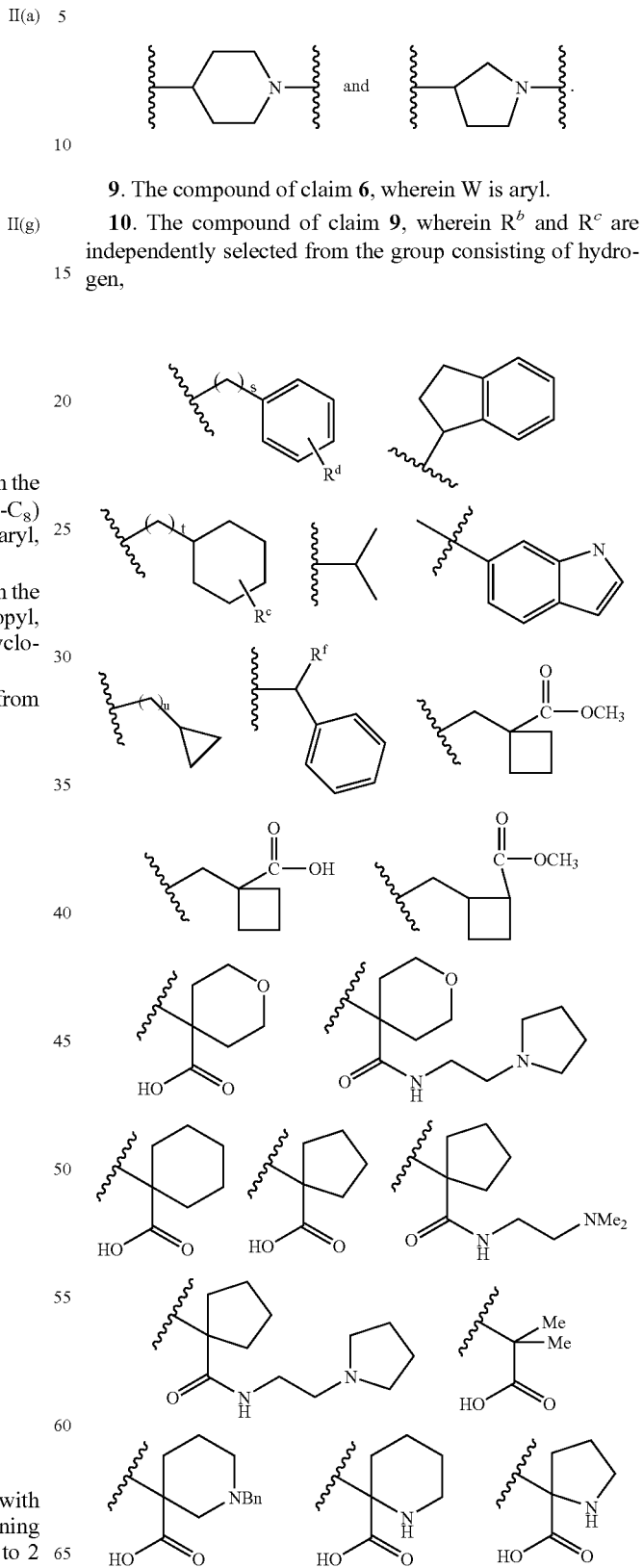

-continued

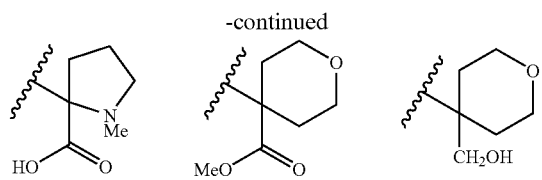
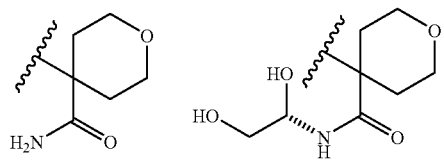
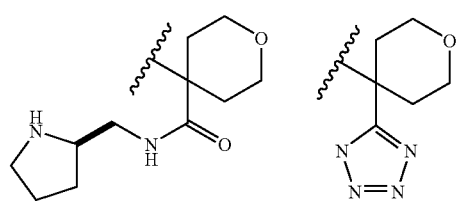
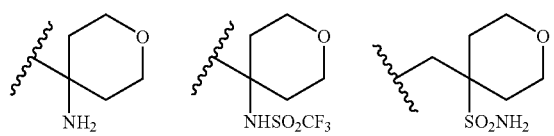
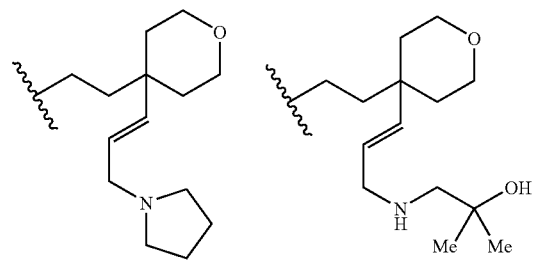
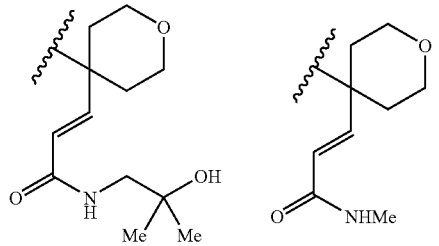
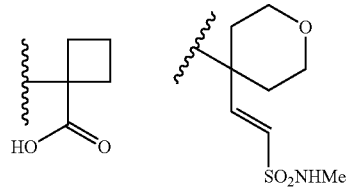
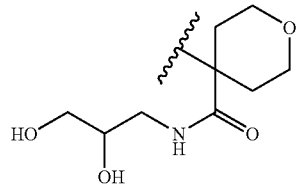

-continued

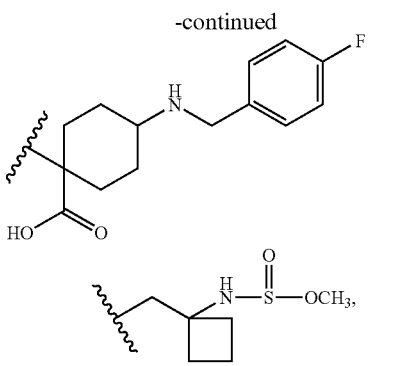

and wherein the subscripts s, t, and u are independently an integer from 0 to 5, and $R^d$, $R^e$, and $R^f$ are independently selected from the group consisting of hydrogen, halogen, hydroxyl, amine, ($C_1$-$C_8$) alkyl and ($C_2$-$C_8$) alkenyl.

11. The compound of claim 8, wherein W is aryl.

12. The compound of claim 11, wherein $R^c$ is selected from the group consisting of hydrogen,

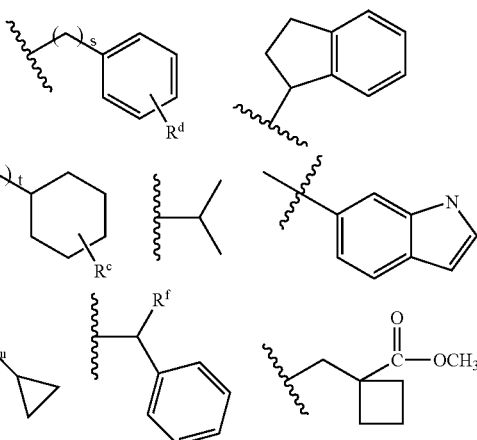
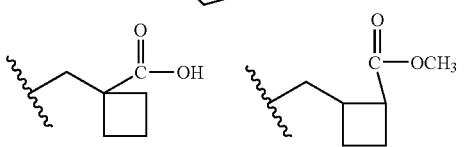
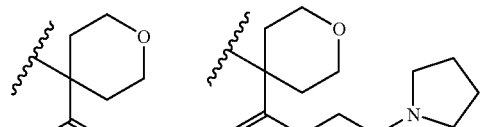
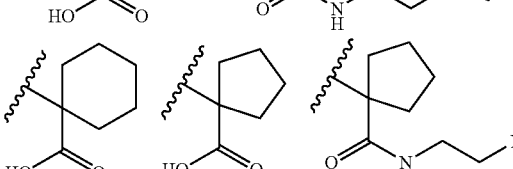
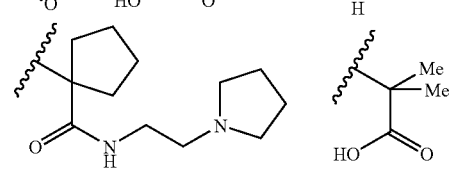

-continued

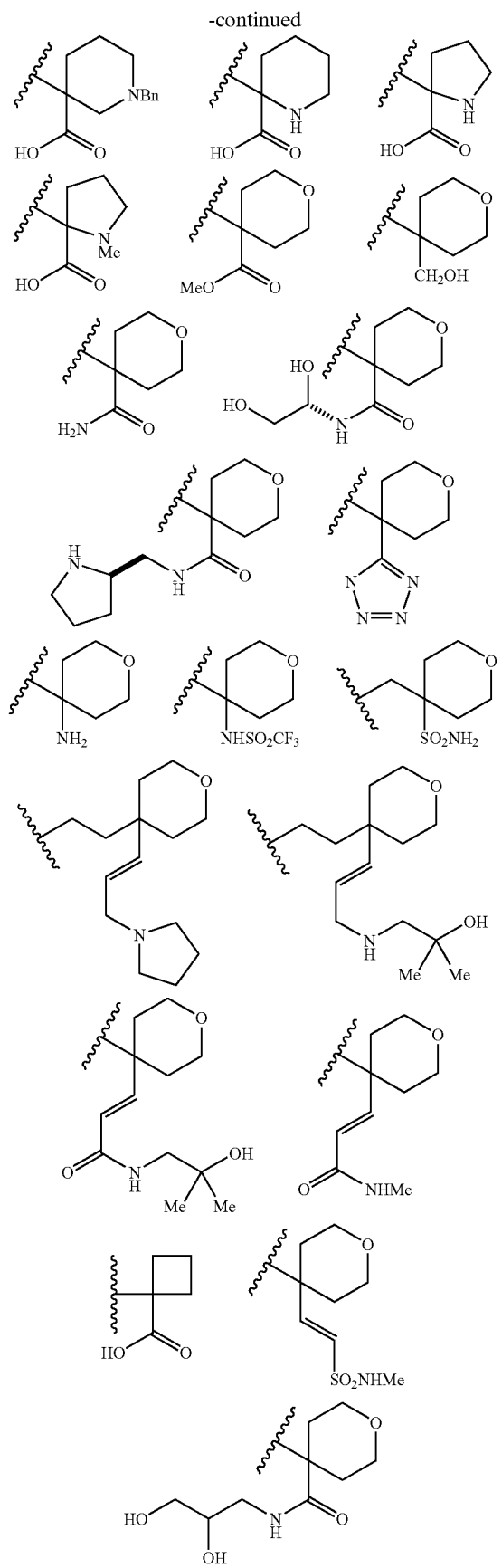

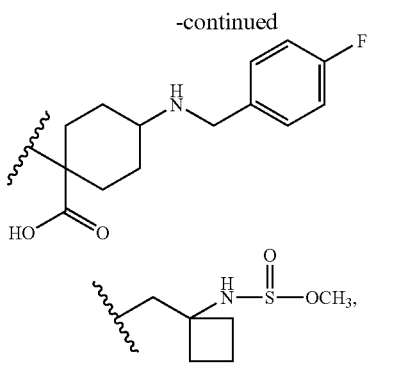

wherein the subscripts s, t, and u are independently an integer from 0 to 5, and $R^d$, $R^e$, and $R^f$ are independently selected from the group consisting of hydrogen, halogen, hydroxyl, amine, ($C_1$-$C_8$) alkyl and ($C_2$-$C_8$) alkenyl.

13. The compound as set forth in claim 1, wherein the compound is selected from the group consisting of:

N-(1-benzyl-piperidin-4-yl)-2-(2,5-dioxo-7-phenoxy-1,2,3,5-tetrahydro-benzo[e][1,4]diazepin-4-yl)-3-methyl-butyramide, N-(1-benzyl-piperidin-4-yl)-2-(2,5-dioxo-7-phenoxy-1,2,3,5-tetrahydro-benzo[e][1,4]diazepin-4-yl)-3,3-dimethyl-butyramide, 2-[7-(2,6-dimethyl-phenoxy)-2,5-dioxo-1,2,3,5-tetrahydro-benzo[e][1,4]diazepin-4-yl]-3-methyl-N-[1-(1-phenyl-ethyl)-piperidin-4-yl]-butyramide, 2-[7-(2,6-dimethyl-phenoxy)-2,5-dioxo-1,2,3,5-tetrahydro-benzo[e][1,4]diazepin-4-yl]-N-(1-indan-1-yl-piperidin-4-yl)-3-methyl-butyramide, 4-{1-[2-(1-cyclopropylmethyl-piperidin-4-yl)-ethyl]-2-methyl-propyl}-7-(2,6-difluoro-phenoxy)-3,4-dihydro-1H-benzo[e][1,4]diazepine-2,5-dione, 7-(2-ethyl-phenoxy)-4-{1-[4-(4-fluoro-benzylamino)-piperidine -1-carbonyl]-2-methyl-propyl}-3,4-dihydro-1H-benzo[e][1,4]diazepine-2,5-dione, 4-[1-(4-cyclopropylamino-piperidine-1-carbonyl)-2-methyl-propyl]-7-(2-ethyl-phenoxy)-3,4-dihydro-1H-benzo[e][1,4]diazepine-2,5-dione, 7-(2,4-difluoro-phenoxy)-4-[1-(3-dimethylaminomethyl-phenyl)-2-methyl-propyl]-3,4-dihydro-1H-benzo[e][1,4]diazepine-2,5-dione, 7-(2,4-difluoro-phenoxy)-4-{1-[3-(isopropylamino-methyl)-phenyl]-2-methyl-propyl}-3,4-dihydro-1H-benzo[e][1,4]diazepine-2,5-dione, 2-(2,5-dioxo-7-phenoxy-1,2,3,5-tetrahydrobenzo[e][1,4]diazepin-4-yl)-3-methyl-butyric acid 1-benzyl-piperidin-4-yl ester, 1-benzyl-piperidine-4-carboxylic acid 2-[7-(4-fluoro-phenoxy)-2,5-dioxo-1,2,3,5-tetrahydro-benzo[e][1,4]diazepin-4-yl]-3-methyl-butyl ester, (1-benzyl-piperidin-4-yl)-carbamic acid 2-[7-(4-fluoro-phenoxy)-2,5-dioxo-1,2,3,5-tetrahydro-benzo[e][1,4]diazepin-4-yl]-3-methyl-butyl ester,

[1-(4-fluoro-benzyl)-piperidin-4-yl]-carbamic acid 2-[7-(4-fluoro-phenoxy)-2,5-dioxo-1,2,3,5-tetrahydro-benzo[e][1,4]diazepin-4-yl]-3-methyl-butyl ester, N-(1-benzyl-piperidin-4-yl)-2-(2,5-dioxo-7-phenoxy-1,2,3,5-tetrahydro-benzo[e][1,4]diazepin-4-yl)-3-methyl-butyramide, 7-(2-tert-butyl-phenoxy)-4-[1-(4-cyclopropylamino-piperidine-1-carbonyl)-2-methyl-propyl]-3,4-dihydro-1H-benzo[e][1,4]diazepine-2,5-dione,
N-(1-benzyl-piperidin-4-yl)-2-(2,5-dioxo-7-phenoxy-1,2,3,5-tetrahydro-benzo[e][1,4]diazepin-4-yl)-2-thiophen-2-yl-acetamide,
N-(1-benzyl-piperidin-4-yl)-2-cyclohexyl-2-(2,5-dioxo-7-phenoxy-1,2,3,5-tetrahydro-benzo[e][1,4]diazepin-4-yl)-acetamide,
2-[7-(4-fluoro-phenoxy)-2,5-dioxo-1,2,3,5-tetrahydro-benzo[e][1,4]diazepin-4-yl]-3-methyl-N-(1-phenyl-piperidin-4-yl)-butyramide;
7-(2,6-dimethyl-phenoxy)-4-{1-[4-(4-fluoro-benzylamino)-piperidine-1-carbonyl]-2-methyl-propyl}-3,4-dihydro-1H-benzo[e][1,4]diazepine-2,5-dione;
7-(2,6-dimethyl-phenoxy)-4-(1-{4-[2-(4-fluoro-phenyl)-ethylamino]-piperidine-1-carbonyl}-2-methyl-propyl)-3,4-dihydro-1H-benzo[e][1,4]diazepine-2,5-dione;
7-(2-tert-butyl-phenoxy)-4-(1-{4-[2-(4-fluoro-phenyl)-ethylamino]-piperidine-1-carbonyl}-2-methyl-propyl)-3,4-dihydro-1H-benzo[e][1,4]diazepine-2,5-dione;
2-{1-[2-(1-cyclopropylmethyl-piperidin-4-yl)-ethyl]-2-methyl-propyl}-7-(2,4-difluoro-phenoxy)-3,4-dihydro-2H-isoquinolin-1-one,
2-[1-(4-cyclopropylamino-piperidine-1-carbonyl)-2-methyl-propyl]-7-(2,4-difluoro-phenoxy)-3,4-dihydro-2H-isoquinolin-1-one,
7-(2,4-difluoro-phenoxy)-2-{1-[4-(4-fluoro-benzylamino)-piperidine-1-carbonyl]-2-methyl-propyl}-3,4-dihydro-2H-isoquinolin-1-one,
7-(2,4-difluoro-phenoxy)-2-(1-{4-[2-(4-fluoro-phenyl)-ethylamino]-piperidine-1-carbonyl}-2-methyl-propyl)-3,4-dihydro-2H-isoquinolin-1-one,
2-[1-(1-cyclopropylmethyl-piperidin-4-yloxymethyl)-2-methyl-propyl]-7-(2,4-difluoro-phenoxy)-3,4-dihydro-2H-isoquinolin-1-one,
2-(cyclopropyl-{3-[2-(cyclopropylmethyl-amino)-ethyl]-phenyl}-methyl)-7-(2,4-difluoro-phenoxy)-3,4-dihydro-2H-isoquinolin-1-one,
2-{1-[4-(cyclopropylmethyl-amino)-piperidine-1-carbonyl]-2-methyl-propyl}-7-(2,4-difluoro-phenoxy)-3,4-dihydro-2H-isoquinolin-1-one,
N-(1-benzyl-piperidin-4-yl)-3-methyl-2-(4-oxo-6-o-tolyloxy-4H-quinazolin-3-yl)-butyramide,
N-(1-benzyl-piperidin-4-yl)-2-[8-(4-fluoro-2-methyl-phenoxy)-1-methyl-6-oxo-4H, 6H-3,5,10b-triaza-benzo[e]azulen-5-yl]-3-methyl-butyramide,
4-{1-[4-(indan-2-ylamino)-piperidine-1-carbonyl]-2-methyl-propyl}-7-o-tolyloxy-1,2,3,4-tetrahydro-benzo[e][1,4]diazepin-5-one,
8-(2,4-difluoro-phenoxy)-2-{1 -[4-(4-fluoro-benzylamino)-piperidine-1-carbonyl]-2-methyl-propyl}-2,3-dihydro-benzo[c]azepin-1-one,
2-[1-(4-cyclopropylamino-cyclohexylmethyl)-2-methyl-propyl]-8-(2,4-difluoro-phenoxy)-2,3,4,5-tetrahydro-benzo[c]azepin-1-one,
2-(1-{4-[(cyclopropylmethyl-amino)-methyl]-thiazol-2-yl }-2-methyl-propyl)-8-(2,4-difluoro-phenoxy)-2,3,4,5-tetrahydro-benzo[c]azepin-1-one,
2-{1-[4-(cyclopropylmethyl-amino)-piperidine-1-carbonyl]-2-methyl-propyl}-8-(2,4-difluoro-phenoxy)-1,2,4,5-tetrahydro-benzo[c]azepin-3-one,
4-(1-{4-[2-(4-fluoro-phenyl)-ethylamino]-piperidine-1-carbonyl}-2-methyl-propyl)-1-methyl-7-o-tolyloxy-1,2,3,4-tetrahydroenzo[e][1,4]diazepin-5-one, 2-(cyclopropyl(6-((cyclopropylmethylamino)methyl)pyridin-2-yl)methyl)-7-(2,4-difluorophenoxy)-3,4-dihydroisoquinolin-1(2H)-one,
2-(cyclopropyl(6-((cyclopropylamino)methyl)pyridin-2-yl)methyl)-7-(2,4-difluorophenoxy)-3,4-dihydroisoquinolin-1(2H)-one,
2-(cyclopropyl(6-(((1-hydroxypropan-2-ylamino)methyl)pyridin-2-yl)methyl)-7-(2,4-difluorophenoxy)-3,4-dihydroisoquinolin-1(2H)-one,
2-(cyclopropyl(6-(((1-hydroxy-2-methylpropan-2-ylamino)methyl)pyridin-2-yl)methyl)-7-(2,4-difluorophenoxy)-3,4-dihydroisoquinolin-1 (2H)-one,
2-(cyclopropyl(6-(((2-fluoroethylamino)methyl)pyridine-2-yl)methyl)-7-(2,4-difluorophenoxy)-3,4-dihydroisoquinolin-1(2H)-one and
2-(cyclopropyl(6-((2,2-difluoroethylamino) methyl)pyridin-2-yl)methyl)-7-(2,4-difluorophenoxy)-3,4-dihydroisoquinolin-1(2H)-one.

14. A compound of formula I

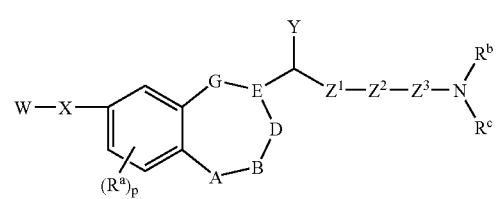

or a pharmaceutically acceptable salt thereof, wherein:

A, B, and D are independently selected from the group consisting of a direct bond, —C(R$^1$)(R$^2$)—, —C(R$^3$)═, —C(O)—, —N(R$^4$)—, —N═, —O—, and —S(O)$_m$—, wherein m is an integer from 0 to 2, and provided that at least one of A, B, and D is other than a bond; and further provided that when one of A and B is —C(R$^1$)(R$^2$)— and the other is —N(R$^4$)—, R$^4$ can be optionally combined with R$^1$, R$^2$ or R$^3$ to form a five or six-membered fused ring containing the nitrogen atom to which R$^4$ is attached and from 0 to 2 additional heteroatoms selected from the group consisting of N, O and S;

E is N;

R$^1$, R$^2$, R$^3$ and R$^4$ are independently selected from the group consisting of hydrogen, halogen, amine, hydroxyl, cyano, (C$_1$-C$_8$) alkyl, (C$_2$-C$_8$) alkenyl, (C$_2$-C$_8$) alkynyl, and (C$_1$-C$_8$) alkoxy;

G is selected from the group consisting of —C(O)—, —C(S)—, —C(NOR$^5$)—, —C(N—NHR$^6$)—, and —C(R$^7$)(R$^8$)—;

Each R$^a$ is independently selected from the group consisting of halogen, hydroxyl, cyano, (C$_1$-C$_8$) alkyl, (C$_2$-C$_8$) alkenyl, (C$_2$-C$_8$) alkynyl, (C$_1$-C$_8$) alkoxy and —NR$^9$R$^{10}$;

p is an integer from 0 to 3;

X is selected from the group consisting of —O— and —S(O)$_n$—, wherein n is an integer from 0 to 2;

R$^5$, R$^6$, and R$^{14}$ are independently selected from the group consisting of hydrogen, (C$_1$-C$_8$) alkyl, (C$_2$-C$_8$) alkenyl, and (C$_2$-C$_8$) alkynyl;

R$^7$, R$^8$, R$^9$, R$^{10}$, R$^{11}$, R$^{12}$, and R$^{13}$ are independently selected from the group consisting of hydrogen, (C$_1$-C$_8$) alkyl, (C$_2$-C$_8$) alkenyl, (C$_2$-C$_8$) alkynyl, and (C$_1$-C$_8$) alkoxy;

W is a ring selected from the group consisting of aryl, heteroaryl, ($C_3$-$C_8$) cycloalkyl, ($C_5$-$C_6$) heterocycloalkyl, ($C_5$-$C_8$) cycloalkenyl, and ($C_5$-$C_6$) heterocycloalkenyl;

Y is selected from the group consisting of ($C_1$-$C_8$) alkyl, ($C_2$-$C_8$) alkenyl, ($C_2$-$C_8$) alkynyl, aryl, heteroaryl, ($C_3$-$C_8$) cycloalkyl, ($C_3$-$C_8$) heterocycloalkyl, ($C_5$-$C_8$) cycloalkenyl and ($C_5$-$C_8$) heterocycloalkenyl;

$Z^1$ and $Z^3$ are independently selected from the group consisting of a bond and ($C_1$-$C_8$) alkylene;

optionally, $Z^3$ can be combined with $R^b$ or $R^c$ to form a 3-, 4-, 5-, 6-, 7- or 8-membered ring containing the nitrogen atom to which $Z^3$ is attached and from 0 to 2 additional heteroatoms selected from the group consisting of N, O, and S;

$Z^2$ is selected from the group consisting of ($C_2$-$C_8$), alkenylene ($C_2$-$C_8$) alkynylene, —C(O)O—, —N(R') (R")—, —C(O)N(R')—, —O—, —S(O)$_k$—, —N(R')C (O)N(R")—, —N(R')C(O)O—, —OC(O)O—, arylene, heteroarylene, aryl-($C_1$-$C_5$) alkylene, ($C_3$-$C_8$) cycloalkylene, ($C_3$-$C_8$) heterocycloalkylene, ($C_5$-$C_8$) cycloalkenylene, ($C_5$-$C_8$) heterocycloalkenylene, and ($C_5$-$C_8$) heterocycloalkylene-C(O)—, wherein k is 0, 1, or 2;

R' and R" are independently selected from the group consisting of hydrogen, ($C_1$-$C_8$) alkyl, ($C_2$-$C_8$) alkenyl, and ($C_2$-$C_8$) alkynyl;

$R^b$ and $R^C$ are independently selected from the group consisting of hydrogen, ($C_1$-$C_8$) alkyl, ($C_2$-$C_8$) alkenyl, ($C_2$-$C_8$) alkynyl, ($C_3$-$C_8$) cycloalkyl, ($C_3$-$C_8$) heterocycloalkyl, ($C_3$-$C_8$) cycloalkenyl, ($C_3$-$C_8$) heterocycloalkenyl, aryl, heteroaryl, halo-($C_1$-$C_8$) alkyl, aryl-($C_1$-$C_5$) alkyl, ($C_3$-$C_8$) cycloalkyl-($C_1$-$C_5$)alkyl, ($C_3$-$C_8$) heterocycloalkyl-($C_1$-$C_5$) alkyl, ($C_3$-$C_8$) heterocycloalkenyl-($C_1$-$C_5$) alkyl, heteroaryl-($C_1$-$C_5$) alkyl, —$CR^{15}CO_2R^{16}$, —$CR^{15}N(R^{16})SO_2R^{17}$, —$CO_2R^{15}$, —$C(O)NR^{15}R^{16}$, —$C(O)N(R^{15})OR^{16}$, —$C(=NOR^{15})$ $NR^{16}R^{17}$, —$C(R^{15})=NOR^{16}$, —$C(O)R^{17}C(O)$ $NR^{15}R^{16}$, —$NR^{15}R^{16}$, —$NR^{15}SO_2R^{16}$, —$NR^{15}(OR^{16})$, —$NR^{17}C(O)NR^{15}C(O)R^{16}$, —$NR^{15}C(O)NR^{16}R^{17}$, —$OR^{15}$, and —$SO_2NR^{15}R^{16}$; optionally, $R^b$ and $R^c$ may be combined to form a 3-, 4-, 5-, 6-, 7-, or 8-membered ring containing the nitrogen atom to which they are attached from 0 to 3 additional heteroatoms selected from the group consisting of N, O and S; and $R^{15}$, $R^{16}$, and $R^{17}$ are independently selected from the group consisting of hydrogen, ($C_1$-$C_8$) alkyl, ($C_2$-$C_8$) alkenyl, ($C_2$-$C_8$) alkynyl, halo-($C^1$-$C4$)alkyl, hetero($C_1$-$C_4$)alkyl, ($C_3$-$C_8$) cycloalkyl, ($C_3$-$C_8$) heterocycloalkyl, ($C_3$-$C_8$) cycloalkenyl, ($C_3$-$C_8$) heterocycloalkenyl, aryl, heteroaryl and aryl-($C_1$-$C_4$)alkyl.

15. A pharmaceutical composition comprising the compound of any one of claims 1, 13 or 14 and a pharmaceutically acceptable carrier, diluent or excipient.

16. A pharmaceutical composition comprising the compound of any one of claims 1, 13 or 14 and an additional anti-obesity agent.

17. The pharmaceutical composition of claim 16, wherein the additional anti-obesity agent is selected from the group consisting of a serotonin transporter inhibitor, a norepinephrine transporter inhibitor, a cannabinoid-1 antagonist/inverse agonist, a histamine 3 antagonist/inverse agonist, a melanin concentrating hormone 1R antagonist, a melanin concentrating hormone 2R agonist/antagonist, leptin, a leptin derivative, an opioid antagonist, an orexin antagonist, a bombesin receptor subtype 3, a cholecystokinin-A agonist, a Ciliary neurotrophic factor, a Ciliary neurotrophic factor derivative, a growth hormone secretagogue receptor agonist/antagonist, a serotonin receptor 2C agonist, a melanocortin 4 receptor agonist, a monoamide reuptake inhibitor, an uncoupling protein-1, -2, or -3 activator, a beta adrenergic receptor 3 agonist, a thyroid hormone β agonist, a phosphodiesterase inhibitor, a fatty acid synthase inhibitor, a diacylglycerol acyltransferase-1 inhibitor, a diacylglycerol acyltransferase-2 inhibitor, an acetyl-CoA carboxylase 2 inhibitor, a glucocorticoid antagonist, an acyl-estrogen, a lipase inhibitor, a fatty acid transporter inhibitor, a dicarboxylate transporter inhibitor, a glucose transporter inhibitor, metformin and topiramate.

18. A method for treating a condition or disorder selected from the group consisting of obesity and an eating disorder, comprising administering to a subject in need thereof a therapeutically effective amount of a compound of any one of claims 1, 13 or 14.

19. A method for treating a condition or disorder selected from the group consisting of obesity and an eating disorder, comprising administering to a subject in need thereof a therapeutically effective amount of a compound of any one of claims 1, 13 or 14 and an additional anti-obesity agent.

20. The method of claim 19, wherein the additional anti-obesity agent is selected from the group consisting of a serotonin transporter inhibitor, a norepinephrine transporter inhibitor, a cannabinoid-1 antagonist/inverse agonist, a histamine 3 antagonist/inverse agonist, a melanin concentrating hormone 1R antagonist, a melanin concentrating hormone 2R agonist/antagonist, leptin, a leptin derivative, an opioid antagonist, an orexin antagonist, a bombesin receptor subtype 3, a cholecystokinin-A agonist, a Ciliary neurotrophic factor, a Ciliary neurotrophic factor derivative, a growth hormone secretagogue receptor agonist/antagonist, a serotonin receptor 2C agonist, a melanocortin 4 receptor agonist, a monoamide reuptake inhibitor, an uncoupling protein-1,-2, or -3 activator, a beta adrenergic receptor 3 agonist, a thyroid hormone β agonist, a phosphodiesterase inhibitor, a fatty acid synthase inhibitor, a diacylglycerol acyltransferase-1 inhibitor, a diacylglycerol acyltransferase-2 inhibitor, an acetyl-CoA carboxylase 2 inhibitor, a glucocorticoid antagonist, an acyl-estrogen, a lipase inhibitor, a fatty acid transporter inhibitor, a dicarboxylate transporter inhibitor, a glucose transporter inhibitor, metformin and topiramate.

* * * * *